US007335755B2

(12) United States Patent
Nakagawara

(10) Patent No.: US 7,335,755 B2
(45) Date of Patent: Feb. 26, 2008

(54) NUCLEIC ACIDS ISOLATED IN NEUROBLASTOMA

(75) Inventor: Akira Nakagawara, Chiba (JP)

(73) Assignees: Hisamitsu Pharmaceutical Co., Inc., Saga (JP); Chiba-Prefecture, Chiba-Shi, Chiba (JP)

( * ) Notice: Subject to any disclaimer, the term of this patent is extended or adjusted under 35 U.S.C. 154(b) by 374 days.

(21) Appl. No.: 10/478,914

(22) PCT Filed: May 30, 2002

(86) PCT No.: PCT/JP02/05294

§ 371 (c)(1),
(2), (4) Date: Jun. 14, 2004

(87) PCT Pub. No.: WO02/097093

PCT Pub. Date: Dec. 5, 2002

(65) Prior Publication Data

US 2004/0265812 A1 Dec. 30, 2004

(30) Foreign Application Priority Data

May 30, 2001 (JP) ............................ 2001-162775
Aug. 24, 2001 (JP) ............................ 2001-255226

(51) Int. Cl.
*C07H 21/02* (2006.01)

(52) U.S. Cl. .................................................... 536/23.1

(58) Field of Classification Search ..................... None
See application file for complete search history.

(56) References Cited

U.S. PATENT DOCUMENTS 5,605,662 A 2/1997 Heller et al.
6,569,662 B1 * 5/2003 Tang et al. ................. 435/212

FOREIGN PATENT DOCUMENTS

WO WO 01/66719 A1 3/2001
WO WO 01/27269 A2 4/2001

OTHER PUBLICATIONS

Buck et al., "Design Strategies and Performance of Custom DNA Sequencing Primers," BioTechniques, 1999, vol. 27, No. 3, pp. 528-536.*

Murphy, "Gene Expression Studies using Microarrays: Principles, Problems, and Prospects," Advances in Physiological Education, Dec. 2002, vol. 26, No. 4, pp. 256-270.*

Heilig et al., "Human Chromosome 14 DNA Sequence BAC R-909M7 of Library RPCI-11 From Chromosome 14 of *Homo sapiens* (Human)", Database EMBL, Database Accession No. AL132709—Document No. XP002301383 (Oct. 28, 1999).

Hillier et al., "zh52hll.rl Soares_fetal_liver_spleen_1NFLS_S1 *Homo sapiens* cDNA Clone IMAGE:415749 5', mRNA Sequence", Database EMBL, Database Accession No. W78947—Document No. XP002301384 (Jun. 25, 1996).

Tsuda et al., "Retrospective Study on Amplification of N-*MYC* and c-*MYC* Genes in Pediatric Solid Tumors and its Association With Prognosis and Tumor Differentiation", Laboratory Investigation, United States and Canadian Academy of Pathology, vol. 50, No. 3, pp. 321-327 (Sep. 1998).

Nakagawara et al., "Inverse Relationship Between *TRK* Expression and N-*MYC* Amplification in Human Neuroblastomas," Cancer Research, vol. 52, No. 5, pp. 1364-1368 (Mar. 1, 1992.

Human Polynucleotide SEQ ID No. 979, Geneseq Database, retrieved from EBI Accession No. GSN:AAI58776 (Database Accession No.), Oct. 22, 2001.

Human Polynucleotide SEQ ID No. 4551, Geneseq Database, retrieved from EBI Accession No. GSN:AAI60562 (Database Accession No.), Oct. 22, 2001.

*Homo sapiens* neuronal specific transcription factor DAT1 mRNA, complete cds., EMBL Database, EBI Accession No. EMBL:AF258348 (May 24, 2000).

*Homo sapiens* 12p13.3 BAC RCPI11-424M22 (Roswell Park Cancer Institute Human BAC Library) complete sequence, EMBL Database, retrieved from EBI Accession No. EMBL:AC007552 (May 17, 1999).

*Homo sapiens* mRNA; cDNA DKFZp586B2223 (from clone DKFZp586B2223), EMBL Database, retrieved from EBI Accession No. EMBL:AL050188 (May 20, 1999).

Human full-length cDNA 3-Prime end of clone CS0DL005YA17 of B Cells (Ramos Cell Line) COT 25-Normalized of *Homo sapiens* (human), EMBL Database,retrieved ffrom EBI Accession No. EMBL:AL582210 (Feb. 12, 2001).

Nakagawara, Shinkeigashu no Hassei to Sono Bunshi Kito, "Neuroblastoma Develpment and Molecular Mechanism," Shoni Naiki 30, 143 (1998).

Knudson AG, et al., Regression of Neuroblastoma IV-S: A Genetic Hypothesis, N. Engl. J. Med. 302, 1254 (1980).

Nakagawara A., The NGF Story and Neuroblastoma, Med. Pediatr. Oncol., 31, 113 (1998).

Nakagawara, et al., Shinkeigasaiboushu ni Okeru Neurotrophin Juyoutai no Hatsugen to Yogo, "Expression of Neurotrophin Receptors and Prognosis in Neuroblastoma," Shoni Geka (Pediatric Surgery), 29:425-432, (1997).

(Continued)

*Primary Examiner*—Young J. Kim
(74) *Attorney, Agent, or Firm*—Fitch Even Tabin & Flannery

(57) ABSTRACT

There are disclosed a nucleic acid whose expression is enhanced in human neuroblastoma with unfavorable prognosis based on comparison between human neuroblastoma with favorable prognosis and human neuroblastoma with unfavorable prognosis, the nucleic acid comprising any one of base sequences set forth in SEQ ID NO:1 to NO:69 in the Sequence Listing, a nucleic acid comprising a portion of any of those base sequences, and an isolated nucleic acid capable of hybridizing to a complementary base sequence of the foregoing under stringent conditions. It discloses gene sequences relating to favorable or unfavorable prognosis of neuroblastoma and will enable the provision of their genetic information and the diagnosis of favorable or unfavorable prognosis.

2 Claims, 2 Drawing Sheets

OTHER PUBLICATIONS

Nakagawara, Nou-shinkeishuyo no Tadankai Hatsugan, “Multistage Oncogenesis of Cerebral and Neural Tumors,” Molecular Medicine, vol. 36, No. 4, 366-372 (1999).

Naldini, L., et al., Science 272, 263-267 (1996).

Medical and Pediatric Oncology, 35:547-549, Dec. 1, 2000.

Kawamoto, et al., “Association Between Favorable Neuroblastoma and High Expression of the Novel Metalloproteinase Gene, *nbla3145/XCE*, Cloned By Differential Screening of the Full-Length-Enriched Oligo-Capping Neuroblastoma cDNA Libraries,” Medical and Pediatric Oncology, 35:628-631 (2000).

Ohira et al., Hunting the Subset-Specific Genes of Neuroblastoma: Expression Profiling and Differential Screening of the Full-Length-Enriched Oligo-Capping cDNA Libraries, Medical and Pediatric Oncology, 35:547-549 (2000).

Aoyama et al., “Human Neuroblastomas With Unfavorable Biologies Express High Levels of Brain-Derived Neurotrophic Factor mRNA And A Variety of Its Variants,” Cancer Letters 164:51-60 (2001).

Nakagawara et al., “Prediction of Prognosis and Molecular Diagnosis of Neuroblastoma,” Igaku no Ayumi, vol. 197, No. 13, pp. 1169-1174 (2001).

Medical and Pediatric Oncology, 35:547-549.

* cited by examiner

DAY 0
+NGF
DAY 5
+NGF
-NGF
AFTER 24 HOURS
AFTER 24 HOURS
AFTER 36 HOURS
DIFFERENTIATION
AFTER 36 HOURS
APOPTOSIS

NUCLEIC ACIDS ISOLATED IN NEUROBLASTOMA

CROSS-REFERENCED APPLICATIONS

This application is a National phase of International Application PCT/JP02/05294, filed May 30, 2002, which designated the U.S. and that International Application was not published under PCT Article 21(2) in English.

TECHNICAL FIELD

This invention relates to nucleic acids whose expression is enhanced in human neuroblastoma with unfavorable prognosis based on comparison between human neuroblastoma with favorable prognosis and human neuroblastoma with unfavorable prognosis.

BACKGROUND ART (Tumorgenesis and Genes)

Individual tumors exhibit distinct characteristic natures, and their biological properties are not necessarily identical even though the basic principle of oncogenesis is the same. Rapid advances in the understanding of cancer from a molecular biological and molecular genetic perspective in recent year have opened the way to an explanation of oncogenesis and tumor cell biology on the genetic level.

(Neuroblastomas)

Neuroblastoma is a pediatric cancer occurring in sympathetic gangliocytes and adrenal medullary cells which originate from cells of the peripheral sympathetic nervous system. Of these sympathetic nervous system cells, neural crest cells in the initial stage of development migrate to the abdomen, differentiating and maturing at sites where sympathetic ganglia are formed. Some of these cells migrate further to the adrenal bodies, penetrating through the adrenal cortex which is already in the process of formation, and reaching the medulla and forming medullary substance there. The neural crest cells also serve as a source of other peripheral nerve cells, differentiating into dorsal root ganglia (sensory nerves), skin pigment cells, thyroid C cells, some pulmonary cells, intestinal gangliocytes, and the like.

(Prognosis for Neuroblastoma)

Neuroblastoma is characterized by a varied clinical profile (Nakagawara, Shinkeigashu no Hassei to Sono Bunshi Kiko [Neuroblastoma Development and Molecular Mechanism], Shoni Naika 30, 143, 1998). For example, neuroblastomas occurring at less than one year of age have very favorable prognosis, with the majority undergoing differentiation and cell death, and spontaneous regression. Currently, most neuroblastomas discovered by a positive result in the commonly performed mass screening of 6-month-old infant urine are of the type which tend to undergo this spontaneous regression. On the other hand, neuroblastomas occurring at age 1 or higher are highly malignant and lead to death of the infant in the majority of cases. It is also hypothesized that a somatic mutation occurs in highly malignant neuroblastomas in infants older than one year of age, which are of monoclonal nature, whereas in naturally regressing neuroblastomas, the genetic mutation remains at only a germline mutation. See Knudson AG, et al.: Regression of neuroblastoma IV-S: A genetic hypothesis, N. Engl. J. Med. 302, 1254 (1980)).

(Tumor Markers which Allow the Diagnosis of Prognosis for Neuroblastoma)

With recent advances in molecular biology research, it has become clear that expression of the high affinity nerve growth factor (NGF) receptor TrkA is closely connected with control of differentiation and cell death. See Nakagawara A., The NGF story and neuroblastoma, Med. Pediatr. Oncol., 31, 113 (1998). Trk is a membrane-spanning receptor, existing as the three main types, Trk-A, -B and -C. These Trk family receptors play an important role in specific nerve cell differentiation and survival in the central nervous and peripheral nervous systems. See Nakagawara, et al., Shinkeigasaiboushu ni Okeru Neurotrophin Juyoutai no Hatsugen to Yogo [Expression of Neurotrophin Receptors and Prognosis in Neuroblastoma], Shoni Geka (Pediatric Surgery), 29:425-432, 1997. The survival and differentiation of tumor cells is controlled by signals from Trk tyrosine kinase and Ret tyrosine kinase. In particular, the role of TrkA receptor is most significant, with TrkA expression being notably high in neuroblastomas with favorable prognosis, and its signals exerting a powerful control over survival and differentiation of tumor cells, and cell death (apoptosis). In neuroblastomas with unfavorable prognosis, on the other hand, TrkA expression is significantly suppressed, while tumor development is aided by a mechanism in which survival is promoted by signals from TrkB and Ret.

It has become clear that amplification of the neural oncogene N-myc has become clearly associated with the prognosis of neuroblastoma. See Nakagawara, Noushinkeishuyo no Tadankai Hatsugan [Multistage Oncogenesis of Cerebral and Neural Tumors], Molecular Medicine, 364, 366(1999). This gene, first cloned in neuroblastoma, is ordinarily only present in a single copy per haploid set in normal cells and neuroblastomas with favorable prognosis, whereas it has been found to be amplified several dozen times in neuroblastomas with unfavorable prognosis.

Up till the present time, however, no oncogene other than N-myc is known to be expressed in neuroblastomas, and absolutely no genetic information other than that of N-myc has been known in relation to favorable or unfavorable prognosis.

DISCLOSURE OF THE INVENTION

This invention has been accomplished in light of the circumstances described above, and its object is to identify the gene sequences which are related to favorable or unfavorable prognosis of neuroblastoma, and to allow the provision of their genetic information as well as the diagnosis for favorable or unfavorable prognosis.

As a result of conducting diligent research, the present inventors have examined the prognoses of neuroblastomas and have succeeded in constructing cDNA libraries from both clinical tissues with favorable prognosis and with unfavorable prognosis. Approximately 2400 clones were respectively obtained from these two types of cDNA libraries and were classified according to the prognosis of neuroblastoma (whether favorable or unfavorable).

Moreover, the present inventors found that the expression of a considerable number of the genes is enhanced only in clinical tissues of neuroblastoma with unfavorable prognosis among the classified genes.

Based on such knowledge, the present inventors have succeeded in providing base sequence information for the detection and cloning of the genes only expressed in clinical tissues with unfavorable prognosis.

Furthermore, based on the aforementioned base sequence information on the regions it has been made possible to carry out the method for detection of prognosis and to design tumor markers which can be used therefor, and this invention has thereupon been completed.

Specifically, this invention aims at providing a nucleic acid whose expression is enhanced in human neuroblastoma with unfavorable prognosis based on comparison between human neuroblastoma with favorable prognosis and human neuroblastoma with unfavorable prognosis, the nucleic acid comprising any one of base sequences set forth in SEQ ID NO:1 to NO:69 in the Sequence Listing as well as providing a nucleic acid comprising a portion of the base sequence. This invention also provides an isolated nucleic acid characterized in that it hybridizes to the nucleic acid described above or its complementary nucleic acid under stringent conditions.

The nucleic acids of this invention are those whose expression is enhanced in human neuroblastoma with unfavorable prognosis based on comparison between human neuroblastoma with favorable prognosis and human neuroblastoma with unfavorable prognosis and those nucleic acids are characterized by their capabilities of being used in the diagnosis for prognosis of human neuroblastoma. The preferred nucleic acid for this purpose is a nucleic acid comprising the base sequence set forth in SEQ ID NO:21 or the base sequence set forth in SEQ ID NO:64 in the Sequence Listing or a nucleic acid related thereto (e.g., a nucleic acid comprising a portion of the base sequence).

This invention also provides a diagnostic agent for the detection of a neurological disease characterized by containing at least one nucleic acid comprising a portion or the whole of a base sequence set forth in SEQ ID NO:1 to SEQ ID NO:69 in the Sequence Listing. Specifically, such tumor detection diagnostic agents include DNA chips and microarrays both of which are produced using the above-mentioned nucleic acids, for example. Accordingly, this invention also provides a microarray composition characterized by containing plural numbers of nucleic acids comprising a portion or the whole of the base sequence set forth in SEQ ID NO:1 to SEQ ID NO:69 in the Sequence Listing. Preferably, such composition comprises all the nucleic acids, i.e., a total of 69 nucleic acids each of which comprises a portion or the whole of a base sequence set forth in SEQ ID NO:1 to SEQ ID NO:69 in the Sequence Listing.

Further according to this invention there is provided an isolated nucleic acid which is DNA characterized by hybridizing to the nucleic acid mentioned above or to its complementary nucleic acid under stringent conditions. There is also provided a diagnostic kit for the prognosis of human neuroblastoma containing as the effective ingredient, a primer set comprising a pair of those nucleic acids (DNA).

In addition, this invention provides a method of diagnosing the prognosis of human neuroblastoma, the method comprising detecting the presence or absence of a nucleic acid comprising any one of base sequences set forth in SEQ ID NO:1 to NO:69 in the Sequence Listing from a clinical tissue sample of the neuroblastoma.

BEST MODE FOR CARRYING OUT THE INVENTION

Figure 1:
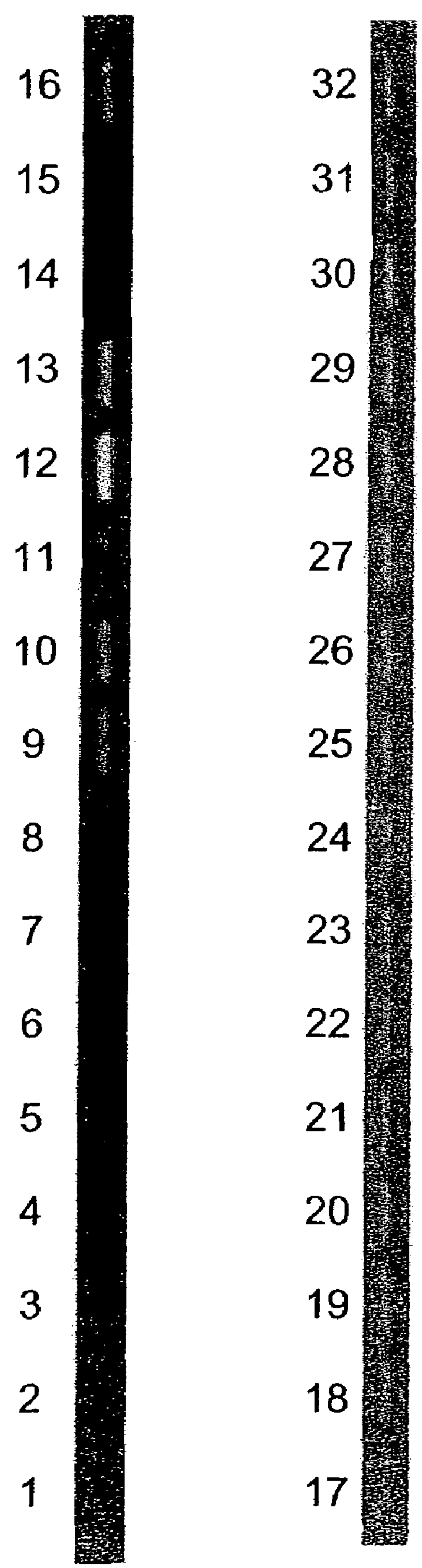
FIG. 1 is a figure corresponding to an electrophoregram showing an example of the results of determination of the gene expression levels in human neuroblastomas with favorable prognosis and with unfavorable prognosis by semi-quantitative PCR.

The term "nucleic acid(s)" as used in this invention refers to, for example, DNA or RNA, or polynucleotides derived therefrom which are active as DNA or RNA, and preferably they are DNA or RNA.

The term "hybridize under stringent conditions" means that two nucleic acid fragments hybridize to each other under the hybridization conditions described by Sambrook, J. et al. in "Expression of cloned genes in *E. coli*", Molecular Cloning: A Laboratory Manual (1989), Cold Spring Harbor Laboratory Press, New York, USA, 9.47-9.62 and 11.45-11.61.

More specifically, the "stringent conditions" refers to hybridization at approximately 45° C., 6.0×SSC, followed by washing at 50° C., 2.0×SSC. The stringency may be selected by choosing a salt concentration in the washing step from approximately 2.0×SSC, 50° C. as low stringency to approximately 0.2×SSC, 50° C. as high stringency. Also, the temperature in the washing step may be increased from room temperature, or approximately 22° C. as low stringency conditions, to approximately 65° C. as high stringency conditions.

The term "isolated nucleic acid(s)" as used in the present specification refers to a nucleic acid or a polynucleotide containing substantially no cellular substances or culture medium, if prepared by recombinant DNA techniques, or containing substantially no precursor chemical substances or other chemical substances, if prepared by chemical synthesis.

The term "favorable prognosis" as used in the present specification refers to a condition of human neuroblastoma in which the tumor is localized or has become a regressing or benign sympathetic ganglion neoplasm, and is judged to have low malignancy based on N-myc or other tumor markers. According to a preferred embodiment of the invention, a favorable prognosis is a case of stage 1 or 2, with an onset age of less than one year and survival without recurrence for 5 or more years after surgery, and with no noted amplification of N-myc in the clinical tissue; however, there is no limitation to such specific cases. The term "unfavorable prognosis" as used in the present specification refers to a condition of human neuroblastoma in which progression of the tumor has been observed, and it is judged to have high malignancy based on N-myc or other tumor markers. According to a preferred embodiment of the invention, an unfavorable prognosis is a case of stage 4, with an onset age of greater than one year, death within 3 years after surgery and noted amplification of N-myc in the clinical tissue; however, there is no limitation to such specific cases.

The nucleic acids of this invention have been found in the clinical tissues of human neuroblastoma and such nucleic acids have the characteristics described below.

Neuroblastoma is a tumor consisting of actual nerve cells, of which only two types of tumor are known in humans, and analysis of the genes expressed therein is expected to provide very useful knowledge for understanding the biology of nerve cells. Specifically, it is extremely difficult, and practically impossible, to obtain site-specific homogeneous tissue from the brain or peripheral nerves. On the other hand, a neuroblastoma consists of an almost homogeneous nerve cell population (though tumorized) derived from peripheral sympathetic nerve cells, and thus offers a high possibility of obtaining homogeneous expression of neuro-related genes. Furthermore, since neuroblastoma is a type of cancer, it will characteristically have many important genes expressed in the immature stage of neurogenesis.

Clinically and biologically, neuroblastoma can be neatly classified into favorable prognosis and unfavorable prognosis types. Cancer cells from neuroblastoma with favorable prognosis are characterized by having a very slow rate of proliferation, with spontaneous regression beginning at some point. Findings to date have confirmed that nerve cell differentiation and apoptosis (nerve cell death) occur in the spontaneous regression, and that the differentiation which occurs in the maturation stages of normal nerve cells and programmed cell death are phenomena very closely resembling each other. Consequently, it is highly probable that the analysis of genes expressed in such tumors will lead to obtaining important information relating to nerve cell differentiation and apoptosis.

Neuroblastomas with unfavorable prognosis are tumors consisting of cancer cells which continue to exhibit definitely malignant proliferation. The probability is very high, therefore, that they have a large number of important genes connected with nerve cell proliferation or genes expressed in undifferentiated nerve cells. In other words, it is highly probable that these will allow the obtainment of genetic information completely different from the profile of genes expressed in neuroblastomas with favorable prognosis.

It is commonly reported that nerve cells contain more expressed gene types than cells derived from other organs. Neuroblastoma cell lines are derived from clinical tissues with unfavorable prognosis, and it is believed that the gene expression profile in the case of tumor development and progression is substantially altered from that of normal nerve cells.

Neuroblastoma is characteristically a pediatric tumor, and because of the very low possibility of effects by acquired factors, it is expected that analysis of the mechanism of cancerization will also yield embryological information with high probability. More surprisingly, the genes or the gene fragments according to this invention include genes whose expression is enhanced only in specific cell cycle phases, and this further suggests the very strong possibility of obtaining genetic information highly useful for the analysis of cancerization mechanisms and related to development and differentiation.

The nucleic acids, having the characteristics mentioned above and from which the aforementioned information can be obtained, are available from human neuroblastoma clinical tissues and have any of the base sequences set forth in SEQ ID NO:1 to NO:69 in the Sequence Listing, or a portion thereof.

As a result of comparing gene expression levels in clinical tissues from human neuroblastomas with favorable prognosis and with unfavorable prognosis, a highly significant difference was found in each of the nucleic acids having base sequences set forth in SEQ ID NO:1 to NO:69 in the Sequence Listing. That is, the expression of these nucleic acids was enhanced in human neuroblastomas with unfavorable prognosis. Thus, in addition to providing the useful genetic information described above, the base sequences set forth in SEQ ID NO:1 to NO:69 can also be utilized as data for tumor markers to diagnose favorable or unfavorable prognosis of neuroblastoma, by detecting DNA and/or RNA having any of these base sequences.

Specifically, this invention will make it possible to obtain various forms of diagnosis for prognosis on or relating to human neuroblastoma through the following means.

(1) Probes for Hybridization

The nucleic acid comprising a portion or the whole of a base sequence disclosed in this invention (which may be referred to as "nucleic acid(s) of the invention") may be at least used as a probe for hybridization in order to detect genes expressed in human neuroblastoma. The nucleic acids of the invention can also be used as probes for hybridization in order to determine gene expression in various tumors and normal tissues, to identify the distribution of the gene expression.

When the nucleic acid comprising a portion or the whole of a base sequence disclosed in this invention is used as a probe for hybridization, there are no particular limitations on the actual method of hybridization. As preferred methods there may be mentioned, for example, Northern hybridization, Southern hybridization, colony hybridization, dot hybridization, fluorescence in situ hybridization (FISH), in situ hybridization (ISH), DNA chip methods, and microarray methods.

As one application example of the hybridization, the nucleic acid of this invention can be used as a probe for Northern hybridization to measure the length of mRNA or to quantitatively detect gene expression in an assayed sample.

When the nucleic acid of the invention is used as a probe for Southern hybridization, it enables the detection of the presence or absence of the base sequence in genomic DNA of an assayed sample.

The nucleic acid comprising a portion or the whole of a base sequence disclosed in this invention can also be used as a probe for fluorescence in situ hybridization (FISH) to identify the location of the gene on a chromosome.

The nucleic acid of the invention can also be used as a probe for in situ hybridization (ISH) to identify the tissue distribution of gene expression.

When the nucleic acid of the invention is used as a probe for hybridization, a nucleic acid residue length of at least 40 is necessary; and among the gene sequences according to the invention, a nucleic acid having 40 or more contiguous residues is preferably used. More preferably, one having 60 or more nucleic acid residues is used.

Nucleic acid probe techniques are well known to one skilled in the art, and for example, conditions suitable for hybridization between a probe of specific length according to the invention and the target polynucleotide may be readily determined. In order to obtain hybridization conditions optimal to probes of various lengths, Sambrook et al. "Molecular Cloning: A Laboratory Manual, 2nd Edition, Cold Spring Harbor (1989) may be followed for such manipulations which are well known to one skilled in the art.

The probe of the invention is preferably labeled in an easily detectable fashion. The detectable label may be any type or portion which can be detected either visually or using devices. As commonly used detectable labels there may be mentioned radioactive isotopes such as $^{32}P$, $^{14}C$, $^{125}I$, $^{3}H$ and $^{35}S$. Biotin-labeled nucleotides may be incorporated into DNA or RNA by nick translation, chemical or enzymatic means. The biotin-labeled probes are detected after hybridization using labeling means such as avidin/streptavidin, fluorescent labels, enzymes, gold colloidal complexes or the like. The nucleic acid may also be labeled by binding with a protein. Nucleic acid cross-linked to a radioactive or fluorescent histone single-stranded DNA binding protein may also be used.

(2) Primers for Use in PCR

For other possible methods of detecting genes, DNA that is the nucleic acid comprising a portion or the whole of a base sequence disclosed in this invention can be used as a primer in a polymerase chain reaction (PCR). For example, RNA may be extracted from a sample to be assayed, and the gene expression can be semi-quantitatively measured by RT-PCR. This may be carried out by a method well known to one skilled in the art. For example, "Molecular Cloning: A Laboratory Manual," (T. Maniatis, Cold Spring Harbor Laboratory Press) or Idenshibyo Nyumon [Introduction to Genetic Diseases] (Takahisa, S.: Nankodo Publishing) may be followed.

When the DNA that is a nucleic acid of the invention is used as a PCR primer, a base length of 10 to 60 is necessary; and among the gene sequences according to the invention, the nucleic acid having 10 to 60 contiguous bases is preferably used. More preferably, one having 15 to 30 bases is used. Generally, a primer sequence with a GC content of 40-60% is preferred. Also, there is preferably no difference in the Tm values of the two primers used for amplification. Preferably there is no annealing at the 3' ends of the primers and no secondary structure is formed in the primers.

(3) Nucleic Acid Screening

The nucleic acid comprising a portion or the whole of a base sequence disclosed in this invention can also be used to detect the expression distribution of a gene which is expressed in various tissues or cells. This can be accomplished, for example, by using the nucleic acid of the invention as a probe for hybridization or as a primer for PCR.

Expression distribution of a gene can also be detected using a DNA chip, microarray or the like. That is, the nucleic acid of the invention may be directly attached to the chip or array. RNA extracted from cells of a tissue may be labeled there with a fluorescent substance or the like, hybridized, and an analysis can be made of the type of tissue cells with high expression of the gene. The DNA attached to the chip or array may be the reaction product of PCR using the nucleic acid of the invention. U.S. Pat. No. 5,605,662 to Heller et al. describes an example of the method for attaching nucleic acids to a chip or array.

By utilizing the aforementioned technology, it is possible to use as a diagnostic agent, at least one among the nucleic acids comprising portions or the whole of base sequences disclosed in this invention. In recent years, it has becoming clear that the genetic information possessed by individuals governs their susceptibility to a certain disease as well as governs the effectiveness of a particular drug. The DNA chips or microarrays produced using the aforementioned nucleic acids are used to clarify the cause-effect relationship between the disease of a subject and the nucleic acid, which will enable not only the diagnosis of that disease but also the selection of a drug to be administered. Specifically, if the result detected using the DNA chip or microarray is employed as an indicator of selection of a drug to be administered, the expression level of one nucleic acid among the nucleic acids of the invention can be examined but also the expression levels of two or more nucleic acids can be comparatively examined to select the drug to be administered, which will then enable more accurate judgment. As used herein, the disease is not particularly limited insofar as it is that which can be diagnosed by the nucleic acids of this invention. Preferably, the disease is a neurological disease and more preferably, neuroblastoma.

(4) DNA Cloning

The nucleic acid comprising a portion or the whole of a base sequence disclosed in this invention can be at least used for cloning a gene which is expressed in human neuroblastoma. For example, by using the nucleic acid of the invention as a probe for Northern hybridization or Southern hybridization, or as a primer for PCR, cloning of a gene containing the nucleic acid comprising a portion or the whole of a base sequence disclosed in this invention is possible. As the genes capable of being subjected to cloning there may be mentioned genes with differing levels of expression particularly between neuroblastoma with favorable prognosis and neuroblastoma with unfavorable prognosis, genes whose forms of expression differ in other tissues or cancer cells, genes whose expression is cell cycle phase-dependent, genes induced upon neurodifferentiation and genes whose expression is regulated by oncogenes or tumor suppressor genes.

(5) Methods of Diagnosing Tumor Prognosis and Tumor Markers to be Used Therefor

The nucleic acid comprising a portion or the whole of a base sequence disclosed in this invention can be used as a probe for hybridization, or as a primer for PCR to determine the presence or absence of enhancement in the gene expression in sample cells, which enables the identification of prognosis. To determine the presence or absence of enhancement in the gene expression, any method that utilizes nucleic acids (probes) capable of hybridizing to the nucleic acid comprising any given sequence of the base sequence disclosed in this invention is provided for use. Prognosis can be diagnosed as favorable if the amount of nucleic acid hybridizing to the probe is increased in the sample cell. When the nucleic acid is used as a primer for PCR, RNA is extracted from the sample to be assayed and the gene expression can be semi-quantitatively measured by the RT-PCR method.

(6) Antisense Oligonucleotides

According to another embodiment of this invention there are provided antisense oligonucleotides having the base sequences according to the invention. As will be considered in practicing this invention, the antisense oligonucleotides may readily be prepared such that they can bind to RNA corresponding to the base sequence of this invention and can thereby inhibit the synthesis of RNA.

(7) Gene Therapy

According to a further embodiment of this invention, there are provided therapeutic genes to be used in gene therapy. As will be considered in practicing this invention, the gene according to this invention may be transferred into a vector for use in gene transportation, whereby the transgene can be expressed by an arbitrary expression promoter and can be used for the gene therapy of cancers, for example.

1. Vectors

The transferable viral vectors may be prepared from DNA viruses or RNA viruses. They may be any viral vector of an MoMLV vector, a herpes virus vector, an Adenovirus vector, an AAV vector, a HIV vector, a Seidai virus vector and the like. One or more proteins among the constituent protein group of a viral vector are substituted by the constituent proteins of a different species of virus, or alternatively a part of the base sequence constituting genetic information is substituted by the base sequence of a different species of virus to form a viral vector of the pseudo-type which can also be used in this invention. For example, there is mentioned a pseudo-type viral vector wherein the Env protein (an envelop protein of HIV) is substituted by the VSV-G protein (an envelop protein of vesicular stomatitis virus or VSV) (Naldini L., et al., Science 272, 263-267, 1996). Further, virues having a host spectrum other than human is usable as the viral vector insofar as they are efficacious. As for the vectors other than those of viral origin, there may be used complexes of calcium phosphate and nucleic acid, ribosomes, cation-lipid complexes, Seidai virus liposomes, polymer carriers having polycation as the backbone main chain and others. In addition, methods such as electroporation and gene guns may be used as a gene transfer system.

2. Expression Promoters

As for the expression cassettes to be used for the therapeutic gene, any cassettes without any particular limitations may be used insofar as they can cause genes to express in the target cells. One skilled in the art can readily select such expression cassettes. Preferably, they are expression cassettes capable of gene expression in the cells derived from an animal, more preferably, expression cassettes capable of gene expression in the cells derived from a mammal, and most preferably expression cassettes capable of gene expression in the cells derived from a human. The gene promoters that can be used as expression cassettes include: for example, virus-derived promoters from an Adenovirus, a cytomegalovirus, a human immunodeficiency virus, a simian virus 40, a Rous sarcoma virus, a herpes simplex virus, a murine leukemia virus, a sinbis virus, a hepatitis type A virus, a hepatitis type B virus, a hepatitis type C virus, a papilloma virus, a human T cell leukemia virus, an influenza virus, a Japanese encephalitis virus, a JC virus, parbovirus B19, a poliovirus, and the like; mammal-derived promoters such as albumin, SR α, a heat shock protein, and an elongation factor; chimera type promoters such as a CAG promoter; and the promoters whose expression can be induced by tetracyclines, steroids and the like.

EXAMPLES

This invention will now be explained in greater detail by way of the examples and production examples; however, the invention will not be restricted to those example.

Production Example 1 Construction of cDNA Library from Human Neuroblastoma

1. Obtaining Samples

Human neuroblastoma clinical tissue specimens were quasi-aseptically frozen immediately after surgical extraction and then preserved at −80° C.

2. Selecting Samples with Favorable Prognosis

Prognosis of the samples obtained in 1. above was carried out based on the following criteria.

Favorable prognosis:
Stage 1 or 2
Age of onset less than one year
Survival for longer than 5 years after surgery without recurrence
No amplification of N-myc
Unfavorable prognosis:
Stage 4
Age of onset older than 4 years
Death within 3 years after surgery
Amplification of N-myc Amplification of N-myc in the aforementioned sample types was confirmed in the following manner.

The clinical tissue obtained in 1. above was thinly sliced with a scalpel and then thoroughly homogenized after addition of 5 ml of TEN buffer (50 mM Tris-HCl (pH=8.0)/1 mM EDTA/100 mM NaCl). Upon adding 750 μl of SDS (10%) and 125 μl of proteinase K (20 mg/ml) to the mixture, it was gently stirred and allowed to stand at 50° C. for 8 hours. This was followed by phenol/chloroform treatment and finally ethanol precipitation to obtain purified genomic DNA. A 5 μg portion of the obtained genomic DNA was completely digested with the restriction endonuclease EcoRI (NEB Inc.), and an N-myc probe was used to determine amplification of N-myc by Southern hybridization.

3. Preparation of mRNA from Clinical Tissue of Human Neuroblastoma with Favorable Prognosis A 2-3 g portion of the clinical tissue sample of human neuroblastoma judged to have favorable prognosis in 2. above was treated using a Total RNA Extraction Kit (QIAGEN Inc.) and the total RNA was extracted. The extracted total RNA was purified using an oligo dT cellulose column (Collaborative Research, Inc.) to obtain a pool of mRNA with a polyA structure.

4. Dephosphorylation of mRNA

A 100-200 μg portion of the mRNA pool prepared in 3. above was dissolved in 67.3 μl of distilled sterile water containing 0.1% diethyl pyrocarbonate (DEPC), and then 20 μl of 5×BAP buffer (Tris-HCl (500 mM, pH=7.0)/mercaptoethanol (50 mM)), 2.7 μl of RNasin (40 unit/μl: Promega Inc.) and 10 μl of BAP (0.25 unit/μl, bacteria-derived alkali phosphatase: Takara Shuzo Co. Ltd.) were added. The mixture was reacted at 37° C. for 1 hour to effect dephosphorylation of the 5' end of the mRNA. This was followed by phenol/chloroform treatment two times, and finally ethanol precipitation to obtain a purified dephosphorylated mRNA pool.

5. Decapping of Dephosphorylated mRNA

The total amount of the dephosphorylated mRNA pool prepared in 4. above was dissolved in 75.3 μl of distilled sterile water containing 0.1% DEPC, and then 20 μl of 5×TAP buffer (sodium acetate (250 mM, pH=5.5)/mercaptoethanol (50 mM), EDTA (5 mM, pH=8.0)), 2.7 μl of RNasin (40 unit/μl) and 2 μl of TAP (tobacco acid pyrophosphatase: 20 unit/μl) were added. The mixture was reacted at 37° C. for 1 hour to effect decapping treatment of the 5' end of the dephosphorylated mRNA. The dephosphorylated mRNA of incomplete length with no capped structure remained without decapping, and with the 5' end dephosphorylated. This was followed by phenol/chloroform treatment and ethanol precipitation to obtain a purified decapped mRNA pool.

6. Preparation of Oligo-Capped mRNA

The total amount of the decapped mRNA pool prepared in 5. above was dissolved in 11 μl of distilled sterile water containing 0.1% DEPC, and then 4 μl of 5'-oligo RNA (5'-AGCAUCGAGUGGGCGUUGGCCUACUGG-3' (SEQ ID NO: 70): 100 ng/μl), 10 μl of 10× ligation buffer (Tris-HCl (500 mM, pH=7.0)/mercaptoethanol (100 mM)), 10 μl of magnesium chloride (50 mM), 2.5 μl of ATP (24 mM), 2.5 μl of RNasin (40 unit/μl), 10 μl of T4 RNA ligase (25 unit/μl: Takara Shuzo Co. Ltd.) and 50 μl of polyethylene glycol (50% w/v, PEG8000: Sigma Corporation) were added. The mixture was reacted at 20° C. for 3 hours for ligation of the 5'-oligo RNA to the 5' end of the decapped mRNA. The dephosphorylated mRNA of incomplete length with no capped structure resulted in no ligation to the 5'-oligo RNA. This was followed by phenol/chloroform treatment and ethanol precipitation to obtain a purified oligo-capped mRNA pool.

7. Removal of DNA from Oligo-Capped mRNA

The oligo-capped mRNA pool prepared in 6. above was dissolved in 70.3 μl of distilled sterile water containing 0.1% DEPC, and then 4 μl of Tris-HCl (1 M, pH=7.0), 5.0 μl of DTT (0.1 M), 16 μl of magnesium chloride (50 mM), 2.7 μl of RNasin (40 unit/μl) and 2 μl of DNaseI (5 unit/μl: Takara Shuzo Co. Ltd.) were added. The mixture was reacted at 37° C. for 10 minutes to dissolve the excess DNA. This was followed by phenol/chloroform treatment and ethanol precipitation and column purification (S-400HR: Pharmacia Biotech Inc.), to obtain a purified DNA(−) oligo-capped mRNA pool.

8. Preparation of 1st Strand cDNA

The DNA(−) oligo-capped mRNA pool prepared in 7. above was reverse transcribed using SuperScript II (kit by Life Tech Oriental, Inc.) to obtain a pool of 1st strand cDNA. The pool of DNA(−) oligo-capped mRNA was dissolved in 21 μl of sterile distilled water, and then 10 μl of 10× First Strand buffer (kit accessory), 8 μl of dNTP mix (5 mM, kit accessory), 6 μl of DTT (0.1 M, kit accessory), 2.5 μl of oligo-dT adapter primer (5 pmol/μl, 5'-GCGGCTGAAGACGGCGTATGTGGCCTTTTTTTTTTTTTTTTT-3' (SEQ ID NO: 71)), 2.0 μl of RNasin (40 unit/μl) and 2 μl of Superscript II RTase (kit accessory) were added. The mixture was reacted at 42° C. for 3 hours to effect reverse transcription. This was followed by phenol/chloroform treatment, alkali treatment and neutralization treatment to dissolve all the RNA and purification was carried out by ethanol precipitation.

9. Preparation of 2nd Strand cDNA

The 1st strand cDNA pool prepared in 8. above was subjected to PCR amplification using Gene Amp (kit by Perkin Elmer Inc.). The pool of 1st strand cDNA was dissolved in 52.4 μl of sterile distilled water, and then 30 μl of 3.3× Reaction buffer (kit accessory), 8 μl of dNTP mix (2.5 mM, kit accessory), 4.4 μl of magnesium acetate (25 mM, kit accessory), 1.6 μl of Primer F (10 pmol/μl, 5'-AGCATCGAGTCGGCCTTGTTG-3' (SEQ ID NO: 72)), 1.6 μl of Primer R (10 pmol/μl, 5'-GCGCTGAAGACGGCCTATGT-3' (SEQ ID NO: 73)) and 2 μl of rTth (kit accessory) were added. A 100 μl portion of mineral oil was gently added to the mixture and overlayed thereon. After denaturing the reaction solution at 94° C. for 5 minutes, a cycle of 94° C. for 1 minute, 52° C. for 1 minute and 72° C. for 10 minutes was repeated 12 times, and then the solution was allowed to stand at 72° C. for 10 minutes to complete the PCR reaction. This was followed by phenol/chloroform treatment and ethanol precipitation to obtain a 2nd strand cDNA pool.

10. SfiI Treatment of 2nd Strand cDNA

The 2nd strand cDNA pool prepared in 9. above was dissolved in 87 μl of sterile distilled water, and then 10×NEB buffer (NEB Inc.), 100×BSA (bovine serum albumin available from NEB Inc.) and 2 μl of SfiI (restriction endonuclease, 20 unit/μl, NEB Inc.) were added. The mixture was reacted overnight at 50° C. to effect SfiI restriction endonuclease treatment. This was followed by phenol/chloroform treatment and ethanol precipitation to obtain a pool of cDNA which had been SfiI-treated at both ends.

11. Size Fractionation of SfiI-treated cDNA

The SfiI-treated cDNA pool prepared in 10. above was electrophoresed on 1% agarose gel and a fraction with >2 kb was purified using Geneclean II (Bio101 Inc.). The purified cDNA pool was dissolved in 100 μl of sterile distilled water and allowed to stand at 37° C. for 6 hours. This was followed by phenol/chloroform treatment and ethanol precipitation to obtain a long-chain cDNA pool.

12. Preparation of cDNA Library

The long-chain cDNA pool prepared in 11. above was ligated into the cloning vector pME18S-FL3 (provided by Prof. Sumio Kanno of the Institute of Medical Science, Tokyo University) using a DNA Ligation Kit ver.1 (kit by Takara Shuzo Co. Ltd.). The long-chain cDNA pool was dissolved in 8 μl of sterile distilled water, and then 1 μl of pME18S-FL3 pretreated with restriction endonuclease DraIII, 80 μl of Solution A (kit accessory) and 10 μl of Solution B (kit accessory) were added and reaction was conducted at 16° C. for 3 hours. This was followed by phenol/chloroform treatment and ethanol precipitation for purification to obtain a cDNA library.

Example 1

Transformation into *E. coli*

The cDNA library prepared in Production Example 1 above was used for transformation into *E. coli* (TOP-10: Invitrogen Corporation). The cDNA library was dissolved in 10 μl of sterile distilled water and mixed with TOP-10. The mixture was then incubated on ice for 30 minutes, at 40° C. for 1 minute and on ice for 5 minutes. After adding 500 μl of SOB medium, shake culturing was performed at 37° C. for 60 minutes. Appropriate amounts thereof were seeded onto ampicillin-containing agar media and culturing was continued at 37° C. for a day and a night to obtain *E. coli* clones.

The *E. coli* clones on agar media obtained were collected with toothpick and suspended in 120 μl of LB medium prepared in a 96-well plate. The 96-well plate was then allowed to stand overnight at 37° C. for culturing of the *E. coli*. A 72 μl portion of 60% glycerol solution was then added and preserved at −20° C. (glycerol stock).

Example 2

Base Sequence Determination

1. Preparation of Plasmid

The 10 μl of glycerol stock prepared in Example 1 was transferred to a 15 ml centrifugation tube, and then 3 ml of LB medium and 50 μg/ml of ampicillin were added and shaking was carried out overnight at 37° C. for culturing of the *E. coli*. A QIAprep Spin Miniprep Kit (QIAGEN Inc.) was then used to extract and purify a plasmid DNA from the *E. coli*.

2. Analysis of Both End Sequences

Both end sequences of the plasmid DNA prepared in 1. above were determined using a DNA Sequencing Kit (kit by ABI). There were combined 600 ng of plasmid DNA, 8 μl of premix (kit accessory) and 3.2 pmol of primers, and sterile distilled water was added to a total of 20 μl. After denaturing the mixture at 96° C. for 2 minutes, a cycle of 96° C. for 10 seconds, 50° C. for 5 seconds and 60° C. for 4 minutes was repeated 25 times for reaction. The product was then purified by ethanol precipitation. Sequencing was carried out by polyacrylamide gel electrophoresis under denaturing conditions, using ABI377 (ABI).

Example 3

Homology Search Using Database

An Internet-mediated DNA sequence homology search was conducted for the samples on which the both end-sequences were analyzed in Example 2. The homology search was conducted using the BLAST of the NCBI (National Center of Biotechnology Information, USA).

Example 4

Determination of Gene Expression Levels in Human Neuroblastomas with Favorable Prognosis and Unfavorable Prognosis by Semi-Quantitative PCR PCR primers were synthesized from portions of the genes obtained in Example 3, and the expression levels in the clinical tissues of human neuroblastomas with favorable prognosis and unfavorable prognosis were comparatively quantitated. mRNA was extracted from the human neuroblastoma clinical tissues by the method described in Example 1, and rTaq (Takara Shuzo Co. Ltd.) was used for PCR reaction. Specifically, 5 μl of sterile distilled water, 2 μl of mRNA, 1 μl of 10×rTaq buffer, 1 μl of 2 mM dNTPs, 0.5 μl each of the synthesized primer set and 0.5 μl of rTaq were combined. After denaturing the mixture at 95° C. for 2 minutes, a cycle of 95° C. for 15 seconds, 55° C. for 15 seconds and 72° C. for 20 seconds was repeated 35 times, and then the mixture was allowed to stand at 72° C. for 6 minutes for PCR reaction. The reaction solution was subjected to 1% agarose gel electrophoresis. One example of the results of determination of the gene expression levels in human neuroblastomas with favorable prognosis and unfavorable prognosis by semi-quantitative PCR is shown in FIG. 1. Here, the explanations of the respective lanes are as follows:

Lanes 1-8: expression of the gene corresponding to the nucleic acid comprising the base sequence set forth in SEQ ID NO: 21 in the Sequence Listing in a clinical sample of neuroblastoma with favorable prognosis;

Lanes 9-16: expression of the gene corresponding to the nucleic acid comprising the base sequence set forth in SEQ ID NO: 21 in the Sequence Listing in a clinical sample of neuroblastoma with unfavorable prognosis;

Lanes 17-24: expression of GAPDH in a clinical sample of neuroblastoma with favorable prognosis; and Lanes 25-32: expression of GAPDH in a clinical sample of neuroblastoma with unfavorable prognosis.

Consequently, nucleic acids whose expression is enhanced only in human neuroblastoma with unfavorable prognosis have been identified in the base sequences set forth in SEQ ID NO:1 to SEQ ID NO:69.

Example 5

Gene Group with Varying Gene Expression Levels by NGF Regulated Apoptosis in Murine Superior Cervical Gangliocytes.

It is known that NGF (nerve growth factor) exerts protective action against apoptosis in human neuroblastoma induced by an antimitotic agent (such as neocarzinostatin). (Cortazzo M H, J. Neurosci, 16, 3895-3899 (1996)). This action is believed to be due to the inhibition of apoptosis by the binding of NGF to p75. It has also been pointed out that the regression of neuroblastoma (causing favorable prognosis) at clinical stage is connected to the apoptosis of the tumor cells.

In order to identify the apoptosis-associated genes in neuroblastoma, the gene group with varying gene expression levels by NGF regulated apoptosis in murine superior cervical gangliocytes was examined.

Superior cervical gangliocytes (SCG neurons) were first isolated from C57BL/6J mice (0 to 1 day of age) in 7 to 10 animals. Seven wells of cells were arranged to be grown on a 24-well cell culture plate at about 1 to about $2\times10^4$ cells per well. RNA was further collected from about 1 to about $2\times10^4$ cells (Day 1 as control).

Figure 2:
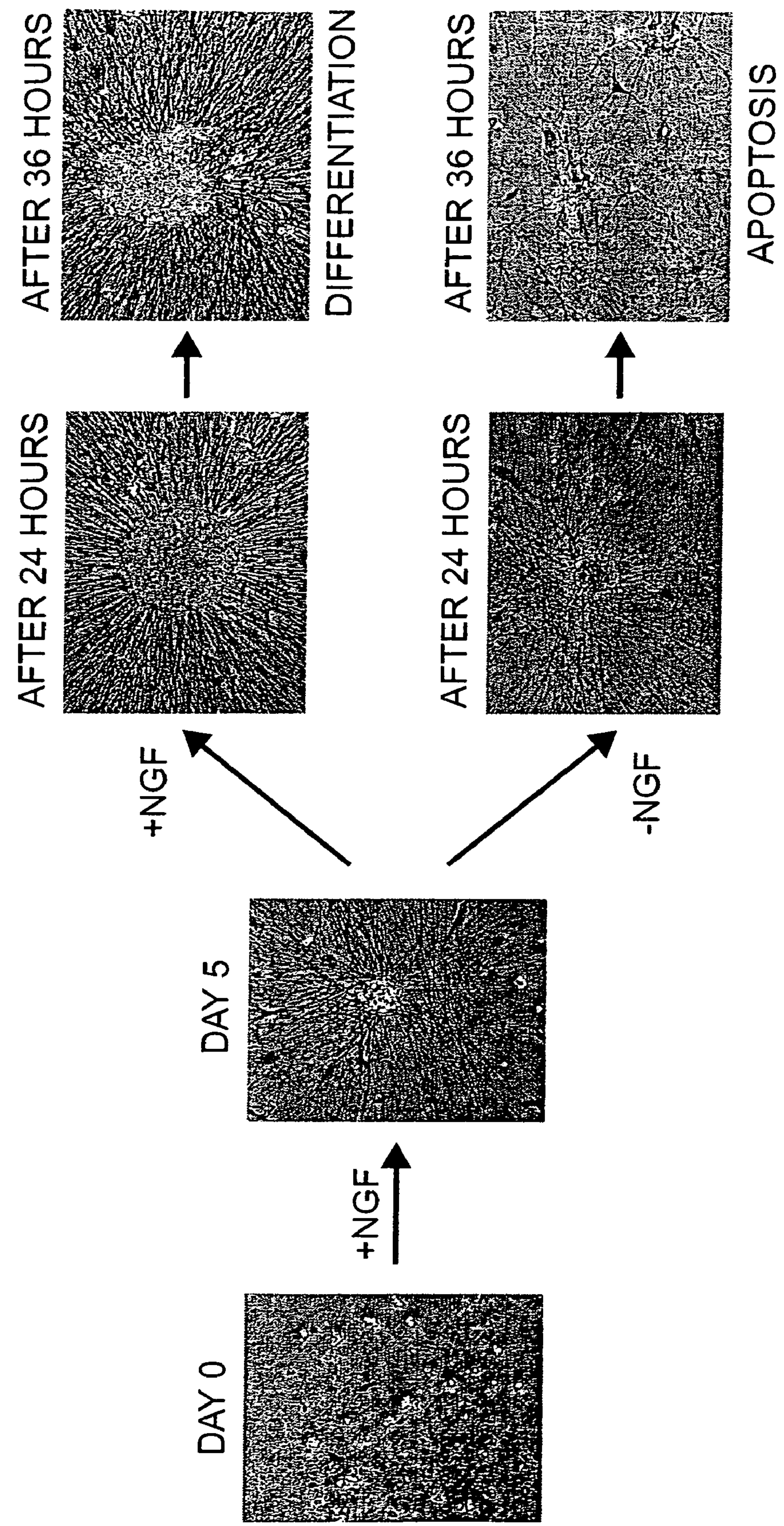
FIG. 2 is a figure corresponding to electron micrographs showing a primary culture containing SCG neurons of a new born mouse.

After the culture obtained by adding NGF (5 mg/ml) to the 7-well cells was incubated for 5 days, RNA was collected from one-well cells (+NGF; after 5 days). Cultures in three wells each of the 6 wells were exchanged with cultures with addition of NGF (5 mg/ml) or anti-NGF antibodies (1%), and they were respectively incubated for 12 hours, 24 hours and 48 hours. Using portions of the samples, cells were examined under an electron microscope to identify the morphological differences between the case where NGF had been added and the case where anti-NGF antibodies had been added. The results are shown in FIG. 2. NGF induced differentiation was observed in the cells with NGF addition, whereas apoptosis was observed in the cells with anti-NGF antibody addition. As a result of NGF depletion by the anti-NGF antibodies, it was apparent that apoptosis was induced. RNA was collected from the respective well cells after 12 hr, 24 hr, and 48 hr culturing. These samples were denoted +NGF 12 hrs, +NGF 24 hrs, +NGF 48 hrs, −NGF 12 hrs, −NGF 24 hrs, and −NGF 48 hrs.

As described above, RNAs of the respectively treated cells from approximately 160 mice were concentrated by ethanol precipitation and cDNAs were synthesized from 1 g RNAs using reverse transcriptase. These cDNAs were used as templates and gene expression levels were compared by PCR. The primers used were constructed from the homologous genes in mice based on the genes found in human neuroblastoma cells. The base sequences of the primers used for the comparison of expression are summarized in Table 1 together with the gene identification numbers (ID) for the targeted genes for comparison.

TABLE 1

| primer | SEQ ID NO | primer sequence | primer | SEQ ID NO | primer sequence |
|---|---|---|---|---|---|
| nbla00031m-F3 | 74 | TCAGAAGGCTTCGAGACTG | nbla00031m-R3 | 75 | GCAGATATCTTGTCAAAGGT |
| nbla00100m-f | 76 | GGTGAGCCCTAACATCCACA | nbla00100m-r | 77 | AGCCCGTAAGCCATCAATC |
| nbla00115m-F3 | 78 | ATCATGGTGAAAGGCACGTC | nbla00115m-R3 | 79 | CATAATTTCCACGTGTTGTG |

TABLE 1-continued

| primer | SEQ ID NO | primer sequence | primer | SEQ ID NO | primer sequence |
|---|---|---|---|---|---|
| nbla00116m-F3 | 80 | AGAGGTTAGCCCTGAGACAG | nbla00116m-R3 | 81 | TCTATGCTTCCAGCAGGTAC |
| nbla00124m-F3 | 82 | CCTTTATATTAGAACGTGGC | nbla00124m-R3 | 83 | TAGGTTTTCAGGACTTGG |
| nbla00144m-F | 84 | GCAGGATAGCAACCTTGACA | nbla00144m-R | 85 | ATGCATGCTTTCGTGTGTTC |
| nbla00150m-2f | 86 | CACCCTGGAGAAACACAAACTC | nbla00150m-2r | 87 | ATGCCGTCCATCTTCATCAC |
| nbla00170m-F3 | 88 | AACATGAATCTGTGGGTGAC | nbla00170m-R3 | 89 | TCAATCGCTTGACCTTTCCTC |
| nbla00204m-F3 | 90 | AAGCATTGAAGTAACAACCG | nbla00204m-R3 | 91 | TGCATTTGACATATGAGAGC |
| nbla00225m-F2 | 92 | TATTAGAACGTGGCCCTCCA | nbla00225m-R2 | 93 | TCGGGACTAGCAGGACAGAA |
| nbla00301m-F3 | 94 | TAAACCAGCAACCCTAACAG | nbla00301m-R3 | 95 | ACTAGAATCAGACCTGCCTT |
| nbla00315m-F | 96 | AACTGGCAGCAAAGAAGGTC | nbla00315m-R | 97 | AGCAGAAGCACGTCAGTAAGG |
| nbla00402m-F2 | 98 | TCACCCAGAATGAGACATGG | nbla00402m-R2 | 99 | GTCAGAAGGTGACACGGTGA |
| nbla00433m-F3 | 100 | CCCAAGGAGGTAAGAGCCTG | nbla00433m-R3 | 101 | AAGCGCTGGAGCTTGTCGGT |
| nbla00437m-F3 | 102 | AGAACGGTGTAATTCAGAGA | nbla00437m-R3 | 103 | GTCATCAGCAAGCTCGAATA |
| nbla00537m-F3 | 104 | TTTATATTAGAACGTGGCCC | nbla00537m-R3 | 105 | AGGACTTGGTAGCTTCTCGG |
| nbla00551m-F | 106 | AATTTTAAAAAGGCAGGATATACAAC | nbla00551m-R | 107 | AAGGAGAGGTAGCATTTTATGTGC |
| ori00660m-F | 108 | GGCATCCTCATCTCCTCAGA | ori00660m-R | 109 | TCTGAAGCAGTTCGAAGCAC |
| nbla00761m-f | 110 | TGGTTCAAACTCTTCCCTCCT | nbla00761m-r | 111 | CTTCCACCTGTGCGTTTTCT |
| nbla00831m-F3 | 112 | TGGGAAATCCACCTGCATC | nbla00831m-R3 | 113 | ACCAGCTCACCCTGAATGTG |
| nbla00908m-2f | 114 | CGTGGCAACACCTTTTTATTC | nbla00908m-2r | 115 | ACACGGCATGGGTTTGTT |
| nbla02874m-f | 116 | TGAGGAGTTGAATGCTGACCT | nbla02874m-r | 117 | CATCGGGGTTAATGCTCTTG |
| nbla03086m-f | 118 | ACTTGCTCATGGTGCTGTCTC | nbla03086m-r | 119 | CGCAGAGCCTGGTAATCTTC |
| nbla03113m-F | 120 | CCTCAAGAACCAGACCAAGC | nbla03113m-R | 121 | CTGATGCTGAGGAGCTGACA |
| nbla03199m-f | 122 | GGCCACCAGAGAGGTAATG | nbla03199m-r | 123 | GTGCTGACCTAAGACCCAAAG |
| nbla03267m-f | 124 | CTGCCTTTGAGATGGTGATG | nbla03267m-r | 125 | TGTAGTGCTTTGCATTGTTGG |
| nbla03646m-f | 126 | TACCTCTTCGGCTGGATGG | nbla03646m-r | 127 | GCTTGGGCAGGATGAATG |
| nbla03755m-F | 128 | AGCCGATGAAGTGTCTGCTT | nbla03755m-R | 129 | RAGCCACAAAAGCAGGTTAGG |
| nbla03771m-f | 130 | GCAGCAGATATAGGGACACAGA | nbla03771m-r | 131 | CACGCATAAATGGCTACACC |
| nbla03777m-F3 | 132 | AGATTATTCACCTGTAAGC | nbla03777m-R3 | 133 | TTTTCCACATGTCCAGCACC |
| nbla03831m-f | 134 | GTGACCAGCAAGGAAACACA | nbla03831m-r | 135 | GAGGATTCAGCCACGAACA |
| nbla03862m-F | 136 | GCATGGAGGAAACCATTAGG | nbla03862m-R | 137 | TGGCTCTTCAACCAAACCTT |
| nbla04021m-F2 | 138 | ATGACCTGGCACTAGGCTTG | nbla04021m-R2 | 139 | AACACATCTGCTGGCTTCTG |
| nbla04137m-f | 140 | ACGACGACACTGACAACCAC | nbla04137m-r | 141 | GCTTGACCTCCGACTCATCT |
| nbla04196m-f | 142 | CACCCATCTGTGTCTGTGGT | nbla04196m-r | 143 | CGTGCTGACGATGATGTTG |
| nbla04261m-2f | 144 | GTGTTTGGCACTACATCACCA | nbla04261m-2r | 145 | CCGGGTTTTCCATTTTCAC |
| nbla04300m-f | 146 | TACAGTGGGAACTGCGTTTG | nbla04300m-r | 147 | CAGGGTTCGTATGCAGGAG |
| nbla10058m-f | 148 | AGCCATTACAGGTGGCAAGA | nbla10058m-r | 149 | GTTGGGTCGATCTTAGGAGGTAG |
| nbla10070m-F3 | 150 | TAACAACTCTAGCACCATC | nbla10070m-R3 | 151 | TACTTAGCAGAACAGAAGAG |
| nbla10071m-f | 152 | GTGGACACCAAGAATGCAAG | nbla10071m-r | 153 | CAGCCAACTGTGGTAAGAAGG |
| nbla10120m-F | 154 | CAGTGCAGCCTTGGAAGTGT | nbla10120m-R | 155 | TCAAAAGCTGCGTGTGTCTC |

TABLE 1-continued

| primer | SEQ ID NO | primer sequence | primer | SEQ ID NO | primer sequence |
|---|---|---|---|---|---|
| nbla10143m-F3 | 156 | TTAGTGAGTACACGAGCTGG | nbla10143m-R3 | 157 | ACTTAACCCAGACTGACCAC |
| nbla10283m-F3 | 158 | AGATGTTTAAGGGCAAACC | nbla10283m-R3 | 159 | TGGAGCCTCTTGGATCTC |
| nbla10300m-F3 | 160 | AACATCCTGGTGGAACAGC | nbla10300m-R3 | 161 | CTCTATAGTAACGACCAAAC |
| nbla10314m-f | 162 | GCTTGAGGACAGTGAAAACCA | nbla10314m-r | 163 | TGGAGTGAGAGGATGGGAAG |
| nbla10317m-2f | 164 | GCAGGGGACACAGGACTCTAC | nbla10317m-2r | 165 | AAGCTCCTTCTGGCTCAACA |
| nbla10329m-F | 166 | CCGAGATCTTCTGCCTTCAT | nbla10329m-R | 167 | TCCTTGCCGTCTCAAACTCT |
| nbla10363m-F3 | 168 | ATCTCTCTAGTGCCATGAC | nbla10363m-R3 | 169 | AGTCTTGCTAAGACTTTCAG |
| nbla10383m-f | 170 | CAGTGCGGTTGTGGTCTATCT | nbla10383m-r | 171 | TGAGGCGTTGACTTTCTGG |
| nbla10388m-F | 172 | TTCAGCAGGTCCTAGCCAAG | nbla10388m-R | 173 | RTGGAAGCTGCTGAAGAAACA |
| nbla10457m-F | 174 | GCCTTTCTTTGTCTGGAACG | nbla10457m-R | 175 | GGGTGAAGCAATTTCACAGG |
| nbla10485m-F | 176 | AAATGGCAGTTTGACTGTGG | nbla10485m-R | 177 | TTGGCTGAGTTCTCCCTCAT |
| nbla10527m-F3 | 178 | ATTAATCCTGCACTCTTACG | nbla10527m-R3 | 179 | AGTTCCATTTCTACAGCAAG |
| nbla10535m-F | 180 | TTGGTCGTGAGGTGGATTCT | nbla10535m-R | 181 | ATCTTGCCAGCCACAGACTT |
| nbla10545m-F | 182 | AGAGTCACCTGCGACCCTTA | nbla10545m-R | 183 | AGCTCTAGCAGCCAGCACAT |
| nbla10677m-f | 184 | CATAATCTTCTCCGGCTTCATC | nbla10677m-r | 185 | GTCTGGTATTTCCGTGAGGTTT |
| nbla1087m-F3 | 186 | ATCTCCCATCGACTCACTGC | nbla10687m-R3 | 187 | TGGCTTTACTGGTCATACAG |
| nbla10696m-f | 188 | TGATTCTCCAAGGCAAGGT | nbla10696m-r | 189 | GATTTCCCCATTGACTGCT |
| nbla10988m-2f | 190 | AGCCTTTGCTACCCTCTTCC | nbla10988m-2r | 191 | GGCGAAACACTCCTCTCGT |
| nbla11030m-F3 | 192 | AACCTCGTAAAAACCATGGC | nbla11030m-R3 | 193 | AGCAGTGACTTGAGCATTTG |
| nbla11042m-2f | 194 | CGACACCTCTCATTGCACAC | nbla11042m-2r | 195 | TCCGTCTCAAATCCACACAC |
| nbla11051m-f | 196 | AGCACAATTCCCCAGACAC | nbla11051m-r | 197 | CTGTAGCCCTTACTGTTTGACC |
| nbla11189m-F | 198 | CTGTGTTCTGATGCCAATGC | nbla11189m-R | 199 | TGCAACTTTCTCCACCAAGA |
| nbla11589m-F2 | 200 | GGAGCTAGCCAAGATGATCG | nbla11589m-R2 | 201 | CTGGCCATCCTAGAGGAGAA |
| nbla11882m-F | 202 | AATTTTAAAAAGGCAGGATATACAAC | nbla11882m-R | 203 | AAGGAGAGGTAGCATTTTATGTGC |
| nbla11895m-F3 | 204 | AATCTTCCTCCCAACCCATG | nbla11895m-R3 | 205 | TGACCCTGCTGAAGGAAGCG |
| nbla20001m-F2 | 206 | CCCTGAATGTTGAACGAGTG | nbla20001m-R2 | 207 | TGCACATTGAAGAGGCAAAC |
| nbla20019m-F1 | 208 | CCGAGGTCAACATTTGTTCC | nbla20019m-R1 | 209 | GAGCAGAGCACAGACAGTGG |
| nbla20125m-F1 | 210 | CTGGAATCATCCAGGCTTTG | nbla20125m-R1 | 211 | GCGTCCAGGATAACAGCACT |
| nbla20134m-F1 | 212 | GTCTTCAAGCAGCGACAGTG | nbla20134m-R1 | 213 | CCTTCAGGGTCTGGTTGATG |
| nbla20146m-F1 | 214 | GGGACCACTAACCAGCTGAA | nbla20146m-R1 | 215 | AAATGTCTGACCCCTCCTCA |
| nbla20181m-F1 | 216 | CCAGGATGGAGTAGCCAAGA | nbla20181m-R1 | 217 | GCCAGTGATCTCCAGGTTTG |
| nbla20182m-F1 | 218 | ACTGGGGAGGAATGGCTAGT | nbla20182m-R1 | 219 | CTGGCTGGAGGAAAAAGGAC |
| nbla20211m-F1 | 220 | CTGAGGTGCTGATGATCCTG | nbla20211m-R1 | 221 | CCAAACTCCTGCTCTTCTCG |
| nbla20231m-F1 | 222 | AGCAGTTTGGTGCTGTTGGT | nbla20231m-R1 | 223 | GCTTGTTCCATGGTTGGACT |
| nbla20250m-F2 | 224 | ACGAGGACCACAGGACTCAA | nbla20250m-R2 | 225 | TGGGCTCCATAGTTTGTTCC |
| nbla20268m-F1 | 226 | ATTCTCTCTGGAGGCGATGA | nbla20268m-R1 | 227 | TTTCCTCACAGCTCCCTCTC |
| nbla20378m-F2 | 228 | TTTAGCTGTTTGCAAATAAGATGT | nbla20378m-R2 | 229 | AATGCAGTGTGTGGGATGTG |
| nbla20421m-F1 | 230 | TCCGACATGATGGTTCTCCT | nbla20421m-R1 | 231 | AGATCCAGGAGTCACCCAAA |

TABLE 1-continued

| primer | SEQ ID NO | primer sequence | primer | SEQ ID NO | primer sequence |
|---|---|---|---|---|---|
| nbla20487m-F3 | 232 | CACAGGTGTCAAAGCACGTT | nbla20487m-R3 | 233 | TGTAGCACTCGCTGTTGCTC |
| nbla20511m-F1 | 234 | TCCTGAAGCCTTCTTGCCTA | nbla20511m-R1 | 235 | GCTTGTGGCAACCAGAAAGT |
| nbla20541m-F1 | 236 | AGGTGGGAGTCGACCTTTCT | nbla20541m-R1 | 237 | GCATCCTTCAACTTGGTCCT |
| nbla20638m-F1 | 238 | GCAGCAAGGAAGAGGACAAG | nbla20638m-R1 | 239 | AGCAATCTTCGTCTGGGAAG |
| nbla20688m-F1 | 240 | AGAAGGACCTCCTCCCAAAG | nbla20688m-R1 | 241 | TGCAACAGTCCTCTTCCTTG |
| nbla20709m-F2 | 242 | ATTAGTTGGGACCTGCCTTG | nbla20709m-R2 | 243 | GCCCATTTTCTTCAGCAGAG |
| nbla20765m-F1 | 244 | AGAGCAGCTCAGCTACCACA | nbla20765m-R1 | 245 | GAAGGCAACTTTGGTGTTGG |
| nbla20798m-F1 | 246 | AAACGGGTACAGGATGGAGA | nbla20798m-R1 | 247 | CAACTGGAGGTCGGAGGATA |
| nbla20874m-F1 | 248 | TGGTCTGTTTAACAATTGACCTG | nbla20874m-R1 | 249 | GCTGCATCTTCCAACATTCTT |
| nbla20968m-F1 | 250 | CCGTGCAGTTTGACATGAAT | nbla20968m-R1 | 251 | TGTGGCATCTCATTCAGCAT |
| nbla21013m-F1 | 252 | CACCCTTTGAAGTGACGGTA | nbla21013m-R1 | 253 | CTGAAAAACCAGCCCACACT |
| nbla21024m-F1 | 254 | CTCTGTGGGATGACACATGC | nbla21024m-R1 | 255 | TTTGGCACCTTGTCATTTTG |
| nbla21077fm-F1 | 256 | CCTGCTTAAGAGTAAGCCTGGT | nbla21077fm-R1 | 257 | AGTTCTGTGGGCTATAGGATCG |
| nbla21130m-F1 | 258 | TGTGTCTTCCGACTTTCTGG | nbla21130m-R1 | 259 | TCTTTCCCTGAGTGCTTGGT |
| nbla21189m-F1 | 260 | AGAGGTGGAAGCACTTCAGG | nbla21189m-R1 | 261 | AAAGTCCTTGGTGCTCTCGT |
| nbla21233m-F1 | 262 | CTGGAGCCTGTTTGATGGTT | nbla21233m-R1 | 263 | TGCTTTCCTTACTGGCAGGT |
| nbla21266m-F1 | 264 | GAACATGGGCACTGACTGG | nbla21266m-R1 | 265 | CATCAGGGCTAGGAGACTCG |
| nbla21297m-F3 | 266 | CAGCAATGAATCCTCCAATGT | nbla21297m-R3 | 267 | TGGTGGTTCTCCCTGTGATT |
| nbla21298m-F2 | 268 | AGACCAGTGGCTCGTCAAAC | nbla21298m-R2 | 269 | TTGCAGACATCAGGGGTGT |
| nbla21337m-F2 | 270 | TCTGCACCAGAGAATCCACA | nbla21337m-R2 | 271 | ATAGGGCTTTTCTCCCGTGT |
| nbla21367m-F1 | 272 | CAGAAAAACGGTGGAGGACT | nbla21367m-R1 | 273 | CCCTGCCTTGTTCTCCATAA |
| nbla21375m-F1 | 274 | CAAGCATGCAGGAAGAACTC | nbla21375m-R1 | 275 | AATGTTCGTAGCCGATCCAG |
| nbla21413m-F1 | 276 | TGTGTTTGCTGGGGAGTATG | nbla21413m-R1 | 277 | TCATTTGCAGCCACTCTACG |
| nbla21569m-F1 | 278 | TGGAGCTCAGAAGAGGAGGA | nbla21569m-R1 | 279 | CGCAACATGAAGTCCATCAG |
| nbla21681m-F1 | 280 | CAAAGTCCCTCTCCTTCAGC | nbla21681m-R1 | 281 | CCCTAGTGGCCAACTCTGAT |
| nbla21761m-F1 | 282 | TTACCCAGGTGGTTCAGCAT | nbla21761m-R1 | 283 | TACCCATCAGGGTGATGACA |
| nbla21843m-F1 | 284 | GCCAGGAAGTGAGGAATGAG | nbla21843m-R1 | 285 | CCCGGATGACCTGAATGTAG |
| nbla21855m-F1 | 286 | AACACACTGGCGTTCATCTG | nbla21855m-R1 | 287 | GACTCCCACTTGCGTCTCTG |
| nbla21922m-F1 | 288 | GACATGGAAGGCATGCTGTA | nbla21922m-R1 | 289 | GACAGACGCTTCAGCGAAAT |
| nbla21934m-F1 | 290 | AGCCTTGGTGCTGAAGATGT | nbla21934m-R1 | 291 | CTTATGTGACCGTGCACCTG |
| nbla21936m-F1 | 292 | CGCCTGACAATCTCAATTCC | nbla21936m-R1 | 293 | CTCACGTGTCTGCGTTTGAT |
| nbla21950m-F1 | 294 | AGGGGATCCGGAAGTATGAC | nbla21950m-R1 | 295 | AAGCCGCTCATCTGGTAGAG |
| nbla22027m-F1 | 296 | TGAGAAAACGGTCCTGAAGC | nbla22027m-R1 | 297 | TGTCAGACCCTTGGCATCTT |
| nbla22028m-F1 | 298 | TACCTGAGTCGGACACGATG | nbla22028m-R1 | 299 | GAGAGCCAGACAAGCTTTGG |
| nbla22093m-F1 | 300 | ACAAGGACCCCTGTGCTAAC | nbla22093m-R1 | 301 | TGAGGACAGTGGCAGGTGTA |
| nbla22153m-F1 | 302 | TGCGAGGATTAACTCCAAGG | nbla22153m-R1 | 303 | GGCAACTTTGGCTGAAGAGT |
| nbla22182m-F2 | 304 | AGTCCCCATTGGGATACTGC | nbla22182m-R2 | 305 | TGGGCAATAATTTGGAAACC |
| nbla22218m-F1 | 306 | AGCCACACTGTTAGCAGCAA | nbla22218m-R1 | 307 | CGAATGTCCAGAAGGGAGAG |

TABLE 1-continued

| primer | SEQ ID NO | primer sequence | primer | SEQ ID NO | primer sequence |
|---|---|---|---|---|---|
| nbla22228m-F1 | 308 | CAGCCTGTGAATGGTGTGAA | nbla22228m-R1 | 309 | TGAGGGAAGCTGTGGAAGAG |
| nbla22298m-F1 | 310 | TGACATCTGCTTGTCCTTGG | nbla22298m-R1 | 311 | GGACGGCAGTACCAAGAGTG |
| nbla22344m-F2 | 312 | GAGTCTGCCATTGGCTTTGT | nbla22344m-R2 | 313 | CTGCTTGCTCTGTTCCACTG |
| nbla22351m-F1 | 314 | AGACAGGGTCTGGCTGTGTT | nbla22351m-R1 | 315 | TGAGGCCAGGAGTTCAAGAC |
| nbla22352m-F1 | 316 | CTGGCACAATGTCTTCACAA | nbla22352m-R1 | 317 | TTGAAAGGGGAGATTCCTGA |
| nbla22361m-F1 | 318 | CGACAGATGACCTTGATTCG | nbla22361m-R1 | 319 | GCCTCAGAAGCCTTTCTCAA |
| nbla22382m-F1 | 320 | GTTGGCGAGCTAGCAAAACT | nbla22382m-R1 | 321 | TGCCATCCTTCTCACAGATG |
| nbla22394m-F1 | 322 | TTACCCATAATGCCCTCCAC | nbla22394m-R1 | 323 | CAAAACGACAGCAGCAGAAC |
| nbla22451m-F1 | 324 | GGCATTGGAGGTTGTCATTC | nbla22451m-R1 | 325 | GCTTGCTCTTCACCAGGAAC |
| nbla22455m-F1 | 326 | GAAGACCCTGGTTTTTGCAG | nbla22455m-R1 | 327 | CAACTCGGTTGGTGAAATCAG |
| nbla22465m-F1 | 328 | AGGAGAAGCCTCATCAACCA | nbla22465m-R1 | 329 | TCAGGCAGACATTCCCAGAT |
| nbla22474m-F1 | 330 | AATGTGCCGGTTTTCTCATC | nbla22474m-R1 | 331 | CCAACCCCTTAGACATGCAC |
| nbla22549m-F1 | 332 | TCTGTGAAAGGGCATGTGAG | nbla22549m-R1 | 333 | GGAGGGATTTCATTGCTCTG |
| nbla22704m-F1 | 334 | TCTCAGTTGGGTTTGGAAGC | nbla22704m-R1 | 335 | GGAGAAAAGCCAGAGTGTCG |
| nbla22832m-F1 | 336 | CACGGGAACCCATTTGTATG | nbla22832m-R1 | 337 | GTGGAAGGAGCCGTTGATAA |
| nbla22886m-F1 | 338 | ATCGGCAGAGTGCATACCTT | nbla22886m-R1 | 339 | TCTGTGGCTCAATACGCTTG |
| nbla23020m-F1 | 340 | TTCCCACCAAATCAGTCTCC | nbla23020m-R1 | 341 | TGGCCACTGAAGTCTCAGGT |
| nbla23028m-F1 | 342 | ATGGTGAAAGTGGTTCAGTGC | nbla23038m-R1 | 343 | TGCATTTGCTGTGGATTACC |
| nbla23060m-F1 | 344 | GTGGCACAGTGGGAGCTATT | nbla23060m-R1 | 345 | GCCCAATCCTCTAAACAACG |
| nbla23218m-F1 | 346 | GTAAACAGCCCCTTGGTCAG | nbla23218m-R1 | 347 | ATGTGCAGTGTTCCCCACTT |
| nbla23394m-F1 | 348 | CAAGCGGTGGAGTACTTGAA | nbla23394m-R1 | 349 | CCTGCAGTTCCCAGTCTTTC |
| nbla23512m-F1 | 350 | CCCAGCCAGCCAAGTAGATA | nbla23512m-R1 | 351 | ACCCCACTCTTTGGGTCTCT |
| nbla23653m-F1 | 352 | ACTGGGCATCTGGATAGCAG | nbla23653m-R1 | 353 | CTTCGGAACCAGCCAACTTA |
| nbla23664m-F1 | 354 | TGAGGGGCTTCAAGCAGTAG | nbla23664m-R1 | 355 | GCACACTCACTTCCCAAGGA |
| nbla23666m-F1 | 356 | CGTGGTGGTGTGTATTTTGG | nbla23666m-R1 | 357 | GCGGTGACATAAAAGGCTGA |
| nbla23718m-F1 | 358 | ATGGAGAACTTGCCTGCACT | nbla23718m-R1 | 359 | TCAGCTTCACCCACACTTTG |
| nbla23719m-F1 | 360 | CTGTGGAGGAGTGGGATGTT | nbla23719m-R1 | 361 | GTTGCTTTTGGTTTCCCATC |
| nbla23760m-F1 | 362 | TGTGAGTCCTCCTGTTGTGG | nbla23760m-R1 | 363 | GAGCTGTCAAAATGGCTTCC |
| nbla23951m-F1 | 364 | TCACAGTTGCTGCCAAAGAG | nbla23951m-R1 | 365 | CGTCCCATTTTCCAGAGATG |
| nbla23973m-F1 | 366 | ACCAGTGTGAGGTGGTCAGA | nbla23973m-R1 | 367 | GTGGGAGGCCACAAACTTAG |
| nbla24082m-F1 | 368 | GGAGCAATCCAAGGAGATGA | nbla24082m-R1 | 369 | TGGACAGCCTCCTTCAGTTT |
| nbla24084m-F1 | 370 | GGTCGTTTAGGTGGCAAATG | nbla24084m-R1 | 371 | CCCAGGAATCTGCAAGGATA |
| nbla24104m-F1 | 372 | GTTGATGGAGCACCACAGAA | nbla24104m-R1 | 373 | CTGCATTGTTCAGCCAGGTT |
| nbla24131m-F1 | 374 | CACCAATGCTGTGAACTTGC | nbla24131m-R1 | 375 | TGACAGTCCAGCCTCACAGA |
| nbla24239m-F1 | 376 | TGGACACGCATAAGAAGCAG | nbla24239m-R1 | 377 | TGTCGAAGAAACTCCTGACG |
| nbla24285m-F1 | 378 | GTGGTGTGATGTCTGCCATT | nbla24285m-R1 | 379 | CCTTGTTGGACCTTGATTCC |
| nbla24297m-F1 | 380 | AAGGCTCTTTCCAGGAGGTC | nbla24297m-R1 | 381 | CCTTCAGGACACACAGGCTTA |
| nbla24348m-F1 | 382 | TAGTCCCCAAACCTGCTGTT | nbla24348m-R1 | 383 | GGCGAAGAAGAATTTGAACG |

TABLE 1-continued

| primer | SEQ ID NO | primer sequence | primer | SEQ ID NO | primer sequence |
|---|---|---|---|---|---|
| nbla24434m-F1 | 384 | GCCTGTGGTCAAAATCCAGT | nbla24434m-R1 | 385 | CTTTGCCTCAGTGGCTCTTC |
| nbla24460m-F1 | 386 | TTTCCAGGAGGTCAGGTTTG | nbla24460m-R1 | 387 | CCTTCAGGACACACAGGCTTA |
| nbla24468m-F1 | 388 | TGACAAAGACGCTGAACTGG | nbla24468m-R1 | 389 | GGGTTGTCAGAAAGCCTGAG |
| nbla24521m-F1 | 390 | TAATGGGAGTGCTGCCTCTG | nbla24521m-R1 | 391 | CATCTTTAAGGCTAACATGC |
| nbla24526m-F1 | 392 | AAGGAGCGCACCAACAGTAT | nbla24526m-R1 | 393 | ATAGGGTGGCTCAGGGAAAT |
| nbla24622m-F1 | 394 | GCACTTGGACCTCCCTTGTA | nbla24622m-R1 | 395 | GGTCCTGCACATTTCAACAG |
| nbla24672m-F1 | 396 | GGGCAGGACAATAAGACTGC | nbla24672m-R1 | 397 | TGTCCACAGCAGACACCCTA |
| nbla24686m-F1 | 398 | AAGAAGGCTCCGAGCTCAAT | nbla24686m-R1 | 399 | TCTGTGAGCTCCAGGCAGTA |
| nbla24709m-F1 | 400 | GCAGCATTCTGAGACACAGG | nbla24709m-R1 | 401 | GCTGGAGAGACCCAAGGACT |
| nbla24719m-F1 | 402 | CAGGGGATAACCTTCGTCAA | nbla24719m-R1 | 403 | AAGCAGCAACGTGGGATAAC |
| nbla24756m-F1 | 404 | ACATTGACAACCCTCCCAAG | nbla24756m-R1 | 405 | AAAGCAGCAGCCTCAGAGAA |
| nbla24831m-F1 | 406 | AAACGCTTGAGCTCTTCCAC | nbla24831m-R1 | 407 | AGCTCAGCAACCGCTCTAAA |
| nbla24893m-F1 | 408 | AGAGGGGCCAAGGGATATAA | nbla24893m-R1 | 409 | TACGAGGGCCTGTTTCAGAT |
| nbla24908m-F1 | 410 | TTCAGAGCATCGAGTTCACG | nbla24908m-R1 | 411 | TCATCCTCCTGGGTGAAGTT |
| nbla24972m-F1 | 412 | TCACCAAAACTGGCACAGAG | nbla24972m-R1 | 413 | TCGGACTGTGCTGCATTCTA |
| nbla24973m-F1 | 414 | CTGCACACCTCTCAATGCAG | nbla24973m-R1 | 415 | GAAGCAGCCCGATGTGTT |
| nbla24986m-F1 | 416 | CAGAGCAGTAACCGTGACCA | nbla24986m-R1 | 417 | ACCAGGACGGACACTGTTGT |

The results described below were obtained with the genes for which variations in the gene expression level were observed. The genes whose expression levels were decreased notably by NGF depletion (−NGF) were nbla-03267 (SEQ ID NO:21)(−NGF 12 hrs): note 24-48 hrs/−NGF24 hrs to −NGF48 hrs. An increase in expression level was observed under different conditions (−NGF12 hrs) for this gene. Addition of NGF also decreased the expression level. In a similar manner nbla-11589 (SEQ ID NO:64) displayed an increase in the expression level by NGF depletion, but displayed a decrease in the expression level by NGF addition.

The primer sets used to amplify those particular genes are shown in Table 2.

TABLE 2

| primer | primer sequence | primer | primer sequence |
|---|---|---|---|
| nbla03267m-f | CTGCCTTTGAGATGGTGATG (SEQ ID NO: 124) | nbla03267m-r | TGTAGTGCTTTGCATTGTTGG (SEQ ID NO: 125) |
| nbla11589m-F2 | GGAGCTAGCCAAGATGATCG (SEQ ID NO: 200) | nbla11589m-R2 | CTGGCCATCCTAGAGGAGAA (SEQ ID NO: 201) |

As described above, because the superior cervical gangliocytes are known to die (apoptosis) through NGF depletion, the genes that display variations in the expression level are closely connected to the mechanism of apoptosis.

INDUSTRIAL APPLICABILITY

As described above, this invention discloses gene sequences relating to favorable or unfavorable prognosis of neuroblastoma and will enable the provision of their genetic information and the diagnosis of favorable or unfavorable prognosis.

The invention claimed is:

1. An isolated nucleic acid of SEQ ID NO:21.

2. A diagnostic agent for the detection of a neurological disease containing an isolated nucleic acid of SEQ ID NO:21.

* * * * *

SEQUENCE LISTING

<160> NUMBER OF SEQ ID NOS: 417

<210> SEQ ID NO 1
<211> LENGTH: 889
<212> TYPE: DNA
<213> ORGANISM: Homo sapiens
<220> FEATURE:
<221> NAME/KEY: modified_base
<222> LOCATION: (2)..(2)
<223> OTHER INFORMATION: n is a, c, g, or t
<220> FEATURE:
<221> NAME/KEY: modified_base
<222> LOCATION: (4)..(13)
<223> OTHER INFORMATION: n is a, c, g, or t
<220> FEATURE:
<221> NAME/KEY: modified_base
<222> LOCATION: (15)..(19)
<223> OTHER INFORMATION: n is a, c, g, or t
<220> FEATURE:
<221> NAME/KEY: modified_base
<222> LOCATION: (22)..(26)
<223> OTHER INFORMATION: n is a, c, g, or t
<220> FEATURE:
<221> NAME/KEY: modified_base
<222> LOCATION: (31)..(32)
<223> OTHER INFORMATION: n is a, c, g, or t
<220> FEATURE:
<221> NAME/KEY: modified_base
<222> LOCATION: (34)..(34)
<223> OTHER INFORMATION: n is a, c, g, or t
<220> FEATURE:
<221> NAME/KEY: modified_base
<222> LOCATION: (628)..(628)
<223> OTHER INFORMATION: n is a, c, g, or t
<220> FEATURE:
<221> NAME/KEY: modified_base
<222> LOCATION: (647)..(647)
<223> OTHER INFORMATION: n is a, c, g, or t
<220> FEATURE:
<221> NAME/KEY: modified_base
<222> LOCATION: (692)..(692)
<223> OTHER INFORMATION: n is a, c, g, or t
<220> FEATURE:
<221> NAME/KEY: modified_base
<222> LOCATION: (734)..(734)
<223> OTHER INFORMATION: n is a, c, g, or t
<220> FEATURE:
<221> NAME/KEY: modified_base
<222> LOCATION: (736)..(736)
<223> OTHER INFORMATION: n is a, c, g, or t
<220> FEATURE:
<221> NAME/KEY: modified_base
<222> LOCATION: (780)..(780)
<223> OTHER INFORMATION: n is a, c, g, or t
<220> FEATURE:
<221> NAME/KEY: modified_base
<222> LOCATION: (799)..(799)
<223> OTHER INFORMATION: n is a, c, g, or t
<220> FEATURE:
<221> NAME/KEY: modified_base
<222> LOCATION: (806)..(806)
<223> OTHER INFORMATION: n is a, c, g, or t
<220> FEATURE:
<221> NAME/KEY: modified_base
<222> LOCATION: (819)..(819)
<223> OTHER INFORMATION: n is a, c, g, or t
<220> FEATURE:
<221> NAME/KEY: modified_base
<222> LOCATION: (839)..(839)
<223> OTHER INFORMATION: n is a, c, g, or t
<220> FEATURE:
<221> NAME/KEY: modified_base
<222> LOCATION: (843)..(843)
<223> OTHER INFORMATION: n is a, c, g, or t
<220> FEATURE:
<221> NAME/KEY: modified_base -continued

```
<222> LOCATION: (868)..(868)
<223> OTHER INFORMATION: n is a, c, g, or t
<220> FEATURE:
<221> NAME/KEY: modified_base
<222> LOCATION: (878)..(878)
<223> OTHER INFORMATION: n is a, c, g, or t
<220> FEATURE:
<221> NAME/KEY: modified_base
<222> LOCATION: (883)..(883)
<223> OTHER INFORMATION: n is a, c, g, or t
<220> FEATURE:
<221> NAME/KEY: modified_base
<222> LOCATION: (889)..(889)
<223> OTHER INFORMATION: n is a, c, g, or t

<400> SEQUENCE: 1

gngnnnnnnn nnngnnnnnt tnnnnnggcc nngnatcctc gagcacggtt ggcctactgg      60

ttattactct tgcattgggt gggatttaag ggttcattat attaagaatt aaacagtaag     120

taaattcata cataaaaggt atggttattc ttgagtcaat aatgagaatg tgttaggaac     180

caaggtttat gattaatcta aaataatttc taaaagaagt taagtctttg ctgtttcgtt     240

ctttctaaaa tgtgtatttt ccttcacaca atgaacatgc cacagctaat tattcgataa     300

caataaagac attggtgttt tgcctctgtg gttaaggagc tcagagtctg ttgtagataa     360

tagttaaagt tcatgtcctg ggtttaggtg gcttgttcat cactaaatta tgttagaaga     420

ataaaccgct aaatatatac atatataaaa agcataccat acaagaacca ataatggaag     480

tgaaccaagg tttatgatta gtttaattca gcccaactta ggtccattac aaatgatgga     540

gggcttttat taatttcaga ggtttttaac attgtatttt attttgtgcc gtggttgatt     600

tacacacatt tctttaaagt taaagatnaa ggctattcac tcctccnagg gagaagcaga     660

taggaaaagg aagatagtgt cagtgtcctc antgtgaagt taagatgggg ggtcacaagt     720

tgtcaatcca atgnantaat aacctttgct gtgtaatgaa ttactggaca atttaatggn     780

ttaaaacaac aataaacant tgtcanttcc cacggttcna agtggcaaga atccaagana     840

ggntactggg gggaaattta cctaaggntc cttggaantt cangcaaan                 889


<210> SEQ ID NO 2
<211> LENGTH: 888
<212> TYPE: DNA
<213> ORGANISM: Homo sapiens
<220> FEATURE:
<221> NAME/KEY: modified_base
<222> LOCATION: (2)..(2)
<223> OTHER INFORMATION: n is a, c, g, or t
<220> FEATURE:
<221> NAME/KEY: modified_base
<222> LOCATION: (4)..(4)
<223> OTHER INFORMATION: n is a, c, g, or t
<220> FEATURE:
<221> NAME/KEY: modified_base
<222> LOCATION: (7)..(12)
<223> OTHER INFORMATION: n is a, c, g, or t
<220> FEATURE:
<221> NAME/KEY: modified_base
<222> LOCATION: (29)..(29)
<223> OTHER INFORMATION: n is a, c, g, or t
<220> FEATURE:
<221> NAME/KEY: modified_base
<222> LOCATION: (412)..(412)
<223> OTHER INFORMATION: n is a, c, g, or t
<220> FEATURE:
<221> NAME/KEY: modified_base
<222> LOCATION: (452)..(452)
<223> OTHER INFORMATION: n is a, c, g, or t
<220> FEATURE:
<221> NAME/KEY: modified_base
<222> LOCATION: (491)..(491)
```

<223> OTHER INFORMATION: n is a, c, g, or t
<220> FEATURE:
<221> NAME/KEY: modified_base
<222> LOCATION: (513)..(513)
<223> OTHER INFORMATION: n is a, c, g, or t
<220> FEATURE:
<221> NAME/KEY: modified_base
<222> LOCATION: (543)..(543)
<223> OTHER INFORMATION: n is a, c, g, or t
<220> FEATURE:
<221> NAME/KEY: modified_base
<222> LOCATION: (570)..(570)
<223> OTHER INFORMATION: n is a, c, g, or t
<220> FEATURE:
<221> NAME/KEY: modified_base
<222> LOCATION: (604)..(604)
<223> OTHER INFORMATION: n is a, c, g, or t
<220> FEATURE:
<221> NAME/KEY: modified_base
<222> LOCATION: (627)..(627)
<223> OTHER INFORMATION: n is a, c, g, or t
<220> FEATURE:
<221> NAME/KEY: modified_base
<222> LOCATION: (654)..(654)
<223> OTHER INFORMATION: n is a, c, g, or t
<220> FEATURE:
<221> NAME/KEY: modified_base
<222> LOCATION: (657)..(657)
<223> OTHER INFORMATION: n is a, c, g, or t
<220> FEATURE:
<221> NAME/KEY: modified_base
<222> LOCATION: (663)..(663)
<223> OTHER INFORMATION: n is a, c, g, or t
<220> FEATURE:
<221> NAME/KEY: modified_base
<222> LOCATION: (674)..(674)
<223> OTHER INFORMATION: n is a, c, g, or t
<220> FEATURE:
<221> NAME/KEY: modified_base
<222> LOCATION: (691)..(691)
<223> OTHER INFORMATION: n is a, c, g, or t
<220> FEATURE:
<221> NAME/KEY: modified_base
<222> LOCATION: (708)..(708)
<223> OTHER INFORMATION: n is a, c, g, or t
<220> FEATURE:
<221> NAME/KEY: modified_base
<222> LOCATION: (725)..(725)
<223> OTHER INFORMATION: n is a, c, g, or t
<220> FEATURE:
<221> NAME/KEY: modified_base
<222> LOCATION: (728)..(728)
<223> OTHER INFORMATION: n is a, c, g, or t
<220> FEATURE:
<221> NAME/KEY: modified_base
<222> LOCATION: (739)..(739)
<223> OTHER INFORMATION: n is a, c, g, or t
<220> FEATURE:
<221> NAME/KEY: modified_base
<222> LOCATION: (750)..(750)
<223> OTHER INFORMATION: n is a, c, g, or t
<220> FEATURE:
<221> NAME/KEY: modified_base
<222> LOCATION: (771)..(771)
<223> OTHER INFORMATION: n is a, c, g, or t
<220> FEATURE:
<221> NAME/KEY: modified_base
<222> LOCATION: (788)..(788)
<223> OTHER INFORMATION: n is a, c, g, or t
<220> FEATURE:
<221> NAME/KEY: modified_base
<222> LOCATION: (798)..(798)
<223> OTHER INFORMATION: n is a, c, g, or t
<220> FEATURE:
<221> NAME/KEY: modified_base
<222> LOCATION: (803)..(803)
<223> OTHER INFORMATION: n is a, c, g, or t
<220> FEATURE:
<221> NAME/KEY: modified_base -continued
<222> LOCATION: (834)..(834)
<223> OTHER INFORMATION: n is a, c, g, or t
<220> FEATURE:
<221> NAME/KEY: modified_base
<222> LOCATION: (836)..(836)
<223> OTHER INFORMATION: n is a, c, g, or t
<220> FEATURE:
<221> NAME/KEY: modified_base
<222> LOCATION: (840)..(840)
<223> OTHER INFORMATION: n is a, c, g, or t
<220> FEATURE:
<221> NAME/KEY: modified_base
<222> LOCATION: (845)..(845)
<223> OTHER INFORMATION: n is a, c, g, or t
<220> FEATURE:
<221> NAME/KEY: modified_base
<222> LOCATION: (850)..(850)
<223> OTHER INFORMATION: n is a, c, g, or t
<220> FEATURE:
<221> NAME/KEY: modified_base
<222> LOCATION: (852)..(852)
<223> OTHER INFORMATION: n is a, c, g, or t
<220> FEATURE:
<221> NAME/KEY: modified_base
<222> LOCATION: (854)..(854)
<223> OTHER INFORMATION: n is a, c, g, or t
<220> FEATURE:
<221> NAME/KEY: modified_base
<222> LOCATION: (861)..(861)
<223> OTHER INFORMATION: n is a, c, g, or t
<220> FEATURE:
<221> NAME/KEY: modified_base
<222> LOCATION: (885)..(885)
<223> OTHER INFORMATION: n is a, c, g, or t

<400> SEQUENCE: 2
gngntgnnnn nngtggcttt ttttttggnt tttttttttt gagacagagt ctcactgtgt 60
tgccaaggct gggagtacag tgggcgcgat cacagcacag agcttttttta ctttatttaa 120 atatgtgccc atttatttct ctaaaataat aaaaagcatg aacaagccca cacgaatcaa 180
gaatataaaa attaacttaa atccattcct acacttttta cccacagaag taaaagccat 240
aattttcacc actgaaaaat aattaaatca ggtatggtgc atctattgtg taaagtaaga 300
gtagatttaa gaaagaacag cctacatgca tttaaatctt tcaagggaca tttgtaggac 360
agtactaaga ttaattataa actcttattc acaccacatt ttaatcagtg gnccaagaat 420
ggcctggaat attatttact gatttatctg gnacccaaca cgagaataaa agctactaca 480
agtatccatc natgtgtttt ctacccagat ggnaaaaatc tgaactttat tcccaataat 540
ggntccaatt atacagtaca agaattaggn aaatttaacc actttttta agggaaattt 600 tcancaaaat agtccatgct agactcnccc ttaagtgttt ccttaatcaa ttgncanttc 660
acntatcaat taanaagtac tcatgaacaa ntccttggtt tttccggnga aaacacagta 720
tggtnagncc atcaacaanc cagaatccgn atacaattta atgcaactat ncacatgaac 780
ctgacccntt gggggaanaa ccnattttag gcccttggtt tgcctttccc ttancnggan 840
aaccnttagn tncnccaggg naataattca aacgttttta cacangcc 888

<210> SEQ ID NO 3
<211> LENGTH: 2083
<212> TYPE: DNA
<213> ORGANISM: Homo sapiens

<400> SEQUENCE: 3
cactgttggc ctactggaga ttacctacaa aggaacaata gtaatattgg ctgtaataag 60
ataacggagc ggcatcttcg tagtgccaag gaaaagtaac tgccaatctg aaattttatg 120

-continued

```
cccagctaaa ctattactca agagtgaggg gaaaaagtta aaacaccaga aacaaaggac    180

tcaaagatta acaaccatga gttcttgctg aaagaacttc tgaaggatgt actccaagaa    240

aaatgaacct taaataacaa gcctccaaaa aaaatgataa aattggtaaa acatattgat    300

aaatctgaat caatgtactg attggaaata aaataaattg gtagaaaatc ggggtagaac    360

taattctaga agatgatatg aagagaagga cagaagagag catgggtatg tgtttgagac    420

tgagagagta caacgaaaat tgaagggggt aactcctggc aaaatagaaa tagcatatac    480

agttcaaaac agtagaagta gagggaaaag aacaaaaata gacttgagga gcacaataag    540

aagcagaact aaagggaaaa ggtatgtgga gagacaccat gataatagaa aacacaagtc    600

cgaacatatc aatcttcaaa ttatgcttca tttataaaaa tttacactta aaataaaaat    660

acaccaataa gttataagta aagggatagg aaatgatgta ccaggcaaat ctgtcatttc    720

tcatctgaag tactggatta ggctccagtc tgcttttcct ccttctattc ctgcccacag    780

tgctccccta accacttctc cagttgtttg ccactcaata gccaaagtga tccttctaaa    840

gagtaagtca agttaaatga ctaacctttg ctcagaactg ttttttcaaa acgctcttac    900

agaggcccaa aggacattct gtgatgtggc cttcccaggc tacctctctg atctctttga    960

tgaccacagt cccacctcag tcattctgat ctactcatct agtcaaactg gctgtgttgc   1020

tgtttcacaa cacaccaatc acttttccat tggggtttgt actcagtcat ttagatctct   1080

gttcagatgt catctcctaa gagaaacttt ttctgtccac cctctctaga gtgtaacttc   1140

catcactatc tgattgctcc cccttttttct ttgtgacatt taaaactatc tggcataatg   1200

gacatgttat tgatttattg tctgtcttct cactaaaatg taaacttatt caggtcaaga   1260

acttgaactt atttacattc tattccctag aatggtgcct ggcacattgt aggtgttagt   1320

tcatatttgt taactgggca ttttatatga tagataatat tattccattt ttaaaaggaa   1380

gaaactgcaa gattaagtaa ctgatccaaa tttttatact ggtaagttgt agagctggga   1440

ttgaatgaaa taaataccaa caaaaataaa actggtaagc agtgttgata atcagaggac   1500

atagatttca gggcaaaagg tatttaaaat aaaaaataga ggccaggcac cgtggctcac   1560

gcccgtaatc ccagcacttt gggaggctga ggtgggcgga tcacctgagg tcaggaattc   1620

gagaccagct tggctaacat ggtgaaaccc catctctact aaaaatacaa aaattactca   1680

ggcatggtgg cagggacctg taatcctagc tcctcgggag gctgaggcag aagaattgct   1740

tgacctaact cgtgaggcag aggttgcagt gagccgagat catgccagtg cactccagcc   1800

tgggcgacag agtaagagtc tgtctcaaaa aaaaaagaac aaatagaaat gattcgtatg   1860

aattaaggct catttcagga agtttttagc agtcatgagc ttgaatgtat ctgtagtata   1920

acttctgtat attaatgaga aaaaaagtaa agattgacag gactctgaag ggaagaagga   1980

aaatcatgtt tatagtagga gactaaccac cagagcaaga aggcaaaata aaaaaaaaaa   2040

aaaaaaggcc acatgtgctc gagctgcagg tcgcggccgc tag                     2083


<210> SEQ ID NO 4
<211> LENGTH: 3210
<212> TYPE: DNA
<213> ORGANISM: Homo sapiens

<400> SEQUENCE: 4

gcactgttgg cctactggcc caggccttgc acacgcaggt gctctcttag tgctccctgg     60

caaggatggg aaggcatgtt cagtcctagg agtaggaagg ggcagaggtg ttgatggccc    120

ctacagagcg gccaaggaca aggagctgct gttcgaaaca gccttcctgc tccccaacct    180
```

-continued

```
gcctcccacc caacaggttt tgcatatact ctactgggaa gagggacaca cccgactgca    240
tcactgccct ccaagtctct ccctgccctg tccagcatcc aggagcaccc ctagttgggg    300
aagcttctgt gactccccct acaacagcct aggatggagt ggggtttgtg aacaaatgca    360
gaaggcagtc ttagggaggt cagctgacat gcccctggcc tgtggctggg aagtagcaga    420
ggctaaggtt cttccccgct ctggggttgc caggagtagc actggatcag tcaggtgaca    480
gggctctcct ctctctgagc aggtccggtg gcagccttca aggtcgccac gccgtattcc    540
ctgtatgtct gtcccgaggg gcagaacgtc accctcacct gcaggctctt gggccctgtg    600
gacaaagggc acgatgtgac cttctacaag acgtggtacc gcagctcgag ggcgaggtg    660
cagacctgct cagagcgccg gcccatccgc aacctcacgt tccaggacct tcacctgcac    720
catggaggcc accaggctgc caacaccagc cacgacctgg ctcagcgcca cgggctggag    780
tcggcctccg accaccatgg caacttctcc atcaccatgc gcaacctgac cctgctggat    840
agcggcctct actgctgcct ggtggtggag atcaggcacc accactcgga gcacagggtc    900
catggtgcca tggagctgca ggtgcagaca ggcaaagatg caccatccaa ctgtgtggtg    960
tacccatcct cctcccagga gagtgaaagt aagggaccaa cctcttgccc cttttgggtt   1020
ctctgttttc ttctgtcctc atcctgcacc cagaccctgt ttggaactct ggcctcatca   1080
ccccaagccc tcagaacccc ccggtcctcc tccttttctg ctgctgcaca tcccttctgc   1140
ttcctccttg gtgcaatccc cagaagccca ctctccttcc atctgctctg gagtctctgc   1200
tcctcttgac tctctggagt ggctgtgcct tggcagtgac ctttggccag ggcaagtgcc   1260
tcatgacagg tactgggtgc cccaggcagc taagtgccgc cctgcccacc agccccctat   1320
ggcttgggaa ggctgggggt cctcttggcc aacagggtga aaccccatct ctactaaaaa   1380
cacaaaaatt agccaggcat ggtggtgcgc gcctgtagtc ccagctactc aagaggctga   1440
ggcaagagaa tcgcttgaac ccgggagtca gaggttgcag tgagccgaga tcgcgccact   1500
gcactccagc ctgctgatag agcaagactc catctcaaaa aaaacaaccc aaaatttgcc   1560
tggcatggtg gcaggcatct gtaatcccag ctactcggga ggctgagaca tgagagctgc   1620
ttgaacctgg gaggcagaag ttgcagtgag ccgagatcac accactgcac tccagcctgg   1680
gtgacagagc gagactctgt cccaaaaaat caaaaaaatc acttttggta gagatgcact   1740
ctcgctatgt tgcccaggct ggtcttgaac tcctgggctc aattgatctt cccaccttga   1800
cctccaaagt gctgggatta caggtgtgag ccaccatgcc tagcctcagg gaattcttat   1860
aagaactcta tgaagtaggc atcaccatct tctctgtatc catggaaaga gaggcctaga   1920
gatgtatgct aacttgccca agctcacata gcccagggta gcatagctgg gatgttgagc   1980
tgaggccgga ggagaagtag cagtcgctgg cagagcacac aggctgctct gggggatgag   2040
ctggtgcgtt taaggaacag gccagcactg gcattcgcaa gcagtgggga aggggagaga   2100
tgccgaggtg gtcagtatcc tgactttcag aggccttttt ttgtttgttt taatttttgc   2160
tagattgata ttaaaaactc atgtggagga actcaaggaa tgtttagaag accaaaagtc   2220
cccaatgaca ggaacaaaag caaccaattt ttaactttct cttctcattc ctgttttcat   2280
tgatttccca catgtagtcc ttttgctcag gaagtctttg gggaaattaa ggatctttga   2340
agctctgaaa taggtgatca ggttagtggt gtctgtcagc tgtctaagag gttggaaaat   2400
gaactactca agatagtcac gaaaatactg aaagtttgat ttttctttcc atatttgaat   2460
taatttttc tgtttgactg gaaggggttt ttgtataact aaaacctcag cgcataaagg   2520
```

-continued

```
agatttaaaa ggagcacatg atttagtggg tgggccatga aactagagat gggatttggg   2580

ggtgaatttg tcaatatctg gattttaatc cagacatctc tgctaacgag cctttggtaa   2640

gtcacttcag atacttttcc tcctttttac aaagagaggg ctggcttagt tatttgccaa   2700

agccccttcc aggcctgaat tccacaagta cgatttactg tagtgtctta tcactctttc   2760

atgtcacaat agcgtggagc attagagaaa agcctagact tttagttgat agccagttga   2820

aatatcattg atagaatttt agttttagga aaaattggtt tgatttctag ctttattact   2880

attaggtatg tgagcttggg caaatcgctt aatctttgag tctagttttc tctcaaaatg   2940

agaacattag gctaaatgat ttccgagttt ccagctagtc ctagagttct atatttctac   3000

atagttgaat tattttatca tgctgttgct ggggaatatg actaaccctt ttgaagctac   3060

taattttatg tcgagcttta aagtccataa ttgttatctt cagaaaatat tatttgacct   3120

acagtatgtc caaatcaatt taataaaatc gctttataac aggaaaaaaa aaaaaaaaaa   3180

aaaaaaaaaa aaaaggccac atgtgctcga                                    3210
```

```
<210> SEQ ID NO 5
<211> LENGTH: 889
<212> TYPE: DNA
<213> ORGANISM: Homo sapiens
<220> FEATURE:
<221> NAME/KEY: modified_base
<222> LOCATION: (3)..(6)
<223> OTHER INFORMATION: n is a, c, g, or t
<220> FEATURE:
<221> NAME/KEY: modified_base
<222> LOCATION: (8)..(17)
<223> OTHER INFORMATION: n is a, c, g, or t
<220> FEATURE:
<221> NAME/KEY: modified_base
<222> LOCATION: (24)..(25)
<223> OTHER INFORMATION: n is a, c, g, or t
<220> FEATURE:
<221> NAME/KEY: modified_base
<222> LOCATION: (38)..(38)
<223> OTHER INFORMATION: n is a, c, g, or t
<220> FEATURE:
<221> NAME/KEY: modified_base
<222> LOCATION: (47)..(47)
<223> OTHER INFORMATION: n is a, c, g, or t
<220> FEATURE:
<221> NAME/KEY: modified_base
<222> LOCATION: (55)..(55)
<223> OTHER INFORMATION: n is a, c, g, or t
<220> FEATURE:
<221> NAME/KEY: modified_base
<222> LOCATION: (74)..(74)
<223> OTHER INFORMATION: n is a, c, g, or t
<220> FEATURE:
<221> NAME/KEY: modified_base
<222> LOCATION: (476)..(476)
<223> OTHER INFORMATION: n is a, c, g, or t
<220> FEATURE:
<221> NAME/KEY: modified_base
<222> LOCATION: (484)..(484)
<223> OTHER INFORMATION: n is a, c, g, or t
<220> FEATURE:
<221> NAME/KEY: modified_base
<222> LOCATION: (503)..(503)
<223> OTHER INFORMATION: n is a, c, g, or t
<220> FEATURE:
<221> NAME/KEY: modified_base
<222> LOCATION: (514)..(514)
<223> OTHER INFORMATION: n is a, c, g, or t
<220> FEATURE:
<221> NAME/KEY: modified_base
<222> LOCATION: (605)..(605)
<223> OTHER INFORMATION: n is a, c, g, or t
<220> FEATURE:
<221> NAME/KEY: modified_base
```

<222> LOCATION: (662)..(662)
<223> OTHER INFORMATION: n is a, c, g, or t
<220> FEATURE:
<221> NAME/KEY: modified_base
<222> LOCATION: (680)..(680)
<223> OTHER INFORMATION: n is a, c, g, or t
<220> FEATURE:
<221> NAME/KEY: modified_base
<222> LOCATION: (686)..(686)
<223> OTHER INFORMATION: n is a, c, g, or t
<220> FEATURE:
<221> NAME/KEY: modified_base
<222> LOCATION: (719)..(719)
<223> OTHER INFORMATION: n is a, c, g, or t
<220> FEATURE:
<221> NAME/KEY: modified_base
<222> LOCATION: (738)..(738)
<223> OTHER INFORMATION: n is a, c, g, or t
<220> FEATURE:
<221> NAME/KEY: modified_base
<222> LOCATION: (755)..(755)
<223> OTHER INFORMATION: n is a, c, g, or t
<220> FEATURE:
<221> NAME/KEY: modified_base
<222> LOCATION: (786)..(786)
<223> OTHER INFORMATION: n is a, c, g, or t
<220> FEATURE:
<221> NAME/KEY: modified_base
<222> LOCATION: (808)..(808)
<223> OTHER INFORMATION: n is a, c, g, or t
<220> FEATURE:
<221> NAME/KEY: modified_base
<222> LOCATION: (814)..(814)
<223> OTHER INFORMATION: n is a, c, g, or t
<220> FEATURE:
<221> NAME/KEY: modified_base
<222> LOCATION: (832)..(832)
<223> OTHER INFORMATION: n is a, c, g, or t
<220> FEATURE:
<221> NAME/KEY: modified_base
<222> LOCATION: (835)..(835)
<223> OTHER INFORMATION: n is a, c, g, or t
<220> FEATURE:
<221> NAME/KEY: modified_base
<222> LOCATION: (855)..(855)
<223> OTHER INFORMATION: n is a, c, g, or t
<220> FEATURE:
<221> NAME/KEY: modified_base
<222> LOCATION: (864)..(864)
<223> OTHER INFORMATION: n is a, c, g, or t
<220> FEATURE:
<221> NAME/KEY: modified_base
<222> LOCATION: (887)..(887)
<223> OTHER INFORMATION: n is a, c, g, or t

<400> SEQUENCE: 5
ggnnnntnnn nnnnnnnggt tttnnggccc gatctcgntc aaatggncct actgncattg 60
atcagctgaa ccanggctct gaagacccgc tcaagaggcc ggtggtgtat gtgaagggtg 120
cagatgccat taagctgatg aacatcgtca acaagcagaa agtggctcga gcaaggatcc 180
agcaccgccc tcctcgacaa cccactgaat actttgacat ggggattttc ctggctttct 240
tcgtcgtggt ctccttggtc tgcctcatcc tccttgtcaa aatcaagctg aagcagcgac 300
gcagtcagaa ttccatgaac aggctggctg tgcaggctct agagaagatg gaaaccagaa 360
agttcaactc caagagcaag ggcgccgggg aggggagctg tggggccctg gacacactca 420
gcagcagctc cacgtccgac tgtgccatct gtctggagaa gtacattgat ggagangagc 480
tgcnggtcat cccctgtact cancggtttc acangaagtg cgtggacccc tggctgctgc 540
aacaacacac ctgccccact gtcggcacaa catcatagaa caaaagggaa accaagcccc 600
gtgtntgttg agaccaacaa cctctcactt gtccgcaaca aaaggtgacc ctgccggtgc 660

```
antaccccgc cgctgcacan gacaangcca tccaacctaa cctacaaggc aaacatggnc    720

tcccacggga aacccgtnac cttgctgacc atggnccggc acggggaaca aaacctctaa    780

tccccncaaa acccccgcct aaatccgnaa gttnccaacc ctccaacttg gncanaacct    840

ggccgctcaa cgctncggct tgancaaccg ggctaatccc aacccancc                889
```

```
<210> SEQ ID NO 6
<211> LENGTH: 867
<212> TYPE: DNA
<213> ORGANISM: Homo sapiens
<220> FEATURE:
<221> NAME/KEY: modified_base
<222> LOCATION: (3)..(3)
<223> OTHER INFORMATION: n is a, c, g, or t
<220> FEATURE:
<221> NAME/KEY: modified_base
<222> LOCATION: (5)..(5)
<223> OTHER INFORMATION: n is a, c, g, or t
<220> FEATURE:
<221> NAME/KEY: modified_base
<222> LOCATION: (9)..(9)
<223> OTHER INFORMATION: n is a, c, g, or t
<220> FEATURE:
<221> NAME/KEY: modified_base
<222> LOCATION: (13)..(13)
<223> OTHER INFORMATION: n is a, c, g, or t
<220> FEATURE:
<221> NAME/KEY: modified_base
<222> LOCATION: (24)..(24)
<223> OTHER INFORMATION: n is a, c, g, or t
<220> FEATURE:
<221> NAME/KEY: modified_base
<222> LOCATION: (27)..(28)
<223> OTHER INFORMATION: n is a, c, g, or t
<220> FEATURE:
<221> NAME/KEY: modified_base
<222> LOCATION: (33)..(33)
<223> OTHER INFORMATION: n is a, c, g, or t
<220> FEATURE:
<221> NAME/KEY: modified_base
<222> LOCATION: (40)..(40)
<223> OTHER INFORMATION: n is a, c, g, or t
<220> FEATURE:
<221> NAME/KEY: modified_base
<222> LOCATION: (70)..(70)
<223> OTHER INFORMATION: n is a, c, g, or t
<220> FEATURE:
<221> NAME/KEY: modified_base
<222> LOCATION: (74)..(74)
<223> OTHER INFORMATION: n is a, c, g, or t
<220> FEATURE:
<221> NAME/KEY: modified_base
<222> LOCATION: (190)..(190)
<223> OTHER INFORMATION: n is a, c, g, or t
<220> FEATURE:
<221> NAME/KEY: modified_base
<222> LOCATION: (386)..(386)
<223> OTHER INFORMATION: n is a, c, g, or t
<220> FEATURE:
<221> NAME/KEY: modified_base
<222> LOCATION: (389)..(389)
<223> OTHER INFORMATION: n is a, c, g, or t
<220> FEATURE:
<221> NAME/KEY: modified_base
<222> LOCATION: (427)..(427)
<223> OTHER INFORMATION: n is a, c, g, or t
<220> FEATURE:
<221> NAME/KEY: modified_base
<222> LOCATION: (476)..(476)
<223> OTHER INFORMATION: n is a, c, g, or t
<220> FEATURE:
<221> NAME/KEY: modified_base
<222> LOCATION: (551)..(551)
<223> OTHER INFORMATION: n is a, c, g, or t
<220> FEATURE:
<221> NAME/KEY: modified_base
```

<222> LOCATION: (557)..(557)
<223> OTHER INFORMATION: n is a, c, g, or t
<220> FEATURE:
<221> NAME/KEY: modified_base
<222> LOCATION: (622)..(622)
<223> OTHER INFORMATION: n is a, c, g, or t
<220> FEATURE:
<221> NAME/KEY: modified_base
<222> LOCATION: (650)..(650)
<223> OTHER INFORMATION: n is a, c, g, or t
<220> FEATURE:
<221> NAME/KEY: modified_base
<222> LOCATION: (663)..(663)
<223> OTHER INFORMATION: n is a, c, g, or t
<220> FEATURE:
<221> NAME/KEY: modified_base
<222> LOCATION: (695)..(695)
<223> OTHER INFORMATION: n is a, c, g, or t
<220> FEATURE:
<221> NAME/KEY: modified_base
<222> LOCATION: (697)..(697)
<223> OTHER INFORMATION: n is a, c, g, or t
<220> FEATURE:
<221> NAME/KEY: modified_base
<222> LOCATION: (747)..(747)
<223> OTHER INFORMATION: n is a, c, g, or t
<220> FEATURE:
<221> NAME/KEY: modified_base
<222> LOCATION: (764)..(764)
<223> OTHER INFORMATION: n is a, c, g, or t
<220> FEATURE:
<221> NAME/KEY: modified_base
<222> LOCATION: (769)..(769)
<223> OTHER INFORMATION: n is a, c, g, or t
<220> FEATURE:
<221> NAME/KEY: modified_base
<222> LOCATION: (797)..(797)
<223> OTHER INFORMATION: n is a, c, g, or t
<220> FEATURE:
<221> NAME/KEY: modified_base
<222> LOCATION: (802)..(802)
<223> OTHER INFORMATION: n is a, c, g, or t
<220> FEATURE:
<221> NAME/KEY: modified_base
<222> LOCATION: (809)..(809)
<223> OTHER INFORMATION: n is a, c, g, or t
<220> FEATURE:
<221> NAME/KEY: modified_base
<222> LOCATION: (823)..(823)
<223> OTHER INFORMATION: n is a, c, g, or t
<220> FEATURE:
<221> NAME/KEY: modified_base
<222> LOCATION: (831)..(831)
<223> OTHER INFORMATION: n is a, c, g, or t
<220> FEATURE:
<221> NAME/KEY: modified_base
<222> LOCATION: (843)..(844)
<223> OTHER INFORMATION: n is a, c, g, or t

<400> SEQUENCE: 6
ggngntttnt ggncgttttc cttntgnnac tanagaatcn agatggctct ggccccagtt 60
cccaatttcn aaantaagag ttcctcctga gctcaggctc ccgggctgct gctgtctgct 120
gagtgagatc tcggtcctgc agcctcagtg gcagtggtgc tggactcctg agtgtcctgg 180
agggcactan ggaagttggc cctgacagca cccgcctcct ccggagggca accaggccgc 240
agtagggcct aacctggcaa cacagagccc gctcctcttc ccgggttgct cccaagcccc 300
tgtggggccg tggggtatcc gggcctcgcg tcccaaccca agagccgagg ctgtgggtcc 360
cttggcagtc cgaagggcaa ggccanatna cagtccacat cctctggaat gatggggatg 420
cgctggntca agtcccgggc cccggggtaa caaccgggcg gtggttcctc ggtgancgtg 480
tactgcacac tcaccgagta tcctcaatgt acaaccgctg cccctccgcc ccgcgggcca 540

-continued

```
actgcttctc ntcatanaac aacaaggcag acctcgtatt tcacccatct gtcctgggca    600

aatggtccgg gtgaaaggcg tncaaaccct gggaacttcc tgactggggn tccccaaccg    660

ccnggcaaaa ccctcgtaaa gtggggccca agaanangtg ctgctgcaac tgtccggggc    720

taagcccggt tgggaaggct ggggtcnaac aacaaggaaa caanggaant cctgggcccc    780

cttcaagtcc tccttangtc anggggggnc caagaaaaac tcnagcccca nttttaggtt    840

aanntattgg gccccttgtc aaggaag                                        867
```

<210> SEQ ID NO 7
<211> LENGTH: 854
<212> TYPE: DNA
<213> ORGANISM: Homo sapiens
<220> FEATURE:
<221> NAME/KEY: modified_base
<222> LOCATION: (2)..(3)
<223> OTHER INFORMATION: n is a, c, g, or t
<220> FEATURE:
<221> NAME/KEY: modified_base
<222> LOCATION: (5)..(7)
<223> OTHER INFORMATION: n is a, c, g, or t
<220> FEATURE:
<221> NAME/KEY: modified_base
<222> LOCATION: (9)..(13)
<223> OTHER INFORMATION: n is a, c, g, or t
<220> FEATURE:
<221> NAME/KEY: modified_base
<222> LOCATION: (18)..(18)
<223> OTHER INFORMATION: n is a, c, g, or t
<220> FEATURE:
<221> NAME/KEY: modified_base
<222> LOCATION: (27)..(27)
<223> OTHER INFORMATION: n is a, c, g, or t
<220> FEATURE:
<221> NAME/KEY: modified_base
<222> LOCATION: (29)..(29)
<223> OTHER INFORMATION: n is a, c, g, or t
<220> FEATURE:
<221> NAME/KEY: modified_base
<222> LOCATION: (35)..(35)
<223> OTHER INFORMATION: n is a, c, g, or t
<220> FEATURE:
<221> NAME/KEY: modified_base
<222> LOCATION: (38)..(38)
<223> OTHER INFORMATION: n is a, c, g, or t
<220> FEATURE:
<221> NAME/KEY: modified_base
<222> LOCATION: (51)..(51)
<223> OTHER INFORMATION: n is a, c, g, or t
<220> FEATURE:
<221> NAME/KEY: modified_base
<222> LOCATION: (64)..(64)
<223> OTHER INFORMATION: n is a, c, g, or t
<220> FEATURE:
<221> NAME/KEY: modified_base
<222> LOCATION: (69)..(69)
<223> OTHER INFORMATION: n is a, c, g, or t
<220> FEATURE:
<221> NAME/KEY: modified_base
<222> LOCATION: (75)..(75)
<223> OTHER INFORMATION: n is a, c, g, or t
<220> FEATURE:
<221> NAME/KEY: modified_base
<222> LOCATION: (78)..(78)
<223> OTHER INFORMATION: n is a, c, g, or t
<220> FEATURE:
<221> NAME/KEY: modified_base
<222> LOCATION: (82)..(82)
<223> OTHER INFORMATION: n is a, c, g, or t
<220> FEATURE:
<221> NAME/KEY: modified_base
<222> LOCATION: (91)..(91)
<223> OTHER INFORMATION: n is a, c, g, or t
<220> FEATURE:
<221> NAME/KEY: modified_base
<222> LOCATION: (124)..(124)
<223> OTHER INFORMATION: n is a, c, g, or t
<220> FEATURE:
<221> NAME/KEY: modified_base
<222> LOCATION: (126)..(126)
<223> OTHER INFORMATION: n is a, c, g, or t
<220> FEATURE:
<221> NAME/KEY: modified_base
<222> LOCATION: (131)..(131)
<223> OTHER INFORMATION: n is a, c, g, or t
<220> FEATURE:
<221> NAME/KEY: modified_base
<222> LOCATION: (140)..(140)
<223> OTHER INFORMATION: n is a, c, g, or t
<220> FEATURE:
<221> NAME/KEY: modified_base
<222> LOCATION: (167)..(167)
<223> OTHER INFORMATION: n is a, c, g, or t
<220> FEATURE:
<221> NAME/KEY: modified_base
<222> LOCATION: (220)..(220)
<223> OTHER INFORMATION: n is a, c, g, or t
<220> FEATURE:
<221> NAME/KEY: modified_base
<222> LOCATION: (236)..(236)
<223> OTHER INFORMATION: n is a, c, g, or t
<220> FEATURE:
<221> NAME/KEY: modified_base
<222> LOCATION: (269)..(269)
<223> OTHER INFORMATION: n is a, c, g, or t
<220> FEATURE:
<221> NAME/KEY: modified_base
<222> LOCATION: (276)..(276)
<223> OTHER INFORMATION: n is a, c, g, or t
<220> FEATURE:
<221> NAME/KEY: modified_base
<222> LOCATION: (301)..(301)
<223> OTHER INFORMATION: n is a, c, g, or t
<220> FEATURE:
<221> NAME/KEY: modified_base
<222> LOCATION: (312)..(312)
<223> OTHER INFORMATION: n is a, c, g, or t
<220> FEATURE:
<221> NAME/KEY: modified_base
<222> LOCATION: (346)..(346)
<223> OTHER INFORMATION: n is a, c, g, or t
<220> FEATURE:
<221> NAME/KEY: modified_base
<222> LOCATION: (349)..(349)
<223> OTHER INFORMATION: n is a, c, g, or t
<220> FEATURE:
<221> NAME/KEY: modified_base
<222> LOCATION: (355)..(355)
<223> OTHER INFORMATION: n is a, c, g, or t
<220> FEATURE:
<221> NAME/KEY: modified_base
<222> LOCATION: (403)..(403)
<223> OTHER INFORMATION: n is a, c, g, or t
<220> FEATURE:
<221> NAME/KEY: modified_base
<222> LOCATION: (445)..(445)
<223> OTHER INFORMATION: n is a, c, g, or t
<220> FEATURE:
<221> NAME/KEY: modified_base
<222> LOCATION: (474)..(474)
<223> OTHER INFORMATION: n is a, c, g, or t
<220> FEATURE:
<221> NAME/KEY: modified_base
<222> LOCATION: (501)..(501)
<223> OTHER INFORMATION: n is a, c, g, or t
<220> FEATURE:
<221> NAME/KEY: modified_base
<222> LOCATION: (503)..(503)
<223> OTHER INFORMATION: n is a, c, g, or t
<220> FEATURE:
<221> NAME/KEY: modified_base
<222> LOCATION: (511)..(512)
<223> OTHER INFORMATION: n is a, c, g, or t
<220> FEATURE:

<221> NAME/KEY: modified_base
<222> LOCATION: (544)..(544)
<223> OTHER INFORMATION: n is a, c, g, or t
<220> FEATURE:
<221> NAME/KEY: modified_base
<222> LOCATION: (558)..(558)
<223> OTHER INFORMATION: n is a, c, g, or t
<220> FEATURE:
<221> NAME/KEY: modified_base
<222> LOCATION: (570)..(570)
<223> OTHER INFORMATION: n is a, c, g, or t
<220> FEATURE:
<221> NAME/KEY: modified_base
<222> LOCATION: (609)..(609)
<223> OTHER INFORMATION: n is a, c, g, or t
<220> FEATURE:
<221> NAME/KEY: modified_base
<222> LOCATION: (634)..(634)
<223> OTHER INFORMATION: n is a, c, g, or t
<220> FEATURE:
<221> NAME/KEY: modified_base
<222> LOCATION: (644)..(644)
<223> OTHER INFORMATION: n is a, c, g, or t
<220> FEATURE:
<221> NAME/KEY: modified_base
<222> LOCATION: (647)..(647)
<223> OTHER INFORMATION: n is a, c, g, or t
<220> FEATURE:
<221> NAME/KEY: modified_base
<222> LOCATION: (654)..(654)
<223> OTHER INFORMATION: n is a, c, g, or t
<220> FEATURE:
<221> NAME/KEY: modified_base
<222> LOCATION: (656)..(656)
<223> OTHER INFORMATION: n is a, c, g, or t
<220> FEATURE:
<221> NAME/KEY: modified_base
<222> LOCATION: (665)..(665)
<223> OTHER INFORMATION: n is a, c, g, or t
<220> FEATURE:
<221> NAME/KEY: modified_base
<222> LOCATION: (672)..(672)
<223> OTHER INFORMATION: n is a, c, g, or t
<220> FEATURE:
<221> NAME/KEY: modified_base
<222> LOCATION: (688)..(688)
<223> OTHER INFORMATION: n is a, c, g, or t
<220> FEATURE:
<221> NAME/KEY: modified_base
<222> LOCATION: (710)..(710)
<223> OTHER INFORMATION: n is a, c, g, or t
<220> FEATURE:
<221> NAME/KEY: modified_base
<222> LOCATION: (715)..(715)
<223> OTHER INFORMATION: n is a, c, g, or t
<220> FEATURE:
<221> NAME/KEY: modified_base
<222> LOCATION: (725)..(725)
<223> OTHER INFORMATION: n is a, c, g, or t
<220> FEATURE:
<221> NAME/KEY: modified_base
<222> LOCATION: (735)..(735)
<223> OTHER INFORMATION: n is a, c, g, or t
<220> FEATURE:
<221> NAME/KEY: modified_base
<222> LOCATION: (740)..(740)
<223> OTHER INFORMATION: n is a, c, g, or t
<220> FEATURE:
<221> NAME/KEY: modified_base
<222> LOCATION: (750)..(750)
<223> OTHER INFORMATION: n is a, c, g, or t
<220> FEATURE:
<221> NAME/KEY: modified_base
<222> LOCATION: (760)..(760)
<223> OTHER INFORMATION: n is a, c, g, or t
<220> FEATURE:
<221> NAME/KEY: modified_base
<222> LOCATION: (768)..(768)
<223> OTHER INFORMATION: n is a, c, g, or t -continued

```
<220> FEATURE:
<221> NAME/KEY: modified_base
<222> LOCATION: (774)..(774)
<223> OTHER INFORMATION: n is a, c, g, or t
<220> FEATURE:
<221> NAME/KEY: modified_base
<222> LOCATION: (776)..(776)
<223> OTHER INFORMATION: n is a, c, g, or t
<220> FEATURE:
<221> NAME/KEY: modified_base
<222> LOCATION: (779)..(780)
<223> OTHER INFORMATION: n is a, c, g, or t
<220> FEATURE:
<221> NAME/KEY: modified_base
<222> LOCATION: (784)..(784)
<223> OTHER INFORMATION: n is a, c, g, or t
<220> FEATURE:
<221> NAME/KEY: modified_base
<222> LOCATION: (787)..(787)
<223> OTHER INFORMATION: n is a, c, g, or t
<220> FEATURE:
<221> NAME/KEY: modified_base
<222> LOCATION: (799)..(799)
<223> OTHER INFORMATION: n is a, c, g, or t
<220> FEATURE:
<221> NAME/KEY: modified_base
<222> LOCATION: (801)..(801)
<223> OTHER INFORMATION: n is a, c, g, or t
<220> FEATURE:
<221> NAME/KEY: modified_base
<222> LOCATION: (804)..(804)
<223> OTHER INFORMATION: n is a, c, g, or t
<220> FEATURE:
<221> NAME/KEY: modified_base
<222> LOCATION: (810)..(810)
<223> OTHER INFORMATION: n is a, c, g, or t
<220> FEATURE:
<221> NAME/KEY: modified_base
<222> LOCATION: (831)..(831)
<223> OTHER INFORMATION: n is a, c, g, or t
<220> FEATURE:
<221> NAME/KEY: modified_base
<222> LOCATION: (833)..(833)
<223> OTHER INFORMATION: n is a, c, g, or t
<220> FEATURE:
<221> NAME/KEY: modified_base
<222> LOCATION: (836)..(837)
<223> OTHER INFORMATION: n is a, c, g, or t
<220> FEATURE:
<221> NAME/KEY: modified_base
<222> LOCATION: (839)..(839)
<223> OTHER INFORMATION: n is a, c, g, or t
<220> FEATURE:
<221> NAME/KEY: modified_base
<222> LOCATION: (848)..(848)
<223> OTHER INFORMATION: n is a, c, g, or t
<220> FEATURE:
<221> NAME/KEY: modified_base
<222> LOCATION: (854)..(854)
<223> OTHER INFORMATION: n is a, c, g, or t

<400> SEQUENCE: 7

gnngnnntnn nnnggccngg atcctcntnc acggngcncc tactggttgg ncgaggacta     60

ctancggane gcggncgngt gnggcgacga ngctgacggc ggccagcagg aggatgattc    120

tggngnagga naggatgatn cggaggttca gcaagaatgc ctgcatnaat tttccacccg    180

ggattatatc atggaaccct ccatcttcaa cactctgaan aggtattttc aggcangagg    240

gtctccagag aatgttatcc agctcttanc tgaaanctac accgctgtgg cccaaactgt    300

naacctgctg gncgagtggc tcattcagac aggtgttgag ccagtncang ttcangagac    360

tgtttgatgc tggacttcac cgttaagctt atttctgacg canggtacca gggggagatc    420

accagtgtgt ccacagcatg ccacncagct agaagtgttc tctagagtgc tccngacctc    480
```

-continued

```
tctaactaca attttacatg nangagaaca nnaccttgaa aaaaatctcc ctgaatttgc    540

caanatggtg tgccaccngg agcacacatn ctgtttgccc aagccatgat gtccgttctg    600

ggccaagang acaaggggc tccgctgttc gcangattgc caanaanttg aacncnttgc     660

ccacnaaaaa gnccatgccc caatcaantt aaaataaccc ttgggaaaan tgccncctaa    720

cccanggcct gcaangttcn cggggcaatn ctgtcaaaan gacccctnaa cccngntgnn    780

aacnccntcc cgtttaaana nttntaaaan catggccccc cccccggttt nanttnncng    840

gttccaancc ttcn                                                      854
```

<210> SEQ ID NO 8
<211> LENGTH: 870
<212> TYPE: DNA
<213> ORGANISM: Homo sapiens
<220> FEATURE:
<221> NAME/KEY: modified_base
<222> LOCATION: (3)..(3)
<223> OTHER INFORMATION: n is a, c, g, or t
<220> FEATURE:
<221> NAME/KEY: modified_base
<222> LOCATION: (6)..(12)
<223> OTHER INFORMATION: n is a, c, g, or t
<220> FEATURE:
<221> NAME/KEY: modified_base
<222> LOCATION: (15)..(15)
<223> OTHER INFORMATION: n is a, c, g, or t
<220> FEATURE:
<221> NAME/KEY: modified_base
<222> LOCATION: (28)..(28)
<223> OTHER INFORMATION: n is a, c, g, or t
<220> FEATURE:
<221> NAME/KEY: modified_base
<222> LOCATION: (50)..(50)
<223> OTHER INFORMATION: n is a, c, g, or t
<220> FEATURE:
<221> NAME/KEY: modified_base
<222> LOCATION: (72)..(72)
<223> OTHER INFORMATION: n is a, c, g, or t
<220> FEATURE:
<221> NAME/KEY: modified_base
<222> LOCATION: (98)..(98)
<223> OTHER INFORMATION: n is a, c, g, or t
<220> FEATURE:
<221> NAME/KEY: modified_base
<222> LOCATION: (139)..(139)
<223> OTHER INFORMATION: n is a, c, g, or t
<220> FEATURE:
<221> NAME/KEY: modified_base
<222> LOCATION: (166)..(166)
<223> OTHER INFORMATION: n is a, c, g, or t
<220> FEATURE:
<221> NAME/KEY: modified_base
<222> LOCATION: (170)..(170)
<223> OTHER INFORMATION: n is a, c, g, or t
<220> FEATURE:
<221> NAME/KEY: modified_base
<222> LOCATION: (200)..(200)
<223> OTHER INFORMATION: n is a, c, g, or t
<220> FEATURE:
<221> NAME/KEY: modified_base
<222> LOCATION: (206)..(206)
<223> OTHER INFORMATION: n is a, c, g, or t
<220> FEATURE:
<221> NAME/KEY: modified_base
<222> LOCATION: (218)..(218)
<223> OTHER INFORMATION: n is a, c, g, or t
<220> FEATURE:
<221> NAME/KEY: modified_base
<222> LOCATION: (224)..(224)
<223> OTHER INFORMATION: n is a, c, g, or t
<220> FEATURE:
<221> NAME/KEY: modified_base
<222> LOCATION: (246)..(246)
<223> OTHER INFORMATION: n is a, c, g, or t -continued
<220> FEATURE:
<221> NAME/KEY: modified_base
<222> LOCATION: (261)..(261)
<223> OTHER INFORMATION: n is a, c, g, or t
<220> FEATURE:
<221> NAME/KEY: modified_base
<222> LOCATION: (353)..(353)
<223> OTHER INFORMATION: n is a, c, g, or t
<220> FEATURE:
<221> NAME/KEY: modified_base
<222> LOCATION: (390)..(390)
<223> OTHER INFORMATION: n is a, c, g, or t
<220> FEATURE:
<221> NAME/KEY: modified_base
<222> LOCATION: (406)..(406)
<223> OTHER INFORMATION: n is a, c, g, or t
<220> FEATURE:
<221> NAME/KEY: modified_base
<222> LOCATION: (454)..(454)
<223> OTHER INFORMATION: n is a, c, g, or t
<220> FEATURE:
<221> NAME/KEY: modified_base
<222> LOCATION: (479)..(479)
<223> OTHER INFORMATION: n is a, c, g, or t
<220> FEATURE:
<221> NAME/KEY: modified_base
<222> LOCATION: (497)..(497)
<223> OTHER INFORMATION: n is a, c, g, or t
<220> FEATURE:
<221> NAME/KEY: modified_base
<222> LOCATION: (538)..(538)
<223> OTHER INFORMATION: n is a, c, g, or t
<220> FEATURE:
<221> NAME/KEY: modified_base
<222> LOCATION: (572)..(572)
<223> OTHER INFORMATION: n is a, c, g, or t
<220> FEATURE:
<221> NAME/KEY: modified_base
<222> LOCATION: (593)..(593)
<223> OTHER INFORMATION: n is a, c, g, or t
<220> FEATURE:
<221> NAME/KEY: modified_base
<222> LOCATION: (603)..(603)
<223> OTHER INFORMATION: n is a, c, g, or t
<220> FEATURE:
<221> NAME/KEY: modified_base
<222> LOCATION: (616)..(616)
<223> OTHER INFORMATION: n is a, c, g, or t
<220> FEATURE:
<221> NAME/KEY: modified_base
<222> LOCATION: (618)..(618)
<223> OTHER INFORMATION: n is a, c, g, or t
<220> FEATURE:
<221> NAME/KEY: modified_base
<222> LOCATION: (644)..(644)
<223> OTHER INFORMATION: n is a, c, g, or t
<220> FEATURE:
<221> NAME/KEY: modified_base
<222> LOCATION: (647)..(647)
<223> OTHER INFORMATION: n is a, c, g, or t
<220> FEATURE:
<221> NAME/KEY: modified_base
<222> LOCATION: (649)..(649)
<223> OTHER INFORMATION: n is a, c, g, or t
<220> FEATURE:
<221> NAME/KEY: modified_base
<222> LOCATION: (655)..(655)
<223> OTHER INFORMATION: n is a, c, g, or t
<220> FEATURE:
<221> NAME/KEY: modified_base
<222> LOCATION: (657)..(657)
<223> OTHER INFORMATION: n is a, c, g, or t
<220> FEATURE:
<221> NAME/KEY: modified_base
<222> LOCATION: (663)..(663)
<223> OTHER INFORMATION: n is a, c, g, or t
<220> FEATURE:
<221> NAME/KEY: modified_base
<222> LOCATION: (666)..(666)

<223> OTHER INFORMATION: n is a, c, g, or t
<220> FEATURE:
<221> NAME/KEY: modified_base
<222> LOCATION: (677)..(677)
<223> OTHER INFORMATION: n is a, c, g, or t
<220> FEATURE:
<221> NAME/KEY: modified_base
<222> LOCATION: (694)..(694)
<223> OTHER INFORMATION: n is a, c, g, or t
<220> FEATURE:
<221> NAME/KEY: modified_base
<222> LOCATION: (697)..(697)
<223> OTHER INFORMATION: n is a, c, g, or t
<220> FEATURE:
<221> NAME/KEY: modified_base
<222> LOCATION: (701)..(701)
<223> OTHER INFORMATION: n is a, c, g, or t
<220> FEATURE:
<221> NAME/KEY: modified_base
<222> LOCATION: (706)..(706)
<223> OTHER INFORMATION: n is a, c, g, or t
<220> FEATURE:
<221> NAME/KEY: modified_base
<222> LOCATION: (711)..(711)
<223> OTHER INFORMATION: n is a, c, g, or t
<220> FEATURE:
<221> NAME/KEY: modified_base
<222> LOCATION: (714)..(714)
<223> OTHER INFORMATION: n is a, c, g, or t
<220> FEATURE:
<221> NAME/KEY: modified_base
<222> LOCATION: (718)..(718)
<223> OTHER INFORMATION: n is a, c, g, or t
<220> FEATURE:
<221> NAME/KEY: modified_base
<222> LOCATION: (721)..(721)
<223> OTHER INFORMATION: n is a, c, g, or t
<220> FEATURE:
<221> NAME/KEY: modified_base
<222> LOCATION: (726)..(726)
<223> OTHER INFORMATION: n is a, c, g, or t
<220> FEATURE:
<221> NAME/KEY: modified_base
<222> LOCATION: (735)..(735)
<223> OTHER INFORMATION: n is a, c, g, or t
<220> FEATURE:
<221> NAME/KEY: modified_base
<222> LOCATION: (738)..(739)
<223> OTHER INFORMATION: n is a, c, g, or t
<220> FEATURE:
<221> NAME/KEY: modified_base
<222> LOCATION: (746)..(746)
<223> OTHER INFORMATION: n is a, c, g, or t
<220> FEATURE:
<221> NAME/KEY: modified_base
<222> LOCATION: (752)..(752)
<223> OTHER INFORMATION: n is a, c, g, or t
<220> FEATURE:
<221> NAME/KEY: modified_base
<222> LOCATION: (762)..(762)
<223> OTHER INFORMATION: n is a, c, g, or t
<220> FEATURE:
<221> NAME/KEY: modified_base
<222> LOCATION: (765)..(766)
<223> OTHER INFORMATION: n is a, c, g, or t
<220> FEATURE:
<221> NAME/KEY: modified_base
<222> LOCATION: (773)..(773)
<223> OTHER INFORMATION: n is a, c, g, or t
<220> FEATURE:
<221> NAME/KEY: modified_base
<222> LOCATION: (779)..(780)
<223> OTHER INFORMATION: n is a, c, g, or t
<220> FEATURE:
<221> NAME/KEY: modified_base
<222> LOCATION: (785)..(786)
<223> OTHER INFORMATION: n is a, c, g, or t
<220> FEATURE:
<221> NAME/KEY: modified_base
<222> LOCATION: (789)..(789)
<223> OTHER INFORMATION: n is a, c, g, or t
<220> FEATURE:
<221> NAME/KEY: modified_base
<222> LOCATION: (793)..(796)
<223> OTHER INFORMATION: n is a, c, g, or t
<220> FEATURE:
<221> NAME/KEY: modified_base
<222> LOCATION: (802)..(802)
<223> OTHER INFORMATION: n is a, c, g, or t
<220> FEATURE:
<221> NAME/KEY: modified_base
<222> LOCATION: (808)..(809)
<223> OTHER INFORMATION: n is a, c, g, or t
<220> FEATURE:
<221> NAME/KEY: modified_base
<222> LOCATION: (812)..(812)
<223> OTHER INFORMATION: n is a, c, g, or t
<220> FEATURE:
<221> NAME/KEY: modified_base
<222> LOCATION: (818)..(818)
<223> OTHER INFORMATION: n is a, c, g, or t
<220> FEATURE:
<221> NAME/KEY: modified_base
<222> LOCATION: (827)..(827)
<223> OTHER INFORMATION: n is a, c, g, or t
<220> FEATURE:
<221> NAME/KEY: modified_base
<222> LOCATION: (834)..(836)
<223> OTHER INFORMATION: n is a, c, g, or t
<220> FEATURE:
<221> NAME/KEY: modified_base
<222> LOCATION: (838)..(838)
<223> OTHER INFORMATION: n is a, c, g, or t
<220> FEATURE:
<221> NAME/KEY: modified_base
<222> LOCATION: (840)..(841)
<223> OTHER INFORMATION: n is a, c, g, or t
<220> FEATURE:
<221> NAME/KEY: modified_base
<222> LOCATION: (855)..(855)
<223> OTHER INFORMATION: n is a, c, g, or t
<220> FEATURE:
<221> NAME/KEY: modified_base
<222> LOCATION: (857)..(857)
<223> OTHER INFORMATION: n is a, c, g, or t
<220> FEATURE:
<221> NAME/KEY: modified_base
<222> LOCATION: (861)..(863)
<223> OTHER INFORMATION: n is a, c, g, or t
<220> FEATURE:
<221> NAME/KEY: modified_base
<222> LOCATION: (866)..(866)
<223> OTHER INFORMATION: n is a, c, g, or t
<220> FEATURE:
<221> NAME/KEY: modified_base
<222> LOCATION: (869)..(870)
<223> OTHER INFORMATION: n is a, c, g, or t

<400> SEQUENCE: 8
ggntgnnnnn nntgntggct tttttttngc tttggctttt taaaaatttn cttattactt 60
gttcttagca anttaagaca attacaataa aacatcanac taactgggtt cttgtgatga 120
aaactgaggt cagcttggna aggagttccc cgagtggagt tcccancggn ccgcggctga 180
cggccatgat ctgtcctgan gggtcntggg agcccagngc ctgncttgag ggaaatgaac 240
actganaaca ggatttggga ncagtattgg attgacagca gataaaggac tgtttgtaag 300
ggcagtttct cactgaagct gctaccattt tcctttgtaa agaagtcatc canctcctcc 360
cagcggtgcc cattttcaag acgctgccan aacctcttaa aacagnttct tgaaagggtt 420
tttccacaac gggttctgga atgttctgct tcanctctgg agggatgctc caaattagnt 480
caccaagatg aagttanatt tgcaatgagc tataaactcc gtcacaaggt catgctcncc 540

-continued

```
ttccgttttg atggtacctg cgaagctgtc antcccaaga tggggaagga aanttgcacg    600

aantcagagg gataangngg agcaatggac ttcaacaact caantgncna aatancnaat    660

gantgnaatg tcagtgncca actttccaaa aaanttncgg ngttantggc nacnggantt    720

naaaancccc caatnaanna aggggnacca ancctgtcca anaanngtct tcnttaaann    780

caagnngtnc aannnnttca antggggnng gncaattntc aaaaagntta aaannnantn    840

naaggccttg ggggncnaaa nnntgntgnn                                     870


<210> SEQ ID NO 9
<211> LENGTH: 889
<212> TYPE: DNA
<213> ORGANISM: Homo sapiens
<220> FEATURE:
<221> NAME/KEY: modified_base
<222> LOCATION: (2)..(2)
<223> OTHER INFORMATION: n is a, c, g, or t
<220> FEATURE:
<221> NAME/KEY: modified_base
<222> LOCATION: (4)..(11)
<223> OTHER INFORMATION: n is a, c, g, or t
<220> FEATURE:
<221> NAME/KEY: modified_base
<222> LOCATION: (15)..(16)
<223> OTHER INFORMATION: n is a, c, g, or t
<220> FEATURE:
<221> NAME/KEY: modified_base
<222> LOCATION: (629)..(629)
<223> OTHER INFORMATION: n is a, c, g, or t
<220> FEATURE:
<221> NAME/KEY: modified_base
<222> LOCATION: (735)..(735)
<223> OTHER INFORMATION: n is a, c, g, or t
<220> FEATURE:
<221> NAME/KEY: modified_base
<222> LOCATION: (741)..(741)
<223> OTHER INFORMATION: n is a, c, g, or t
<220> FEATURE:
<221> NAME/KEY: modified_base
<222> LOCATION: (781)..(781)
<223> OTHER INFORMATION: n is a, c, g, or t
<220> FEATURE:
<221> NAME/KEY: modified_base
<222> LOCATION: (797)..(797)
<223> OTHER INFORMATION: n is a, c, g, or t
<220> FEATURE:
<221> NAME/KEY: modified_base
<222> LOCATION: (826)..(826)
<223> OTHER INFORMATION: n is a, c, g, or t
<220> FEATURE:
<221> NAME/KEY: modified_base
<222> LOCATION: (839)..(839)
<223> OTHER INFORMATION: n is a, c, g, or t
<220> FEATURE:
<221> NAME/KEY: modified_base
<222> LOCATION: (851)..(851)
<223> OTHER INFORMATION: n is a, c, g, or t
<220> FEATURE:
<221> NAME/KEY: modified_base
<222> LOCATION: (862)..(862)
<223> OTHER INFORMATION: n is a, c, g, or t
<220> FEATURE:
<221> NAME/KEY: modified_base
<222> LOCATION: (868)..(868)
<223> OTHER INFORMATION: n is a, c, g, or t
<220> FEATURE:
<221> NAME/KEY: modified_base
<222> LOCATION: (885)..(885)
<223> OTHER INFORMATION: n is a, c, g, or t

<400> SEQUENCE: 9

gngnnnnnnn nggcnnggat ctcgagcacg tggggcctac tgatctcggt tgctaccagt     60

ggtgaatcct atgtccctga tttctttaga ctgggagcag ctgcaacagg agtttaactt    120
```

```
tgtttcagat caagaattaa atagatccaa acgatttagg cttcttcatc ttagaagcca    180

agaggtgcca agaattccga aatataagca agttccagtc tatgaccgag aaattatgga    240

aaaggtattc caggactatg agaaacggtt acgaagacag aaatgtaata gaaaccaagg    300

aacacacaga cacccatagg gccatagtag ccaagtacct ccagcaggtt agagaatcag    360

tgataaatcg tttcttaatt gcaaaacaat attttcttct tgctgatatg atagtagaag    420

aagaagttcc caatatcagc attttgggcc taagcctttt cgagctggca agaacaaaag    480

cgaccactgc ggccaaggag aaaaggtcgg aagaaggtga cagcccaaaa cctgtctgat    540

ggagacataa agctgctggt gaacattgtg cgagcttacg acattccagt gaggaagccg    600

gcagtgagca aattccagca gccgtcgang tcctcaagga tgttcagtga aaagcatgct    660

gcttccccaa gcacgtacag cccaacccac aatgctgact acccctcggg caagttttag    720

tacgtccctt tgtanaagtc nctttcaacg aacaatttgc catacgacta cggctgaagg    780

nccaaaccct aactggnatg aagaactaga acttccattt agggcnctaa tggggattnt    840

agcacaacca ntctgaatca antgaaanat gttgggtcat tacantttg               889
```

```
<210> SEQ ID NO 10
<211> LENGTH: 891
<212> TYPE: DNA
<213> ORGANISM: Homo sapiens
<220> FEATURE:
<221> NAME/KEY: modified_base
<222> LOCATION: (2)..(2)
<223> OTHER INFORMATION: n is a, c, g, or t
<220> FEATURE:
<221> NAME/KEY: modified_base
<222> LOCATION: (4)..(4)
<223> OTHER INFORMATION: n is a, c, g, or t
<220> FEATURE:
<221> NAME/KEY: modified_base
<222> LOCATION: (7)..(11)
<223> OTHER INFORMATION: n is a, c, g, or t
<220> FEATURE:
<221> NAME/KEY: modified_base
<222> LOCATION: (18)..(18)
<223> OTHER INFORMATION: n is a, c, g, or t
<220> FEATURE:
<221> NAME/KEY: modified_base
<222> LOCATION: (27)..(27)
<223> OTHER INFORMATION: n is a, c, g, or t
<220> FEATURE:
<221> NAME/KEY: modified_base
<222> LOCATION: (33)..(33)
<223> OTHER INFORMATION: n is a, c, g, or t
<220> FEATURE:
<221> NAME/KEY: modified_base
<222> LOCATION: (52)..(52)
<223> OTHER INFORMATION: n is a, c, g, or t
<220> FEATURE:
<221> NAME/KEY: modified_base
<222> LOCATION: (456)..(456)
<223> OTHER INFORMATION: n is a, c, g, or t
<220> FEATURE:
<221> NAME/KEY: modified_base
<222> LOCATION: (548)..(548)
<223> OTHER INFORMATION: n is a, c, g, or t
<220> FEATURE:
<221> NAME/KEY: modified_base
<222> LOCATION: (589)..(589)
<223> OTHER INFORMATION: n is a, c, g, or t
<220> FEATURE:
<221> NAME/KEY: modified_base
<222> LOCATION: (602)..(602)
<223> OTHER INFORMATION: n is a, c, g, or t
<220> FEATURE:
<221> NAME/KEY: modified_base
<222> LOCATION: (605)..(605)
```

<223> OTHER INFORMATION: n is a, c, g, or t
<220> FEATURE:
<221> NAME/KEY: modified_base
<222> LOCATION: (618)..(618)
<223> OTHER INFORMATION: n is a, c, g, or t
<220> FEATURE:
<221> NAME/KEY: modified_base
<222> LOCATION: (620)..(620)
<223> OTHER INFORMATION: n is a, c, g, or t
<220> FEATURE:
<221> NAME/KEY: modified_base
<222> LOCATION: (622)..(622)
<223> OTHER INFORMATION: n is a, c, g, or t
<220> FEATURE:
<221> NAME/KEY: modified_base
<222> LOCATION: (644)..(644)
<223> OTHER INFORMATION: n is a, c, g, or t
<220> FEATURE:
<221> NAME/KEY: modified_base
<222> LOCATION: (679)..(679)
<223> OTHER INFORMATION: n is a, c, g, or t
<220> FEATURE:
<221> NAME/KEY: modified_base
<222> LOCATION: (684)..(684)
<223> OTHER INFORMATION: n is a, c, g, or t
<220> FEATURE:
<221> NAME/KEY: modified_base
<222> LOCATION: (690)..(690)
<223> OTHER INFORMATION: n is a, c, g, or t
<220> FEATURE:
<221> NAME/KEY: modified_base
<222> LOCATION: (719)..(719)
<223> OTHER INFORMATION: n is a, c, g, or t
<220> FEATURE:
<221> NAME/KEY: modified_base
<222> LOCATION: (738)..(738)
<223> OTHER INFORMATION: n is a, c, g, or t
<220> FEATURE:
<221> NAME/KEY: modified_base
<222> LOCATION: (771)..(771)
<223> OTHER INFORMATION: n is a, c, g, or t
<220> FEATURE:
<221> NAME/KEY: modified_base
<222> LOCATION: (797)..(797)
<223> OTHER INFORMATION: n is a, c, g, or t
<220> FEATURE:
<221> NAME/KEY: modified_base
<222> LOCATION: (824)..(824)
<223> OTHER INFORMATION: n is a, c, g, or t
<220> FEATURE:
<221> NAME/KEY: modified_base
<222> LOCATION: (834)..(834)
<223> OTHER INFORMATION: n is a, c, g, or t
<220> FEATURE:
<221> NAME/KEY: modified_base
<222> LOCATION: (844)..(844)
<223> OTHER INFORMATION: n is a, c, g, or t
<220> FEATURE:
<221> NAME/KEY: modified_base
<222> LOCATION: (878)..(878)
<223> OTHER INFORMATION: n is a, c, g, or t
<220> FEATURE:
<221> NAME/KEY: modified_base
<222> LOCATION: (885)..(885)
<223> OTHER INFORMATION: n is a, c, g, or t
<220> FEATURE:
<221> NAME/KEY: modified_base
<222> LOCATION: (888)..(888)
<223> OTHER INFORMATION: n is a, c, g, or t
<220> FEATURE:
<221> NAME/KEY: modified_base
<222> LOCATION: (890)..(890)
<223> OTHER INFORMATION: n is a, c, g, or t

<400> SEQUENCE: 10
gngntgnnnn ntgtgggntt ttttttnggc ttncagtttg aaaacagtgg cntaatttta 60
ttatttgcca ataatatgtt cttctgatgt gatgcatata atttaaaatt ttctcatatc 120

```
ctaagtgtag tttttacatg atagagaaag tacagtgaaa aaaattacct gttgcgtata    180

agagaggcaa catagatcca aacagacaaa acatttttgg ggtatgggtg tatgtataca    240

gctaaagcaa attcaacatt aggaacatca atattatgta ctccagtact atacacagcg    300

tcaattaaag gcttcacttc agaataaggc atgtgaagag gaaatccaag agaacctgta    360

gtctcccagc tgttttagca gttctgctct gtggtcatct tctacatctt ctccttgact    420

tttttctaac aagaggcaag aagtgacgca gagtanaggt acaataccta ttccaccgag    480

tcagatggcg tggctccagt ccatgatttt ttcctttagt aatttttcaa tcctgtcctg    540

tagctcanct gcagctgctt gtctgaacgc tggtaaatta actcctcang ctgaacactg    600

gnaanggcaa gatatggnan gnttcctgaa aagaaagatt ccanaacttg ggcctggtga    660

catcaaaatt tatccttang gggngatcan atcgtggata ttaaaccaaa tattgtcang    720

acctattaac agccacantt ttcaagggac aaaatgttca aattgtccaa naaaaatgtc    780

cactgcaggg attccanatt aaataacgac cttgctccaa gttngcaaat aggnattggg    840

cccncaggga aaacattgcc cacaaaaagc aagcctcnta cccanganan a             891
```

```
<210> SEQ ID NO 11
<211> LENGTH: 855
<212> TYPE: DNA
<213> ORGANISM: Homo sapiens
<220> FEATURE:
<221> NAME/KEY: modified_base
<222> LOCATION: (2)..(4)
<223> OTHER INFORMATION: n is a, c, g, or t
<220> FEATURE:
<221> NAME/KEY: modified_base
<222> LOCATION: (9)..(11)
<223> OTHER INFORMATION: n is a, c, g, or t
<220> FEATURE:
<221> NAME/KEY: modified_base
<222> LOCATION: (18)..(18)
<223> OTHER INFORMATION: n is a, c, g, or t
<220> FEATURE:
<221> NAME/KEY: modified_base
<222> LOCATION: (20)..(20)
<223> OTHER INFORMATION: n is a, c, g, or t
<220> FEATURE:
<221> NAME/KEY: modified_base
<222> LOCATION: (29)..(29)
<223> OTHER INFORMATION: n is a, c, g, or t
<220> FEATURE:
<221> NAME/KEY: modified_base
<222> LOCATION: (36)..(36)
<223> OTHER INFORMATION: n is a, c, g, or t
<220> FEATURE:
<221> NAME/KEY: modified_base
<222> LOCATION: (577)..(577)
<223> OTHER INFORMATION: n is a, c, g, or t
<220> FEATURE:
<221> NAME/KEY: modified_base
<222> LOCATION: (620)..(620)
<223> OTHER INFORMATION: n is a, c, g, or t
<220> FEATURE:
<221> NAME/KEY: modified_base
<222> LOCATION: (680)..(680)
<223> OTHER INFORMATION: n is a, c, g, or t
<220> FEATURE:
<221> NAME/KEY: modified_base
<222> LOCATION: (706)..(706)
<223> OTHER INFORMATION: n is a, c, g, or t
<220> FEATURE:
<221> NAME/KEY: modified_base
<222> LOCATION: (723)..(723)
<223> OTHER INFORMATION: n is a, c, g, or t
<220> FEATURE:
<221> NAME/KEY: modified_base
<222> LOCATION: (725)..(725)
```

-continued

<223> OTHER INFORMATION: n is a, c, g, or t
<220> FEATURE:
<221> NAME/KEY: modified_base
<222> LOCATION: (727)..(727)
<223> OTHER INFORMATION: n is a, c, g, or t
<220> FEATURE:
<221> NAME/KEY: modified_base
<222> LOCATION: (732)..(732)
<223> OTHER INFORMATION: n is a, c, g, or t
<220> FEATURE:
<221> NAME/KEY: modified_base
<222> LOCATION: (736)..(736)
<223> OTHER INFORMATION: n is a, c, g, or t
<220> FEATURE:
<221> NAME/KEY: modified_base
<222> LOCATION: (773)..(773)
<223> OTHER INFORMATION: n is a, c, g, or t
<220> FEATURE:
<221> NAME/KEY: modified_base
<222> LOCATION: (798)..(799)
<223> OTHER INFORMATION: n is a, c, g, or t
<220> FEATURE:
<221> NAME/KEY: modified_base
<222> LOCATION: (803)..(803)
<223> OTHER INFORMATION: n is a, c, g, or t
<220> FEATURE:
<221> NAME/KEY: modified_base
<222> LOCATION: (829)..(829)
<223> OTHER INFORMATION: n is a, c, g, or t
<220> FEATURE:
<221> NAME/KEY: modified_base
<222> LOCATION: (834)..(834)
<223> OTHER INFORMATION: n is a, c, g, or t
<220> FEATURE:
<221> NAME/KEY: modified_base
<222> LOCATION: (846)..(846)
<223> OTHER INFORMATION: n is a, c, g, or t

<400> SEQUENCE: 11
gnnnttttnn ngggcccngn atcccgaana ctgttngcct actggaaaga tggtgggagg 60
aggagaacat ccgcgtggtt cgttgtggcg gcagcgagtt gaactttagg agagctgtgt 120
tctctgcaga ttctaagtat atcttctgtg tctctggaga ctttgttaaa gtttacagca 180
cagttacaga agagtgtgta cacatactgc atggacacag aaatctggtg actggaatcc 240
agcttaaccc caacaaccat ctacagctgt attcttgttc ccttgatggc acaattaaac 300
tgtgggacta tatagatggc atcttaataa agactttcat agttggatgt aaacttcatg 360
ccctctttac tcttgcccaa gctgaggatt ctgtctttgt tatagtgaat aaagaaaaac 420
caagatatat ttcagctggt ttcagtgaaa ctgccaaaat cctcaagcca ggaagtagaa 480
gccaaggagc tgtcctttgt tttggattac ataaaccagt cacccaagtg cattgccttt 540
ggaaacgaag gagtatatgt tgctgcaata cgggaanttt acttgtccgt ttaatttttc 600
aaaaagaaaa caacatcaan ggttacttta acatcatcaa agaaataaga aacatgctaa 660
aaacaatttt acatgtgtan caagtcaacc aacggaagac tgaacncaac ctggtcacat 720
ggntngnaaa antccncctt tgggggaatt tttatgatga taagaaatat acnttcacat 780
ggttacaatt ggaccaanna aanggttaag gattttggtt tttcaattnc aagnaacaat 840
ctgccnaatg ggggc 855

<210> SEQ ID NO 12
<211> LENGTH: 860
<212> TYPE: DNA
<213> ORGANISM: Homo sapiens
<220> FEATURE:
<221> NAME/KEY: modified_base
<222> LOCATION: (4)..(11)
<223> OTHER INFORMATION: n is a, c, g, or t
<220> FEATURE:
<221> NAME/KEY: modified_base
<222> LOCATION: (14)..(15)
<223> OTHER INFORMATION: n is a, c, g, or t
<220> FEATURE:
<221> NAME/KEY: modified_base
<222> LOCATION: (18)..(18)
<223> OTHER INFORMATION: n is a, c, g, or t
<220> FEATURE:
<221> NAME/KEY: modified_base
<222> LOCATION: (26)..(27)
<223> OTHER INFORMATION: n is a, c, g, or t
<220> FEATURE:
<221> NAME/KEY: modified_base
<222> LOCATION: (34)..(35)
<223> OTHER INFORMATION: n is a, c, g, or t
<220> FEATURE:
<221> NAME/KEY: modified_base
<222> LOCATION: (39)..(39)
<223> OTHER INFORMATION: n is a, c, g, or t
<220> FEATURE:
<221> NAME/KEY: modified_base
<222> LOCATION: (41)..(42)
<223> OTHER INFORMATION: n is a, c, g, or t
<220> FEATURE:
<221> NAME/KEY: modified_base
<222> LOCATION: (44)..(44)
<223> OTHER INFORMATION: n is a, c, g, or t
<220> FEATURE:
<221> NAME/KEY: modified_base
<222> LOCATION: (53)..(53)
<223> OTHER INFORMATION: n is a, c, g, or t
<220> FEATURE:
<221> NAME/KEY: modified_base
<222> LOCATION: (428)..(428)
<223> OTHER INFORMATION: n is a, c, g, or t
<220> FEATURE:
<221> NAME/KEY: modified_base
<222> LOCATION: (512)..(512)
<223> OTHER INFORMATION: n is a, c, g, or t
<220> FEATURE:
<221> NAME/KEY: modified_base
<222> LOCATION: (554)..(554)
<223> OTHER INFORMATION: n is a, c, g, or t
<220> FEATURE:
<221> NAME/KEY: modified_base
<222> LOCATION: (655)..(655)
<223> OTHER INFORMATION: n is a, c, g, or t
<220> FEATURE:
<221> NAME/KEY: modified_base
<222> LOCATION: (667)..(667)
<223> OTHER INFORMATION: n is a, c, g, or t
<220> FEATURE:
<221> NAME/KEY: modified_base
<222> LOCATION: (673)..(673)
<223> OTHER INFORMATION: n is a, c, g, or t
<220> FEATURE:
<221> NAME/KEY: modified_base
<222> LOCATION: (716)..(716)
<223> OTHER INFORMATION: n is a, c, g, or t
<220> FEATURE:
<221> NAME/KEY: modified_base
<222> LOCATION: (723)..(723)
<223> OTHER INFORMATION: n is a, c, g, or t
<220> FEATURE:
<221> NAME/KEY: modified_base
<222> LOCATION: (741)..(741)
<223> OTHER INFORMATION: n is a, c, g, or t
<220> FEATURE:
<221> NAME/KEY: modified_base
<222> LOCATION: (750)..(750)
<223> OTHER INFORMATION: n is a, c, g, or t
<220> FEATURE:
<221> NAME/KEY: modified_base
<222> LOCATION: (754)..(754)
<223> OTHER INFORMATION: n is a, c, g, or t
<220> FEATURE:
<221> NAME/KEY: modified_base
<222> LOCATION: (758)..(758)

<223> OTHER INFORMATION: n is a, c, g, or t
<220> FEATURE:
<221> NAME/KEY: modified_base
<222> LOCATION: (765)..(765)
<223> OTHER INFORMATION: n is a, c, g, or t
<220> FEATURE:
<221> NAME/KEY: modified_base
<222> LOCATION: (771)..(771)
<223> OTHER INFORMATION: n is a, c, g, or t
<220> FEATURE:
<221> NAME/KEY: modified_base
<222> LOCATION: (775)..(775)
<223> OTHER INFORMATION: n is a, c, g, or t
<220> FEATURE:
<221> NAME/KEY: modified_base
<222> LOCATION: (784)..(785)
<223> OTHER INFORMATION: n is a, c, g, or t
<220> FEATURE:
<221> NAME/KEY: modified_base
<222> LOCATION: (818)..(819)
<223> OTHER INFORMATION: n is a, c, g, or t
<220> FEATURE:
<221> NAME/KEY: modified_base
<222> LOCATION: (821)..(822)
<223> OTHER INFORMATION: n is a, c, g, or t
<220> FEATURE:
<221> NAME/KEY: modified_base
<222> LOCATION: (835)..(835)
<223> OTHER INFORMATION: n is a, c, g, or t
<220> FEATURE:
<221> NAME/KEY: modified_base
<222> LOCATION: (840)..(841)
<223> OTHER INFORMATION: n is a, c, g, or t
<220> FEATURE:
<221> NAME/KEY: modified_base
<222> LOCATION: (850)..(852)
<223> OTHER INFORMATION: n is a, c, g, or t
<220> FEATURE:
<221> NAME/KEY: modified_base
<222> LOCATION: (856)..(856)
<223> OTHER INFORMATION: n is a, c, g, or t

<400> SEQUENCE: 12

```
tggnnnnnnn nttnntgngg cttttnnagc gctnntttnt nnantttttt ggnccagcaa      60

agtttgttaa aatttattat cttattttta gaacagaaat aacattaaaa tagatgtttt     120

tagaatatca acatacaatc aaaaacacaa agtccaagga tcctccccat ctccaaggct     180

taaagggcag ctatccagct gtagtctatt ttcctaaatt ttctcagttc tttttcttca     240

gattttgaca actgatgtat aatgtcttct cctaaacctg tgttacttgt atcctggact     300

ttttcggtaa aatcattttc ttcatctgaa tcttcacttt ctttttcttc ttccatatct     360

acatcttcag gaatttcctt agcactctta gtctctttag acagcagcaa tgagtttaca     420

aacatggngc acaggaaagc agcagatggc aggacatggg ctggagtgtg aagaagctca     480

ctaattgcgg gtatgttttc tgttaagggt anttgtacca agctcattct ccaaagtttc     540

gtttagtttt tcancctgct gttgcctgtg ttttcccaat atgaaataaa atggggttgt     600

gggaagactt cctctgctaa caactgtttg cctggtggtg tgagtttttc ctccnggaga     660

ctttgtnctg aangtcaata aactccggga ttttgttagg aagttaaact gggatntatt     720

tanccccggg aaacctctga nggggaaggn tcangganat ctccntggga naaanactcc     780

ccannggcc tttccccccg ggggaaaacc ctttgganna nnaaagggcc ttggnccccn     840

nggtttaaan nnaaanaaag                                                 860
```

<210> SEQ ID NO 13
<211> LENGTH: 794
<212> TYPE: DNA
<213> ORGANISM: Homo sapiens
<220> FEATURE:
<221> NAME/KEY: modified_base
<222> LOCATION: (6)..(6)
<223> OTHER INFORMATION: n is a, c, g, or t
<220> FEATURE:
<221> NAME/KEY: modified_base
<222> LOCATION: (162)..(162)
<223> OTHER INFORMATION: n is a, c, g, or t
<220> FEATURE:
<221> NAME/KEY: modified_base
<222> LOCATION: (557)..(557)
<223> OTHER INFORMATION: n is a, c, g, or t
<220> FEATURE:
<221> NAME/KEY: modified_base
<222> LOCATION: (644)..(644)
<223> OTHER INFORMATION: n is a, c, g, or t
<220> FEATURE:
<221> NAME/KEY: modified_base
<222> LOCATION: (674)..(674)
<223> OTHER INFORMATION: n is a, c, g, or t
<220> FEATURE:
<221> NAME/KEY: modified_base
<222> LOCATION: (749)..(749)
<223> OTHER INFORMATION: n is a, c, g, or t
<220> FEATURE:
<221> NAME/KEY: modified_base
<222> LOCATION: (752)..(752)
<223> OTHER INFORMATION: n is a, c, g, or t
<220> FEATURE:
<221> NAME/KEY: modified_base
<222> LOCATION: (766)..(766)
<223> OTHER INFORMATION: n is a, c, g, or t
<220> FEATURE:
<221> NAME/KEY: modified_base
<222> LOCATION: (768)..(768)
<223> OTHER INFORMATION: n is a, c, g, or t
<220> FEATURE:
<221> NAME/KEY: modified_base
<222> LOCATION: (771)..(771)
<223> OTHER INFORMATION: n is a, c, g, or t
<220> FEATURE:
<221> NAME/KEY: modified_base
<222> LOCATION: (793)..(793)
<223> OTHER INFORMATION: n is a, c, g, or t

<400> SEQUENCE: 13

```
atctcnagca ctgttggcct actggggaga ccgtccatcc agaggaaggc aagtttttgg     60

gctcgggcgg ctgagaagac cgcgcggggc tggagacagg tagcagtacg gggcggggc    120

ttcatgccgg atgtgatagt ctgcagtcgt ttcggttggc ancctggcgg gtgggagatg    180

cggcggccac ctgctgcaaa gaaccgaagg gaaggttaga agtacgaagg cagtttggag    240

ctggggctaa gcagctgtcg cacggtcaga tcatgggctc caccaagcac tggggcgaat    300

ggctcctgaa cttgaaggtg gctccagccg gcgtctttgg tgtggccttt ctagccagag    360

tcgccctggt tttctatggc gtcttccagg accggacct gcacgtgagg tatacggaca    420

tcgactacca ggtcttcacc gacgccgcgc gcttcgtcac ggaggggcgc tcgccttacc    480

tgagagccac gtaccgttac accccgctgc tgggttggct cctcactccc aacatctacc    540

tcaacgagct ccttggnaaa tttctcctca tcaactgcga actcctcaac gctttcctcc    600

ttataccgcc tgctgctgct gaaagggctt gggcgcccca agcnttttgc tactgtgtcc    660

ttttggcttc taanccctgc ctatggaata tcaaaccgcg taattcggct ccaatgtcgc    720

tccctgggcc tgaagggcct cactttatna anaaaaaacc ctcccntntt naccgtatcc    780

aagggtttcc cgng                                                     794
```

<210> SEQ ID NO 14
<211> LENGTH: 740
<212> TYPE: DNA

-continued

<213> ORGANISM: Homo sapiens
<220> FEATURE:
<221> NAME/KEY: modified_base
<222> LOCATION: (3)..(7)
<223> OTHER INFORMATION: n is a, c, g, or t
<220> FEATURE:
<221> NAME/KEY: modified_base
<222> LOCATION: (12)..(12)
<223> OTHER INFORMATION: n is a, c, g, or t
<220> FEATURE:
<221> NAME/KEY: modified_base
<222> LOCATION: (14)..(14)
<223> OTHER INFORMATION: n is a, c, g, or t
<220> FEATURE:
<221> NAME/KEY: modified_base
<222> LOCATION: (22)..(23)
<223> OTHER INFORMATION: n is a, c, g, or t
<220> FEATURE:
<221> NAME/KEY: modified_base
<222> LOCATION: (50)..(50)
<223> OTHER INFORMATION: n is a, c, g, or t
<220> FEATURE:
<221> NAME/KEY: modified_base
<222> LOCATION: (406)..(406)
<223> OTHER INFORMATION: n is a, c, g, or t
<220> FEATURE:
<221> NAME/KEY: modified_base
<222> LOCATION: (447)..(447)
<223> OTHER INFORMATION: n is a, c, g, or t
<220> FEATURE:
<221> NAME/KEY: modified_base
<222> LOCATION: (538)..(538)
<223> OTHER INFORMATION: n is a, c, g, or t
<220> FEATURE:
<221> NAME/KEY: modified_base
<222> LOCATION: (561)..(561)
<223> OTHER INFORMATION: n is a, c, g, or t
<220> FEATURE:
<221> NAME/KEY: modified_base
<222> LOCATION: (608)..(608)
<223> OTHER INFORMATION: n is a, c, g, or t
<220> FEATURE:
<221> NAME/KEY: modified_base
<222> LOCATION: (610)..(610)
<223> OTHER INFORMATION: n is a, c, g, or t
<220> FEATURE:
<221> NAME/KEY: modified_base
<222> LOCATION: (630)..(631)
<223> OTHER INFORMATION: n is a, c, g, or t
<220> FEATURE:
<221> NAME/KEY: modified_base
<222> LOCATION: (653)..(653)
<223> OTHER INFORMATION: n is a, c, g, or t
<220> FEATURE:
<221> NAME/KEY: modified_base
<222> LOCATION: (707)..(707)
<223> OTHER INFORMATION: n is a, c, g, or t
<220> FEATURE:
<221> NAME/KEY: modified_base
<222> LOCATION: (717)..(717)
<223> OTHER INFORMATION: n is a, c, g, or t
<220> FEATURE:
<221> NAME/KEY: modified_base
<222> LOCATION: (730)..(730)
<223> OTHER INFORMATION: n is a, c, g, or t
<220> FEATURE:
<221> NAME/KEY: modified_base
<222> LOCATION: (733)..(733)
<223> OTHER INFORMATION: n is a, c, g, or t
<220> FEATURE:
<221> NAME/KEY: modified_base
<222> LOCATION: (740)..(740)
<223> OTHER INFORMATION: n is a, c, g, or t

<400> SEQUENCE: 14
ttnnnnngcc tntnttttttt tnntttttttt ttgcgactag gtctcaccan cttgccccag 60
gtgggtctag aactcctgaa ctcaagcgac cctcccacct cagcctccca aagtgctgag 120

```
actacaggca agggccacca tacacagttt aagaatattt tttggatttt cacagctgtc    180

aggaaagctt tagaaagaaa agatgggtgt taaaagttaa gacacagctt aagacagaag    240

cattgtaaaa caggaacaaa tactggctta aacctgatgt ctctaactat attcctctat    300

tttaagaatg ttttagtatc tgatagtttc atcagccttt ccattttcca atatgtgacc    360

tttattccca ccatgtccca aataaacgag tcctaggatt tcctanaagg tggacctcaa    420

ttattgtgtc ccttttatat ataaggnaaa cattgctttt aagttctgtt ggaacatggg    480

aactttcact agaatgctta gaatgttcag aaaaaatgtc ccaaagctct cttccggncc    540

atacaagaca atcagaatgt nacacagtag caaagggtgt gggacataca ctagtcatat    600

ttgattcncn ctgtcaaggg gtctccttgn natgggaaat aatttgatca ggntgggaca    660

attgataaga aagaaagaac aaaccaagta accaaattaa caagaangggg ttccttncct    720

gaaactccan aanaaaaggn                                                740
```

<210> SEQ ID NO 15
<211> LENGTH: 816
<212> TYPE: DNA
<213> ORGANISM: Homo sapiens
<220> FEATURE:
<221> NAME/KEY: modified_base
<222> LOCATION: (5)..(5)
<223> OTHER INFORMATION: n is a, c, g, or t
<220> FEATURE:
<221> NAME/KEY: modified_base
<222> LOCATION: (7)..(7)
<223> OTHER INFORMATION: n is a, c, g, or t
<220> FEATURE:
<221> NAME/KEY: modified_base
<222> LOCATION: (16)..(16)
<223> OTHER INFORMATION: n is a, c, g, or t
<220> FEATURE:
<221> NAME/KEY: modified_base
<222> LOCATION: (434)..(434)
<223> OTHER INFORMATION: n is a, c, g, or t
<220> FEATURE:
<221> NAME/KEY: modified_base
<222> LOCATION: (448)..(448)
<223> OTHER INFORMATION: n is a, c, g, or t
<220> FEATURE:
<221> NAME/KEY: modified_base
<222> LOCATION: (486)..(486)
<223> OTHER INFORMATION: n is a, c, g, or t
<220> FEATURE:
<221> NAME/KEY: modified_base
<222> LOCATION: (593)..(593)
<223> OTHER INFORMATION: n is a, c, g, or t
<220> FEATURE:
<221> NAME/KEY: modified_base
<222> LOCATION: (612)..(612)
<223> OTHER INFORMATION: n is a, c, g, or t
<220> FEATURE:
<221> NAME/KEY: modified_base
<222> LOCATION: (616)..(616)
<223> OTHER INFORMATION: n is a, c, g, or t
<220> FEATURE:
<221> NAME/KEY: modified_base
<222> LOCATION: (620)..(620)
<223> OTHER INFORMATION: n is a, c, g, or t
<220> FEATURE:
<221> NAME/KEY: modified_base
<222> LOCATION: (633)..(633)
<223> OTHER INFORMATION: n is a, c, g, or t
<220> FEATURE:
<221> NAME/KEY: modified_base
<222> LOCATION: (642)..(642)
<223> OTHER INFORMATION: n is a, c, g, or t
<220> FEATURE:
<221> NAME/KEY: modified_base
<222> LOCATION: (659)..(659)

-continued

<223> OTHER INFORMATION: n is a, c, g, or t
<220> FEATURE:
<221> NAME/KEY: modified_base
<222> LOCATION: (662)..(662)
<223> OTHER INFORMATION: n is a, c, g, or t
<220> FEATURE:
<221> NAME/KEY: modified_base
<222> LOCATION: (677)..(678)
<223> OTHER INFORMATION: n is a, c, g, or t
<220> FEATURE:
<221> NAME/KEY: modified_base
<222> LOCATION: (710)..(710)
<223> OTHER INFORMATION: n is a, c, g, or t
<220> FEATURE:
<221> NAME/KEY: modified_base
<222> LOCATION: (737)..(737)
<223> OTHER INFORMATION: n is a, c, g, or t
<220> FEATURE:
<221> NAME/KEY: modified_base
<222> LOCATION: (752)..(752)
<223> OTHER INFORMATION: n is a, c, g, or t
<220> FEATURE:
<221> NAME/KEY: modified_base
<222> LOCATION: (769)..(769)
<223> OTHER INFORMATION: n is a, c, g, or t
<220> FEATURE:
<221> NAME/KEY: modified_base
<222> LOCATION: (781)..(781)
<223> OTHER INFORMATION: n is a, c, g, or t
<220> FEATURE:
<221> NAME/KEY: modified_base
<222> LOCATION: (800)..(801)
<223> OTHER INFORMATION: n is a, c, g, or t
<220> FEATURE:
<221> NAME/KEY: modified_base
<222> LOCATION: (806)..(807)
<223> OTHER INFORMATION: n is a, c, g, or t
<220> FEATURE:
<221> NAME/KEY: modified_base
<222> LOCATION: (811)..(811)
<223> OTHER INFORMATION: n is a, c, g, or t
<220> FEATURE:
<221> NAME/KEY: modified_base
<222> LOCATION: (816)..(816)
<223> OTHER INFORMATION: n is a, c, g, or t

<400> SEQUENCE: 15
tctcntngca ctgttngcct actggggtta ttgggcagaa gcctcccatt acggagcacg 60
aaagagtcca tgaaggtccc cgcgactccc ggactggaga aaacggctct tgcgatgggg 120
cgaagtccga gctgcggcgg gcgttggtcc gtgcagggaa gtgggaatcg ttaggttcgt 180
tctggacccg ccgccccatg gcccaggcgt ctcgctcagg tagcctgcct ccactcgtta 240
tcgtgccccc gctgagggcg caacccgggg gcactgggag gagcagtggg agagaagtcg 300
aacgggcggt cttcgctggg aggttcactg ctggccgagc ggaacttctg gagggacgcc 360
gtggtggccg acgccggcgg atgtgagcga ggactacgag gctgatgctg cggcctggag 420
gcgggggccc gcangtggcg gcccgatncc tcccgcgctg cagcgtctcc gggcggtgtt 480
gctgcnggtg catcgcgagc gggaacaact cctccaagcc cgagactgcg cctacaccta 540
cagtcggctg tgcgactcat gaagacctga gtcctggctc gccatccggc ggncctaacc 600
ccttccccaa angtgncgcn actgcaactg cancettcca angggcggtt ctgcgaatng 660
gncctgggga aactctnnaa cccgctgctg ctacgcgccc catcggactn accgccaatt 720
cctggagggt gtcatcnaaa atgcaacttc cnggtcttcg gccggggganc ccgccaaccc 780 ngggcctttt gtcccaaatn nccganntgt nctttn 816

<210> SEQ ID NO 16
<211> LENGTH: 839

-continued

<212> TYPE: DNA
<213> ORGANISM: Homo sapiens
<220> FEATURE:
<221> NAME/KEY: modified_base
<222> LOCATION: (3)..(12)
<223> OTHER INFORMATION: n is a, c, g, or t
<220> FEATURE:
<221> NAME/KEY: modified_base
<222> LOCATION: (27)..(27)
<223> OTHER INFORMATION: n is a, c, g, or t
<220> FEATURE:
<221> NAME/KEY: modified_base
<222> LOCATION: (44)..(44)
<223> OTHER INFORMATION: n is a, c, g, or t
<220> FEATURE:
<221> NAME/KEY: modified_base
<222> LOCATION: (586)..(586)
<223> OTHER INFORMATION: n is a, c, g, or t
<220> FEATURE:
<221> NAME/KEY: modified_base
<222> LOCATION: (606)..(606)
<223> OTHER INFORMATION: n is a, c, g, or t
<220> FEATURE:
<221> NAME/KEY: modified_base
<222> LOCATION: (670)..(670)
<223> OTHER INFORMATION: n is a, c, g, or t
<220> FEATURE:
<221> NAME/KEY: modified_base
<222> LOCATION: (697)..(697)
<223> OTHER INFORMATION: n is a, c, g, or t
<220> FEATURE:
<221> NAME/KEY: modified_base
<222> LOCATION: (703)..(703)
<223> OTHER INFORMATION: n is a, c, g, or t
<220> FEATURE:
<221> NAME/KEY: modified_base
<222> LOCATION: (747)..(747)
<223> OTHER INFORMATION: n is a, c, g, or t
<220> FEATURE:
<221> NAME/KEY: modified_base
<222> LOCATION: (757)..(757)
<223> OTHER INFORMATION: n is a, c, g, or t
<220> FEATURE:
<221> NAME/KEY: modified_base
<222> LOCATION: (795)..(795)
<223> OTHER INFORMATION: n is a, c, g, or t
<220> FEATURE:
<221> NAME/KEY: modified_base
<222> LOCATION: (816)..(816)
<223> OTHER INFORMATION: n is a, c, g, or t

<400> SEQUENCE: 16
ggnnnnnnnn nntgtggctt ttttttngcc tttttttttt ttgntgacag agtcttgctc 60
tgtcacccag gctggagtgc tgtggctgga tctcagctca ctgcaagctc cgcctcccag 120
gttcacacca ttctcctgcc tcagcctccc gagtagctgg gactacaggc acccgccacc 180
acgcccggct aattttttgt atttttagtg gaaacagggt ttcaccgtgt tagccaggat 240
ggtcttgatc tcctgacctc atgatccgcc tgcctcggtc tcccaaagtg ctggattaca 300
ggcgtgagcc acctcgccca gcccctaatc ttggattctt aagcccaggc tctttgtagc 360
ttattctcca gtatgctttc ctccaagctt ccagttctgg gcttccttaa tatgcaattc 420
caaatgtctg gattttccag ctagagatgg ggagctctta actttctggc tcctggtccc 480
aggctcctta ggattcagga ctggttccca agcaggaaaa aaacggcagg tgccaacggg 540
gtcgctggtg ttgcctgagg gcaagccaag cctgctgatt tcccancaag tagccctccg 600
ggctangtcc ccttcctcct aatgtgcttt gcaactgacc tgtctgggct ggagatgttc 660
caagctggan ccgggggtcc aaactctcca aggctantga ggnaactgct gggcaaattt 720
cgtgggcctg gacctcctga caagcanctg gtaaggnaag gattggaaag gtaggtggtg 780

-continued

```
ctgggggata tactngaaac ccaattaatg ggggananaa agggtttggg aacaacaaa     839


<210> SEQ ID NO 17
<211> LENGTH: 2198
<212> TYPE: DNA
<213> ORGANISM: Homo sapiens

<400> SEQUENCE: 17

cctactggtc ttgtgtgggt gttttccagc acggaaaagt cgagataatt gccaatgatc     60

agggaaaccg aaccactcca agctatgtcg cctttacgga cactgaacgg ttgatcggtg    120

atgccgcaaa gaatcaagtt gcaatgaacc ccaccaacac agtttttgat gccaaacgtc    180

tgattggacg cagatttgat gatgctgttg tccagtctga tatgaaacat tggcccttta    240

tggtggtgaa tgatgctggc aggcccaagg tccaagtaga atacaaggga gagaccaaaa    300

gcttctatcc agaggaggtg tcttctatgg ttctgacaaa gatgaaggaa attgcagaag    360

cctaccttgg gaagactgtt accaatgctg tggtcacagt gccagcttac tttaatgact    420

ctcagcgtca ggctaccaaa gatgctggaa ctattgctgg tctcaatgta cttagaatta    480

ttaatgagcc aactgctgct gctattgctt acggcttaga caaaaaggtt ggagcagaaa    540

gaaacgtgct catctttgac ctgggaggtg gcacttttga tgtgtcaatc ctcactattg    600

aggatggaat ctttgaggtc aagtctacag ctggagacac ccacttgggt ggagaagatt    660

ttgacaaccg aatggtcaac cattttattg ctgagtttaa gcgcaagcat aagaaggaca    720

tcagtgagaa caagagagct gtaagacgcc tccgtactgc ttgtgaacgt gctaagcgta    780

ccctctcttc cagcacccag gccagtattg agatcgattc tctctatgaa ggaatcgact    840

tctatacctc cattacccgt gcccgatttg aagaactgaa tgctgacctg ttccgtggca    900

ccctggaccc agtagagaaa gcccttcgag atgccaaact agacaagtca cagattcatg    960

atattgtcct ggttggtggt tctactcgta tccccaagat tcagaagctt ctccaagact   1020

tcttcaatgg aaaagaactg aataagagca tcaaccctga tgaagctgtt gcttatggtg   1080

cagctgtcca ggcagccatc ttgtctggag acaagtctga gaatgttcaa gatttgctgc   1140

tcttggatgt cactcctctt tcccttggta ttgaaactgc tggtggagtc atgactgtcc   1200

tcatcaagcg taataccacc attcctacca agcagacaca gaccttcact acctattctg   1260

acaaccagcc tggtgtgctt attcaggttt atgaaggcga gcgtgccatg acaaaggata   1320

acaacctgct tggcaagttt gaactcacag gcatacctcc tgcaccccga ggtgttcctc   1380

agattgaagt cacttttgac attgatgcca atggtatact caatgtctct gctgtggaca   1440

agagtacggg aaaagagaac aagattacta tcactaatga caagggccgt ttgagcaagg   1500

aagacattga acgtatggtc caggaagctg agaagtacaa agctgaagat gagaagcaga   1560

gggacaaggt gtcatccaag aattcacttg agtcctatgc cttcaacatg aaagcaactg   1620

ttgaagatga gaaacttcaa ggcaagatta acgatgagga caaacagaag attctggaca   1680

agtgtaatga aattatcaac tggcttgata agaatcagac tgctgagaag gaagaatttg   1740

aacatcaaca gaaagagctg gagaaagttt gcaaccccat catcaccaag ctgtaccaga   1800

gtgcaggagg catgccagga ggaatgcctg gggggatttcc tggtggtgga gctcctccct   1860

ctggtggtgc ttcctcaggg cccaccattg aagaggttga ttaagccaac caagtgtaga   1920

tgtagcattg ttccacacat ttaaaacatt tgaaggacct aaattcgtag caaattctgt   1980

ggcagtttta aaaagttaag ctgctatagt aagttactgg gcattctcaa tacttgaata   2040

tggaacatat gcacagggga aggaaataac attgcacttt ataaacactg tattgtaagt   2100
```

```
ggaaaatgca atgtcttaaa taaaactatt taaaattggc accataaaaa aaaaaaaaaa   2160

aaaaaaaaaa ggccacatgt gctcgagctg caggtcgc                           2198


<210> SEQ ID NO 18
<211> LENGTH: 845
<212> TYPE: DNA
<213> ORGANISM: Homo sapiens
<220> FEATURE:
<221> NAME/KEY: modified_base
<222> LOCATION: (580)..(580)
<223> OTHER INFORMATION: n is a, c, g, or t
<220> FEATURE:
<221> NAME/KEY: modified_base
<222> LOCATION: (674)..(674)
<223> OTHER INFORMATION: n is a, c, g, or t
<220> FEATURE:
<221> NAME/KEY: modified_base
<222> LOCATION: (704)..(704)
<223> OTHER INFORMATION: n is a, c, g, or t
<220> FEATURE:
<221> NAME/KEY: modified_base
<222> LOCATION: (715)..(715)
<223> OTHER INFORMATION: n is a, c, g, or t
<220> FEATURE:
<221> NAME/KEY: modified_base
<222> LOCATION: (743)..(744)
<223> OTHER INFORMATION: n is a, c, g, or t
<220> FEATURE:
<221> NAME/KEY: modified_base
<222> LOCATION: (792)..(792)
<223> OTHER INFORMATION: n is a, c, g, or t
<220> FEATURE:
<221> NAME/KEY: modified_base
<222> LOCATION: (811)..(811)
<223> OTHER INFORMATION: n is a, c, g, or t
<220> FEATURE:
<221> NAME/KEY: modified_base
<222> LOCATION: (839)..(839)
<223> OTHER INFORMATION: n is a, c, g, or t
<220> FEATURE:
<221> NAME/KEY: modified_base
<222> LOCATION: (841)..(841)
<223> OTHER INFORMATION: n is a, c, g, or t

<400> SEQUENCE: 18

tcctcgagca cgttggccta ctggcctaat gtactttggg tgctctttgt gcctaaaatt     60

tttcatttag gtaagataat aacttctcag ttttgcttaa acacatttaa actgagtttt    120

tatcttttgc aacagaaaga atcctgactt aggcagtcgt tttctttgga attcaaatgc    180

ctacatcatc tgaggcttgg tctcaatcag gtgaaatgca gcaacataac acaataaaat    240

taacttgtgt agaatgcctt ctggggtcca gagccaggtg cttcctcaag gactgcctct    300

cagagcacaa tggtgatgtg gtactgactg tggaagctga gagcaaaact ataactgtgc    360

cctgaatgca catgctcaaa ctgagcctct ggttcgataa gtgccagatg ttttggaccc    420

tatgggaaca ctgctgtgtt cttatcattg acagaaagaa atgttcctca cattattaag    480

gttcgatagt attatttaag gaagtaaata cagtatatgt atcaaatagt aaaagttaag    540

aattttggtt ggttttgagg gaacaaagta aaagcctgan ggaaatgaag ccagacttcc    600

tagtagtaaa ttacaaagtt acaatcctgc ccatggtcaa ctgagaaggg atcatccaac    660

aacgatggat ctcntgagaa actaaatacc ttcgctaccc aagntactcc ttcantgggc    720

attaatgatt gacaatacat gtnnagtgtc tgagttatca tcactccata attaaagttt    780

cctttgccct cncctgactt cgggaacttg ncacatatta ctcaaccttc ccttgccana    840

ntttg                                                                845
```

<210> SEQ ID NO 19
<211> LENGTH: 868
<212> TYPE: DNA
<213> ORGANISM: Homo sapiens
<220> FEATURE:
<221> NAME/KEY: modified_base
<222> LOCATION: (2)..(2)
<223> OTHER INFORMATION: n is a, c, g, or t
<220> FEATURE:
<221> NAME/KEY: modified_base
<222> LOCATION: (4)..(4)
<223> OTHER INFORMATION: n is a, c, g, or t
<220> FEATURE:
<221> NAME/KEY: modified_base
<222> LOCATION: (7)..(10)
<223> OTHER INFORMATION: n is a, c, g, or t
<220> FEATURE:
<221> NAME/KEY: modified_base
<222> LOCATION: (29)..(29)
<223> OTHER INFORMATION: n is a, c, g, or t
<220> FEATURE:
<221> NAME/KEY: modified_base
<222> LOCATION: (535)..(535)
<223> OTHER INFORMATION: n is a, c, g, or t
<220> FEATURE:
<221> NAME/KEY: modified_base
<222> LOCATION: (609)..(609)
<223> OTHER INFORMATION: n is a, c, g, or t
<220> FEATURE:
<221> NAME/KEY: modified_base
<222> LOCATION: (616)..(616)
<223> OTHER INFORMATION: n is a, c, g, or t
<220> FEATURE:
<221> NAME/KEY: modified_base
<222> LOCATION: (739)..(739)
<223> OTHER INFORMATION: n is a, c, g, or t
<220> FEATURE:
<221> NAME/KEY: modified_base
<222> LOCATION: (751)..(751)
<223> OTHER INFORMATION: n is a, c, g, or t
<220> FEATURE:
<221> NAME/KEY: modified_base
<222> LOCATION: (754)..(754)
<223> OTHER INFORMATION: n is a, c, g, or t
<220> FEATURE:
<221> NAME/KEY: modified_base
<222> LOCATION: (760)..(760)
<223> OTHER INFORMATION: n is a, c, g, or t
<220> FEATURE:
<221> NAME/KEY: modified_base
<222> LOCATION: (776)..(776)
<223> OTHER INFORMATION: n is a, c, g, or t
<220> FEATURE:
<221> NAME/KEY: modified_base
<222> LOCATION: (784)..(784)
<223> OTHER INFORMATION: n is a, c, g, or t
<220> FEATURE:
<221> NAME/KEY: modified_base
<222> LOCATION: (787)..(787)
<223> OTHER INFORMATION: n is a, c, g, or t
<220> FEATURE:
<221> NAME/KEY: modified_base
<222> LOCATION: (815)..(816)
<223> OTHER INFORMATION: n is a, c, g, or t
<220> FEATURE:
<221> NAME/KEY: modified_base
<222> LOCATION: (835)..(835)
<223> OTHER INFORMATION: n is a, c, g, or t
<220> FEATURE:
<221> NAME/KEY: modified_base
<222> LOCATION: (847)..(847)
<223> OTHER INFORMATION: n is a, c, g, or t
<220> FEATURE:
<221> NAME/KEY: modified_base
<222> LOCATION: (856)..(856)
<223> OTHER INFORMATION: n is a, c, g, or t
<220> FEATURE:
<221> NAME/KEY: modified_base
<222> LOCATION: (858)..(858)
<223> OTHER INFORMATION: n is a, c, g, or t
<220> FEATURE:
<221> NAME/KEY: modified_base
<222> LOCATION: (862)..(862)
<223> OTHER INFORMATION: n is a, c, g, or t
<220> FEATURE:
<221> NAME/KEY: modified_base
<222> LOCATION: (866)..(866)
<223> OTHER INFORMATION: n is a, c, g, or t

<400> SEQUENCE: 19
gngntgnnnn tgtggctttt ttttttgtnt tgttgttgtt gttgttgaca tttaataagt 60
caatatatgt gactacagga cggaaactgt aaaaagggtc cacagctgga aggtgaagat 120
attacacctg gagtagtaag gtgacaaata cctgttgata gactggtttc ttgataagaa 180
tttattcatg cctcctctac ctttccattt acttccgagt ttttgaacct cagcactgct 240
gacgttttaa accagatgat tccttgctgg ggagtagggt gggggccacc agtgcattgt 300
agaatgtcca agaaactgaa catcctacta cctctacaca ctagatgcca gtagcagccg 360
ccccacccta ctcccatgaa ttgggacaag caaaaatgtt cccagacatt gcctgatgtc 420
tccatgaagg tgggtgcagg tgcaaaattg tccttcggtt gagaagaact ggtttaactt 480
aagagaccaa atctcagtag tatattctga aaaagccata tgagttttgt tttcnctatc 540
cctgaatcac aaatgagagc caattttaat tgtgattata aaataaactg tgattttaat 600
tgtgattanc ctgcanaagt cactccgctg atctgtttac atggattaac tcatttaatc 660
ctacaagaag gaggtcaact gatcctcact ttaaaaatga agaaattgaa gcttaaagag 720
ttgaagtgac ttcccaagnt caaaactagg ntanacacan cttttgtccg gatccnctcc 780
gtangantcc aaaaccttgc ttttaacaat cctgnngtgc tccctacatg catanatggt 840
taaaatnacc ccccgntnaa cntaanaa 868

<210> SEQ ID NO 20
<211> LENGTH: 2495
<212> TYPE: DNA
<213> ORGANISM: Homo sapiens

<400> SEQUENCE: 20
cactgttggc ctactggcta ctatcaggat cgtggctatt ttgaagagct gatcaccatg 60
ttggaagcag cactgggact tgagcgagct cacatgggaa tgtttactga attagctatt 120
ctatactcta aatttaagcc tcagaaaatg agggagcacc tggagctgtt ctggtctaga 180
gtgaatattc ccaaggtgct aagagctgca gaacaagctc atctttgggc agaactggtg 240
tttttgtatg acaagtatga agaatatgat aatgccataa ttaccatgat gaatcatcca 300
actgatgcct ggaaagaagg gcaattcaaa gatatcatta ccaaggttgc caatgtggaa 360
ctatactaca gagcaataca gttctactta gaattcaagc ctctgttgtt aaatgatttg 420
ctgatggtgc tgtctccacg gttggatcac actcgtgcag tcaattattt cagcaaggtt 480
aaacagctac cactggtgaa accgtatttg cgttcagttc agaaccataa caacaaatct 540
gtgaatgaat cattgaacaa tctttttatt acagaagaag attatcaggc tctgcgaaca 600
tcaatagatg cttatgacaa ctttgacaat atctcgcttg ctcagcgttt ggaaaaacat 660
gaactcattg agttcaggag aattgctgct tatctcttca aaggcaacaa tcgctggaaa 720
cagagtgtag agctgtgcaa gaaagacagc ctttacaagg atgcaatgca gtatgcttct 780
gaatctaaag atactgaatt ggctgaagaa ctcctgcagt ggtttttgca ggaagaaaaa 840

-continued

```
agagagtgct ttggagcttg tctgtttacc tgttacgatc ttttaaggcc agatgtcgtc    900

ctagaaactg catggaggca caatatcatg gattttgcca tgccctattt catccaggtc    960

atgaaggagt acttgacaaa ggtggataaa ttagatgctt cagaatcact gagaaaagaa   1020

gaagaacaag ctacagagac acaacccatt gtttatggtc agccccagtt gatgctgaca   1080

gcaggaccca gtgttgccgt ccctccccag gcaccttttg gttatggtta taccgcacca   1140

ccgtatggac agccacagcc tggctttggg tacagcatgt gagatgaagc gctgatcctg   1200

tagtcaccta ttttcgtact gaaacatcgt ctttacccac ttctcagttt ataatggggg   1260

aaaacaggca acgtgttctt gtaaccttta tttcatgaag gacttctttt tgtttctaac   1320

tataaacttg gatcacctat gttaaaacct tatttcacat tccacatcat tttagaattt   1380

attttcgaag ggaatagtt tcaatgtttt attcacttgg gcttttttc ttcccctct    1440

ttctttaaag aactgctcaa tattcaatct gttgtgaaga acctgatttg cactctgtag   1500

tgtttaaaga aacaaagaaa ctctaatatt gaatctctta aatttagtgt atgtaaacag   1560

cttacaaata cgtattgtct aaatgcattt aaatctgttt tattcaaaga aaagctaaag   1620

caaaaacact ggcatatgac catgcaagac tgtcagtgcc aacaaagaca acactaatca   1680

gcacatcgta cactggattg cagtgcttcc cagattattg aaaaatgtta cagacaactt   1740

gcctgatttt taaatgagcg taaaaggccc tctaacctat gcaggtttcc ccattatgca   1800

tatagaaaat gctagtatgt tttgctcact tcatatgtaa caggtgccct tatgttgtgc   1860

tgtatcctgt gctttttctg tgggaccatt ccattcagga gcaaagagca ccatgattcc   1920

aatcttgtgt gtgtttacta acccttccct gaggtttgtg tatgttggat attgtggtgt   1980

tttagatcac tgagtgtaca gaagagagaa attcaaacaa aatattgctg ttcttcagtt   2040

ttgtttgtgg aatttgaaat tactcaaatt taaaataaat tactggactg tggaaataac   2100

atagaattga agttttaatt aaataccact caaacgaaaa gaacagtagt ttttgtagtt   2160

ttatattgga tactgaggca ttagggaggc atgaaaggaa gaggaatgag gattgagaca   2220

tgtgaagaca ttgtgcatta tatcaatgtg cattcctgta gttcattaac aaggtacatg   2280

caatagtcta aagaaccaga gtcactacta tagtggctta acatttaatc tgtctccaat   2340

attttaacca agtgacaccg gggtttttat cgaagcattt cacttaaatg aacaaatcat   2400

ggctgttata ttaacttgaa ataaaatata tttaaacatg taaaaaaaaa aaaaaaaagg   2460

ccacatgtgc tcgagctgca ggtcgcggcc gctag                              2495


<210> SEQ ID NO 21
<211> LENGTH: 3589
<212> TYPE: DNA
<213> ORGANISM: Homo sapiens

<400> SEQUENCE: 21

gcctactgga ttcgccatca ttttgcacac tgcgaggggc tccgtgtgtg cgccctgtct     60

tgtctggccg tcctcatccc ttcccccacc ccctgccgcc actccgaccc gctcccaaag    120

tggcttcaca atagtcggtc ctcggcggtg taggctgcgc accaggtcca cacttaagcg    180

aaatcaagga gacccccttc tacttctacc tttgggtttg gtgctcaatg cgaagctgct    240

gcaactcaga cacgcctaag tcaactcatg cagaaaaagg agaaaagttt tggtatacaa    300

atgctctcag tccagccaga caccaagccg aaaggttgtg ctggctgcaa ccgaaagatc    360

aaggaccggt atcttctaaa ggcactggac aaatactggc atgaagactg cctgaagtgt    420

gcctgctgtg actgtcgctt gggggaggtg ggctccaccc tgtacactaa agctaatctt    480
```

-continued

```
atcctttgtc gcagagacta tctgaggctc tttggtgtaa cgggaaactg cgctgcctgt    540
agtaagctca tccctgcctt tgagatggtg atgcgtgcca aggacaatgt ttaccacctg    600
gactgctttg catgtcagct ttgtaatcag agattttgtg ttggagacaa atttttccta    660
aagaataaca tgatcctttg ccagacggac tacgaggaag gtttaatgaa agaaggttat    720
gcaccccagg ttcgctgatc tatcaacatc accccattaa gaatacagag cactacattc    780
ttttatcttt tttgctccac atgtacataa gaattgacac aggaacctac tgaatagcgt    840
agatatagga aggcaggatg gttatatgga ataaaaggcg gactgcatct gtatgtagtg    900
aaattgcccc agttcagagt tgaatgttta ttattaaaga aaaaagtaat gtacatatgg    960
ctggattttt ttgcttgcta ttcgtttttg tgtcacttgg catgagatgt ttattttgga   1020
ctattgtata taatgtattg taatatttga agcacaaatg taatacagtt ttattgtgtt   1080
accatttgtg ttccatttgc ttctttgtat tgttgcattt agtacaatca gtgtttaaac   1140
ttactgtata tttatgcttt ctgtatttac cagctatttt aaatgagctg taactttcta   1200
gtaaagaatt gaaaagcaaa tctcactaat gatacacaga tagataaagc aagtctatca   1260
acattaaaaa tactaaaaaa taaagacaca cacagagcat tttagtgaca tccactactt   1320
attgccgcta tgagttagag tctatcagtg ttcttgttat aaccccctat tttcaggggg   1380
ttaaaaatca gctttaaaaa aatacataaa aatttcatct taaagcactt tcattttata   1440
ccaacgtgaa aagtgccatt tttagaataa ctttaaagct taacaggttt cctttttaata   1500
tccttttttt gtgtgctctt tacttacaca atggctttgt tttgcttttt cagccacacc   1560
ccttatgtga actagtgcct ttgggtatca cgtaaaattt tttccaaagg gttactttaa   1620
aaatctgtta ccacaattat gagatgattt ttaagtgata aattaaactt cttcttgtat   1680
aaattctgcc cagatctctc cacaagagct gagggtttca taactttatg gcttaataaa   1740
tgtatgacac tgaaaagatt tgagtgtgaa tctactgaaa tcactataat gcacattgaa   1800
gctatgatgg tatttgagta gtgaggttac ttttgatcgg agcaacataa tgctcataga   1860
atcttctaga agaagagaaa caaagggatt gataaaatgc tgagaactag tgattatata   1920
tttttctgta tttacctgac atttatttta atgttcaaaa agtaaacact ttaagtttga   1980
tgtgttttac tctctcattg ttttaagtaa ttgccaactc agaatacatc attcttaggc   2040
tgaaatttgt ctttccattt tttaaggtga aatagtacta ccttacgtga tagcatacaa   2100
agaagaaagc tctagaaaga gaaattatgg agaatgatta tttaaattac aattaaggaa   2160
atgagaatat gatcccctct tccgagttgc ccacaaactt gcttctttgc ttttgctccc   2220
tgtaatagaa ctacttttca acaaatctaa ttttgcacgg caccgttaac catattttca   2280
ctacagcaaa cttagtgcta tgggttttct ttttctttgt ttttttcttg atcacttgta   2340
taggaaacaa cattttccag tgttatttgc atatatattt tgtccttcca atatatgcat   2400
tacagatgaa aattaaatgt tatacctgaa ttcttgggtt ggggccaaaa tattaagctg   2460
aaaataatgc tggtgtggat ttgttttaaa acaaagcttt attatgaaca tgcatgtgaa   2520
tctggatatt gcctcttatt tttaagaaaa tggttctgtg aaaagtgaat gatatgtatt   2580
tttccaaatg cttcatggtt aggagtcttc aagttccatg ttccccagat ttgagatata   2640
ctaaagaaag aaattcaaaa gtagctattt ggggcccaca aaaataacta ttattttagc   2700
cttagagcct tacacttgtt tcatgaagag aaaggacttg cataaccaaa ataaacaaag   2760
caagacaaat taaaaatatg tgggggagag atcagtgaaa agtggttttc ttaatgcagc   2820
```

-continued

```
cctgctggtc cccattaaca attgcttgaa attcacatgg atgtaaaatt ataattgtca   2880

ggatcttatt cagatgatct tttaaggttt aactggtttt gcttttgttt atctatatgt   2940

caaaatactt gtaaattggg aacaaacttc tctcagcttc ttgaagttgt tcaactatcc   3000

ttgccactgg aagaccaaac aaggttttca ctgctttttc ttttacataa tatgctgaga   3060

attatttctt atgcttttta ctacaaacaa aattactcac ctggattaaa gattaaggcc   3120

ttaatctgtt tagattatct ttaatctcca tgaaatcgtg aaataagaca agaatagtgt   3180

ttcagctgta ggccatttta cagctaattg cccataaatt gtagcattta ttgacctgaa   3240

gtactaagct aattgtcttg actactcaaa gcccctgaat tgttgtcaac tttccccttt   3300

gtgttgtgta gccctaacgt catttagctt gttgtctgat gcctccagta ggacacctcc   3360

gatggagctt tgatttctga gcagcgaaag ctcccttcct aagatgcatc tcgcataggc   3420

tgcctatgat gaaggaccgt gcacctccac tccaacagag tgctgagttt aaaagttgac   3480

ctgtgtttgt aatttcactt tcatcttgct taataaatat ctgctggatt ctttcaaaaa   3540

aaaaaaaaaa aaaaaaaaaa aaaaaaggcc acatgtgctc gagctgcag               3589
```

<210> SEQ ID NO 22
<211> LENGTH: 767
<212> TYPE: DNA
<213> ORGANISM: Homo sapiens
<220> FEATURE:
<221> NAME/KEY: modified_base
<222> LOCATION: (67)..(67)
<223> OTHER INFORMATION: n is a, c, g, or t
<220> FEATURE:
<221> NAME/KEY: modified_base
<222> LOCATION: (99)..(100)
<223> OTHER INFORMATION: n is a, c, g, or t
<220> FEATURE:
<221> NAME/KEY: modified_base
<222> LOCATION: (592)..(592)
<223> OTHER INFORMATION: n is a, c, g, or t
<220> FEATURE:
<221> NAME/KEY: modified_base
<222> LOCATION: (627)..(636)
<223> OTHER INFORMATION: n is a, c, g, or t
<220> FEATURE:
<221> NAME/KEY: modified_base
<222> LOCATION: (676)..(676)
<223> OTHER INFORMATION: n is a, c, g, or t
<220> FEATURE:
<221> NAME/KEY: modified_base
<222> LOCATION: (692)..(692)
<223> OTHER INFORMATION: n is a, c, g, or t
<220> FEATURE:
<221> NAME/KEY: modified_base
<222> LOCATION: (724)..(724)
<223> OTHER INFORMATION: n is a, c, g, or t
<220> FEATURE:
<221> NAME/KEY: modified_base
<222> LOCATION: (751)..(751)
<223> OTHER INFORMATION: n is a, c, g, or t
<220> FEATURE:
<221> NAME/KEY: modified_base
<222> LOCATION: (758)..(758)
<223> OTHER INFORMATION: n is a, c, g, or t

<400> SEQUENCE: 22

```
actggtttga tgtttctact gctacggaat gtattttaaa cacatatcgt ttctttttct     60

tggaaantaa gttgattagg accacagatt tggtttagnn agggtaatat tttgaaatac    120

tacaaggttt agacagtcca tgaaatcgac ctgtttaata atttaccatc ctgaaagtcc    180

agaattaaaa tatggaagca agaactatat aattgattag gatgcttggt aggttttttt    240

cattgttcaa atattcattg cacagtggat tgttttgatt agttagtatg cttttttttt    300
```

-continued

```
aattaattca gtcttctgtt aatttttaag ttttggttag tgccacaagg aatttaactt    360

tttgatttgt ataatagaaa actgaactag gaattgttag cggggttttg aaggatgtgt    420

actttccttc aaaataaagt ggtagatttt caaaatttta cactagtcag ttctttatat    480

tctaagttaa atgtaagttt gtaaaattat tttgggtttc ttctacaaag gaaaaaattg    540

gatttatata tataagggta ctgcataatg atttcatttt gataatgtgc anaatggcct    600

cataagctca cagaaggtaa aaaaaannnn nnnnnnagga aaaatcagga tttcactggt    660

ttaaaagaaa tctcantttt aattttggaa tntaaaaggg gatttgggat ttgtgaccat    720

tttnttttcc aaaaaacacc cattctttag naatgggntt gaattaa                  767
```

<210> SEQ ID NO 23
<211> LENGTH: 767
<212> TYPE: DNA
<213> ORGANISM: Homo sapiens
<220> FEATURE:
<221> NAME/KEY: modified_base
<222> LOCATION: (13)..(13)
<223> OTHER INFORMATION: n is a, c, g, or t
<220> FEATURE:
<221> NAME/KEY: modified_base
<222> LOCATION: (60)..(60)
<223> OTHER INFORMATION: n is a, c, g, or t
<220> FEATURE:
<221> NAME/KEY: modified_base
<222> LOCATION: (92)..(93)
<223> OTHER INFORMATION: n is a, c, g, or t
<220> FEATURE:
<221> NAME/KEY: modified_base
<222> LOCATION: (354)..(354)
<223> OTHER INFORMATION: n is a, c, g, or t
<220> FEATURE:
<221> NAME/KEY: modified_base
<222> LOCATION: (559)..(559)
<223> OTHER INFORMATION: n is a, c, g, or t
<220> FEATURE:
<221> NAME/KEY: modified_base
<222> LOCATION: (639)..(639)
<223> OTHER INFORMATION: n is a, c, g, or t
<220> FEATURE:
<221> NAME/KEY: modified_base
<222> LOCATION: (642)..(642)
<223> OTHER INFORMATION: n is a, c, g, or t
<220> FEATURE:
<221> NAME/KEY: modified_base
<222> LOCATION: (646)..(646)
<223> OTHER INFORMATION: n is a, c, g, or t
<220> FEATURE:
<221> NAME/KEY: modified_base
<222> LOCATION: (652)..(652)
<223> OTHER INFORMATION: n is a, c, g, or t
<220> FEATURE:
<221> NAME/KEY: modified_base
<222> LOCATION: (656)..(656)
<223> OTHER INFORMATION: n is a, c, g, or t
<220> FEATURE:
<221> NAME/KEY: modified_base
<222> LOCATION: (660)..(660)
<223> OTHER INFORMATION: n is a, c, g, or t
<220> FEATURE:
<221> NAME/KEY: modified_base
<222> LOCATION: (671)..(671)
<223> OTHER INFORMATION: n is a, c, g, or t
<220> FEATURE:
<221> NAME/KEY: modified_base
<222> LOCATION: (676)..(676)
<223> OTHER INFORMATION: n is a, c, g, or t
<220> FEATURE:
<221> NAME/KEY: modified_base
<222> LOCATION: (681)..(681)
<223> OTHER INFORMATION: n is a, c, g, or t
<220> FEATURE:

<221> NAME/KEY: modified_base
<222> LOCATION: (691)..(691)
<223> OTHER INFORMATION: n is a, c, g, or t
<220> FEATURE:
<221> NAME/KEY: modified_base
<222> LOCATION: (696)..(696)
<223> OTHER INFORMATION: n is a, c, g, or t
<220> FEATURE:
<221> NAME/KEY: modified_base
<222> LOCATION: (705)..(705)
<223> OTHER INFORMATION: n is a, c, g, or t
<220> FEATURE:
<221> NAME/KEY: modified_base
<222> LOCATION: (729)..(729)
<223> OTHER INFORMATION: n is a, c, g, or t
<220> FEATURE:
<221> NAME/KEY: modified_base
<222> LOCATION: (735)..(735)
<223> OTHER INFORMATION: n is a, c, g, or t
<220> FEATURE:
<221> NAME/KEY: modified_base
<222> LOCATION: (740)..(740)
<223> OTHER INFORMATION: n is a, c, g, or t
<220> FEATURE:
<221> NAME/KEY: modified_base
<222> LOCATION: (747)..(747)
<223> OTHER INFORMATION: n is a, c, g, or t
<220> FEATURE:
<221> NAME/KEY: modified_base
<222> LOCATION: (767)..(767)
<223> OTHER INFORMATION: n is a, c, g, or t

<400> SEQUENCE: 23

```
cctttgagtt tcnttataac ttcctgtaca aatcacttat ctataaaata atggttaacn     60

tttactcctt aattcacaaa aagatcacaa anngcaagat ccttcccaag aaaaccttac    120

tgtaaaccaa gacattccca ctatttagac taggttttaa ctcaaaggtt aagaactcaa    180

aggttgagaa agacaaactg gagcatttgt cttttattta ccagttgcat accttaattc    240

tgcagatgga taatctggtt gagataagca ttgccatctc tcaattttta caaaacaaaa    300

agctaccaac aagaagttaa tggtgaagaa aaatttgtct caaaaataac acanttgaga    360

aatagctttg tattaagtgc agtacttata acatccctga tgtcaaatgt acaaaattta    420

gctttaggtc actaaagcat gtttaccctt ttgaagaaac atgtattgct aggtcagcca    480

tcctacttca ctggaaataa cgttaaactt gtagactggt caaatggcca atcaaaatga    540

ctaagaaaca ttatcgggng gtttttggt tggttgggtt ttcatccttt ctctttcctt    600

tcggtcaaaa attcagttcc catcctaaac caaactctnt gncctnttgc angggnttan    660

aaaagttgcc ntttgncact nttgaacctt naaganggat ttgcntggta ttgaataaga    720

atccggagna tattntaatn gggtttnaaa attttccccc taacctn                767
```

<210> SEQ ID NO 24
<211> LENGTH: 802
<212> TYPE: DNA
<213> ORGANISM: Homo sapiens
<220> FEATURE:
<221> NAME/KEY: modified_base
<222> LOCATION: (2)..(3)
<223> OTHER INFORMATION: n is a, c, g, or t
<220> FEATURE:
<221> NAME/KEY: modified_base
<222> LOCATION: (5)..(6)
<223> OTHER INFORMATION: n is a, c, g, or t
<220> FEATURE:
<221> NAME/KEY: modified_base
<222> LOCATION: (8)..(10)
<223> OTHER INFORMATION: n is a, c, g, or t
<220> FEATURE:
<221> NAME/KEY: modified_base
<222> LOCATION: (14)..(14)
<223> OTHER INFORMATION: n is a, c, g, or t
<220> FEATURE:
<221> NAME/KEY: modified_base
<222> LOCATION: (22)..(22)
<223> OTHER INFORMATION: n is a, c, g, or t
<220> FEATURE:
<221> NAME/KEY: modified_base
<222> LOCATION: (25)..(28)
<223> OTHER INFORMATION: n is a, c, g, or t
<220> FEATURE:
<221> NAME/KEY: modified_base
<222> LOCATION: (42)..(42)
<223> OTHER INFORMATION: n is a, c, g, or t
<220> FEATURE:
<221> NAME/KEY: modified_base
<222> LOCATION: (587)..(587)
<223> OTHER INFORMATION: n is a, c, g, or t
<220> FEATURE:
<221> NAME/KEY: modified_base
<222> LOCATION: (612)..(612)
<223> OTHER INFORMATION: n is a, c, g, or t
<220> FEATURE:
<221> NAME/KEY: modified_base
<222> LOCATION: (632)..(632)
<223> OTHER INFORMATION: n is a, c, g, or t
<220> FEATURE:
<221> NAME/KEY: modified_base
<222> LOCATION: (640)..(640)
<223> OTHER INFORMATION: n is a, c, g, or t
<220> FEATURE:
<221> NAME/KEY: modified_base
<222> LOCATION: (694)..(694)
<223> OTHER INFORMATION: n is a, c, g, or t
<220> FEATURE:
<221> NAME/KEY: modified_base
<222> LOCATION: (706)..(706)
<223> OTHER INFORMATION: n is a, c, g, or t
<220> FEATURE:
<221> NAME/KEY: modified_base
<222> LOCATION: (723)..(723)
<223> OTHER INFORMATION: n is a, c, g, or t
<220> FEATURE:
<221> NAME/KEY: modified_base
<222> LOCATION: (743)..(743)
<223> OTHER INFORMATION: n is a, c, g, or t
<220> FEATURE:
<221> NAME/KEY: modified_base
<222> LOCATION: (751)..(751)
<223> OTHER INFORMATION: n is a, c, g, or t
<220> FEATURE:
<221> NAME/KEY: modified_base
<222> LOCATION: (771)..(771)
<223> OTHER INFORMATION: n is a, c, g, or t
<220> FEATURE:
<221> NAME/KEY: modified_base
<222> LOCATION: (779)..(779)
<223> OTHER INFORMATION: n is a, c, g, or t
<220> FEATURE:
<221> NAME/KEY: modified_base
<222> LOCATION: (796)..(796)
<223> OTHER INFORMATION: n is a, c, g, or t

<400> SEQUENCE: 24
gnngnngnnn gttnggggcg gnttnnnntt tggaattcct tnagcactgt tggcctactg 60
gaatacattt tttctttgtc ttttgaagac atggtttcca actgtgctca gatgcgagat 120
aggaagtctg tggtctttat aagtaatagt aatggctctc agcagatgct tgtgttgttt 180
ttagagagta tcatcttaaa tacaattatc gaaattaatg taaaattatg gtactgcctt 240
cattcctaaa aagatacatg agaaatgtcc tgcaaatctc cttgaaattt atgactttga 300
tggaggtata ccctcacctt ctgatttgtt ggcattcaaa agttttaaag acagagtgag 360
caacagataa gcacttttga agtagactgg tattgtagca tagtaaaaat aattttacat 420

-continued

```
gatggatgat ttgtgaatgt ttatcttgaa cctctggaag aagaggaata gaataattaa    480

cttataatta gccaccagta ttaagagggt ggagactggg gagggacagg tgagtaaact    540

gatagagggt caagtgggtt aagaaaatgt caacatggga gaatttncta aattaagtgg    600

aattagactt gncttgccaa tcttttgagt gnattaatgn gctagaatat gataatcaac    660

aaccaaaaag ggaatatatg ccagttgaca aaantttcaa aaatgnattc ctaactgtag    720

ttncaactgg ttaaatcctt tangatttag ntaaaatcct tgggattaag nccatcttna    780

aaaggaactt aaaatntgat tt                                              802
```

```
<210> SEQ ID NO 25
<211> LENGTH: 795
<212> TYPE: DNA
<213> ORGANISM: Homo sapiens
<220> FEATURE:
<221> NAME/KEY: modified_base
<222> LOCATION: (7)..(7)
<223> OTHER INFORMATION: n is a, c, g, or t
<220> FEATURE:
<221> NAME/KEY: modified_base
<222> LOCATION: (9)..(10)
<223> OTHER INFORMATION: n is a, c, g, or t
<220> FEATURE:
<221> NAME/KEY: modified_base
<222> LOCATION: (31)..(31)
<223> OTHER INFORMATION: n is a, c, g, or t
<220> FEATURE:
<221> NAME/KEY: modified_base
<222> LOCATION: (36)..(36)
<223> OTHER INFORMATION: n is a, c, g, or t
<220> FEATURE:
<221> NAME/KEY: modified_base
<222> LOCATION: (560)..(560)
<223> OTHER INFORMATION: n is a, c, g, or t
<220> FEATURE:
<221> NAME/KEY: modified_base
<222> LOCATION: (576)..(576)
<223> OTHER INFORMATION: n is a, c, g, or t
<220> FEATURE:
<221> NAME/KEY: modified_base
<222> LOCATION: (587)..(587)
<223> OTHER INFORMATION: n is a, c, g, or t
<220> FEATURE:
<221> NAME/KEY: modified_base
<222> LOCATION: (603)..(603)
<223> OTHER INFORMATION: n is a, c, g, or t
<220> FEATURE:
<221> NAME/KEY: modified_base
<222> LOCATION: (614)..(614)
<223> OTHER INFORMATION: n is a, c, g, or t
<220> FEATURE:
<221> NAME/KEY: modified_base
<222> LOCATION: (632)..(632)
<223> OTHER INFORMATION: n is a, c, g, or t
<220> FEATURE:
<221> NAME/KEY: modified_base
<222> LOCATION: (641)..(641)
<223> OTHER INFORMATION: n is a, c, g, or t
<220> FEATURE:
<221> NAME/KEY: modified_base
<222> LOCATION: (645)..(645)
<223> OTHER INFORMATION: n is a, c, g, or t
<220> FEATURE:
<221> NAME/KEY: modified_base
<222> LOCATION: (653)..(653)
<223> OTHER INFORMATION: n is a, c, g, or t
<220> FEATURE:
<221> NAME/KEY: modified_base
<222> LOCATION: (665)..(665)
<223> OTHER INFORMATION: n is a, c, g, or t
<220> FEATURE:
<221> NAME/KEY: modified_base
<222> LOCATION: (676)..(676)
<223> OTHER INFORMATION: n is a, c, g, or t
```

-continued

<220> FEATURE:
<221> NAME/KEY: modified_base
<222> LOCATION: (683)..(683)
<223> OTHER INFORMATION: n is a, c, g, or t
<220> FEATURE:
<221> NAME/KEY: modified_base
<222> LOCATION: (700)..(700)
<223> OTHER INFORMATION: n is a, c, g, or t
<220> FEATURE:
<221> NAME/KEY: modified_base
<222> LOCATION: (709)..(709)
<223> OTHER INFORMATION: n is a, c, g, or t
<220> FEATURE:
<221> NAME/KEY: modified_base
<222> LOCATION: (713)..(713)
<223> OTHER INFORMATION: n is a, c, g, or t
<220> FEATURE:
<221> NAME/KEY: modified_base
<222> LOCATION: (729)..(729)
<223> OTHER INFORMATION: n is a, c, g, or t
<220> FEATURE:
<221> NAME/KEY: modified_base
<222> LOCATION: (736)..(736)
<223> OTHER INFORMATION: n is a, c, g, or t
<220> FEATURE:
<221> NAME/KEY: modified_base
<222> LOCATION: (739)..(739)
<223> OTHER INFORMATION: n is a, c, g, or t
<220> FEATURE:
<221> NAME/KEY: modified_base
<222> LOCATION: (742)..(742)
<223> OTHER INFORMATION: n is a, c, g, or t
<220> FEATURE:
<221> NAME/KEY: modified_base
<222> LOCATION: (746)..(746)
<223> OTHER INFORMATION: n is a, c, g, or t
<220> FEATURE:
<221> NAME/KEY: modified_base
<222> LOCATION: (749)..(749)
<223> OTHER INFORMATION: n is a, c, g, or t
<220> FEATURE:
<221> NAME/KEY: modified_base
<222> LOCATION: (759)..(760)
<223> OTHER INFORMATION: n is a, c, g, or t
<220> FEATURE:
<221> NAME/KEY: modified_base
<222> LOCATION: (770)..(772)
<223> OTHER INFORMATION: n is a, c, g, or t
<220> FEATURE:
<221> NAME/KEY: modified_base
<222> LOCATION: (776)..(776)
<223> OTHER INFORMATION: n is a, c, g, or t
<220> FEATURE:
<221> NAME/KEY: modified_base
<222> LOCATION: (780)..(780)
<223> OTHER INFORMATION: n is a, c, g, or t
<220> FEATURE:
<221> NAME/KEY: modified_base
<222> LOCATION: (783)..(783)
<223> OTHER INFORMATION: n is a, c, g, or t
<220> FEATURE:
<221> NAME/KEY: modified_base
<222> LOCATION: (785)..(785)
<223> OTHER INFORMATION: n is a, c, g, or t
<220> FEATURE:
<221> NAME/KEY: modified_base
<222> LOCATION: (794)..(795)
<223> OTHER INFORMATION: n is a, c, g, or t

<400> SEQUENCE: 25
gaggggngnn cttgtggcct tttttttttg ntttanggta aggtctcact ctgttgccta 60
ggctggaatg cagtggcaca accatggctc actgcagcca tgacctcctg ggctccagtg 120
agcctcctgc ctctcagcct cccaagtagc caagactata cacacatgcc ataaagcctg 180
gctaattttc ttattttttc gtagagatgg ggtcttgcta ttgccccaga tggtcttgaa 240

-continued

```
ctcctggcct caagtgattc tcccagcttg gttccccaaa gtgctagaat tataggcgtg    300

agccactgta ccttgcctac aaccaaattt gagtaacaga ttatatttgt gaaactgttt    360

agtatacatg gcttccatgt aacattttat ttggggaaag aatgtttcat tgcttaaaaa    420

agctcataaa tcacgaatgc atgttagtta tcattttata gggtacaata tcagaaaaag    480

aaatctcctt ttgcaccaag aatgggttca aaccaacact tttgcactct tatttagaat    540

agattaatac ttgtaagcan gaaatagtac ctcttntggg caacagntat gggaaacctt    600

ctnctttgaa atgncatttc ttaagaacca anccaaaaca ncttnttact ttngggccat    660

tgganttaga atctgnttca ttnatccata atagttctan ttttttggnt ggnccccttta   720

acactttgnt ccaaanttng gngganctng ctggccttnn aaagctgaan nngttnccan    780

tanantttttc cgtnn                                                    795
```

<210> SEQ ID NO 26
<211> LENGTH: 804
<212> TYPE: DNA
<213> ORGANISM: Homo sapiens
<220> FEATURE:
<221> NAME/KEY: modified_base
<222> LOCATION: (1)..(2)
<223> OTHER INFORMATION: n is a, c, g, or t
<220> FEATURE:
<221> NAME/KEY: modified_base
<222> LOCATION: (4)..(7)
<223> OTHER INFORMATION: n is a, c, g, or t
<220> FEATURE:
<221> NAME/KEY: modified_base
<222> LOCATION: (10)..(12)
<223> OTHER INFORMATION: n is a, c, g, or t
<220> FEATURE:
<221> NAME/KEY: modified_base
<222> LOCATION: (16)..(16)
<223> OTHER INFORMATION: n is a, c, g, or t
<220> FEATURE:
<221> NAME/KEY: modified_base
<222> LOCATION: (18)..(18)
<223> OTHER INFORMATION: n is a, c, g, or t
<220> FEATURE:
<221> NAME/KEY: modified_base
<222> LOCATION: (20)..(21)
<223> OTHER INFORMATION: n is a, c, g, or t
<220> FEATURE:
<221> NAME/KEY: modified_base
<222> LOCATION: (23)..(29)
<223> OTHER INFORMATION: n is a, c, g, or t
<220> FEATURE:
<221> NAME/KEY: modified_base
<222> LOCATION: (36)..(36)
<223> OTHER INFORMATION: n is a, c, g, or t
<220> FEATURE:
<221> NAME/KEY: modified_base
<222> LOCATION: (43)..(43)
<223> OTHER INFORMATION: n is a, c, g, or t
<220> FEATURE:
<221> NAME/KEY: modified_base
<222> LOCATION: (570)..(570)
<223> OTHER INFORMATION: n is a, c, g, or t
<220> FEATURE:
<221> NAME/KEY: modified_base
<222> LOCATION: (617)..(617)
<223> OTHER INFORMATION: n is a, c, g, or t
<220> FEATURE:
<221> NAME/KEY: modified_base
<222> LOCATION: (650)..(650)
<223> OTHER INFORMATION: n is a, c, g, or t
<220> FEATURE:
<221> NAME/KEY: modified_base
<222> LOCATION: (695)..(695)
<223> OTHER INFORMATION: n is a, c, g, or t
<220> FEATURE:
<221> NAME/KEY: modified_base

```
<222> LOCATION: (738)..(738)
<223> OTHER INFORMATION: n is a, c, g, or t
<220> FEATURE:
<221> NAME/KEY: modified_base
<222> LOCATION: (743)..(743)
<223> OTHER INFORMATION: n is a, c, g, or t
<220> FEATURE:
<221> NAME/KEY: modified_base
<222> LOCATION: (749)..(749)
<223> OTHER INFORMATION: n is a, c, g, or t
<220> FEATURE:
<221> NAME/KEY: modified_base
<222> LOCATION: (759)..(759)
<223> OTHER INFORMATION: n is a, c, g, or t
<220> FEATURE:
<221> NAME/KEY: modified_base
<222> LOCATION: (779)..(779)
<223> OTHER INFORMATION: n is a, c, g, or t

<400> SEQUENCE: 26

nngnnnnagn nngttngngn ngnnnnnnnt ttggantcct tgncactgtt ggcctactgg      60

tatgtatgta gcaaacctgc acattctgca catgtacccc agaatgtttt ttaaaaaata     120

aaatactttt aaaaagagag aattgttatc ataattttaa acttcctctg ctttcccttg     180

cctgaaaatt ggagataatg atatttcctg ttaatatacc tcttgaggat tagaaaaaaa     240

gttatatttg tcatcatgat tgttgtgatc aaaaccatag tcaatctcaa ccagttactg     300

aatgctcttg attttggcta ttagacttta atgagtaaat atgaacataa agagtcatcc     360

agaaaaggca ttctgctctc cctatccttt ccttcctctc accctctttt cttttaaatc     420

actaagaatc actccattcc cagtgttttt gccagcagtc atttcatagg aggcaaatat     480

tacttttaag cagtatatgc ctgaccttta aaaaaatggt agatatatgt ttggcaactt     540

aaggtaacag aatactaagt actggattgn cagtcaaata atgaagtcca tattctggtt     600

taacatcttt aagttgncat tgcagtcatt taatatcatt cattaaaagn atactaatta     660

catttcaggg gcactatata tggaaaatca gaatncaaat ataagggtaa tttttcctc      720

atgcaaaagg gaaaaccnca aancctttna atgggatcnt taataattaa aaaggaccnt     780

ttcattacta ggagaaaaag gttt                                            804


<210> SEQ ID NO 27
<211> LENGTH: 766
<212> TYPE: DNA
<213> ORGANISM: Homo sapiens
<220> FEATURE:
<221> NAME/KEY: modified_base
<222> LOCATION: (4)..(4)
<223> OTHER INFORMATION: n is a, c, g, or t
<220> FEATURE:
<221> NAME/KEY: modified_base
<222> LOCATION: (7)..(12)
<223> OTHER INFORMATION: n is a, c, g, or t
<220> FEATURE:
<221> NAME/KEY: modified_base
<222> LOCATION: (34)..(34)
<223> OTHER INFORMATION: n is a, c, g, or t
<220> FEATURE:
<221> NAME/KEY: modified_base
<222> LOCATION: (515)..(515)
<223> OTHER INFORMATION: n is a, c, g, or t
<220> FEATURE:
<221> NAME/KEY: modified_base
<222> LOCATION: (528)..(528)
<223> OTHER INFORMATION: n is a, c, g, or t
<220> FEATURE:
<221> NAME/KEY: modified_base
<222> LOCATION: (625)..(625)
<223> OTHER INFORMATION: n is a, c, g, or t
<220> FEATURE:
```

<221> NAME/KEY: modified_base
<222> LOCATION: (666)..(666)
<223> OTHER INFORMATION: n is a, c, g, or t
<220> FEATURE:
<221> NAME/KEY: modified_base
<222> LOCATION: (694)..(694)
<223> OTHER INFORMATION: n is a, c, g, or t
<220> FEATURE:
<221> NAME/KEY: modified_base
<222> LOCATION: (726)..(726)
<223> OTHER INFORMATION: n is a, c, g, or t
<220> FEATURE:
<221> NAME/KEY: modified_base
<222> LOCATION: (747)..(747)
<223> OTHER INFORMATION: n is a, c, g, or t

<400> SEQUENCE: 27
gagnggnnnn nnctttgtgg cctttttttt tttnttttga aatggatttt tgctcttgtt 60
gcccaggctg gagtgcaatg gtgtgatctt ggctcaccac cacctccgct tccctggttc 120
aagacattct cctgctgcag cctcctgagt agctgggatt acaggcatgc accaccatgc 180
ctagccaatt ttgtatttct tgtagagatg gggtttctcc acgttggtca agctggtctc 240
gaactcccaa cctcaggtga tccgcccacc tcggcctccc aaagtgctgg gattacaggc 300
atgagccacc gcgcctggcc catttgttct ttttgtagtc ttgattttag attgcatata 360
gaagagagac caaactgcat agaaaagggc ctttcacaaa agaaagaaaa tctgcacttg 420
catttctctg gctcaatgtc ccttctcctc aaagcattct ccttcctctc ctacctcttt 480
tcagaacaaa ccaatttttc cttcatctct acttntggta cccagctnac tttccaaatc 540
ctagacacgt tatctaagtt atgaagcttg atgtcatccc aagaacttta ttagcccatg 600
ctccaaaaaa tgggggatct tgcanggagg aagcaagtaa cacattgaaa ggcacattgc 660
cccaanggaa aagccagacc ttgacagaga cacntgaacg ttggtcaagg aagctaggag 720
tctggnctaa tggtgaaaaa tggaacngga ggctactaaa tgggca 766

<210> SEQ ID NO 28
<211> LENGTH: 751
<212> TYPE: DNA
<213> ORGANISM: Homo sapiens
<220> FEATURE:
<221> NAME/KEY: modified_base
<222> LOCATION: (436)..(436)
<223> OTHER INFORMATION: n is a, c, g, or t
<220> FEATURE:
<221> NAME/KEY: modified_base
<222> LOCATION: (515)..(515)
<223> OTHER INFORMATION: n is a, c, g, or t
<220> FEATURE:
<221> NAME/KEY: modified_base
<222> LOCATION: (603)..(603)
<223> OTHER INFORMATION: n is a, c, g, or t
<220> FEATURE:
<221> NAME/KEY: modified_base
<222> LOCATION: (613)..(613)
<223> OTHER INFORMATION: n is a, c, g, or t
<220> FEATURE:
<221> NAME/KEY: modified_base
<222> LOCATION: (691)..(691)
<223> OTHER INFORMATION: n is a, c, g, or t
<220> FEATURE:
<221> NAME/KEY: modified_base
<222> LOCATION: (699)..(699)
<223> OTHER INFORMATION: n is a, c, g, or t
<220> FEATURE:
<221> NAME/KEY: modified_base
<222> LOCATION: (705)..(705)
<223> OTHER INFORMATION: n is a, c, g, or t
<220> FEATURE:
<221> NAME/KEY: modified_base -continued
<222> LOCATION: (711)..(711)
<223> OTHER INFORMATION: n is a, c, g, or t
<220> FEATURE:
<221> NAME/KEY: modified_base
<222> LOCATION: (717)..(717)
<223> OTHER INFORMATION: n is a, c, g, or t
<220> FEATURE:
<221> NAME/KEY: modified_base
<222> LOCATION: (733)..(733)
<223> OTHER INFORMATION: n is a, c, g, or t
<220> FEATURE:
<221> NAME/KEY: modified_base
<222> LOCATION: (751)..(751)
<223> OTHER INFORMATION: n is a, c, g, or t

<400> SEQUENCE: 28
gcctactgga tattggggat tcatatgctt atgcagaacc ccaaatccta tctttctctg 60
tgttcactct tttggctgta cccatgtttt caccataacc ttttcgtggc aatgtgtaat 120
aatctttggc tagtctatgg tgttgtatac ttgcacggtc atgtaggaca cgtacctcca 180
tttctttcta tgtgtctctc tcttctgcct ctttttatc acattgtcat tatatagaga 240
gagtattata tcctggaata atttatttaa tgaaggggaa gttcttttaa taatcctagt 300
gcttgcaagg tttccccttt aacttttatt tacttttact ttgaagaact aacagtagaa 360
ccttttattg ttccaacata ataggatttt tttctatttt ccattgagct ttttgtgttt 420
gtttatttaa tattgntctt taataacttt ccacaacccg ttatatcttt atgggtaatt 480
attttctcac ttattttata attttggatt ttganatcat ttttaagtga gggttttcaa 540
gtggggaatc tatgtggcat ttggaagatg tgtccttcca gagtttggtt ttggtttttg 600
ggntggtggt ggntttttc tggggatcct ggtgacctca atggttccaa tatatatttg 660
aatgctcaac ctgagtaagg aggcctatgg ngacaaatnt aagangaggc ntggttnctt 720
catccctatg acngccaaaa tcccaatttt n 751

<210> SEQ ID NO 29
<211> LENGTH: 749
<212> TYPE: DNA
<213> ORGANISM: Homo sapiens
<220> FEATURE:
<221> NAME/KEY: modified_base
<222> LOCATION: (89)..(89)
<223> OTHER INFORMATION: n is a, c, g, or t
<220> FEATURE:
<221> NAME/KEY: modified_base
<222> LOCATION: (532)..(532)
<223> OTHER INFORMATION: n is a, c, g, or t
<220> FEATURE:
<221> NAME/KEY: modified_base
<222> LOCATION: (569)..(569)
<223> OTHER INFORMATION: n is a, c, g, or t
<220> FEATURE:
<221> NAME/KEY: modified_base
<222> LOCATION: (572)..(572)
<223> OTHER INFORMATION: n is a, c, g, or t
<220> FEATURE:
<221> NAME/KEY: modified_base
<222> LOCATION: (582)..(582)
<223> OTHER INFORMATION: n is a, c, g, or t
<220> FEATURE:
<221> NAME/KEY: modified_base
<222> LOCATION: (682)..(682)
<223> OTHER INFORMATION: n is a, c, g, or t
<220> FEATURE:
<221> NAME/KEY: modified_base
<222> LOCATION: (688)..(688)
<223> OTHER INFORMATION: n is a, c, g, or t
<220> FEATURE:
<221> NAME/KEY: modified_base
<222> LOCATION: (691)..(691)

<223> OTHER INFORMATION: n is a, c, g, or t
<220> FEATURE:
<221> NAME/KEY: modified_base
<222> LOCATION: (724)..(724)
<223> OTHER INFORMATION: n is a, c, g, or t
<220> FEATURE:
<221> NAME/KEY: modified_base
<222> LOCATION: (734)..(734)
<223> OTHER INFORMATION: n is a, c, g, or t

<400> SEQUENCE: 29

```
gagacagggt ctcattatgt cacccaggct ggagtgtagt gcaatcacag ctcactgcag     60

cctcgacctc ctgggctcaa gtgatcctnc cacctcagcc tcttgagtgg ctgggggcat    120

aggtgcatgc caccacacct ggctagttta tttttcattt tttgcagaga tggggtctca    180

ttatcttgcc caggctggta ttgaatttct gggctcaagc aatcttcctg cctcagcctc    240

ctgaagtgct ggaattacag gtgtgagcca ctgtgcccag ccaatttttt gctttttaaa    300

aatctgattt gctcattgtt gtatctccag tgtgcagaac agtgcctggc acagaaaagc    360

agcctgataa atatttatgg aatgaatgaa tgtctaaagt agtcactgaa attaattata    420

ttctcatttt tatatctcat tcatcaatat catctcttaa acatcaaaag aaacgatgtc    480

caataggttt agctgctttt attaaagcct tttaagttga tatagaacat gnattatgac    540

taggtttaaa tcaatcttct tataaaatnt anccagatgc tnttaaaatt aatcatgtca    600

cttttaaagt tccaatccat tgaaaaagtt tggaaaatta aaggctctct ttatccaaaa    660

ggtactcaac agtaagccaa tnccatantt ngggctataa cctacccgac ttttttaaac    720

ggcntttttt aacnttttgg atttaaaaa                                      749
```

<210> SEQ ID NO 30
<211> LENGTH: 735
<212> TYPE: DNA
<213> ORGANISM: Homo sapiens
<220> FEATURE:
<221> NAME/KEY: modified_base
<222> LOCATION: (581)..(581)
<223> OTHER INFORMATION: n is a, c, g, or t
<220> FEATURE:
<221> NAME/KEY: modified_base
<222> LOCATION: (610)..(610)
<223> OTHER INFORMATION: n is a, c, g, or t
<220> FEATURE:
<221> NAME/KEY: modified_base
<222> LOCATION: (665)..(665)
<223> OTHER INFORMATION: n is a, c, g, or t
<220> FEATURE:
<221> NAME/KEY: modified_base
<222> LOCATION: (695)..(695)
<223> OTHER INFORMATION: n is a, c, g, or t
<220> FEATURE:
<221> NAME/KEY: modified_base
<222> LOCATION: (703)..(703)
<223> OTHER INFORMATION: n is a, c, g, or t
<220> FEATURE:
<221> NAME/KEY: modified_base
<222> LOCATION: (713)..(713)
<223> OTHER INFORMATION: n is a, c, g, or t
<220> FEATURE:
<221> NAME/KEY: modified_base
<222> LOCATION: (724)..(724)
<223> OTHER INFORMATION: n is a, c, g, or t
<220> FEATURE:
<221> NAME/KEY: modified_base
<222> LOCATION: (728)..(728)
<223> OTHER INFORMATION: n is a, c, g, or t

<400> SEQUENCE: 30

```
cactgttggc ctactgggaa gaaacctaga actatgaatc ttagaatgga agtcaagatg     60
```

```
aaaaggcaaa agaaaggatt cttgcatatt cttggatgtt tcaaatgtag ggttttggaa    120

tattcctcta tttgattgat ttcaacgtac gaatctgctc ttggaaagag agagattcct    180

gtgtgtttac aggacatata aatgtgctcc aaaggactga actaacatgc ctggaagtag    240

acatatggaa tgaatattgt catttagtgc agttatcatg gaaagttata tcattttctt    300

gtaatattac aacagctcaa aatgtgtttg gaactctttt ttggaggtgc ctttacagaa    360

tcagcaatac attcaaatca gtgtgtgatt tttttttttc ccttttgagg aggcatttga    420

gttttcagaa acagcctaca gtaatttact gttaattcta gtgactacag tgggtaatca    480

cacattttag ctgtttggga tcaaaagcag acttagattt aaaaaatact aaaaataatt    540

ttctcatgtg gttcataaag cacatggaat tgggttaatg ntttaatgtc aaactttatg    600

tgagccagan gatgaacctt ttggaagcat aaatgcaaat agcaagaagt tttctctcat    660

ttctncatct gaaactgctc atcatgtatc ctcanaatat tancatgcac gtnggactct    720

tctnaaancc ggggc                                                      735
```

```
<210> SEQ ID NO 31
<211> LENGTH: 735
<212> TYPE: DNA
<213> ORGANISM: Homo sapiens
<220> FEATURE:
<221> NAME/KEY: modified_base
<222> LOCATION: (2)..(2)
<223> OTHER INFORMATION: n is a, c, g, or t
<220> FEATURE:
<221> NAME/KEY: modified_base
<222> LOCATION: (627)..(627)
<223> OTHER INFORMATION: n is a, c, g, or t
<220> FEATURE:
<221> NAME/KEY: modified_base
<222> LOCATION: (668)..(668)
<223> OTHER INFORMATION: n is a, c, g, or t
<220> FEATURE:
<221> NAME/KEY: modified_base
<222> LOCATION: (680)..(680)
<223> OTHER INFORMATION: n is a, c, g, or t
<220> FEATURE:
<221> NAME/KEY: modified_base
<222> LOCATION: (682)..(682)
<223> OTHER INFORMATION: n is a, c, g, or t
<220> FEATURE:
<221> NAME/KEY: modified_base
<222> LOCATION: (702)..(702)
<223> OTHER INFORMATION: n is a, c, g, or t
<220> FEATURE:
<221> NAME/KEY: modified_base
<222> LOCATION: (709)..(709)
<223> OTHER INFORMATION: n is a, c, g, or t
<220> FEATURE:
<221> NAME/KEY: modified_base
<222> LOCATION: (723)..(723)
<223> OTHER INFORMATION: n is a, c, g, or t
<220> FEATURE:
<221> NAME/KEY: modified_base
<222> LOCATION: (735)..(735)
<223> OTHER INFORMATION: n is a, c, g, or t

<400> SEQUENCE: 31
```

```
tncccttttg agatggcgtc tcgctctgtc gcccaggctg gagtgcagtg gccgtgatct     60

cggctcactg caagctccac ctcctgggtt cacgccattc tcccgcttca gcctcccgag    120

taactgggac tataggtgcc caccaccacg cccggctaat tttgtttttc tatttgtagt    180

agagacaggg tttcacagta gagccaggat ggtctcgatc tcctgacctc gtgattcgcc    240

tgccccggcc tcccaaagtg ctgggattac aggcgtgagc caccacgccc tgccacattg    300
```

```
ttactttcca ttgaaactaa ataccaaaag agaggttcat agaggccttc agtgtagttt    360

agtaatgaca gtttactgcc ttttgctttt ggaaagaaga aaatatacat agttcacaga    420

gctctgcctt caaaggcaca tggagaatgg gagttagcct gtggcattac cttgggaact    480

ttagtgatag ccacctacaa tttaaaatta tgtaaaattc gtgtcagaaa tgcagctctg    540

taaaacttac ttctacatag agaaaaaata ataatgcatc tggattttat taataccttc    600

ctgaaaaaca ccaggagaaa aaaagcncag gaaaatcaac tcctgattcc atgaagctct    660

ctaaacangt cttgagatan gnaaagctta ccctcctttt cnaacaggng ttccaaaagg    720

ctncctgata ttatn                                                      735
```

<210> SEQ ID NO 32
<211> LENGTH: 738
<212> TYPE: DNA
<213> ORGANISM: Homo sapiens
<220> FEATURE:
<221> NAME/KEY: modified_base
<222> LOCATION: (8)..(8)
<223> OTHER INFORMATION: n is a, c, g, or t
<220> FEATURE:
<221> NAME/KEY: modified_base
<222> LOCATION: (567)..(567)
<223> OTHER INFORMATION: n is a, c, g, or t
<220> FEATURE:
<221> NAME/KEY: modified_base
<222> LOCATION: (597)..(597)
<223> OTHER INFORMATION: n is a, c, g, or t
<220> FEATURE:
<221> NAME/KEY: modified_base
<222> LOCATION: (604)..(604)
<223> OTHER INFORMATION: n is a, c, g, or t
<220> FEATURE:
<221> NAME/KEY: modified_base
<222> LOCATION: (640)..(640)
<223> OTHER INFORMATION: n is a, c, g, or t
<220> FEATURE:
<221> NAME/KEY: modified_base
<222> LOCATION: (650)..(650)
<223> OTHER INFORMATION: n is a, c, g, or t
<220> FEATURE:
<221> NAME/KEY: modified_base
<222> LOCATION: (668)..(668)
<223> OTHER INFORMATION: n is a, c, g, or t
<220> FEATURE:
<221> NAME/KEY: modified_base
<222> LOCATION: (700)..(700)
<223> OTHER INFORMATION: n is a, c, g, or t
<220> FEATURE:
<221> NAME/KEY: modified_base
<222> LOCATION: (729)..(729)
<223> OTHER INFORMATION: n is a, c, g, or t

<400> SEQUENCE: 32

```
ctactggnat gaaaaggatg agcaaggaga aatgccccaa aggagactga cccggcgcgg     60

tgctggcggg agcgctcaag ggcagcggat ttgttgttgt tgctgttttc ctttgtgggt    120

gtttggtgct tgatttccag aaactctcca gcgacttgga cttcttcttt tttttttttt    180

ctttttagat agaagtgact gtgtggttgg tctctgaggt atttggggga ctctgtattt    240

gctcgtttac gtgttggaaa aaccaagtgg ctttggggtt tcgccctatc ccactccctc    300

tctttcctgc tccattggtt ccttaagaaa tgctatattt tgtgagtgca agctggcttg    360

gggagccctc tcttgtgtaa atgtccccca tgtttctgaa aagtgctgta agtttaagtc    420

ccctcacccc cagcactgcc caaacagggg ccaagtgcgc cccaattcca agaatgaagg    480

cagagcgaca acagtgcgga caccccggct gctagcccac ggtgaacccg gcggggttgc    540

ccaccagttg cgaaagcccc ctttctnaag gagcacgcgg acctcggtgg agatctncaa    600
```

tgangcttaa aggaacccaa ggcctcggcc gggttggggn ttggcctcan tgcattggac 660
ccctggtntt ttccctgaag gctggctcgc gtggccggcn cgggtggtgg gccttccggt 720
tcttgcccna ggaccaat 738

<210> SEQ ID NO 33
<211> LENGTH: 785
<212> TYPE: DNA
<213> ORGANISM: Homo sapiens
<220> FEATURE:
<221> NAME/KEY: modified_base
<222> LOCATION: (2)..(3)
<223> OTHER INFORMATION: n is a, c, g, or t
<220> FEATURE:
<221> NAME/KEY: modified_base
<222> LOCATION: (6)..(11)
<223> OTHER INFORMATION: n is a, c, g, or t
<220> FEATURE:
<221> NAME/KEY: modified_base
<222> LOCATION: (40)..(40)
<223> OTHER INFORMATION: n is a, c, g, or t
<220> FEATURE:
<221> NAME/KEY: modified_base
<222> LOCATION: (90)..(90)
<223> OTHER INFORMATION: n is a, c, g, or t
<220> FEATURE:
<221> NAME/KEY: modified_base
<222> LOCATION: (110)..(110)
<223> OTHER INFORMATION: n is a, c, g, or t
<220> FEATURE:
<221> NAME/KEY: modified_base
<222> LOCATION: (115)..(115)
<223> OTHER INFORMATION: n is a, c, g, or t
<220> FEATURE:
<221> NAME/KEY: modified_base
<222> LOCATION: (132)..(132)
<223> OTHER INFORMATION: n is a, c, g, or t
<220> FEATURE:
<221> NAME/KEY: modified_base
<222> LOCATION: (134)..(134)
<223> OTHER INFORMATION: n is a, c, g, or t
<220> FEATURE:
<221> NAME/KEY: modified_base
<222> LOCATION: (154)..(154)
<223> OTHER INFORMATION: n is a, c, g, or t
<220> FEATURE:
<221> NAME/KEY: modified_base
<222> LOCATION: (208)..(208)
<223> OTHER INFORMATION: n is a, c, g, or t
<220> FEATURE:
<221> NAME/KEY: modified_base
<222> LOCATION: (215)..(215)
<223> OTHER INFORMATION: n is a, c, g, or t
<220> FEATURE:
<221> NAME/KEY: modified_base
<222> LOCATION: (217)..(217)
<223> OTHER INFORMATION: n is a, c, g, or t
<220> FEATURE:
<221> NAME/KEY: modified_base
<222> LOCATION: (235)..(235)
<223> OTHER INFORMATION: n is a, c, g, or t
<220> FEATURE:
<221> NAME/KEY: modified_base
<222> LOCATION: (239)..(239)
<223> OTHER INFORMATION: n is a, c, g, or t
<220> FEATURE:
<221> NAME/KEY: modified_base
<222> LOCATION: (291)..(291)
<223> OTHER INFORMATION: n is a, c, g, or t
<220> FEATURE:
<221> NAME/KEY: modified_base
<222> LOCATION: (296)..(296)
<223> OTHER INFORMATION: n is a, c, g, or t
<220> FEATURE:
<221> NAME/KEY: modified_base
<222> LOCATION: (305)..(305)

-continued

<223> OTHER INFORMATION: n is a, c, g, or t
<220> FEATURE:
<221> NAME/KEY: modified_base
<222> LOCATION: (320)..(320)
<223> OTHER INFORMATION: n is a, c, g, or t
<220> FEATURE:
<221> NAME/KEY: modified_base
<222> LOCATION: (336)..(336)
<223> OTHER INFORMATION: n is a, c, g, or t
<220> FEATURE:
<221> NAME/KEY: modified_base
<222> LOCATION: (345)..(345)
<223> OTHER INFORMATION: n is a, c, g, or t
<220> FEATURE:
<221> NAME/KEY: modified_base
<222> LOCATION: (370)..(370)
<223> OTHER INFORMATION: n is a, c, g, or t
<220> FEATURE:
<221> NAME/KEY: modified_base
<222> LOCATION: (376)..(377)
<223> OTHER INFORMATION: n is a, c, g, or t
<220> FEATURE:
<221> NAME/KEY: modified_base
<222> LOCATION: (380)..(380)
<223> OTHER INFORMATION: n is a, c, g, or t
<220> FEATURE:
<221> NAME/KEY: modified_base
<222> LOCATION: (392)..(392)
<223> OTHER INFORMATION: n is a, c, g, or t
<220> FEATURE:
<221> NAME/KEY: modified_base
<222> LOCATION: (406)..(406)
<223> OTHER INFORMATION: n is a, c, g, or t
<220> FEATURE:
<221> NAME/KEY: modified_base
<222> LOCATION: (417)..(417)
<223> OTHER INFORMATION: n is a, c, g, or t
<220> FEATURE:
<221> NAME/KEY: modified_base
<222> LOCATION: (458)..(458)
<223> OTHER INFORMATION: n is a, c, g, or t
<220> FEATURE:
<221> NAME/KEY: modified_base
<222> LOCATION: (539)..(539)
<223> OTHER INFORMATION: n is a, c, g, or t
<220> FEATURE:
<221> NAME/KEY: modified_base
<222> LOCATION: (543)..(543)
<223> OTHER INFORMATION: n is a, c, g, or t
<220> FEATURE:
<221> NAME/KEY: modified_base
<222> LOCATION: (560)..(560)
<223> OTHER INFORMATION: n is a, c, g, or t
<220> FEATURE:
<221> NAME/KEY: modified_base
<222> LOCATION: (579)..(579)
<223> OTHER INFORMATION: n is a, c, g, or t
<220> FEATURE:
<221> NAME/KEY: modified_base
<222> LOCATION: (593)..(593)
<223> OTHER INFORMATION: n is a, c, g, or t
<220> FEATURE:
<221> NAME/KEY: modified_base
<222> LOCATION: (639)..(639)
<223> OTHER INFORMATION: n is a, c, g, or t
<220> FEATURE:
<221> NAME/KEY: modified_base
<222> LOCATION: (643)..(643)
<223> OTHER INFORMATION: n is a, c, g, or t
<220> FEATURE:
<221> NAME/KEY: modified_base
<222> LOCATION: (647)..(647)
<223> OTHER INFORMATION: n is a, c, g, or t
<220> FEATURE:
<221> NAME/KEY: modified_base
<222> LOCATION: (671)..(671)
<223> OTHER INFORMATION: n is a, c, g, or t
<220> FEATURE:
<221> NAME/KEY: modified_base
<222> LOCATION: (687)..(688)
<223> OTHER INFORMATION: n is a, c, g, or t
<220> FEATURE:
<221> NAME/KEY: modified_base
<222> LOCATION: (710)..(712)
<223> OTHER INFORMATION: n is a, c, g, or t
<220> FEATURE:
<221> NAME/KEY: modified_base
<222> LOCATION: (714)..(714)
<223> OTHER INFORMATION: n is a, c, g, or t
<220> FEATURE:
<221> NAME/KEY: modified_base
<222> LOCATION: (719)..(719)
<223> OTHER INFORMATION: n is a, c, g, or t
<220> FEATURE:
<221> NAME/KEY: modified_base
<222> LOCATION: (723)..(723)
<223> OTHER INFORMATION: n is a, c, g, or t
<220> FEATURE:
<221> NAME/KEY: modified_base
<222> LOCATION: (761)..(761)
<223> OTHER INFORMATION: n is a, c, g, or t
<220> FEATURE:
<221> NAME/KEY: modified_base
<222> LOCATION: (765)..(767)
<223> OTHER INFORMATION: n is a, c, g, or t
<220> FEATURE:
<221> NAME/KEY: modified_base
<222> LOCATION: (769)..(769)
<223> OTHER INFORMATION: n is a, c, g, or t
<220> FEATURE:
<221> NAME/KEY: modified_base
<222> LOCATION: (780)..(780)
<223> OTHER INFORMATION: n is a, c, g, or t
<220> FEATURE:
<221> NAME/KEY: modified_base
<222> LOCATION: (785)..(785)
<223> OTHER INFORMATION: n is a, c, g, or t

<400> SEQUENCE: 33
gnntgnnnnn nttttgtggc ctttatttga atcccttttn tttttctttt tttttttttt 60
tttttttttt ttttttttag ggccagcgtn tgggctccat ttgatcaggn cagcntttat 120
tagtaggaag cngnaacatt tacaactggt cctngggcag gaaccgggag ggccaccacc 180
cgcggccgcc cacgcgagcc cagccttnag ggganangagc agcgcgtcca atgcnctgng 240
gacaaacccc aacccgcccg aggccctggg ctcctttaag cctcactgga natctncacc 300
gaggncccgc gtgctccctn aggaaagggg gctttngcaa ctggngggca accccgccgg 360
gctttaccgn gggctnncan ccggggtgtc cncactgttg tcgctntgcc ttcattnttg 420
gaattggggc gcacttggcc cctgtttggg cagtgctngg ggtgagggga ctaaactaca 480
gcacttttca aaaacatggg ggacatttac acaagagagg gctccccaag ccagcttgna 540
ctnacaaaat atagcatttn ttaaggaacc aatggagcng gaaagaaagg gantgggata 600
tgggcgaaac cccaaagccc ttgggttttt caacacgtna acnagcnaat tcagattccc 660
caaatcctta nagaccaacc cacagtnnct ttttttaaa aagaaaaaan nnanggaana 720
atncaaatcc cttggaaagt tttgggaatc aacccccaaa ncccnnnang gaaaaccggn 780 ccccn 785

<210> SEQ ID NO 34
<211> LENGTH: 743
<212> TYPE: DNA
<213> ORGANISM: Homo sapiens
<220> FEATURE:
<221> NAME/KEY: modified_base
<222> LOCATION: (413)..(413)
<223> OTHER INFORMATION: n is a, c, g, or t
<220> FEATURE:

<221> NAME/KEY: modified_base
<222> LOCATION: (539)..(539)
<223> OTHER INFORMATION: n is a, c, g, or t
<220> FEATURE:
<221> NAME/KEY: modified_base
<222> LOCATION: (589)..(589)
<223> OTHER INFORMATION: n is a, c, g, or t
<220> FEATURE:
<221> NAME/KEY: modified_base
<222> LOCATION: (679)..(679)
<223> OTHER INFORMATION: n is a, c, g, or t
<220> FEATURE:
<221> NAME/KEY: modified_base
<222> LOCATION: (739)..(739)
<223> OTHER INFORMATION: n is a, c, g, or t

<400> SEQUENCE: 34
cctactgtga agaagatgaa gaagaagtgt ataaaatggc tggtgtgatg gcccagtgtg 60
ggggcctgga atgcatgctt aacagactcg cagggatcag agatttcaag cagggacgcc 120
accttctaac agtgctactg atattgttca gttactgcgt gaaggtgaaa gtcaaccggc 180
agcaactggt caaactggaa atgaacacct tgaacgtcat gctggggacc ctaaacctgg 240
cccttgtagc tgaacaagaa agcaaggaca gcgggggtgc agctgtggct gagcaggtgc 300
ttagcatcat ggagatcatt ctagatgagt ccaatgctga gcccctgagt gaggacaagg 360
gcaacctcct cctgacaggt gacaaggatc aactggtgat gctcttggac canatcaaca 420
gcacctttgt tcgctccaac cccagtgtgc tccagggcct gcttcgcatc atcccgtacc 480
tttcctttgg agaggtggag aaaatgcaca tcttggtgga gcgattcaaa ccatactgna 540
actttgataa atatgatgaa gatcacaagt ggtgatgata aaagtcttnc tggactgctt 600
ctgtaaaata gctgctggca tcaagaacaa cggcaatggg caccaacttg aaggatctga 660
ttcttcaaaa ggggatcanc cagaatgcct tggctacatg aaaagcacat ccttacgcca 720
agaatttgga tccgacatnt gga 743

<210> SEQ ID NO 35
<211> LENGTH: 778
<212> TYPE: DNA
<213> ORGANISM: Homo sapiens
<220> FEATURE:
<221> NAME/KEY: modified_base
<222> LOCATION: (2)..(3)
<223> OTHER INFORMATION: n is a, c, g, or t
<220> FEATURE:
<221> NAME/KEY: modified_base
<222> LOCATION: (5)..(5)
<223> OTHER INFORMATION: n is a, c, g, or t
<220> FEATURE:
<221> NAME/KEY: modified_base
<222> LOCATION: (8)..(12)
<223> OTHER INFORMATION: n is a, c, g, or t
<220> FEATURE:
<221> NAME/KEY: modified_base
<222> LOCATION: (30)..(32)
<223> OTHER INFORMATION: n is a, c, g, or t
<220> FEATURE:
<221> NAME/KEY: modified_base
<222> LOCATION: (35)..(35)
<223> OTHER INFORMATION: n is a, c, g, or t
<220> FEATURE:
<221> NAME/KEY: modified_base
<222> LOCATION: (515)..(515)
<223> OTHER INFORMATION: n is a, c, g, or t
<220> FEATURE:
<221> NAME/KEY: modified_base
<222> LOCATION: (570)..(570)
<223> OTHER INFORMATION: n is a, c, g, or t
<220> FEATURE:
<221> NAME/KEY: modified_base

```
<222> LOCATION: (573)..(573)
<223> OTHER INFORMATION: n is a, c, g, or t
<220> FEATURE:
<221> NAME/KEY: modified_base
<222> LOCATION: (584)..(584)
<223> OTHER INFORMATION: n is a, c, g, or t
<220> FEATURE:
<221> NAME/KEY: modified_base
<222> LOCATION: (604)..(604)
<223> OTHER INFORMATION: n is a, c, g, or t
<220> FEATURE:
<221> NAME/KEY: modified_base
<222> LOCATION: (622)..(622)
<223> OTHER INFORMATION: n is a, c, g, or t
<220> FEATURE:
<221> NAME/KEY: modified_base
<222> LOCATION: (656)..(656)
<223> OTHER INFORMATION: n is a, c, g, or t
<220> FEATURE:
<221> NAME/KEY: modified_base
<222> LOCATION: (674)..(674)
<223> OTHER INFORMATION: n is a, c, g, or t
<220> FEATURE:
<221> NAME/KEY: modified_base
<222> LOCATION: (683)..(683)
<223> OTHER INFORMATION: n is a, c, g, or t
<220> FEATURE:
<221> NAME/KEY: modified_base
<222> LOCATION: (712)..(714)
<223> OTHER INFORMATION: n is a, c, g, or t
<220> FEATURE:
<221> NAME/KEY: modified_base
<222> LOCATION: (716)..(716)
<223> OTHER INFORMATION: n is a, c, g, or t
<220> FEATURE:
<221> NAME/KEY: modified_base
<222> LOCATION: (752)..(752)
<223> OTHER INFORMATION: n is a, c, g, or t
<220> FEATURE:
<221> NAME/KEY: modified_base
<222> LOCATION: (764)..(764)
<223> OTHER INFORMATION: n is a, c, g, or t

<400> SEQUENCE: 35

gnngnggnnn nnttggtggc ctttttttgan nnccnttttt ttttttcaat gtgtgttaag      60

tcacttgttt atttctcaag atgtgcacac tcaagtatga agctggccgg gacaactcat     120

ggctcctagg tatgtacagg ccctttgatg gcttgggtta cagacaacct catagctggt     180

gcaccacaca cacgagataa aacaggaagc ctaaaaaccc caagccacac caagaaaaat     240

gagagagggg agggcggggt aacaatgcag catcccgcgg agggaactta atgcacaagg     300

agggagaaca gagggtggaa ggcaagccag cttcgtcttc gccgccgcag ctgctgtgtg     360

gtggtcaggg gactgagttc aacaggtcct tcaggaagct ctctggatcg gtgatttctg     420

ataaaagacc ggccacatcg aggaactctg agaaggtctc cactggcatg aactcctcct     480

ggaaggtttt cagggctttg tcggcagctt cgtanatggg catgtcgttg tggcggatgt     540

actcagcgag agagcaggac cagcctcctn tgngttactg gtangcacct tcttaaacat     600

gtgnaaatga gatcgacgag gnccaaaaga gaagggaaga acggtaacgg aatagncctt     660

cattgcttat ctgncaacct ggngggttca cctggagcca ttgcccagcc tnnnanggca     720

ccaacagctt ccgaagattt ccaacctggg gntttcattg ttangggcaa gatttaag        778


<210> SEQ ID NO 36
<211> LENGTH: 814
<212> TYPE: DNA
<213> ORGANISM: Homo sapiens
<220> FEATURE:
<221> NAME/KEY: modified_base
<222> LOCATION: (2)..(2)
```

-continued

<223> OTHER INFORMATION: n is a, c, g, or t
<220> FEATURE:
<221> NAME/KEY: modified_base
<222> LOCATION: (5)..(5)
<223> OTHER INFORMATION: n is a, c, g, or t
<220> FEATURE:
<221> NAME/KEY: modified_base
<222> LOCATION: (7)..(7)
<223> OTHER INFORMATION: n is a, c, g, or t
<220> FEATURE:
<221> NAME/KEY: modified_base
<222> LOCATION: (9)..(10)
<223> OTHER INFORMATION: n is a, c, g, or t
<220> FEATURE:
<221> NAME/KEY: modified_base
<222> LOCATION: (15)..(18)
<223> OTHER INFORMATION: n is a, c, g, or t
<220> FEATURE:
<221> NAME/KEY: modified_base
<222> LOCATION: (30)..(30)
<223> OTHER INFORMATION: n is a, c, g, or t
<220> FEATURE:
<221> NAME/KEY: modified_base
<222> LOCATION: (529)..(529)
<223> OTHER INFORMATION: n is a, c, g, or t
<220> FEATURE:
<221> NAME/KEY: modified_base
<222> LOCATION: (722)..(722)
<223> OTHER INFORMATION: n is a, c, g, or t
<220> FEATURE:
<221> NAME/KEY: modified_base
<222> LOCATION: (748)..(748)
<223> OTHER INFORMATION: n is a, c, g, or t
<220> FEATURE:
<221> NAME/KEY: modified_base
<222> LOCATION: (759)..(759)
<223> OTHER INFORMATION: n is a, c, g, or t
<220> FEATURE:
<221> NAME/KEY: modified_base
<222> LOCATION: (776)..(776)
<223> OTHER INFORMATION: n is a, c, g, or t
<220> FEATURE:
<221> NAME/KEY: modified_base
<222> LOCATION: (785)..(786)
<223> OTHER INFORMATION: n is a, c, g, or t
<220> FEATURE:
<221> NAME/KEY: modified_base
<222> LOCATION: (803)..(804)
<223> OTHER INFORMATION: n is a, c, g, or t
<220> FEATURE:
<221> NAME/KEY: modified_base
<222> LOCATION: (806)..(806)
<223> OTHER INFORMATION: n is a, c, g, or t

<400> SEQUENCE: 36
gnggngngnn ggttnnnntt tgaattcctn tgcactgttg gcctactgga cgaaaaacat 60
attaaaacaa acccagaaga actgagagag attgtgacat ctatacttga agaatacaca 120
agtcaagaaa attggtattt ggttacctgt cttgaaactg aggaaatggg agaggagctg 180
atgatggagc acccaggcct ccaagccatc acgtctggtg aacacacctg ccaagttaca 240
tcttttctag ccttctcaaa gccaagtccc actatttgct ccatgaacag taacatctgg 300
caaatatgca ttcagttgga aggaattggc cagtttgcat atgcactagg aaaagacttc 360
tgtttgctct tgatgtcagc cctttatcca gtactggaga aggctggaga ccaaacccta 420
ctcattagtc aggtggctac cagcaccatg atggacgttt gccgtgcttg tggctacgac 480
tccctgcagc acctgatcaa tcaaaattca gactatttaa gtgaatggna tctctttaaa 540
tctgcgtcat ctggctctgc atcctcatac cccaaaggtc tgggaagtca tgctgcggaa 600
ctcagatgct acctgcttcc tttggtggca gatgtgggtc aagatgtctt tggccacctt 660
ggccaatttt acgatagaga ctgcttcctt tgcagcgtct gcatgctctg atggcacatt 720
anccaatggt tccaacacag taatcttngg cacctcaana gcaaagttag gagaanaggg 780
aagcnnttga accaagacca canntnttgg gaaa 814

<210> SEQ ID NO 37
<211> LENGTH: 811
<212> TYPE: DNA
<213> ORGANISM: Homo sapiens
<220> FEATURE:
<221> NAME/KEY: modified_base
<222> LOCATION: (2)..(2)
<223> OTHER INFORMATION: n is a, c, g, or t
<220> FEATURE:
<221> NAME/KEY: modified_base
<222> LOCATION: (5)..(5)
<223> OTHER INFORMATION: n is a, c, g, or t
<220> FEATURE:
<221> NAME/KEY: modified_base
<222> LOCATION: (7)..(7)
<223> OTHER INFORMATION: n is a, c, g, or t
<220> FEATURE:
<221> NAME/KEY: modified_base
<222> LOCATION: (10)..(10)
<223> OTHER INFORMATION: n is a, c, g, or t
<220> FEATURE:
<221> NAME/KEY: modified_base
<222> LOCATION: (12)..(12)
<223> OTHER INFORMATION: n is a, c, g, or t
<220> FEATURE:
<221> NAME/KEY: modified_base
<222> LOCATION: (15)..(18)
<223> OTHER INFORMATION: n is a, c, g, or t
<220> FEATURE:
<221> NAME/KEY: modified_base
<222> LOCATION: (21)..(21)
<223> OTHER INFORMATION: n is a, c, g, or t
<220> FEATURE:
<221> NAME/KEY: modified_base
<222> LOCATION: (612)..(612)
<223> OTHER INFORMATION: n is a, c, g, or t
<220> FEATURE:
<221> NAME/KEY: modified_base
<222> LOCATION: (640)..(640)
<223> OTHER INFORMATION: n is a, c, g, or t
<220> FEATURE:
<221> NAME/KEY: modified_base
<222> LOCATION: (654)..(654)
<223> OTHER INFORMATION: n is a, c, g, or t
<220> FEATURE:
<221> NAME/KEY: modified_base
<222> LOCATION: (679)..(679)
<223> OTHER INFORMATION: n is a, c, g, or t
<220> FEATURE:
<221> NAME/KEY: modified_base
<222> LOCATION: (724)..(724)
<223> OTHER INFORMATION: n is a, c, g, or t
<220> FEATURE:
<221> NAME/KEY: modified_base
<222> LOCATION: (748)..(748)
<223> OTHER INFORMATION: n is a, c, g, or t
<220> FEATURE:
<221> NAME/KEY: modified_base
<222> LOCATION: (757)..(757)
<223> OTHER INFORMATION: n is a, c, g, or t
<220> FEATURE:
<221> NAME/KEY: modified_base
<222> LOCATION: (763)..(763)
<223> OTHER INFORMATION: n is a, c, g, or t
<220> FEATURE:
<221> NAME/KEY: modified_base
<222> LOCATION: (773)..(773)
<223> OTHER INFORMATION: n is a, c, g, or t
<220> FEATURE:
<221> NAME/KEY: modified_base
<222> LOCATION: (777)..(777)
<223> OTHER INFORMATION: n is a, c, g, or t
<220> FEATURE:

-continued

<221> NAME/KEY: modified_base
<222> LOCATION: (788)..(789)
<223> OTHER INFORMATION: n is a, c, g, or t
<220> FEATURE:
<221> NAME/KEY: modified_base
<222> LOCATION: (807)..(810)
<223> OTHER INFORMATION: n is a, c, g, or t

<400> SEQUENCE: 37

```
gnggngnggn gnttnnnntg ngtggccttt tttttttcc ttttttact tttcatccaa     60

gaagtgtctt tatttccgtt tgtttctcaa agatcaggtt aggtaaaaca aattagttcc    120

atctcattat ttgaagacag ggaggtgtat gcagatggag gggaactgac ctcttgtgtg    180

tgtgtgtgtg tggcctgtga gggagctggg gctatagaga tggtaggcta aggggttaaa    240

cccttagagc caccagacaa tgtcacttga aaacacaagg tatgaaatat aaataatagt    300

cagctacttt ccttcaatcc atttctaagc agttgtgtga tcgatcaatt tataaatcga    360

ttggctaact aattcacctt ctctgctgcc gctgcaccgc ctatggccgg ggtggggtca    420

gcccagcttc tggctggcag taggggaggg atcggtggcc tctgtggtgg gggagcaggg    480

tcactgcagc tccttgagca gctggagcac gttggtcgtg taggggttct gctgccgctg    540

gcccgtgcag ctgcacaggg tggaagctgg ggtggggagg tgtgaactgc acggggcagt    600

aaagctcgtc angaggacca ggtggagtct gggtccaccn tcatcaaagt gganggaaga    660

cgctctggca acctcttgna attcacgggc tggttgacac ttggggaaat aagcagctta    720

accncttatt aggcaacctt acctaggnca agctttnaca aanggggccc agncctntaa    780

aaaagcannt tgaccttgaa ggccacnnnn c                                   811
```

<210> SEQ ID NO 38
<211> LENGTH: 816
<212> TYPE: DNA
<213> ORGANISM: Homo sapiens
<220> FEATURE:
<221> NAME/KEY: modified_base
<222> LOCATION: (2)..(2)
<223> OTHER INFORMATION: n is a, c, g, or t
<220> FEATURE:
<221> NAME/KEY: modified_base
<222> LOCATION: (4)..(4)
<223> OTHER INFORMATION: n is a, c, g, or t
<220> FEATURE:
<221> NAME/KEY: modified_base
<222> LOCATION: (9)..(9)
<223> OTHER INFORMATION: n is a, c, g, or t
<220> FEATURE:
<221> NAME/KEY: modified_base
<222> LOCATION: (14)..(16)
<223> OTHER INFORMATION: n is a, c, g, or t
<220> FEATURE:
<221> NAME/KEY: modified_base
<222> LOCATION: (18)..(18)
<223> OTHER INFORMATION: n is a, c, g, or t
<220> FEATURE:
<221> NAME/KEY: modified_base
<222> LOCATION: (22)..(22)
<223> OTHER INFORMATION: n is a, c, g, or t
<220> FEATURE:
<221> NAME/KEY: modified_base
<222> LOCATION: (577)..(577)
<223> OTHER INFORMATION: n is a, c, g, or t
<220> FEATURE:
<221> NAME/KEY: modified_base
<222> LOCATION: (604)..(604)
<223> OTHER INFORMATION: n is a, c, g, or t
<220> FEATURE:
<221> NAME/KEY: modified_base
<222> LOCATION: (616)..(616)
<223> OTHER INFORMATION: n is a, c, g, or t
<220> FEATURE:
<221> NAME/KEY: modified_base
<222> LOCATION: (646)..(646)
<223> OTHER INFORMATION: n is a, c, g, or t
<220> FEATURE:
<221> NAME/KEY: modified_base
<222> LOCATION: (659)..(659)
<223> OTHER INFORMATION: n is a, c, g, or t
<220> FEATURE:
<221> NAME/KEY: modified_base
<222> LOCATION: (684)..(684)
<223> OTHER INFORMATION: n is a, c, g, or t
<220> FEATURE:
<221> NAME/KEY: modified_base
<222> LOCATION: (697)..(697)
<223> OTHER INFORMATION: n is a, c, g, or t
<220> FEATURE:
<221> NAME/KEY: modified_base
<222> LOCATION: (714)..(714)
<223> OTHER INFORMATION: n is a, c, g, or t
<220> FEATURE:
<221> NAME/KEY: modified_base
<222> LOCATION: (732)..(732)
<223> OTHER INFORMATION: n is a, c, g, or t
<220> FEATURE:
<221> NAME/KEY: modified_base
<222> LOCATION: (743)..(743)
<223> OTHER INFORMATION: n is a, c, g, or t
<220> FEATURE:
<221> NAME/KEY: modified_base
<222> LOCATION: (753)..(753)
<223> OTHER INFORMATION: n is a, c, g, or t
<220> FEATURE:
<221> NAME/KEY: modified_base
<222> LOCATION: (765)..(765)
<223> OTHER INFORMATION: n is a, c, g, or t
<220> FEATURE:
<221> NAME/KEY: modified_base
<222> LOCATION: (781)..(781)
<223> OTHER INFORMATION: n is a, c, g, or t
<220> FEATURE:
<221> NAME/KEY: modified_base
<222> LOCATION: (788)..(788)
<223> OTHER INFORMATION: n is a, c, g, or t
<220> FEATURE:
<221> NAME/KEY: modified_base
<222> LOCATION: (790)..(790)
<223> OTHER INFORMATION: n is a, c, g, or t
<220> FEATURE:
<221> NAME/KEY: modified_base
<222> LOCATION: (793)..(793)
<223> OTHER INFORMATION: n is a, c, g, or t
<220> FEATURE:
<221> NAME/KEY: modified_base
<222> LOCATION: (799)..(799)
<223> OTHER INFORMATION: n is a, c, g, or t
<220> FEATURE:
<221> NAME/KEY: modified_base
<222> LOCATION: (803)..(805)
<223> OTHER INFORMATION: n is a, c, g, or t
<220> FEATURE:
<221> NAME/KEY: modified_base
<222> LOCATION: (816)..(816)
<223> OTHER INFORMATION: n is a, c, g, or t

<400> SEQUENCE: 38
gngnggggng gttnnntntg antcctttgc actgttggcc tactggcgct catcagctac 60
gtgtccctga aaaaggagaa catcttcacc actcccaagt acgccagccc gggggccgcc 120
ccgaatgtac atgttccacg cgggattccg gtgagtgcgg gcctctgtgt tagtgccctc 180
gggaatttgg ttgatggggt gtttggggaa gggaaggcgt gggggagggg tgttttggcc 240
tctccgagac tctttgggcc agataactgc gcggtccttc cactcctctc tctaattctc 300
ccttccccct ccctgttatt tttttttaa cccaaagccc ctagaagccg ctgtccaaat 360

-continued

```
cgatgtgatt gcatttctcg tattcttcct cagcatccct tccctcattt cagaaatggg    420

ggttggggga ggctttcagg agggtgaggg tggagggaaa gacggtgtgt ttgttcggga    480

gggggccggc gagcagagat ggacaggcgt gaggggagcg ccctccccgc gccctgtccg    540

aaacttcgcg gcccggcccg gggccggtgc tggcggntta atggcgcaag cgccagattc    600

cctngcgccc tcttcnttac tccccacgcc tatcaaagga cacgcnggtt tattctcang    660

aagcccctgg gccgttctct tttngacctt tccccgnccg caacgccccc acancttttc    720

gggaattttt gnaatttccc cgnccccttgc ggnaaccaac ccccnaaggg ccgccaccct    780

ngccaggncn gantaccgnt tcnnnttggc cggccn                              816
```

<210> SEQ ID NO 39
<211> LENGTH: 820
<212> TYPE: DNA
<213> ORGANISM: Homo sapiens
<220> FEATURE:
<221> NAME/KEY: modified_base
<222> LOCATION: (2)..(2)
<223> OTHER INFORMATION: n is a, c, g, or t
<220> FEATURE:
<221> NAME/KEY: modified_base
<222> LOCATION: (5)..(5)
<223> OTHER INFORMATION: n is a, c, g, or t
<220> FEATURE:
<221> NAME/KEY: modified_base
<222> LOCATION: (7)..(7)
<223> OTHER INFORMATION: n is a, c, g, or t
<220> FEATURE:
<221> NAME/KEY: modified_base
<222> LOCATION: (10)..(10)
<223> OTHER INFORMATION: n is a, c, g, or t
<220> FEATURE:
<221> NAME/KEY: modified_base
<222> LOCATION: (13)..(13)
<223> OTHER INFORMATION: n is a, c, g, or t
<220> FEATURE:
<221> NAME/KEY: modified_base
<222> LOCATION: (16)..(18)
<223> OTHER INFORMATION: n is a, c, g, or t
<220> FEATURE:
<221> NAME/KEY: modified_base
<222> LOCATION: (22)..(23)
<223> OTHER INFORMATION: n is a, c, g, or t
<220> FEATURE:
<221> NAME/KEY: modified_base
<222> LOCATION: (34)..(34)
<223> OTHER INFORMATION: n is a, c, g, or t
<220> FEATURE:
<221> NAME/KEY: modified_base
<222> LOCATION: (37)..(37)
<223> OTHER INFORMATION: n is a, c, g, or t
<220> FEATURE:
<221> NAME/KEY: modified_base
<222> LOCATION: (43)..(43)
<223> OTHER INFORMATION: n is a, c, g, or t
<220> FEATURE:
<221> NAME/KEY: modified_base
<222> LOCATION: (538)..(538)
<223> OTHER INFORMATION: n is a, c, g, or t
<220> FEATURE:
<221> NAME/KEY: modified_base
<222> LOCATION: (555)..(555)
<223> OTHER INFORMATION: n is a, c, g, or t
<220> FEATURE:
<221> NAME/KEY: modified_base
<222> LOCATION: (646)..(646)
<223> OTHER INFORMATION: n is a, c, g, or t
<220> FEATURE:
<221> NAME/KEY: modified_base
<222> LOCATION: (658)..(658)
<223> OTHER INFORMATION: n is a, c, g, or t
<220> FEATURE:
<221> NAME/KEY: modified_base
<222> LOCATION: (663)..(663)
<223> OTHER INFORMATION: n is a, c, g, or t
<220> FEATURE:
<221> NAME/KEY: modified_base
<222> LOCATION: (702)..(702)
<223> OTHER INFORMATION: n is a, c, g, or t
<220> FEATURE:
<221> NAME/KEY: modified_base
<222> LOCATION: (704)..(704)
<223> OTHER INFORMATION: n is a, c, g, or t
<220> FEATURE:
<221> NAME/KEY: modified_base
<222> LOCATION: (724)..(724)
<223> OTHER INFORMATION: n is a, c, g, or t
<220> FEATURE:
<221> NAME/KEY: modified_base
<222> LOCATION: (734)..(734)
<223> OTHER INFORMATION: n is a, c, g, or t
<220> FEATURE:
<221> NAME/KEY: modified_base
<222> LOCATION: (751)..(751)
<223> OTHER INFORMATION: n is a, c, g, or t
<220> FEATURE:
<221> NAME/KEY: modified_base
<222> LOCATION: (765)..(765)
<223> OTHER INFORMATION: n is a, c, g, or t
<220> FEATURE:
<221> NAME/KEY: modified_base
<222> LOCATION: (774)..(774)
<223> OTHER INFORMATION: n is a, c, g, or t
<220> FEATURE:
<221> NAME/KEY: modified_base
<222> LOCATION: (788)..(788)
<223> OTHER INFORMATION: n is a, c, g, or t
<220> FEATURE:
<221> NAME/KEY: modified_base
<222> LOCATION: (796)..(796)
<223> OTHER INFORMATION: n is a, c, g, or t
<220> FEATURE:
<221> NAME/KEY: modified_base
<222> LOCATION: (798)..(798)
<223> OTHER INFORMATION: n is a, c, g, or t
<220> FEATURE:
<221> NAME/KEY: modified_base
<222> LOCATION: (808)..(808)
<223> OTHER INFORMATION: n is a, c, g, or t

<400> SEQUENCE: 39
gnggngnggn ggnttnnntt tnngtggcct tttntanttt tcntttattg aaattggtcc 60
tgatatgtcc tttttatgag aggacactac acacacagga gaagtttcct gatcattgct 120
ttgtgcagtc atgccaagaa aacaatgcag atacacctga tggtgagggt ggggcgtata 180
gatgtttgtt gttttagatg tttttgtttg cttgtttttg ttttgttttg ttttgagctc 240
ttgaattctt aaaagcacct tttggatctt ttcctcctat cctacctttg atgtaaaaac 300
gctgtccgat taaatgtcca cttagaaggt ttctcttgga gttcctgggt gagagaattc 360
gtaatgggca cgaatgacgg gtctagaaac ttcagcgcaa attgtgacct ggagaggagc 420
atgagcacag acaagcgtgc tggcctcagc tcggggaagc cgaggtagcc attaaagtgc 480
agcggctggg gcgagggcgg ctggtacgcg tgcggctccg ttccgtcccg gacccctntc 540
atttggtcca ccctntggtc cacacacacc cgagagaaaa aaagaaaact agggaacccc 600
atctgcattg ccatcccttc gggtgccgga gagaccataa aatggnccgc atgcgganaa 660
canggcgcac gccggggcgc aaggcttgaa cccgcggcgc tncnagacca gggaataaca 720
ccgnggacag gggncggccc ggcagcctga nccgttaagc ctttnagccc atanaatggt 780
ttttgganaa aggcananga aaccgganac ccaaggaaag 820

<210> SEQ ID NO 40

<211> LENGTH: 717
<212> TYPE: DNA
<213> ORGANISM: Homo sapiens
<220> FEATURE:
<221> NAME/KEY: modified_base
<222> LOCATION: (9)..(9)
<223> OTHER INFORMATION: n is a, c, g, or t
<220> FEATURE:
<221> NAME/KEY: modified_base
<222> LOCATION: (573)..(573)
<223> OTHER INFORMATION: n is a, c, g, or t
<220> FEATURE:
<221> NAME/KEY: modified_base
<222> LOCATION: (602)..(602)
<223> OTHER INFORMATION: n is a, c, g, or t
<220> FEATURE:
<221> NAME/KEY: modified_base
<222> LOCATION: (637)..(637)
<223> OTHER INFORMATION: n is a, c, g, or t
<220> FEATURE:
<221> NAME/KEY: modified_base
<222> LOCATION: (685)..(685)
<223> OTHER INFORMATION: n is a, c, g, or t
<220> FEATURE:
<221> NAME/KEY: modified_base
<222> LOCATION: (692)..(692)
<223> OTHER INFORMATION: n is a, c, g, or t

<400> SEQUENCE: 40
ggcactgcng gcctactggt tgagaagtat cgagcacagc ttgataccaa aactgactcc 60
actggaaccc attctctgta cacaacatac aaagattatg aaattatgtt ccatgtttct 120
accatgctgc catacacacc caacaacaaa caacagctcc tgaggaagcg gcacattgga 180
aatgatatcg taacaattgt tttccaagag cctggagcac agccattcag cccaaaaaac 240
atccgatccc acttccagca cgttttcgtc atcgtcaggg tgcacaatcc gtgctctgac 300
agtgtctgtt atagtgtggc tgttaccagg tccagagatg tgccttcctt tgggcctcca 360
ttcctaaagg ggtcactttc cctaagtcaa atgtgttcag ggacttcctt ttggcgaaag 420
tgattaatgc agaaaatgct gctcataaat cggagaagtt tcgggccatg gcaactcgga 480
cccgccagga atacctgaaa gatctggcag aaaagaatgt caccaacacc cctatcgacc 540
cttctggcaa gtttccgtca tctctctggc ttncaagaag aaggaaaagt ctaagccata 600
tncaggagcc cgagctcagc agcatggggg ccattgnatg gcaagtccgg ctgaagacta 660
caacaagggc atggaactag actgnctttt anggatcttc aatggagttc attgggc 717

<210> SEQ ID NO 41
<211> LENGTH: 717
<212> TYPE: DNA
<213> ORGANISM: Homo sapiens
<220> FEATURE:
<221> NAME/KEY: modified_base
<222> LOCATION: (578)..(578)
<223> OTHER INFORMATION: n is a, c, g, or t
<220> FEATURE:
<221> NAME/KEY: modified_base
<222> LOCATION: (619)..(619)
<223> OTHER INFORMATION: n is a, c, g, or t
<220> FEATURE:
<221> NAME/KEY: modified_base
<222> LOCATION: (652)..(652)
<223> OTHER INFORMATION: n is a, c, g, or t
<220> FEATURE:
<221> NAME/KEY: modified_base
<222> LOCATION: (666)..(666)
<223> OTHER INFORMATION: n is a, c, g, or t
<220> FEATURE:
<221> NAME/KEY: modified_base
<222> LOCATION: (688)..(688)
<223> OTHER INFORMATION: n is a, c, g, or t -continued
<220> FEATURE:
<221> NAME/KEY: modified_base
<222> LOCATION: (694)..(694)
<223> OTHER INFORMATION: n is a, c, g, or t
<220> FEATURE:
<221> NAME/KEY: modified_base
<222> LOCATION: (704)..(704)
<223> OTHER INFORMATION: n is a, c, g, or t
<220> FEATURE:
<221> NAME/KEY: modified_base
<222> LOCATION: (713)..(713)
<223> OTHER INFORMATION: n is a, c, g, or t

<400> SEQUENCE: 41
gattcctttt agcagttaaa cttttatttt actgtttaaa atttttattt actttttttg 60
tttttctttt ctacaaaagg caggtgatga ttgttgatct gcaactattg tgttgtgcac 120
tccccgaaag gggcagagt aggaagccag ggaaggtgct ctgaggatgc tttctatgga 180
gggaataagg gctgcaggac actcactgga gggagtgtct gggcccttct cctgtcctcc 240
tcagccttcc ctagctcatg tctatggtgt tgaagaccca ttctgtgaac ttcttcagct 300
tgtccgaggc gttctgggac tcctcctgta gcctcaggtt gtcctctcgc aggtgctgca 360
cctccgcctg aaggtgagct ttgtcttctt tttccttctt caaatcttcc gaagcatctt 420
cagcatacct tcagctggtc cactttagaa gccagagtgg gagaggagtc tttactgctg 480
taaggcttca tctgggccag aacctggcct cagctgatca ctggtggatg cagcactcaa 540
ggggccgatg gttttcatca ctagcagcaa aaaatgangc tctctggacc tcataagctt 600
tggcaagcat ctaccaagnt ggaccaatcc aagtctgcaa caatgcaagc angggcatca 660
ggccanggtc gggcataagc tggctgcngg gctnctggat gtantgaagg aanctgc 717

<210> SEQ ID NO 42
<211> LENGTH: 717
<212> TYPE: DNA
<213> ORGANISM: Homo sapiens
<220> FEATURE:
<221> NAME/KEY: modified_base
<222> LOCATION: (666)..(666)
<223> OTHER INFORMATION: n is a, c, g, or t

<400> SEQUENCE: 42
cactgttggc cggctctgcc actctcgctc cgaggtcccc gcgccagaga cgcagccgcg 60
ctcccaccac ccacacccac cgcgccctcg ttcgcctctt ctccgggagc cagtccgcgc 120
caccgccgcc gcccagccca tcgccaccct ccgcagccat gtccaccagg tccgtgtcct 180
cgtcctccta ccgcaggatg ttcggcggcc cgggcaccgc gagccggccg agctccagcc 240
ggagctacgt gactacgtcc acccgcacct acagcctggg cagcgcgctg cgccccagca 300
ccagccgcag cctctacgcc tcgtccccgg gcggcgtgta tgccacgcgc tcctctgccg 360
tgcgcctgcg gagcagcgtg cccggggtgc ggctcctgca ggactcggtg gacttctcgc 420
tggccgacgc catcaacacc gagttcaaga acacccgcac caacgagaag gtggagctgc 480
aggagctgaa tgaccgcttc gcaactacat cgacaaggtg cgcttctgga gcagcagaat 540
aagatcctgc tggccgagct cgagcagctc aagggcaagg caagtcgcgc ctgggggacc 600
tctacgagga ggagatgcgg aactgcgccg gcaggtggac agctaaccaa cgacaaagcc 660
cgcgtngagg tggaacgcga caacctggcc gaggacatca tgcgccttcc gggagaa 717

<210> SEQ ID NO 43
<211> LENGTH: 726
<212> TYPE: DNA

<213> ORGANISM: Homo sapiens
<220> FEATURE:
<221> NAME/KEY: modified_base
<222> LOCATION: (13)..(13)
<223> OTHER INFORMATION: n is a, c, g, or t
<220> FEATURE:
<221> NAME/KEY: modified_base
<222> LOCATION: (633)..(633)
<223> OTHER INFORMATION: n is a, c, g, or t
<220> FEATURE:
<221> NAME/KEY: modified_base
<222> LOCATION: (638)..(638)
<223> OTHER INFORMATION: n is a, c, g, or t
<220> FEATURE:
<221> NAME/KEY: modified_base
<222> LOCATION: (696)..(696)
<223> OTHER INFORMATION: n is a, c, g, or t
<220> FEATURE:
<221> NAME/KEY: modified_base
<222> LOCATION: (704)..(704)
<223> OTHER INFORMATION: n is a, c, g, or t
<220> FEATURE:
<221> NAME/KEY: modified_base
<222> LOCATION: (707)..(707)
<223> OTHER INFORMATION: n is a, c, g, or t
<220> FEATURE:
<221> NAME/KEY: modified_base
<222> LOCATION: (719)..(719)
<223> OTHER INFORMATION: n is a, c, g, or t

<400> SEQUENCE: 43

```
ttttcctttt tcnaagattt attgaagcag aaacaagttg gttggatact tgctggaaaa      60

aaaaaagcag ttttaatggt attcaaaata ccttttaaaa agtattctag cacaagattt     120

ttctgtaaac tagattatgt tgtaaacttt tttctaaatc ttgtaggagt gtcggttgtt     180

aagaactaga gcttattcct attccaaatc tatcttgcgc tcctgaaaaa ctgcagaaag     240

gcacttgaaa gctgtttctt taagatatgg atttcttttt tattcttgct ggtaatatat     300

tgctgcactg agtgtgtgca atttttattc aaggtcatcg tgatgctgag aagtttccgt     360

tgataacctg tccatctcta gtttcaaccg tcttaatcag aagtgtcctt tttgagtggg     420

tatcaaccag agggagtgaa tccagattag tttccctcag gttcagggag gaaaagtttg     480

gaagaggcag agaaatcctg ctctcctcgc cttccagcag cttcctgtag gtggcaatct     540

caatgtcaag ggccatctta acattgagca ggcttggtat tcacgaaggt gacgagccat     600

ttcctccttc atattctgaa tctcatcctg cangcggnca atagtggctt ggtagttagc     660

agcttcaacg gcaaaagtct cttccattta cgcatntggc gttncangga ctcattggnt     720

ccttta                                                                726
```

<210> SEQ ID NO 44
<211> LENGTH: 663
<212> TYPE: DNA
<213> ORGANISM: Homo sapiens
<220> FEATURE:
<221> NAME/KEY: modified_base
<222> LOCATION: (12)..(12)
<223> OTHER INFORMATION: n is a, c, g, or t
<220> FEATURE:
<221> NAME/KEY: modified_base
<222> LOCATION: (15)..(15)
<223> OTHER INFORMATION: n is a, c, g, or t
<220> FEATURE:
<221> NAME/KEY: modified_base
<222> LOCATION: (20)..(20)
<223> OTHER INFORMATION: n is a, c, g, or t
<220> FEATURE:
<221> NAME/KEY: modified_base
<222> LOCATION: (528)..(528)
<223> OTHER INFORMATION: n is a, c, g, or t
<220> FEATURE:
<221> NAME/KEY: modified_base
<222> LOCATION: (541)..(541)
<223> OTHER INFORMATION: n is a, c, g, or t
<220> FEATURE:
<221> NAME/KEY: modified_base
<222> LOCATION: (547)..(547)
<223> OTHER INFORMATION: n is a, c, g, or t
<220> FEATURE:
<221> NAME/KEY: modified_base
<222> LOCATION: (582)..(582)
<223> OTHER INFORMATION: n is a, c, g, or t
<220> FEATURE:
<221> NAME/KEY: modified_base
<222> LOCATION: (619)..(619)
<223> OTHER INFORMATION: n is a, c, g, or t
<220> FEATURE:
<221> NAME/KEY: modified_base
<222> LOCATION: (627)..(627)
<223> OTHER INFORMATION: n is a, c, g, or t
<220> FEATURE:
<221> NAME/KEY: modified_base
<222> LOCATION: (632)..(632)
<223> OTHER INFORMATION: n is a, c, g, or t
<220> FEATURE:
<221> NAME/KEY: modified_base
<222> LOCATION: (645)..(645)
<223> OTHER INFORMATION: n is a, c, g, or t
<220> FEATURE:
<221> NAME/KEY: modified_base
<222> LOCATION: (651)..(651)
<223> OTHER INFORMATION: n is a, c, g, or t
<220> FEATURE:
<221> NAME/KEY: modified_base
<222> LOCATION: (656)..(656)
<223> OTHER INFORMATION: n is a, c, g, or t

<400> SEQUENCE: 44
gcttggcctg gngangtgcn gggattacag gcgtgagcca ccacgcccgg ccttgcttga 60
gttttaatca gcctatgtat cctggcagtc agggccagtc tccatacttc agggtgtata 120
gtcaaatcca agtacaactt ttgagcaggc agagaaggaa gtggatatgt gagcgtttcc 180
accaaaggtt tcctgaacgc ttggcctggg tcaggcactg gggccaacag ggtggccgag 240
gcagggccct tactcctcag gagctcctga agacccaacc ctgcaggagg agccagggcc 300
ctgagtgcat gatccttgct tggcacagag tgtgggtcag gtgtaggaaa gagtcggtcg 360
tcatcaggga aagaacactg tctttggaga tagtctagac ctgcggtaaa gttgatgtct 420
gcctgccagc tctgcacaga gggacagtgc ccaactgcat cctgggatgg cagacacagt 480
gctgacatgt tgctggttga aggcaagcca cttctttcca tggctcanta ggaccaaata 540
ngtcacngaa gggaagatcc ttgaagctga atgctgagag tnaattaatc aaacccaagg 600
ggaaaactac acttacctnt ggagttngaa antttatcaa tgacntgagg ntgagnttcc 660
gtg 663

<210> SEQ ID NO 45
<211> LENGTH: 698
<212> TYPE: DNA
<213> ORGANISM: Homo sapiens
<220> FEATURE:
<221> NAME/KEY: modified_base
<222> LOCATION: (2)..(2)
<223> OTHER INFORMATION: n is a, c, g, or t
<220> FEATURE:
<221> NAME/KEY: modified_base
<222> LOCATION: (6)..(6)
<223> OTHER INFORMATION: n is a, c, g, or t
<220> FEATURE:
<221> NAME/KEY: modified_base
<222> LOCATION: (61)..(61)

<223> OTHER INFORMATION: n is a, c, g, or t
<220> FEATURE:
<221> NAME/KEY: modified_base
<222> LOCATION: (513)..(513)
<223> OTHER INFORMATION: n is a, c, g, or t
<220> FEATURE:
<221> NAME/KEY: modified_base
<222> LOCATION: (534)..(534)
<223> OTHER INFORMATION: n is a, c, g, or t
<220> FEATURE:
<221> NAME/KEY: modified_base
<222> LOCATION: (575)..(575)
<223> OTHER INFORMATION: n is a, c, g, or t
<220> FEATURE:
<221> NAME/KEY: modified_base
<222> LOCATION: (595)..(595)
<223> OTHER INFORMATION: n is a, c, g, or t
<220> FEATURE:
<221> NAME/KEY: modified_base
<222> LOCATION: (597)..(597)
<223> OTHER INFORMATION: n is a, c, g, or t
<220> FEATURE:
<221> NAME/KEY: modified_base
<222> LOCATION: (650)..(651)
<223> OTHER INFORMATION: n is a, c, g, or t
<220> FEATURE:
<221> NAME/KEY: modified_base
<222> LOCATION: (673)..(673)
<223> OTHER INFORMATION: n is a, c, g, or t
<220> FEATURE:
<221> NAME/KEY: modified_base
<222> LOCATION: (695)..(695)
<223> OTHER INFORMATION: n is a, c, g, or t

<400> SEQUENCE: 45
gngcangcag atgacagaaa tttctacaga cacttaatag acagacattc cttaggccta 60
nttcaaatat ctaaattcca tctggggact tggctgtcaa aagataatca tctcttgctt 120
catttctcat ataatttcct aaaccctcgg gtctcagcta gtgcaaggtc ctgtcatggt 180
cacctgtggc ttgggccaat tctcacttcc cctgaagggc agctgcgtgt agggagcggg 240
ggctgccaaa gtttcactct gactggaggt aaacttaaca tcatttctgc attagtcatt 300
tagagccctg ggctcagtac tttcccccaa ctgggtttct gcttttgagc tcgctctgca 360
atttcccaat tctgactcaa ttctctctgg gcccagggag ctgcaacagc actcctccca 420
ccatttctca gctgtagccc tcttgcaggt gtctgccaca aaagaaaacc agcatacaac 480
gccatgcagg gccactctga gctggggacc ttntgcagtt gcacctggga tctntgcagg 540
tgccagaaga accttacacc agacatccct acagntgaac gctggtccac caggntntgg 600
actttgggga aagtccaccg gccactactt acccagcaca tgtggcccan ngctctggtt 660
ccaatcatca cgngggcaagc ctggcttttc caganatc 698

<210> SEQ ID NO 46
<211> LENGTH: 776
<212> TYPE: DNA
<213> ORGANISM: Homo sapiens

<400> SEQUENCE: 46
cactgttggc ctactggctt ctaatgtgaa gcaagacaga gcactgctgt aaatgtctag 60
cagcagattt ttttttatt ggtacatatt atccttcaaa tctgagaatt tggactaact 120
gcaccaaaga accctctaat ttggtccctg gcacatgcat acttgtcaat gtttttattc 180
ttttacaaga cctgcatttt atttgaatta cccgaatagc aatatgtaaa atacaagtga 240
caaaatgtga tgagagcttc ttgaaccggt aaactagtac aggtctgaga aagacatatt 300
agaagaatca ttatacttcc ttgaattata tttattttca tgtttctcta atgcaaagaa 360

-continued

```
tgtttcatca aatgtatatt ttctgttgct tactgtttgc tctgagaaga agctgctgtt    420

tcaaagatgg acctctgagt agctaattga ttcaagtagt ttttttatgt tgacacatta    480

ttactgctgt tagcagtcgt tttcaccagg tacttacaga gcagatttca tacatcattc    540

attcaagggc taaatttata ttttttggaa atcatggcaa ctacacagga tgttgcttac    600

caggacggag ttttggtatc ttaagtactg aagttagcac tatggttaca tgcaaaagat    660

taagggaaaa acccttaaag tggacaggta ttcaaaggtc attttctggg actcatcaaa    720

gtgccaaaag acttgtaaca ctttgcctgg actttttcat tttacaacaa gtcatc        776
```

<210> SEQ ID NO 47
<211> LENGTH: 770
<212> TYPE: DNA
<213> ORGANISM: Homo sapiens
<220> FEATURE:
<221> NAME/KEY: modified_base
<222> LOCATION: (1)..(1)
<223> OTHER INFORMATION: n is a, c, g, or t
<220> FEATURE:
<221> NAME/KEY: modified_base
<222> LOCATION: (4)..(4)
<223> OTHER INFORMATION: n is a, c, g, or t
<220> FEATURE:
<221> NAME/KEY: modified_base
<222> LOCATION: (55)..(55)
<223> OTHER INFORMATION: n is a, c, g, or t
<220> FEATURE:
<221> NAME/KEY: modified_base
<222> LOCATION: (57)..(57)
<223> OTHER INFORMATION: n is a, c, g, or t
<220> FEATURE:
<221> NAME/KEY: modified_base
<222> LOCATION: (62)..(62)
<223> OTHER INFORMATION: n is a, c, g, or t
<220> FEATURE:
<221> NAME/KEY: modified_base
<222> LOCATION: (69)..(69)
<223> OTHER INFORMATION: n is a, c, g, or t
<220> FEATURE:
<221> NAME/KEY: modified_base
<222> LOCATION: (73)..(73)
<223> OTHER INFORMATION: n is a, c, g, or t
<220> FEATURE:
<221> NAME/KEY: modified_base
<222> LOCATION: (75)..(76)
<223> OTHER INFORMATION: n is a, c, g, or t
<220> FEATURE:
<221> NAME/KEY: modified_base
<222> LOCATION: (79)..(79)
<223> OTHER INFORMATION: n is a, c, g, or t
<220> FEATURE:
<221> NAME/KEY: modified_base
<222> LOCATION: (81)..(81)
<223> OTHER INFORMATION: n is a, c, g, or t
<220> FEATURE:
<221> NAME/KEY: modified_base
<222> LOCATION: (88)..(88)
<223> OTHER INFORMATION: n is a, c, g, or t
<220> FEATURE:
<221> NAME/KEY: modified_base
<222> LOCATION: (91)..(91)
<223> OTHER INFORMATION: n is a, c, g, or t
<220> FEATURE:
<221> NAME/KEY: modified_base
<222> LOCATION: (93)..(93)
<223> OTHER INFORMATION: n is a, c, g, or t
<220> FEATURE:
<221> NAME/KEY: modified_base
<222> LOCATION: (96)..(96)
<223> OTHER INFORMATION: n is a, c, g, or t
<220> FEATURE:
<221> NAME/KEY: modified_base
<222> LOCATION: (106)..(106)

-continued

<223> OTHER INFORMATION: n is a, c, g, or t
<220> FEATURE:
<221> NAME/KEY: modified_base
<222> LOCATION: (111)..(111)
<223> OTHER INFORMATION: n is a, c, g, or t
<220> FEATURE:
<221> NAME/KEY: modified_base
<222> LOCATION: (117)..(117)
<223> OTHER INFORMATION: n is a, c, g, or t
<220> FEATURE:
<221> NAME/KEY: modified_base
<222> LOCATION: (123)..(123)
<223> OTHER INFORMATION: n is a, c, g, or t
<220> FEATURE:
<221> NAME/KEY: modified_base
<222> LOCATION: (131)..(132)
<223> OTHER INFORMATION: n is a, c, g, or t
<220> FEATURE:
<221> NAME/KEY: modified_base
<222> LOCATION: (134)..(134)
<223> OTHER INFORMATION: n is a, c, g, or t
<220> FEATURE:
<221> NAME/KEY: modified_base
<222> LOCATION: (143)..(143)
<223> OTHER INFORMATION: n is a, c, g, or t
<220> FEATURE:
<221> NAME/KEY: modified_base
<222> LOCATION: (149)..(149)
<223> OTHER INFORMATION: n is a, c, g, or t
<220> FEATURE:
<221> NAME/KEY: modified_base
<222> LOCATION: (155)..(155)
<223> OTHER INFORMATION: n is a, c, g, or t
<220> FEATURE:
<221> NAME/KEY: modified_base
<222> LOCATION: (158)..(158)
<223> OTHER INFORMATION: n is a, c, g, or t
<220> FEATURE:
<221> NAME/KEY: modified_base
<222> LOCATION: (162)..(162)
<223> OTHER INFORMATION: n is a, c, g, or t
<220> FEATURE:
<221> NAME/KEY: modified_base
<222> LOCATION: (164)..(165)
<223> OTHER INFORMATION: n is a, c, g, or t
<220> FEATURE:
<221> NAME/KEY: modified_base
<222> LOCATION: (172)..(172)
<223> OTHER INFORMATION: n is a, c, g, or t
<220> FEATURE:
<221> NAME/KEY: modified_base
<222> LOCATION: (175)..(175)
<223> OTHER INFORMATION: n is a, c, g, or t
<220> FEATURE:
<221> NAME/KEY: modified_base
<222> LOCATION: (180)..(180)
<223> OTHER INFORMATION: n is a, c, g, or t
<220> FEATURE:
<221> NAME/KEY: modified_base
<222> LOCATION: (194)..(194)
<223> OTHER INFORMATION: n is a, c, g, or t
<220> FEATURE:
<221> NAME/KEY: modified_base
<222> LOCATION: (196)..(196)
<223> OTHER INFORMATION: n is a, c, g, or t
<220> FEATURE:
<221> NAME/KEY: modified_base
<222> LOCATION: (198)..(198)
<223> OTHER INFORMATION: n is a, c, g, or t
<220> FEATURE:
<221> NAME/KEY: modified_base
<222> LOCATION: (200)..(200)
<223> OTHER INFORMATION: n is a, c, g, or t
<220> FEATURE:
<221> NAME/KEY: modified_base
<222> LOCATION: (203)..(203)
<223> OTHER INFORMATION: n is a, c, g, or t
<220> FEATURE:
<221> NAME/KEY: modified_base
<222> LOCATION: (206)..(206)
<223> OTHER INFORMATION: n is a, c, g, or t
<220> FEATURE:
<221> NAME/KEY: modified_base
<222> LOCATION: (213)..(213)
<223> OTHER INFORMATION: n is a, c, g, or t
<220> FEATURE:
<221> NAME/KEY: modified_base
<222> LOCATION: (215)..(215)
<223> OTHER INFORMATION: n is a, c, g, or t
<220> FEATURE:
<221> NAME/KEY: modified_base
<222> LOCATION: (219)..(219)
<223> OTHER INFORMATION: n is a, c, g, or t
<220> FEATURE:
<221> NAME/KEY: modified_base
<222> LOCATION: (223)..(224)
<223> OTHER INFORMATION: n is a, c, g, or t
<220> FEATURE:
<221> NAME/KEY: modified_base
<222> LOCATION: (229)..(230)
<223> OTHER INFORMATION: n is a, c, g, or t
<220> FEATURE:
<221> NAME/KEY: modified_base
<222> LOCATION: (233)..(233)
<223> OTHER INFORMATION: n is a, c, g, or t
<220> FEATURE:
<221> NAME/KEY: modified_base
<222> LOCATION: (236)..(236)
<223> OTHER INFORMATION: n is a, c, g, or t
<220> FEATURE:
<221> NAME/KEY: modified_base
<222> LOCATION: (248)..(248)
<223> OTHER INFORMATION: n is a, c, g, or t
<220> FEATURE:
<221> NAME/KEY: modified_base
<222> LOCATION: (250)..(250)
<223> OTHER INFORMATION: n is a, c, g, or t
<220> FEATURE:
<221> NAME/KEY: modified_base
<222> LOCATION: (257)..(257)
<223> OTHER INFORMATION: n is a, c, g, or t
<220> FEATURE:
<221> NAME/KEY: modified_base
<222> LOCATION: (263)..(263)
<223> OTHER INFORMATION: n is a, c, g, or t
<220> FEATURE:
<221> NAME/KEY: modified_base
<222> LOCATION: (274)..(274)
<223> OTHER INFORMATION: n is a, c, g, or t
<220> FEATURE:
<221> NAME/KEY: modified_base
<222> LOCATION: (277)..(277)
<223> OTHER INFORMATION: n is a, c, g, or t
<220> FEATURE:
<221> NAME/KEY: modified_base
<222> LOCATION: (280)..(280)
<223> OTHER INFORMATION: n is a, c, g, or t
<220> FEATURE:
<221> NAME/KEY: modified_base
<222> LOCATION: (284)..(284)
<223> OTHER INFORMATION: n is a, c, g, or t
<220> FEATURE:
<221> NAME/KEY: modified_base
<222> LOCATION: (286)..(286)
<223> OTHER INFORMATION: n is a, c, g, or t
<220> FEATURE:
<221> NAME/KEY: modified_base
<222> LOCATION: (289)..(289)
<223> OTHER INFORMATION: n is a, c, g, or t
<220> FEATURE:
<221> NAME/KEY: modified_base
<222> LOCATION: (292)..(292)
<223> OTHER INFORMATION: n is a, c, g, or t
<220> FEATURE:
<221> NAME/KEY: modified_base
<222> LOCATION: (294)..(294)
<223> OTHER INFORMATION: n is a, c, g, or t
<220> FEATURE:

-continued

<221> NAME/KEY: modified_base
<222> LOCATION: (299)..(299)
<223> OTHER INFORMATION: n is a, c, g, or t
<220> FEATURE:
<221> NAME/KEY: modified_base
<222> LOCATION: (301)..(301)
<223> OTHER INFORMATION: n is a, c, g, or t
<220> FEATURE:
<221> NAME/KEY: modified_base
<222> LOCATION: (309)..(309)
<223> OTHER INFORMATION: n is a, c, g, or t
<220> FEATURE:
<221> NAME/KEY: modified_base
<222> LOCATION: (311)..(311)
<223> OTHER INFORMATION: n is a, c, g, or t
<220> FEATURE:
<221> NAME/KEY: modified_base
<222> LOCATION: (320)..(320)
<223> OTHER INFORMATION: n is a, c, g, or t
<220> FEATURE:
<221> NAME/KEY: modified_base
<222> LOCATION: (332)..(332)
<223> OTHER INFORMATION: n is a, c, g, or t
<220> FEATURE:
<221> NAME/KEY: modified_base
<222> LOCATION: (334)..(334)
<223> OTHER INFORMATION: n is a, c, g, or t
<220> FEATURE:
<221> NAME/KEY: modified_base
<222> LOCATION: (337)..(337)
<223> OTHER INFORMATION: n is a, c, g, or t
<220> FEATURE:
<221> NAME/KEY: modified_base
<222> LOCATION: (340)..(341)
<223> OTHER INFORMATION: n is a, c, g, or t
<220> FEATURE:
<221> NAME/KEY: modified_base
<222> LOCATION: (351)..(351)
<223> OTHER INFORMATION: n is a, c, g, or t
<220> FEATURE:
<221> NAME/KEY: modified_base
<222> LOCATION: (360)..(360)
<223> OTHER INFORMATION: n is a, c, g, or t
<220> FEATURE:
<221> NAME/KEY: modified_base
<222> LOCATION: (373)..(373)
<223> OTHER INFORMATION: n is a, c, g, or t
<220> FEATURE:
<221> NAME/KEY: modified_base
<222> LOCATION: (376)..(376)
<223> OTHER INFORMATION: n is a, c, g, or t
<220> FEATURE:
<221> NAME/KEY: modified_base
<222> LOCATION: (378)..(378)
<223> OTHER INFORMATION: n is a, c, g, or t
<220> FEATURE:
<221> NAME/KEY: modified_base
<222> LOCATION: (380)..(380)
<223> OTHER INFORMATION: n is a, c, g, or t
<220> FEATURE:
<221> NAME/KEY: modified_base
<222> LOCATION: (391)..(391)
<223> OTHER INFORMATION: n is a, c, g, or t
<220> FEATURE:
<221> NAME/KEY: modified_base
<222> LOCATION: (401)..(401)
<223> OTHER INFORMATION: n is a, c, g, or t
<220> FEATURE:
<221> NAME/KEY: modified_base
<222> LOCATION: (407)..(407)
<223> OTHER INFORMATION: n is a, c, g, or t
<220> FEATURE:
<221> NAME/KEY: modified_base
<222> LOCATION: (414)..(414)
<223> OTHER INFORMATION: n is a, c, g, or t
<220> FEATURE:
<221> NAME/KEY: modified_base
<222> LOCATION: (427)..(427)
<223> OTHER INFORMATION: n is a, c, g, or t
<220> FEATURE:
<221> NAME/KEY: modified_base
<222> LOCATION: (433)..(433)
<223> OTHER INFORMATION: n is a, c, g, or t
<220> FEATURE:
<221> NAME/KEY: modified_base
<222> LOCATION: (439)..(439)
<223> OTHER INFORMATION: n is a, c, g, or t
<220> FEATURE:
<221> NAME/KEY: modified_base
<222> LOCATION: (441)..(441)
<223> OTHER INFORMATION: n is a, c, g, or t
<220> FEATURE:
<221> NAME/KEY: modified_base
<222> LOCATION: (443)..(443)
<223> OTHER INFORMATION: n is a, c, g, or t
<220> FEATURE:
<221> NAME/KEY: modified_base
<222> LOCATION: (446)..(447)
<223> OTHER INFORMATION: n is a, c, g, or t
<220> FEATURE:
<221> NAME/KEY: modified_base
<222> LOCATION: (452)..(452)
<223> OTHER INFORMATION: n is a, c, g, or t
<220> FEATURE:
<221> NAME/KEY: modified_base
<222> LOCATION: (460)..(461)
<223> OTHER INFORMATION: n is a, c, g, or t
<220> FEATURE:
<221> NAME/KEY: modified_base
<222> LOCATION: (464)..(464)
<223> OTHER INFORMATION: n is a, c, g, or t
<220> FEATURE:
<221> NAME/KEY: modified_base
<222> LOCATION: (470)..(471)
<223> OTHER INFORMATION: n is a, c, g, or t
<220> FEATURE:
<221> NAME/KEY: modified_base
<222> LOCATION: (476)..(476)
<223> OTHER INFORMATION: n is a, c, g, or t
<220> FEATURE:
<221> NAME/KEY: modified_base
<222> LOCATION: (480)..(480)
<223> OTHER INFORMATION: n is a, c, g, or t
<220> FEATURE:
<221> NAME/KEY: modified_base
<222> LOCATION: (482)..(482)
<223> OTHER INFORMATION: n is a, c, g, or t
<220> FEATURE:
<221> NAME/KEY: modified_base
<222> LOCATION: (487)..(487)
<223> OTHER INFORMATION: n is a, c, g, or t
<220> FEATURE:
<221> NAME/KEY: modified_base
<222> LOCATION: (492)..(492)
<223> OTHER INFORMATION: n is a, c, g, or t
<220> FEATURE:
<221> NAME/KEY: modified_base
<222> LOCATION: (504)..(504)
<223> OTHER INFORMATION: n is a, c, g, or t
<220> FEATURE:
<221> NAME/KEY: modified_base
<222> LOCATION: (507)..(507)
<223> OTHER INFORMATION: n is a, c, g, or t
<220> FEATURE:
<221> NAME/KEY: modified_base
<222> LOCATION: (511)..(511)
<223> OTHER INFORMATION: n is a, c, g, or t
<220> FEATURE:
<221> NAME/KEY: modified_base
<222> LOCATION: (529)..(529)
<223> OTHER INFORMATION: n is a, c, g, or t
<220> FEATURE:
<221> NAME/KEY: modified_base
<222> LOCATION: (531)..(531)
<223> OTHER INFORMATION: n is a, c, g, or t
<220> FEATURE:
<221> NAME/KEY: modified_base
<222> LOCATION: (535)..(535)

-continued

<223> OTHER INFORMATION: n is a, c, g, or t
<220> FEATURE:
<221> NAME/KEY: modified_base
<222> LOCATION: (538)..(538)
<223> OTHER INFORMATION: n is a, c, g, or t
<220> FEATURE:
<221> NAME/KEY: modified_base
<222> LOCATION: (540)..(540)
<223> OTHER INFORMATION: n is a, c, g, or t
<220> FEATURE:
<221> NAME/KEY: modified_base
<222> LOCATION: (545)..(545)
<223> OTHER INFORMATION: n is a, c, g, or t
<220> FEATURE:
<221> NAME/KEY: modified_base
<222> LOCATION: (547)..(547)
<223> OTHER INFORMATION: n is a, c, g, or t
<220> FEATURE:
<221> NAME/KEY: modified_base
<222> LOCATION: (552)..(552)
<223> OTHER INFORMATION: n is a, c, g, or t
<220> FEATURE:
<221> NAME/KEY: modified_base
<222> LOCATION: (556)..(557)
<223> OTHER INFORMATION: n is a, c, g, or t
<220> FEATURE:
<221> NAME/KEY: modified_base
<222> LOCATION: (561)..(561)
<223> OTHER INFORMATION: n is a, c, g, or t
<220> FEATURE:
<221> NAME/KEY: modified_base
<222> LOCATION: (569)..(569)
<223> OTHER INFORMATION: n is a, c, g, or t
<220> FEATURE:
<221> NAME/KEY: modified_base
<222> LOCATION: (573)..(573)
<223> OTHER INFORMATION: n is a, c, g, or t
<220> FEATURE:
<221> NAME/KEY: modified_base
<222> LOCATION: (579)..(579)
<223> OTHER INFORMATION: n is a, c, g, or t
<220> FEATURE:
<221> NAME/KEY: modified_base
<222> LOCATION: (587)..(587)
<223> OTHER INFORMATION: n is a, c, g, or t
<220> FEATURE:
<221> NAME/KEY: modified_base
<222> LOCATION: (593)..(593)
<223> OTHER INFORMATION: n is a, c, g, or t
<220> FEATURE:
<221> NAME/KEY: modified_base
<222> LOCATION: (620)..(620)
<223> OTHER INFORMATION: n is a, c, g, or t
<220> FEATURE:
<221> NAME/KEY: modified_base
<222> LOCATION: (630)..(630)
<223> OTHER INFORMATION: n is a, c, g, or t
<220> FEATURE:
<221> NAME/KEY: modified_base
<222> LOCATION: (633)..(633)
<223> OTHER INFORMATION: n is a, c, g, or t
<220> FEATURE:
<221> NAME/KEY: modified_base
<222> LOCATION: (641)..(641)
<223> OTHER INFORMATION: n is a, c, g, or t
<220> FEATURE:
<221> NAME/KEY: modified_base
<222> LOCATION: (646)..(646)
<223> OTHER INFORMATION: n is a, c, g, or t
<220> FEATURE:
<221> NAME/KEY: modified_base
<222> LOCATION: (669)..(669)
<223> OTHER INFORMATION: n is a, c, g, or t
<220> FEATURE:
<221> NAME/KEY: modified_base
<222> LOCATION: (671)..(671)
<223> OTHER INFORMATION: n is a, c, g, or t
<220> FEATURE:
<221> NAME/KEY: modified_base -continued
<222> LOCATION: (683)..(683)
<223> OTHER INFORMATION: n is a, c, g, or t
<220> FEATURE:
<221> NAME/KEY: modified_base
<222> LOCATION: (694)..(694)
<223> OTHER INFORMATION: n is a, c, g, or t
<220> FEATURE:
<221> NAME/KEY: modified_base
<222> LOCATION: (700)..(701)
<223> OTHER INFORMATION: n is a, c, g, or t
<220> FEATURE:
<221> NAME/KEY: modified_base
<222> LOCATION: (703)..(703)
<223> OTHER INFORMATION: n is a, c, g, or t
<220> FEATURE:
<221> NAME/KEY: modified_base
<222> LOCATION: (705)..(706)
<223> OTHER INFORMATION: n is a, c, g, or t
<220> FEATURE:
<221> NAME/KEY: modified_base
<222> LOCATION: (713)..(713)
<223> OTHER INFORMATION: n is a, c, g, or t
<220> FEATURE:
<221> NAME/KEY: modified_base
<222> LOCATION: (724)..(724)
<223> OTHER INFORMATION: n is a, c, g, or t
<220> FEATURE:
<221> NAME/KEY: modified_base
<222> LOCATION: (737)..(737)
<223> OTHER INFORMATION: n is a, c, g, or t
<220> FEATURE:
<221> NAME/KEY: modified_base
<222> LOCATION: (752)..(752)
<223> OTHER INFORMATION: n is a, c, g, or t
<220> FEATURE:
<221> NAME/KEY: modified_base
<222> LOCATION: (761)..(761)
<223> OTHER INFORMATION: n is a, c, g, or t
<220> FEATURE:
<221> NAME/KEY: modified_base
<222> LOCATION: (766)..(766)
<223> OTHER INFORMATION: n is a, c, g, or t
<220> FEATURE:
<221> NAME/KEY: modified_base
<222> LOCATION: (769)..(769)
<223> OTHER INFORMATION: n is a, c, g, or t

<400> SEQUENCE: 47
nccncttttt tttttttttt tttttttttt tttttttttt tttttttttg gaatnanctt 60
tntttcccnt acngnnaana nctttttngc ntngantttt aaggcnccaa ngtaaantaa 120 aanccccccaa nngncagggt ttnaaaaanc caaanttngt tncnnttttt tnggnaaaan 180
gttcaccctt tttntngntn tgnaanggac ccntntttng ggnnaaaann ganttnttta 240
aatcaaanan ttttttnccc ctnggaaaaa aaantcngcn gtancnttnt cncngaatnt 300
ngaaaattnc nttttttttn ataaaggggc cntnctnttn ngccttttcc nccaaaagcn 360 gggggggtt atnctngntn tttaaaaaaa ngttttttcc nggggcngga aaancccttt 420
ttttttnctt ttnctaaana ncnggnnaaa angttcaagn ntgntaaagn ngcctntaan 480
cnggaanggg ancttgttaa atcnccnttt ncattttagg gctttttttng naatnggncn 540 ttttnancaa angtannaaa ntgcttttng ccntaaagng ggtttcntca aangcttaag 600
ggtttaaaaa atttggggcn gaaaacaaan tcnttgggaa ngggtnaacc gggggaaaag 660
gaaaaagtnc nggcaaagtt gtncaagctt tggnctttgn ngngnncaaa aantgacctt 720 gganccccggc cctttanggg ttttcctaaa cntttggatg naacanagng 770

<210> SEQ ID NO 48
<211> LENGTH: 759
<212> TYPE: DNA

-continued

<213> ORGANISM: Homo sapiens
<220> FEATURE:
<221> NAME/KEY: modified_base
<222> LOCATION: (7)..(7)
<223> OTHER INFORMATION: n is a, c, g, or t
<220> FEATURE:
<221> NAME/KEY: modified_base
<222> LOCATION: (480)..(480)
<223> OTHER INFORMATION: n is a, c, g, or t
<220> FEATURE:
<221> NAME/KEY: modified_base
<222> LOCATION: (487)..(487)
<223> OTHER INFORMATION: n is a, c, g, or t
<220> FEATURE:
<221> NAME/KEY: modified_base
<222> LOCATION: (514)..(514)
<223> OTHER INFORMATION: n is a, c, g, or t
<220> FEATURE:
<221> NAME/KEY: modified_base
<222> LOCATION: (563)..(563)
<223> OTHER INFORMATION: n is a, c, g, or t
<220> FEATURE:
<221> NAME/KEY: modified_base
<222> LOCATION: (586)..(586)
<223> OTHER INFORMATION: n is a, c, g, or t
<220> FEATURE:
<221> NAME/KEY: modified_base
<222> LOCATION: (589)..(589)
<223> OTHER INFORMATION: n is a, c, g, or t
<220> FEATURE:
<221> NAME/KEY: modified_base
<222> LOCATION: (608)..(608)
<223> OTHER INFORMATION: n is a, c, g, or t
<220> FEATURE:
<221> NAME/KEY: modified_base
<222> LOCATION: (613)..(614)
<223> OTHER INFORMATION: n is a, c, g, or t
<220> FEATURE:
<221> NAME/KEY: modified_base
<222> LOCATION: (616)..(616)
<223> OTHER INFORMATION: n is a, c, g, or t
<220> FEATURE:
<221> NAME/KEY: modified_base
<222> LOCATION: (639)..(639)
<223> OTHER INFORMATION: n is a, c, g, or t
<220> FEATURE:
<221> NAME/KEY: modified_base
<222> LOCATION: (650)..(650)
<223> OTHER INFORMATION: n is a, c, g, or t
<220> FEATURE:
<221> NAME/KEY: modified_base
<222> LOCATION: (699)..(699)
<223> OTHER INFORMATION: n is a, c, g, or t
<220> FEATURE:
<221> NAME/KEY: modified_base
<222> LOCATION: (712)..(712)
<223> OTHER INFORMATION: n is a, c, g, or t
<220> FEATURE:
<221> NAME/KEY: modified_base
<222> LOCATION: (736)..(736)
<223> OTHER INFORMATION: n is a, c, g, or t
<220> FEATURE:
<221> NAME/KEY: modified_base
<222> LOCATION: (747)..(747)
<223> OTHER INFORMATION: n is a, c, g, or t
<220> FEATURE:
<221> NAME/KEY: modified_base
<222> LOCATION: (759)..(759)
<223> OTHER INFORMATION: n is a, c, g, or t

<400> SEQUENCE: 48
actgttngcc tactggttct gaataacttc tttttaccta tattccagca ttccagtctc 60
ctaattcagt cttcacttct gtctgagctg ctattaaacc tgagttctta atttggacag 120
ttttattttc cagttctaga agttcttttt gctctttttc agttttgctg tcctttaaag 180
tttcctgttc cttccagata ctttcaggct tttcttttat ttctttaaat agagtaagta 240

```
cgattttata atttggatct gataattcca gcatctgaaa tctctggtgg tctgtgtcca    300

gtcaggaaaa tagaaatcag tgagatgtct caagcagaga gggatttagt gaagtatttg    360

attgcaaagg agctggaagg gttggaggag gaggccatgt tacctggttg ttcttgggct    420

tgttgctgga ggcatggctg ctgatcccct gaaattttcc gcagctgcat tccgtgtggn    480

tgcctgnttt tgcatctggc ttttcctttc ccgntctttc aattttccgc cagggttggc    540

tttggagaac ctgacaagac tgnctagcaa gaattcttct atatgnagnt ttcaagcttc    600

taaccttntg cannanaagc agaaaagatc tgaatacanc agacaaaatn tgaaactgga    660

tatatggcat cccgtggttt tgctggtggg ttttgcttnt aaaggcttgg tnggcctttt    720

atgcctgggt aatttngggg accgggnttt taaaaatan                           759
```

```
<210> SEQ ID NO 49
<211> LENGTH: 808
<212> TYPE: DNA
<213> ORGANISM: Homo sapiens
<220> FEATURE:
<221> NAME/KEY: modified_base
<222> LOCATION: (9)..(9)
<223> OTHER INFORMATION: n is a, c, g, or t
<220> FEATURE:
<221> NAME/KEY: modified_base
<222> LOCATION: (13)..(13)
<223> OTHER INFORMATION: n is a, c, g, or t
<220> FEATURE:
<221> NAME/KEY: modified_base
<222> LOCATION: (26)..(26)
<223> OTHER INFORMATION: n is a, c, g, or t
<220> FEATURE:
<221> NAME/KEY: modified_base
<222> LOCATION: (30)..(30)
<223> OTHER INFORMATION: n is a, c, g, or t
<220> FEATURE:
<221> NAME/KEY: modified_base
<222> LOCATION: (39)..(39)
<223> OTHER INFORMATION: n is a, c, g, or t
<220> FEATURE:
<221> NAME/KEY: modified_base
<222> LOCATION: (43)..(44)
<223> OTHER INFORMATION: n is a, c, g, or t
<220> FEATURE:
<221> NAME/KEY: modified_base
<222> LOCATION: (46)..(46)
<223> OTHER INFORMATION: n is a, c, g, or t
<220> FEATURE:
<221> NAME/KEY: modified_base
<222> LOCATION: (49)..(49)
<223> OTHER INFORMATION: n is a, c, g, or t
<220> FEATURE:
<221> NAME/KEY: modified_base
<222> LOCATION: (52)..(52)
<223> OTHER INFORMATION: n is a, c, g, or t
<220> FEATURE:
<221> NAME/KEY: modified_base
<222> LOCATION: (59)..(59)
<223> OTHER INFORMATION: n is a, c, g, or t
<220> FEATURE:
<221> NAME/KEY: modified_base
<222> LOCATION: (61)..(62)
<223> OTHER INFORMATION: n is a, c, g, or t
<220> FEATURE:
<221> NAME/KEY: modified_base
<222> LOCATION: (66)..(66)
<223> OTHER INFORMATION: n is a, c, g, or t
<220> FEATURE:
<221> NAME/KEY: modified_base
<222> LOCATION: (73)..(74)
<223> OTHER INFORMATION: n is a, c, g, or t
<220> FEATURE:
<221> NAME/KEY: modified_base
<222> LOCATION: (76)..(76)
```

-continued

<223> OTHER INFORMATION: n is a, c, g, or t
<220> FEATURE:
<221> NAME/KEY: modified_base
<222> LOCATION: (79)..(79)
<223> OTHER INFORMATION: n is a, c, g, or t
<220> FEATURE:
<221> NAME/KEY: modified_base
<222> LOCATION: (91)..(92)
<223> OTHER INFORMATION: n is a, c, g, or t
<220> FEATURE:
<221> NAME/KEY: modified_base
<222> LOCATION: (94)..(94)
<223> OTHER INFORMATION: n is a, c, g, or t
<220> FEATURE:
<221> NAME/KEY: modified_base
<222> LOCATION: (97)..(97)
<223> OTHER INFORMATION: n is a, c, g, or t
<220> FEATURE:
<221> NAME/KEY: modified_base
<222> LOCATION: (100)..(100)
<223> OTHER INFORMATION: n is a, c, g, or t
<220> FEATURE:
<221> NAME/KEY: modified_base
<222> LOCATION: (104)..(104)
<223> OTHER INFORMATION: n is a, c, g, or t
<220> FEATURE:
<221> NAME/KEY: modified_base
<222> LOCATION: (111)..(111)
<223> OTHER INFORMATION: n is a, c, g, or t
<220> FEATURE:
<221> NAME/KEY: modified_base
<222> LOCATION: (116)..(116)
<223> OTHER INFORMATION: n is a, c, g, or t
<220> FEATURE:
<221> NAME/KEY: modified_base
<222> LOCATION: (127)..(127)
<223> OTHER INFORMATION: n is a, c, g, or t
<220> FEATURE:
<221> NAME/KEY: modified_base
<222> LOCATION: (133)..(134)
<223> OTHER INFORMATION: n is a, c, g, or t
<220> FEATURE:
<221> NAME/KEY: modified_base
<222> LOCATION: (139)..(139)
<223> OTHER INFORMATION: n is a, c, g, or t
<220> FEATURE:
<221> NAME/KEY: modified_base
<222> LOCATION: (148)..(148)
<223> OTHER INFORMATION: n is a, c, g, or t
<220> FEATURE:
<221> NAME/KEY: modified_base
<222> LOCATION: (150)..(151)
<223> OTHER INFORMATION: n is a, c, g, or t
<220> FEATURE:
<221> NAME/KEY: modified_base
<222> LOCATION: (154)..(154)
<223> OTHER INFORMATION: n is a, c, g, or t
<220> FEATURE:
<221> NAME/KEY: modified_base
<222> LOCATION: (157)..(157)
<223> OTHER INFORMATION: n is a, c, g, or t
<220> FEATURE:
<221> NAME/KEY: modified_base
<222> LOCATION: (159)..(159)
<223> OTHER INFORMATION: n is a, c, g, or t
<220> FEATURE:
<221> NAME/KEY: modified_base
<222> LOCATION: (162)..(162)
<223> OTHER INFORMATION: n is a, c, g, or t
<220> FEATURE:
<221> NAME/KEY: modified_base
<222> LOCATION: (164)..(164)
<223> OTHER INFORMATION: n is a, c, g, or t
<220> FEATURE:
<221> NAME/KEY: modified_base
<222> LOCATION: (166)..(166)
<223> OTHER INFORMATION: n is a, c, g, or t
<220> FEATURE:
<221> NAME/KEY: modified_base
<222> LOCATION: (169)..(169)
<223> OTHER INFORMATION: n is a, c, g, or t
<220> FEATURE:
<221> NAME/KEY: modified_base
<222> LOCATION: (173)..(173)
<223> OTHER INFORMATION: n is a, c, g, or t
<220> FEATURE:
<221> NAME/KEY: modified_base
<222> LOCATION: (176)..(176)
<223> OTHER INFORMATION: n is a, c, g, or t
<220> FEATURE:
<221> NAME/KEY: modified_base
<222> LOCATION: (194)..(195)
<223> OTHER INFORMATION: n is a, c, g, or t
<220> FEATURE:
<221> NAME/KEY: modified_base
<222> LOCATION: (198)..(198)
<223> OTHER INFORMATION: n is a, c, g, or t
<220> FEATURE:
<221> NAME/KEY: modified_base
<222> LOCATION: (205)..(206)
<223> OTHER INFORMATION: n is a, c, g, or t
<220> FEATURE:
<221> NAME/KEY: modified_base
<222> LOCATION: (209)..(210)
<223> OTHER INFORMATION: n is a, c, g, or t
<220> FEATURE:
<221> NAME/KEY: modified_base
<222> LOCATION: (226)..(226)
<223> OTHER INFORMATION: n is a, c, g, or t
<220> FEATURE:
<221> NAME/KEY: modified_base
<222> LOCATION: (229)..(229)
<223> OTHER INFORMATION: n is a, c, g, or t
<220> FEATURE:
<221> NAME/KEY: modified_base
<222> LOCATION: (237)..(237)
<223> OTHER INFORMATION: n is a, c, g, or t
<220> FEATURE:
<221> NAME/KEY: modified_base
<222> LOCATION: (240)..(240)
<223> OTHER INFORMATION: n is a, c, g, or t
<220> FEATURE:
<221> NAME/KEY: modified_base
<222> LOCATION: (246)..(246)
<223> OTHER INFORMATION: n is a, c, g, or t
<220> FEATURE:
<221> NAME/KEY: modified_base
<222> LOCATION: (252)..(253)
<223> OTHER INFORMATION: n is a, c, g, or t
<220> FEATURE:
<221> NAME/KEY: modified_base
<222> LOCATION: (256)..(256)
<223> OTHER INFORMATION: n is a, c, g, or t
<220> FEATURE:
<221> NAME/KEY: modified_base
<222> LOCATION: (261)..(263)
<223> OTHER INFORMATION: n is a, c, g, or t
<220> FEATURE:
<221> NAME/KEY: modified_base
<222> LOCATION: (285)..(285)
<223> OTHER INFORMATION: n is a, c, g, or t
<220> FEATURE:
<221> NAME/KEY: modified_base
<222> LOCATION: (294)..(294)
<223> OTHER INFORMATION: n is a, c, g, or t
<220> FEATURE:
<221> NAME/KEY: modified_base
<222> LOCATION: (299)..(299)
<223> OTHER INFORMATION: n is a, c, g, or t
<220> FEATURE:
<221> NAME/KEY: modified_base
<222> LOCATION: (303)..(303)
<223> OTHER INFORMATION: n is a, c, g, or t
<220> FEATURE:
<221> NAME/KEY: modified_base
<222> LOCATION: (308)..(308)
<223> OTHER INFORMATION: n is a, c, g, or t
<220> FEATURE:

-continued

<221> NAME/KEY: modified_base
<222> LOCATION: (311)..(312)
<223> OTHER INFORMATION: n is a, c, g, or t
<220> FEATURE:
<221> NAME/KEY: modified_base
<222> LOCATION: (324)..(324)
<223> OTHER INFORMATION: n is a, c, g, or t
<220> FEATURE:
<221> NAME/KEY: modified_base
<222> LOCATION: (327)..(327)
<223> OTHER INFORMATION: n is a, c, g, or t
<220> FEATURE:
<221> NAME/KEY: modified_base
<222> LOCATION: (332)..(333)
<223> OTHER INFORMATION: n is a, c, g, or t
<220> FEATURE:
<221> NAME/KEY: modified_base
<222> LOCATION: (335)..(336)
<223> OTHER INFORMATION: n is a, c, g, or t
<220> FEATURE:
<221> NAME/KEY: modified_base
<222> LOCATION: (344)..(346)
<223> OTHER INFORMATION: n is a, c, g, or t
<220> FEATURE:
<221> NAME/KEY: modified_base
<222> LOCATION: (353)..(353)
<223> OTHER INFORMATION: n is a, c, g, or t
<220> FEATURE:
<221> NAME/KEY: modified_base
<222> LOCATION: (355)..(355)
<223> OTHER INFORMATION: n is a, c, g, or t
<220> FEATURE:
<221> NAME/KEY: modified_base
<222> LOCATION: (366)..(367)
<223> OTHER INFORMATION: n is a, c, g, or t
<220> FEATURE:
<221> NAME/KEY: modified_base
<222> LOCATION: (381)..(382)
<223> OTHER INFORMATION: n is a, c, g, or t
<220> FEATURE:
<221> NAME/KEY: modified_base
<222> LOCATION: (385)..(385)
<223> OTHER INFORMATION: n is a, c, g, or t
<220> FEATURE:
<221> NAME/KEY: modified_base
<222> LOCATION: (387)..(387)
<223> OTHER INFORMATION: n is a, c, g, or t
<220> FEATURE:
<221> NAME/KEY: modified_base
<222> LOCATION: (389)..(389)
<223> OTHER INFORMATION: n is a, c, g, or t
<220> FEATURE:
<221> NAME/KEY: modified_base
<222> LOCATION: (391)..(391)
<223> OTHER INFORMATION: n is a, c, g, or t
<220> FEATURE:
<221> NAME/KEY: modified_base
<222> LOCATION: (393)..(393)
<223> OTHER INFORMATION: n is a, c, g, or t
<220> FEATURE:
<221> NAME/KEY: modified_base
<222> LOCATION: (395)..(395)
<223> OTHER INFORMATION: n is a, c, g, or t
<220> FEATURE:
<221> NAME/KEY: modified_base
<222> LOCATION: (398)..(398)
<223> OTHER INFORMATION: n is a, c, g, or t
<220> FEATURE:
<221> NAME/KEY: modified_base
<222> LOCATION: (401)..(403)
<223> OTHER INFORMATION: n is a, c, g, or t
<220> FEATURE:
<221> NAME/KEY: modified_base
<222> LOCATION: (413)..(413)
<223> OTHER INFORMATION: n is a, c, g, or t
<220> FEATURE:
<221> NAME/KEY: modified_base
<222> LOCATION: (418)..(418)
<223> OTHER INFORMATION: n is a, c, g, or t
<220> FEATURE:
<221> NAME/KEY: modified_base
<222> LOCATION: (426)..(426)
<223> OTHER INFORMATION: n is a, c, g, or t
<220> FEATURE:
<221> NAME/KEY: modified_base
<222> LOCATION: (436)..(436)
<223> OTHER INFORMATION: n is a, c, g, or t
<220> FEATURE:
<221> NAME/KEY: modified_base
<222> LOCATION: (446)..(446)
<223> OTHER INFORMATION: n is a, c, g, or t
<220> FEATURE:
<221> NAME/KEY: modified_base
<222> LOCATION: (449)..(449)
<223> OTHER INFORMATION: n is a, c, g, or t
<220> FEATURE:
<221> NAME/KEY: modified_base
<222> LOCATION: (452)..(452)
<223> OTHER INFORMATION: n is a, c, g, or t
<220> FEATURE:
<221> NAME/KEY: modified_base
<222> LOCATION: (454)..(454)
<223> OTHER INFORMATION: n is a, c, g, or t
<220> FEATURE:
<221> NAME/KEY: modified_base
<222> LOCATION: (456)..(456)
<223> OTHER INFORMATION: n is a, c, g, or t
<220> FEATURE:
<221> NAME/KEY: modified_base
<222> LOCATION: (462)..(462)
<223> OTHER INFORMATION: n is a, c, g, or t
<220> FEATURE:
<221> NAME/KEY: modified_base
<222> LOCATION: (465)..(465)
<223> OTHER INFORMATION: n is a, c, g, or t
<220> FEATURE:
<221> NAME/KEY: modified_base
<222> LOCATION: (470)..(470)
<223> OTHER INFORMATION: n is a, c, g, or t
<220> FEATURE:
<221> NAME/KEY: modified_base
<222> LOCATION: (478)..(479)
<223> OTHER INFORMATION: n is a, c, g, or t
<220> FEATURE:
<221> NAME/KEY: modified_base
<222> LOCATION: (484)..(484)
<223> OTHER INFORMATION: n is a, c, g, or t
<220> FEATURE:
<221> NAME/KEY: modified_base
<222> LOCATION: (486)..(486)
<223> OTHER INFORMATION: n is a, c, g, or t
<220> FEATURE:
<221> NAME/KEY: modified_base
<222> LOCATION: (495)..(495)
<223> OTHER INFORMATION: n is a, c, g, or t
<220> FEATURE:
<221> NAME/KEY: modified_base
<222> LOCATION: (498)..(498)
<223> OTHER INFORMATION: n is a, c, g, or t
<220> FEATURE:
<221> NAME/KEY: modified_base
<222> LOCATION: (500)..(500)
<223> OTHER INFORMATION: n is a, c, g, or t
<220> FEATURE:
<221> NAME/KEY: modified_base
<222> LOCATION: (509)..(510)
<223> OTHER INFORMATION: n is a, c, g, or t
<220> FEATURE:
<221> NAME/KEY: modified_base
<222> LOCATION: (519)..(519)
<223> OTHER INFORMATION: n is a, c, g, or t
<220> FEATURE:
<221> NAME/KEY: modified_base
<222> LOCATION: (521)..(521)
<223> OTHER INFORMATION: n is a, c, g, or t
<220> FEATURE:
<221> NAME/KEY: modified_base
<222> LOCATION: (536)..(536)

<223> OTHER INFORMATION: n is a, c, g, or t
<220> FEATURE:
<221> NAME/KEY: modified_base
<222> LOCATION: (543)..(543)
<223> OTHER INFORMATION: n is a, c, g, or t
<220> FEATURE:
<221> NAME/KEY: modified_base
<222> LOCATION: (545)..(545)
<223> OTHER INFORMATION: n is a, c, g, or t
<220> FEATURE:
<221> NAME/KEY: modified_base
<222> LOCATION: (551)..(554)
<223> OTHER INFORMATION: n is a, c, g, or t
<220> FEATURE:
<221> NAME/KEY: modified_base
<222> LOCATION: (557)..(557)
<223> OTHER INFORMATION: n is a, c, g, or t
<220> FEATURE:
<221> NAME/KEY: modified_base
<222> LOCATION: (559)..(560)
<223> OTHER INFORMATION: n is a, c, g, or t
<220> FEATURE:
<221> NAME/KEY: modified_base
<222> LOCATION: (564)..(565)
<223> OTHER INFORMATION: n is a, c, g, or t
<220> FEATURE:
<221> NAME/KEY: modified_base
<222> LOCATION: (569)..(569)
<223> OTHER INFORMATION: n is a, c, g, or t
<220> FEATURE:
<221> NAME/KEY: modified_base
<222> LOCATION: (572)..(574)
<223> OTHER INFORMATION: n is a, c, g, or t
<220> FEATURE:
<221> NAME/KEY: modified_base
<222> LOCATION: (578)..(578)
<223> OTHER INFORMATION: n is a, c, g, or t
<220> FEATURE:
<221> NAME/KEY: modified_base
<222> LOCATION: (580)..(580)
<223> OTHER INFORMATION: n is a, c, g, or t
<220> FEATURE:
<221> NAME/KEY: modified_base
<222> LOCATION: (582)..(584)
<223> OTHER INFORMATION: n is a, c, g, or t
<220> FEATURE:
<221> NAME/KEY: modified_base
<222> LOCATION: (594)..(595)
<223> OTHER INFORMATION: n is a, c, g, or t
<220> FEATURE:
<221> NAME/KEY: modified_base
<222> LOCATION: (597)..(597)
<223> OTHER INFORMATION: n is a, c, g, or t
<220> FEATURE:
<221> NAME/KEY: modified_base
<222> LOCATION: (602)..(602)
<223> OTHER INFORMATION: n is a, c, g, or t
<220> FEATURE:
<221> NAME/KEY: modified_base
<222> LOCATION: (610)..(610)
<223> OTHER INFORMATION: n is a, c, g, or t
<220> FEATURE:
<221> NAME/KEY: modified_base
<222> LOCATION: (615)..(616)
<223> OTHER INFORMATION: n is a, c, g, or t
<220> FEATURE:
<221> NAME/KEY: modified_base
<222> LOCATION: (618)..(619)
<223> OTHER INFORMATION: n is a, c, g, or t
<220> FEATURE:
<221> NAME/KEY: modified_base
<222> LOCATION: (628)..(628)
<223> OTHER INFORMATION: n is a, c, g, or t
<220> FEATURE:
<221> NAME/KEY: modified_base
<222> LOCATION: (633)..(633)
<223> OTHER INFORMATION: n is a, c, g, or t
<220> FEATURE:
<221> NAME/KEY: modified_base -continued
<222> LOCATION: (636)..(636)
<223> OTHER INFORMATION: n is a, c, g, or t
<220> FEATURE:
<221> NAME/KEY: modified_base
<222> LOCATION: (641)..(641)
<223> OTHER INFORMATION: n is a, c, g, or t
<220> FEATURE:
<221> NAME/KEY: modified_base
<222> LOCATION: (647)..(651)
<223> OTHER INFORMATION: n is a, c, g, or t
<220> FEATURE:
<221> NAME/KEY: modified_base
<222> LOCATION: (658)..(658)
<223> OTHER INFORMATION: n is a, c, g, or t
<220> FEATURE:
<221> NAME/KEY: modified_base
<222> LOCATION: (664)..(664)
<223> OTHER INFORMATION: n is a, c, g, or t
<220> FEATURE:
<221> NAME/KEY: modified_base
<222> LOCATION: (666)..(666)
<223> OTHER INFORMATION: n is a, c, g, or t
<220> FEATURE:
<221> NAME/KEY: modified_base
<222> LOCATION: (671)..(671)
<223> OTHER INFORMATION: n is a, c, g, or t
<220> FEATURE:
<221> NAME/KEY: modified_base
<222> LOCATION: (673)..(675)
<223> OTHER INFORMATION: n is a, c, g, or t
<220> FEATURE:
<221> NAME/KEY: modified_base
<222> LOCATION: (677)..(679)
<223> OTHER INFORMATION: n is a, c, g, or t
<220> FEATURE:
<221> NAME/KEY: modified_base
<222> LOCATION: (684)..(684)
<223> OTHER INFORMATION: n is a, c, g, or t
<220> FEATURE:
<221> NAME/KEY: modified_base
<222> LOCATION: (686)..(686)
<223> OTHER INFORMATION: n is a, c, g, or t
<220> FEATURE:
<221> NAME/KEY: modified_base
<222> LOCATION: (688)..(688)
<223> OTHER INFORMATION: n is a, c, g, or t
<220> FEATURE:
<221> NAME/KEY: modified_base
<222> LOCATION: (690)..(691)
<223> OTHER INFORMATION: n is a, c, g, or t
<220> FEATURE:
<221> NAME/KEY: modified_base
<222> LOCATION: (696)..(696)
<223> OTHER INFORMATION: n is a, c, g, or t
<220> FEATURE:
<221> NAME/KEY: modified_base
<222> LOCATION: (699)..(700)
<223> OTHER INFORMATION: n is a, c, g, or t
<220> FEATURE:
<221> NAME/KEY: modified_base
<222> LOCATION: (714)..(714)
<223> OTHER INFORMATION: n is a, c, g, or t
<220> FEATURE:
<221> NAME/KEY: modified_base
<222> LOCATION: (716)..(716)
<223> OTHER INFORMATION: n is a, c, g, or t
<220> FEATURE:
<221> NAME/KEY: modified_base
<222> LOCATION: (718)..(718)
<223> OTHER INFORMATION: n is a, c, g, or t
<220> FEATURE:
<221> NAME/KEY: modified_base
<222> LOCATION: (721)..(721)
<223> OTHER INFORMATION: n is a, c, g, or t
<220> FEATURE:
<221> NAME/KEY: modified_base
<222> LOCATION: (724)..(724)
<223> OTHER INFORMATION: n is a, c, g, or t
<220> FEATURE:

-continued

<221> NAME/KEY: modified_base
<222> LOCATION: (740)..(740)
<223> OTHER INFORMATION: n is a, c, g, or t
<220> FEATURE:
<221> NAME/KEY: modified_base
<222> LOCATION: (742)..(742)
<223> OTHER INFORMATION: n is a, c, g, or t
<220> FEATURE:
<221> NAME/KEY: modified_base
<222> LOCATION: (745)..(745)
<223> OTHER INFORMATION: n is a, c, g, or t
<220> FEATURE:
<221> NAME/KEY: modified_base
<222> LOCATION: (752)..(752)
<223> OTHER INFORMATION: n is a, c, g, or t
<220> FEATURE:
<221> NAME/KEY: modified_base
<222> LOCATION: (755)..(755)
<223> OTHER INFORMATION: n is a, c, g, or t
<220> FEATURE:
<221> NAME/KEY: modified_base
<222> LOCATION: (757)..(760)
<223> OTHER INFORMATION: n is a, c, g, or t
<220> FEATURE:
<221> NAME/KEY: modified_base
<222> LOCATION: (762)..(763)
<223> OTHER INFORMATION: n is a, c, g, or t
<220> FEATURE:
<221> NAME/KEY: modified_base
<222> LOCATION: (765)..(766)
<223> OTHER INFORMATION: n is a, c, g, or t
<220> FEATURE:
<221> NAME/KEY: modified_base
<222> LOCATION: (771)..(771)
<223> OTHER INFORMATION: n is a, c, g, or t
<220> FEATURE:
<221> NAME/KEY: modified_base
<222> LOCATION: (780)..(781)
<223> OTHER INFORMATION: n is a, c, g, or t
<220> FEATURE:
<221> NAME/KEY: modified_base
<222> LOCATION: (783)..(783)
<223> OTHER INFORMATION: n is a, c, g, or t
<220> FEATURE:
<221> NAME/KEY: modified_base
<222> LOCATION: (786)..(787)
<223> OTHER INFORMATION: n is a, c, g, or t
<220> FEATURE:
<221> NAME/KEY: modified_base
<222> LOCATION: (793)..(793)
<223> OTHER INFORMATION: n is a, c, g, or t
<220> FEATURE:
<221> NAME/KEY: modified_base
<222> LOCATION: (798)..(798)
<223> OTHER INFORMATION: n is a, c, g, or t
<220> FEATURE:
<221> NAME/KEY: modified_base
<222> LOCATION: (800)..(801)
<223> OTHER INFORMATION: n is a, c, g, or t
<220> FEATURE:
<221> NAME/KEY: modified_base
<222> LOCATION: (804)..(805)
<223> OTHER INFORMATION: n is a, c, g, or t

<400> SEQUENCE: 49
gaacccttng gantgtccct ctacantttn gggaacccnc ccnntnggng ancttaaang 60
nngagntccc cannanttna accctttttt nnangcnacn atcncctgga nacacngggg 120
ccttttngca aanncatanc cccccccntn ncangtncnc antnanacnt acngtntaat 180
gtcacatttt aaanncantc acatnntann acatacgcac taaaanatna atacagncan 240
aaatancacc anntgntcca nnnatactgt ttataaaaag tctanactgc atanttganc 300
aantgttncc nntataatta atanccntca anncnnccaa ccannntgat tgncnctatg 360
acaaannaac taaagcacgt nnatngnant ngntnccntt nnnaaaactt tcncagtntt 420

```
aaaatntaaa agcatnacta ggggantcta ancntnacca cnccnacccn taagcccnna    480

aagngncatc acatnacntn ctaactctnn ctttaaaant nctggaaacc acccanaccc    540

tantnatgct nnnnccntnn cctnntaanc gnnngaanan tnnnaactct atanngntct    600

anaaacaacn ctcannannt ctactaanta tcnttnacaa ntctacnnnn ntaattcnta    660

accnanttct nannnannnt tttnancntn ncaacntgnn aactaccctc gttntnancc    720

nttnctacct tcagacttan gnttnaattc tntgnannnn gnngnntatc ntctatactn    780

ncntanntcc canttctncn nacnnccc                                        808
```

```
<210> SEQ ID NO 50
<211> LENGTH: 719
<212> TYPE: DNA
<213> ORGANISM: Homo sapiens
<220> FEATURE:
<221> NAME/KEY: modified_base
<222> LOCATION: (4)..(4)
<223> OTHER INFORMATION: n is a, c, g, or t
<220> FEATURE:
<221> NAME/KEY: modified_base
<222> LOCATION: (554)..(554)
<223> OTHER INFORMATION: n is a, c, g, or t
<220> FEATURE:
<221> NAME/KEY: modified_base
<222> LOCATION: (626)..(626)
<223> OTHER INFORMATION: n is a, c, g, or t
<220> FEATURE:
<221> NAME/KEY: modified_base
<222> LOCATION: (662)..(662)
<223> OTHER INFORMATION: n is a, c, g, or t
<220> FEATURE:
<221> NAME/KEY: modified_base
<222> LOCATION: (669)..(669)
<223> OTHER INFORMATION: n is a, c, g, or t
<220> FEATURE:
<221> NAME/KEY: modified_base
<222> LOCATION: (703)..(703)
<223> OTHER INFORMATION: n is a, c, g, or t
<220> FEATURE:
<221> NAME/KEY: modified_base
<222> LOCATION: (719)..(719)
<223> OTHER INFORMATION: n is a, c, g, or t

<400> SEQUENCE: 50

ggantttcct ttttttgtag ttttacaatt ttatttctga aagtaaataa aaatccaagg     60

acaacttttg agaatattat ctaatatgtg gcctgactta aaataataaa gaaaacactt    120

agaaaatctt actgattgtg aacagaaata caatcatatg gaataacact gtatctaatt    180

gtggacatag aaacataaag aaaaactgtg catttcaaat agattcacaa ggctcattct    240

gataacagaa tcacagatat cttcagtgta tcatatagaa aactgtgtgt aaaataaagt    300

attagattaa taccagcagg gcaaactgac agtaatagtt taacaagaga ttgaactaga    360

agtttcacga aagaaaaaca aactgtaaga agtctaacac caatgagtga aggaagaagc    420

aaaaacctac ttacattgta ttgaatgtaa tacattgaag tcatcattga ttgaataaga    480

acataactta ggtttataac agagtttatt atcaggttgg aaaacaggca atttctaatt    540

catgtaagta ttgnctttca aatggttttt tcctaaattg gctacaaaac tagggtaatg    600

ccaaaagcct atttaaaata taatgnatct tgaaatacag atgttcctca actaacgatg    660

gngtacatnc tgataaaccc ctggaaattc aaaatccatt aancaaaaat gcatgcgan     719
```

```
<210> SEQ ID NO 51
<211> LENGTH: 732
<212> TYPE: DNA
```

<213> ORGANISM: Homo sapiens
<220> FEATURE:
<221> NAME/KEY: modified_base
<222> LOCATION: (7)..(8)
<223> OTHER INFORMATION: n is a, c, g, or t
<220> FEATURE:
<221> NAME/KEY: modified_base
<222> LOCATION: (12)..(12)
<223> OTHER INFORMATION: n is a, c, g, or t
<220> FEATURE:
<221> NAME/KEY: modified_base
<222> LOCATION: (471)..(471)
<223> OTHER INFORMATION: n is a, c, g, or t
<220> FEATURE:
<221> NAME/KEY: modified_base
<222> LOCATION: (556)..(556)
<223> OTHER INFORMATION: n is a, c, g, or t
<220> FEATURE:
<221> NAME/KEY: modified_base
<222> LOCATION: (628)..(628)
<223> OTHER INFORMATION: n is a, c, g, or t
<220> FEATURE:
<221> NAME/KEY: modified_base
<222> LOCATION: (651)..(651)
<223> OTHER INFORMATION: n is a, c, g, or t
<220> FEATURE:
<221> NAME/KEY: modified_base
<222> LOCATION: (664)..(664)
<223> OTHER INFORMATION: n is a, c, g, or t
<220> FEATURE:
<221> NAME/KEY: modified_base
<222> LOCATION: (672)..(672)
<223> OTHER INFORMATION: n is a, c, g, or t
<220> FEATURE:
<221> NAME/KEY: modified_base
<222> LOCATION: (724)..(724)
<223> OTHER INFORMATION: n is a, c, g, or t
<220> FEATURE:
<221> NAME/KEY: modified_base
<222> LOCATION: (731)..(732)
<223> OTHER INFORMATION: n is a, c, g, or t

<400> SEQUENCE: 51 tgttgannc cnttttttgga gttttacaat tttatttctg aaagtaaata aaaatccaag 60
gacaactttt gagaatatta tctaatatgt ggcctgactt aaaataataa agaaaacact 120
tagaaaatct tactgattgt gaacagaaat acaatcatat ggaataacac tgtatctaat 180
tgtggacata gaaacataaa gaaaaactgt gcatttcaaa tagattcaca aggctcattc 240
tgataacaga atcacagata tcttcagtgt atcatataga aaactgtgtg taaaataaag 300
tattagatta ataccagcag ggcaaactga cagtaatagt ttaacaagag attgaactag 360
aagtttcacg aaagaaaaac aaactgtaag aagtctaaca ccaatgagtg aaggaagaag 420
caaaaaccta cttacattgt attgaatgta atacattgaa gtcatcattg nattgaataa 480
gaacataact taggtttata acagagttta ttatcaggtt ggaaaacagg caatttctaa 540
ttcatgtaag tattgncttt caaatgtttt tttcctaaat tggctacaaa actagggtaa 600
tgccaaaagc ctatttaaaa tataatgnat cttgaaatac agatgttcct naactaacga 660
tggnggtaca tnctgataaa cccactgtaa attcaaaatc cattaagcaa aaatgcatgc 720
gatntcctaa nn 732

<210> SEQ ID NO 52
<211> LENGTH: 772
<212> TYPE: DNA
<213> ORGANISM: Homo sapiens
<220> FEATURE:
<221> NAME/KEY: modified_base
<222> LOCATION: (3)..(3)
<223> OTHER INFORMATION: n is a, c, g, or t

```
<220> FEATURE:
<221> NAME/KEY: modified_base
<222> LOCATION: (22)..(23)
<223> OTHER INFORMATION: n is a, c, g, or t
<220> FEATURE:
<221> NAME/KEY: modified_base
<222> LOCATION: (627)..(627)
<223> OTHER INFORMATION: n is a, c, g, or t
<220> FEATURE:
<221> NAME/KEY: modified_base
<222> LOCATION: (644)..(644)
<223> OTHER INFORMATION: n is a, c, g, or t
<220> FEATURE:
<221> NAME/KEY: modified_base
<222> LOCATION: (655)..(655)
<223> OTHER INFORMATION: n is a, c, g, or t
<220> FEATURE:
<221> NAME/KEY: modified_base
<222> LOCATION: (666)..(666)
<223> OTHER INFORMATION: n is a, c, g, or t
<220> FEATURE:
<221> NAME/KEY: modified_base
<222> LOCATION: (668)..(668)
<223> OTHER INFORMATION: n is a, c, g, or t
<220> FEATURE:
<221> NAME/KEY: modified_base
<222> LOCATION: (720)..(720)
<223> OTHER INFORMATION: n is a, c, g, or t
<220> FEATURE:
<221> NAME/KEY: modified_base
<222> LOCATION: (723)..(723)
<223> OTHER INFORMATION: n is a, c, g, or t
<220> FEATURE:
<221> NAME/KEY: modified_base
<222> LOCATION: (727)..(727)
<223> OTHER INFORMATION: n is a, c, g, or t

<400> SEQUENCE: 52

ttntgtggcc ttttttttt tnntttttaa gtaatgggta aagtttattt catttttaat     60

aacaattaga ggacaaaatg tttaaaattt gcagtttaaa acatgcacat tcacaaaagg    120

ccaatgacac ataacactgc atagaaataa tattactcaa ttttaataac tataaaacac    180

agtgcatcaa acatcaagat aaacaaacct gagaaaacta ctataaccac agattcaata    240

ctctccactc atgcagcttc acaatttcta cagcagtttc aggaggaatg gtttttcagg    300

gagctgaaaa tactacttta tctttaacgc aaaactgcag ttttctgtag tagctgcctt    360

ccaaggctgc cctgtttttc ttaacctaat aaacttgaaa atgtaaaaaa tgacgattaa    420

agtagttaaa caacagatag tatttactgc atttatggct tccatttaga accatgaaac    480

ataaaaatat tatttttaac tattctgctc acatctttgc aagaacagat ttacctgtgg    540

aaaggtgctg gtaattcaaa gtaagcaaat atgaaatcta agtttctact taagggagat    600

tattgctgag aagtttggga gccttantaa gaaaagtctt aaangcagct taacnggaag    660

atcaantnaa ttggtcaaaa ttctttggaa ataatctact tattaaaaaa gtgggccgan    720

ggnccantaa ttggctctgg aattttaaat tcaggtaggc cgggaaaaac tt            772


<210> SEQ ID NO 53
<211> LENGTH: 779
<212> TYPE: DNA
<213> ORGANISM: Homo sapiens
<220> FEATURE:
<221> NAME/KEY: modified_base
<222> LOCATION: (19)..(19)
<223> OTHER INFORMATION: n is a, c, g, or t
<220> FEATURE:
<221> NAME/KEY: modified_base
<222> LOCATION: (22)..(22)
<223> OTHER INFORMATION: n is a, c, g, or t
<220> FEATURE:
```

-continued

<221> NAME/KEY: modified_base
<222> LOCATION: (175)..(175)
<223> OTHER INFORMATION: n is a, c, g, or t
<220> FEATURE:
<221> NAME/KEY: modified_base
<222> LOCATION: (604)..(604)
<223> OTHER INFORMATION: n is a, c, g, or t
<220> FEATURE:
<221> NAME/KEY: modified_base
<222> LOCATION: (633)..(633)
<223> OTHER INFORMATION: n is a, c, g, or t
<220> FEATURE:
<221> NAME/KEY: modified_base
<222> LOCATION: (646)..(646)
<223> OTHER INFORMATION: n is a, c, g, or t
<220> FEATURE:
<221> NAME/KEY: modified_base
<222> LOCATION: (665)..(665)
<223> OTHER INFORMATION: n is a, c, g, or t
<220> FEATURE:
<221> NAME/KEY: modified_base
<222> LOCATION: (675)..(675)
<223> OTHER INFORMATION: n is a, c, g, or t
<220> FEATURE:
<221> NAME/KEY: modified_base
<222> LOCATION: (694)..(694)
<223> OTHER INFORMATION: n is a, c, g, or t
<220> FEATURE:
<221> NAME/KEY: modified_base
<222> LOCATION: (721)..(721)
<223> OTHER INFORMATION: n is a, c, g, or t
<220> FEATURE:
<221> NAME/KEY: modified_base
<222> LOCATION: (758)..(758)
<223> OTHER INFORMATION: n is a, c, g, or t

<400> SEQUENCE: 53
gcactgttgg cctactggnt gnggttaccc tgctgtgtgc tgaaagccac cctggtatct 60
gcttgtttct ctcttttgca cttgatgaaa tattcacagg tggttacagt ctcagtcacc 120
actgttttca gtatcaagct tggtgctgaa caattgctca gtaaatgtcc atcanatgaa 180
cagtgggtac ctacttggga aaacataata aaatgtattt gtcctatcac ctaactttat 240
ttacaaagga attttaaata gaatcataaa gcgtcagaat aggaaagaaa ccatgaagtc 300
accagaggaa gtggtggtaa ctgtttccca gtgaaaatcc ccaaataggt ttatgtgggc 360
aaatgagaag gaaccttgga aagattccac tggaaggcat tttgatttcc cagagtgggc 420
tggcccctgt aatgcaaaca cagatctgat catgagctct gagccgagca gacttgctct 480
ttttgaacct actcctgcta ggattcttgg gcccttcaag gggcactcca gactagggta 540
acaggggttt ctaccactac agaagtgtgg aatattatgg gaatactata aagtgactct 600
ggtnccttca accccttcac ttccgcttac ctnttcatca ctctgncccc attgctgact 660
tcttntgggt ctgangaagc tcttcttctg actnaggatc aaggccagcc ttagcccttg 720
nccaccatca ttttcatttc acaaggagca cccttcantt ctaagcctgc gtgcggggc 779

<210> SEQ ID NO 54
<211> LENGTH: 788
<212> TYPE: DNA
<213> ORGANISM: Homo sapiens
<220> FEATURE:
<221> NAME/KEY: modified_base
<222> LOCATION: (4)..(4)
<223> OTHER INFORMATION: n is a, c, g, or t
<220> FEATURE:
<221> NAME/KEY: modified_base
<222> LOCATION: (308)..(308)
<223> OTHER INFORMATION: n is a, c, g, or t
<220> FEATURE:
<221> NAME/KEY: modified_base

```
<222> LOCATION: (608)..(608)
<223> OTHER INFORMATION: n is a, c, g, or t
<220> FEATURE:
<221> NAME/KEY: modified_base
<222> LOCATION: (610)..(610)
<223> OTHER INFORMATION: n is a, c, g, or t
<220> FEATURE:
<221> NAME/KEY: modified_base
<222> LOCATION: (637)..(637)
<223> OTHER INFORMATION: n is a, c, g, or t
<220> FEATURE:
<221> NAME/KEY: modified_base
<222> LOCATION: (652)..(652)
<223> OTHER INFORMATION: n is a, c, g, or t
<220> FEATURE:
<221> NAME/KEY: modified_base
<222> LOCATION: (723)..(723)
<223> OTHER INFORMATION: n is a, c, g, or t
<220> FEATURE:
<221> NAME/KEY: modified_base
<222> LOCATION: (743)..(743)
<223> OTHER INFORMATION: n is a, c, g, or t
<220> FEATURE:
<221> NAME/KEY: modified_base
<222> LOCATION: (745)..(745)
<223> OTHER INFORMATION: n is a, c, g, or t

<400> SEQUENCE: 54

gttncccttt tttcaagtct tagcagaggg gagatgtaga acaattttca aaataaaact     60

gattgccatg gagggcttta tgagggtgag atatccatcc agtctaagta cttatgggcc    120

tcagatgaga cctcaggaga ggtcaggggg agcttccatg gggggtaggg ccgtggtcca    180

ttgctgctgt ttatttcctc tttacctgag aaacgtgtgg gctggactcc ctggccctgg    240

gaagggccct ggcagcctgg gtagtggaga tgcctcttct ctatccttat gtaattattt    300

gtggctgngt ggtcttgatt atcttgacat ttaaatgctg agtaattttc tcaaaacatt    360

cacactctct gagggatgaa tgcaatttct gctgtgtttc agacggcagt gtataaatgg    420

ggtaaaaact gcatataagg gcctggagct ggtggggttg ggggactttt gagaacccag    480

aagctaaaag tcaaaagctg ttttgaagaa tttaactgct ttaagcccca tagtgatatt    540

cacaacctga gcacattaat tggaagaagt tgaacagaga atcagaaggg aattctcaga    600

tggggcanan ctggtgcaaa ctcctgggga cacccgnaca actttgaatg anggaaacga    660

gggcagcaaa tctcctcatg ctgatcccaa ggcctaaccc caccttattt gacatttgag    720

ctntaaaatc tagagaagac atntnatttc agtaggaagt aaaaaacggg ctttcacagg    780

gaaggaag                                                             788


<210> SEQ ID NO 55
<211> LENGTH: 781
<212> TYPE: DNA
<213> ORGANISM: Homo sapiens
<220> FEATURE:
<221> NAME/KEY: modified_base
<222> LOCATION: (1)..(1)
<223> OTHER INFORMATION: n is a, c, g, or t
<220> FEATURE:
<221> NAME/KEY: modified_base
<222> LOCATION: (3)..(6)
<223> OTHER INFORMATION: n is a, c, g, or t
<220> FEATURE:
<221> NAME/KEY: modified_base
<222> LOCATION: (8)..(16)
<223> OTHER INFORMATION: n is a, c, g, or t
<220> FEATURE:
<221> NAME/KEY: modified_base
<222> LOCATION: (22)..(22)
<223> OTHER INFORMATION: n is a, c, g, or t
<220> FEATURE:
```

```
<221> NAME/KEY: modified_base
<222> LOCATION: (750)..(750)
<223> OTHER INFORMATION: n is a, c, g, or t
<220> FEATURE:
<221> NAME/KEY: modified_base
<222> LOCATION: (778)..(778)
<223> OTHER INFORMATION: n is a, c, g, or t
<220> FEATURE:
<221> NAME/KEY: modified_base
<222> LOCATION: (780)..(781)
<223> OTHER INFORMATION: n is a, c, g, or t

<400> SEQUENCE: 55

ngnnnntnnn nnnnnnttgg antcctcggc actgttggcc tactggcctt tcagataaat     60

acaagctaag tagcgaaggt accttggaaa tatctaacat acaaattgaa gactcaggaa    120

gatacacatg tgttgcccag aatgtccaag ggcagacac tcgggtggca acaattaagg    180

ttaacgggac ccttctggat ggtacccagg tgctaaaaat atacgtcaag cagacagaat    240

cccattccat cttagtgtcc tggaaagtta attccaatgt catgacgtca aacttaaaat    300

ggtcgtctgc caccatgaag attgataacc ctcacataac atatactgcc agggtcccag    360

tcgatgtcca tgaatacaac ctaacgcatc tgcagccttc cacagattat gaagtgtgtc    420

tcacagtgtc caatattcat cagcagactc aaaagtcatg cgtaaatgtc acaaccaaaa    480

atgccgcctt cgcagtggac atctctgatc aagaaaccag tacagccctt gctgcagtaa    540

tggggtctat gtttgccgtc attagccttg cgtccattgc tgtgtacttt gccaaaagat    600

ttaagagaaa aaactaccac cactcattaa aaaagtatat gcaaaaaacc tcttcaatcc    660

cactaaatga gctgtcccac cactcattaa cctctgggaa ggtgacagcg agaaagacaa    720

agatgggtct gcagacacca agccacccan gtcgcacatt cagaactata catgtggnan    780

n                                                                    781


<210> SEQ ID NO 56
<211> LENGTH: 790
<212> TYPE: DNA
<213> ORGANISM: Homo sapiens
<220> FEATURE:
<221> NAME/KEY: modified_base
<222> LOCATION: (2)..(3)
<223> OTHER INFORMATION: n is a, c, g, or t
<220> FEATURE:
<221> NAME/KEY: modified_base
<222> LOCATION: (5)..(5)
<223> OTHER INFORMATION: n is a, c, g, or t
<220> FEATURE:
<221> NAME/KEY: modified_base
<222> LOCATION: (8)..(11)
<223> OTHER INFORMATION: n is a, c, g, or t
<220> FEATURE:
<221> NAME/KEY: modified_base
<222> LOCATION: (14)..(14)
<223> OTHER INFORMATION: n is a, c, g, or t
<220> FEATURE:
<221> NAME/KEY: modified_base
<222> LOCATION: (33)..(33)
<223> OTHER INFORMATION: n is a, c, g, or t
<220> FEATURE:
<221> NAME/KEY: modified_base
<222> LOCATION: (620)..(620)
<223> OTHER INFORMATION: n is a, c, g, or t
<220> FEATURE:
<221> NAME/KEY: modified_base
<222> LOCATION: (667)..(667)
<223> OTHER INFORMATION: n is a, c, g, or t
<220> FEATURE:
<221> NAME/KEY: modified_base
<222> LOCATION: (707)..(707)
<223> OTHER INFORMATION: n is a, c, g, or t
```

<220> FEATURE:
<221> NAME/KEY: modified_base
<222> LOCATION: (722)..(722)
<223> OTHER INFORMATION: n is a, c, g, or t
<220> FEATURE:
<221> NAME/KEY: modified_base
<222> LOCATION: (738)..(738)
<223> OTHER INFORMATION: n is a, c, g, or t
<220> FEATURE:
<221> NAME/KEY: modified_base
<222> LOCATION: (770)..(770)
<223> OTHER INFORMATION: n is a, c, g, or t
<220> FEATURE:
<221> NAME/KEY: modified_base
<222> LOCATION: (776)..(776)
<223> OTHER INFORMATION: n is a, c, g, or t

<400> SEQUENCE: 56

```
gnngnagnnn nttngtggcc tttttttttt ttnttttatt ttggtagttg tttttatgga     60
tgtgaaaaat attaccactg caactagcaa gaactataaa tgatacatta ttgcaagtgt    120
tctaaaaaat cagaacaaaa ctaatttatt atagttctgt cttcattata caccacgtgt    180
tggtgagtta aacacaacaa aattgtcttt tcttttaaaa gtgtctacta aagataaaaa    240
gaataagata acaattaaca tgtagtttgt tacattaaaa aatctgatat acatatttct    300
attgcctgtt agcttgttct aagcctcttt aactattaca acaaaaaaaa aaaaggaaag    360
aaaaagaaaa ttcattgttt aaaggcaaac attcaattca gttgatacaa cattacagta    420
cagtcaacta acatcattca acgaaggtaa caagtctagc cttagcttct tgagttaaaa    480
gtctatagac cagattgcta caaaagtttc aatgctgctt caaaaccata tgttagcttt    540
ttggaggaca aagtctttct acggatggct tcagaagggg catgctactg gtaaaaagca    600
caggggggaac cccatcctgn cattaatcat tttattgagc actgtagtta gaacagcatt    660
attgagntta agcacaacaa ctaaaataaa ataataatat aataacnatc ataataatgg    720
tnagaattaa aaccaacnca gactgggaag cctaaagcgc tggcagccgn gcaaancctt    780
gcgatccctt                                                           790
```

<210> SEQ ID NO 57
<211> LENGTH: 2336
<212> TYPE: DNA
<213> ORGANISM: Homo sapiens

<400> SEQUENCE: 57

```
gtacggaagt gttacttctg ctctaaaagc tgcggaattc ctcgagcact gttggcctac     60
tggaatgcga gctgagcaga cagggctgca aggaaatctg gcgcggttca atacctcgtc    120
tagcctgggt tccagtatct aatttttttt ttgttttaac tgacaaactc atttctctac    180
tgggacagga tgctgtgctg gctggaagtt ccatttctac agcaagaatc ctatctggaa    240
acacagaagt tgtcctctag ccacagcagc tcgaactttt ttgattgtcg ttgctgcttt    300
ctcccatcac ccccatcccc ttttgacaaa gatccaactg taaaaagtct tacgtaacag    360
ttcaggacta cttcggttct tttactgggt aagcactttc aatttttttt ttttaactaa    420
aagccatttt aaaattgaat ctgttgaggg gcttgactaa aatcttttaa gtaatttgtg    480
taatggaata ctgtcagtgg attttttcgt ctcatttctg cacgtgctcc tttgttctca    540
gaacagaagc tttttataca catcccataa cgcagctgga gagagttatg aagtcagtta    600
ttataaggaa cacaaaggtt gctttccatt ctttgccttt agataattaa tttttttgtt    660
ttcttaaaat ggagtattta aagaaggaag aaattcacaa gaaataaact gttggagaat    720
```

-continued

```
ttagaaaagt ttgaagtttt taccaccttt tctatctcta gttttgtgtg gccaaacact    780

tgtgccgcct ggggcggtgg gggtagaggc aagcatagac agagaggaac taagccagac    840

atggacaaag gcacgagcca aaaccagaca gtcctggccg ttcgataggc cagcagtggg    900

tgagacaggt cagccagctg caggggcggg agcggggggg cgggtaggga catggatgtg    960

tgaggtgctc atgcgtgcga tcgtgactag attctgaaac tgccagccat tttcccagct   1020

ccgctttgtg caatctaaag gaatgcatcc cctctgaagc agtcttgcca gagcctagtg   1080

agggagagaa gtatggtaaa taccacaaca tatggaatca gaaaataccg ggaactggag   1140

tgggcaaggg ggaatgcaga gggtgtggaa atttttagt gatctggaat gtgttgagtg   1200

acaggaagtg ccccaagctt ctcccccacc aactcttctc agtcgcgcct gcttttgtct   1260

aactcttgta atctacacac tactgcttac aaagctgtct gagtttaaga caaaaagaaa   1320

cctaaaagtc tccttacttc atagtacctg tgatatggaa ggaatgtaaa agcatgaccc   1380

tttaagccta tggacatttt ttcaggtata caggagaaag ataaaataat tttccacaga   1440

aaaatgagaa ttatgaatta tatagttcag gttccaaatc taatttttaa aagaattctg   1500

attctgctac actttacaaa tgcttaggtt ggttcctaat ttgaaggaga cttgttttat   1560

ttggttaatg cattgcattt gaacttgttt ctattttctt tgcataaatt tggactttgg   1620

gagaaaaatg caaagtaata agtagaatgc acttggggga aaaaaggagg atttttccct   1680

tcatgggttg gaaagtattt taaagggttg ttttcttgaa aaaacaagct ctctcttact   1740

ttctgcatct atgctataaa gataactatg ctataataaa tgtaaggtag aaaactttaa   1800

agagaaaata acagtgttct aagtgaaaag ctacttagca ttttcccaaa ctcacacatt   1860

atcaacagaa acactaaaaa ttaagagaaa agcggccaac taattaaata gctagcctta   1920

ttttgggggt atgggataga aaattaagtg tgaataaaat gatacttggg aatgtttctc   1980

cctcgtacca caaaggatgt tagtggtcag cctacgagtt aatccttcct agcatggctc   2040

tgagccttca tgccgagcag acgttattca catgacgatt cgaaaagtcc attcatatat   2100

ctcgctacct ggatttgaat agaaaccaga cagcaattct ttagttccag ccaccattcg   2160

ccccactgga caatagcgat ttgttagcac agagtcacag gctgtgggac acaaagcttg   2220

gagctgcaga aagatggggg attcagagaa caggaaatta caggctcgat gcactcctgg   2280

cagctctgag aatacaaaaa aaaaaaaaaa aaaaaaggcc acatgtgctc gagctg       2336
```

<210> SEQ ID NO 58
<211> LENGTH: 779
<212> TYPE: DNA
<213> ORGANISM: Homo sapiens
<220> FEATURE:
<221> NAME/KEY: modified_base
<222> LOCATION: (1)..(3)
<223> OTHER INFORMATION: n is a, c, g, or t
<220> FEATURE:
<221> NAME/KEY: modified_base
<222> LOCATION: (5)..(6)
<223> OTHER INFORMATION: n is a, c, g, or t
<220> FEATURE:
<221> NAME/KEY: modified_base
<222> LOCATION: (9)..(11)
<223> OTHER INFORMATION: n is a, c, g, or t
<220> FEATURE:
<221> NAME/KEY: modified_base
<222> LOCATION: (13)..(16)
<223> OTHER INFORMATION: n is a, c, g, or t
<220> FEATURE:
<221> NAME/KEY: modified_base
<222> LOCATION: (24)..(30)
<223> OTHER INFORMATION: n is a, c, g, or t -continued
<220> FEATURE:
<221> NAME/KEY: modified_base
<222> LOCATION: (43)..(43)
<223> OTHER INFORMATION: n is a, c, g, or t
<220> FEATURE:
<221> NAME/KEY: modified_base
<222> LOCATION: (45)..(45)
<223> OTHER INFORMATION: n is a, c, g, or t
<220> FEATURE:
<221> NAME/KEY: modified_base
<222> LOCATION: (664)..(664)
<223> OTHER INFORMATION: n is a, c, g, or t
<220> FEATURE:
<221> NAME/KEY: modified_base
<222> LOCATION: (684)..(684)
<223> OTHER INFORMATION: n is a, c, g, or t
<220> FEATURE:
<221> NAME/KEY: modified_base
<222> LOCATION: (696)..(696)
<223> OTHER INFORMATION: n is a, c, g, or t
<220> FEATURE:
<221> NAME/KEY: modified_base
<222> LOCATION: (728)..(728)
<223> OTHER INFORMATION: n is a, c, g, or t
<220> FEATURE:
<221> NAME/KEY: modified_base
<222> LOCATION: (732)..(732)
<223> OTHER INFORMATION: n is a, c, g, or t
<220> FEATURE:
<221> NAME/KEY: modified_base
<222> LOCATION: (776)..(776)
<223> OTHER INFORMATION: n is a, c, g, or t
<220> FEATURE:
<221> NAME/KEY: modified_base
<222> LOCATION: (779)..(779)
<223> OTHER INFORMATION: n is a, c, g, or t

<400> SEQUENCE: 58

```
nnngnnggnn ngnnnngtgg gggnnnnnnn tttggaattc ctngngcact gttggcctac      60

tggaacacac gccggagggt cgcacgcggg ttccagttgt gattgctgga gttgtgtatt     120

gccaggaggc tctccgagat tggggtcggg tcactgcctc atccaccgga gcgatggcgt     180

ttctccgaag catgtggggc gtgctgagtg ccctgggaag gtctggagca gagctgtgca     240

ccggctgtgg aagtcgactg cgctccccct tcagttttgt gtatttaccg aggtggtttt     300

catctgtctt ggcaagttgt ccaaagaaac ctgtaagttc ttaccttcga ttttctaaag     360

aacaactacc catatttaaa gctcagaacc cagatgcaaa aactacagaa ctaattagaa     420

gaattgccca gcgttggagg gaacttcctg attcaaagaa aaaaatatat caagatgctt     480

atagggcgga gtggcaggta tataaagaag agataagcag atttaaagaa cagctaactc     540

caagtcagat tatgtctttg gaaaaagaaa tcatggacaa acatttaaaa aggaaagcta     600

tgacaaaaaa aaaagagtta acactgcttg gaaaaccaaa aagacctcgt tcagcttata     660

acgnttatgt agcttgaaag attncaagga gctaanggtg attcaccgca ggaaaagctg     720

aagactgnaa angaaaactg gaaaaatctg gctgactttt gaaaaggaat tatatntcn      779
```

<210> SEQ ID NO 59
<211> LENGTH: 757
<212> TYPE: DNA
<213> ORGANISM: Homo sapiens
<220> FEATURE:
<221> NAME/KEY: modified_base
<222> LOCATION: (4)..(4)
<223> OTHER INFORMATION: n is a, c, g, or t
<220> FEATURE:
<221> NAME/KEY: modified_base
<222> LOCATION: (10)..(10)
<223> OTHER INFORMATION: n is a, c, g, or t
<220> FEATURE:

-continued

<221> NAME/KEY: modified_base
<222> LOCATION: (12)..(14)
<223> OTHER INFORMATION: n is a, c, g, or t
<220> FEATURE:
<221> NAME/KEY: modified_base
<222> LOCATION: (18)..(18)
<223> OTHER INFORMATION: n is a, c, g, or t
<220> FEATURE:
<221> NAME/KEY: modified_base
<222> LOCATION: (28)..(31)
<223> OTHER INFORMATION: n is a, c, g, or t
<220> FEATURE:
<221> NAME/KEY: modified_base
<222> LOCATION: (34)..(34)
<223> OTHER INFORMATION: n is a, c, g, or t
<220> FEATURE:
<221> NAME/KEY: modified_base
<222> LOCATION: (104)..(104)
<223> OTHER INFORMATION: n is a, c, g, or t
<220> FEATURE:
<221> NAME/KEY: modified_base
<222> LOCATION: (116)..(116)
<223> OTHER INFORMATION: n is a, c, g, or t
<220> FEATURE:
<221> NAME/KEY: modified_base
<222> LOCATION: (251)..(251)
<223> OTHER INFORMATION: n is a, c, g, or t
<220> FEATURE:
<221> NAME/KEY: modified_base
<222> LOCATION: (264)..(264)
<223> OTHER INFORMATION: n is a, c, g, or t
<220> FEATURE:
<221> NAME/KEY: modified_base
<222> LOCATION: (296)..(296)
<223> OTHER INFORMATION: n is a, c, g, or t
<220> FEATURE:
<221> NAME/KEY: modified_base
<222> LOCATION: (303)..(303)
<223> OTHER INFORMATION: n is a, c, g, or t
<220> FEATURE:
<221> NAME/KEY: modified_base
<222> LOCATION: (419)..(419)
<223> OTHER INFORMATION: n is a, c, g, or t
<220> FEATURE:
<221> NAME/KEY: modified_base
<222> LOCATION: (551)..(551)
<223> OTHER INFORMATION: n is a, c, g, or t
<220> FEATURE:
<221> NAME/KEY: modified_base
<222> LOCATION: (554)..(554)
<223> OTHER INFORMATION: n is a, c, g, or t
<220> FEATURE:
<221> NAME/KEY: modified_base
<222> LOCATION: (564)..(564)
<223> OTHER INFORMATION: n is a, c, g, or t
<220> FEATURE:
<221> NAME/KEY: modified_base
<222> LOCATION: (599)..(599)
<223> OTHER INFORMATION: n is a, c, g, or t
<220> FEATURE:
<221> NAME/KEY: modified_base
<222> LOCATION: (634)..(634)
<223> OTHER INFORMATION: n is a, c, g, or t
<220> FEATURE:
<221> NAME/KEY: modified_base
<222> LOCATION: (639)..(639)
<223> OTHER INFORMATION: n is a, c, g, or t
<220> FEATURE:
<221> NAME/KEY: modified_base
<222> LOCATION: (657)..(657)
<223> OTHER INFORMATION: n is a, c, g, or t
<220> FEATURE:
<221> NAME/KEY: modified_base
<222> LOCATION: (669)..(670)
<223> OTHER INFORMATION: n is a, c, g, or t
<220> FEATURE:
<221> NAME/KEY: modified_base
<222> LOCATION: (679)..(679)
<223> OTHER INFORMATION: n is a, c, g, or t
<220> FEATURE:
<221> NAME/KEY: modified_base
<222> LOCATION: (705)..(705)
<223> OTHER INFORMATION: n is a, c, g, or t
<220> FEATURE:
<221> NAME/KEY: modified_base
<222> LOCATION: (712)..(712)
<223> OTHER INFORMATION: n is a, c, g, or t
<220> FEATURE:
<221> NAME/KEY: modified_base
<222> LOCATION: (720)..(720)
<223> OTHER INFORMATION: n is a, c, g, or t
<220> FEATURE:
<221> NAME/KEY: modified_base
<222> LOCATION: (724)..(724)
<223> OTHER INFORMATION: n is a, c, g, or t
<220> FEATURE:
<221> NAME/KEY: modified_base
<222> LOCATION: (739)..(739)
<223> OTHER INFORMATION: n is a, c, g, or t
<220> FEATURE:
<221> NAME/KEY: modified_base
<222> LOCATION: (757)..(757)
<223> OTHER INFORMATION: n is a, c, g, or t

<400> SEQUENCE: 59
gagngggggn tnnnttgngg gccttttnnn nccntttttt tttttttttt tttttttttt 60
ttgggtttca acaaacttta tttatgaaca ctaaatattc atgntaattt tcaagnatca 120
taaaagtctt taaaaaaaaa catttaaaat tataaacaca attcctagct cacaggccat 180
aaaaagcagg cagcaggctg gatttgatcc acaggccata gttggctggc tcttaaacag 240
gcttttatac nttatgcaaa gggnttcaaa ttccagagac tttggagact tttcgntttt 300
tanatttctc attttaaaac acacataata caagttttct ttctggatca atatactcac 360
gagagaaaat aattcagaaa aaaataaaat tccttactta aaaaaaggga aaagctatng 420
aacaaatgtt tcgcttaaaa tatatttagg aaatgtaaaa ttaaagatta aaaattttat 480
tctatgcaac ataaaataat atgcataaat ctggcacata atttctttgg ttttacttta 540
gaaaaaagac ngtnagaaaa aagnttataa atttctcaag cccttttata caaaggtgna 600
actaaaaccc gcaatcactt atatgtccac cctnaactnt gaatacaatg ggaattntcc 660
taggaccgnn attacctana agagtctggc tgctttatga aaacnccccct tntttccaan 720 aaancggggg ttttacaant tgggacaatt tgaaacn 757

<210> SEQ ID NO 60
<211> LENGTH: 2022
<212> TYPE: DNA
<213> ORGANISM: Homo sapiens

<400> SEQUENCE: 60
gcctgtacgg aagtgttact tctgctctaa aagctgcgga attcctcgag cactgttggc 60
ctactggcca gctttattta atgatgataa aatacaactc tttctaaatg aaatttttat 120
ttggaaattt tctctccatt acttagttac tatctgagat agaagaacac ctgaactgta 180
ccatttctca ggttgagccg gatataaagg taccagtgga tgaatttgat gggaaagtta 240
cctacggtca gaaaagggct gctggtggta agctttgaat tattttaaat acaattttaa 300
atgtaaatat acctgttttg aacttcggtt tgggaaggca gtactttcat ttcattaggt 360
taagagtata tttttagcgt gttaatcatt ccctccttat taccctcata gtactttgtc 420
catacctgcc ttgtagcatt tttaaattgt gtcatcttta tgtgaatgaa agacttcagc 480
ttagctcttt ctcttgaagt gttaatgtca taagagtagt tgaacatttt gtggaattat 540

-continued

```
taggaaacaa gagcataata ggtgattttg aacaaggaat cagaagcctt tgacttaact    600
caggtggtaa ttcagcatat tatttcctct gcctgggatg cccttttgtt agcttgttcc    660
tgaaaaattg taagactcag gcctaactag ttgtttccga gccaagggtg ggtagaggtg    720
ttgggacagc tgttagtgag gcctaattat ttatttatat tgaaataatt gatttaacat    780
tttttaaagt caaagttctg gagataattt gcccagtagt acattttatt gctgcaagca    840
aagtttaaag tgatataatt gagccaaagt attgctgaca agttatttca agcatgtcat    900
ttacattact ttgttatttg tgtgtgacgc aggtggaagc tataaaggcc atgtggatat    960
tttggcacct actgttcaag agttggctgc ccttgaaaag gaggcgcaga catctttcct   1020
gcatcttggc taccttccta accagctgtt cagaaccttc tgatttttac atttactgaa   1080
taagatttga gtaatgaaag tctgtagtct taaaactcta aaacagttgt actgcttcca   1140
agcagcagta tttatagtaa cgtaagctat taatgctaac tcttgcatgt caagaaacat   1200
tagtcttagg aattcttcaa aaaatggcat cccaatgaaa ataaatttga tgactatatt   1260
ttcatgaagg tttgtgtctt attttaaagt tatattgata tattttttct atttcttttt   1320
taagaacagt atgggcttat gaagtagaat ttatgggtat gtgaatctgg cagaggactt   1380
acgtggaacc actcgggaat attctaaaag taggttttca gatggctaag gttgtctatg   1440
tgtatattga agctagagga gagttggaac atgaagggaa attcgatgat cccaatgtag   1500
aagaactgct tggttagttt ggaagcatgg aagttttgag ggagtcagta aaggttctgt   1560
atctaaggac tgatgactga tgtgatggtg ccagtgaaga tgtatcttct ttttatgacc   1620
cttgctttcc agatgatgca tacccattaa agtagaacta atctgctgtc cctacaggtc   1680
ttaaaatcaa acttaaactc agggtttttt ttgttggtta ttttttttgtt tgtttgtttg   1740
tttgtttttg tttttgagac agggtcttgc tttgtcaccc agcctggagt ccagtggcgt   1800
gaacacagct cactgcaacc tcaacctcct aggctcaagc aatcctctcg cgtcagtcct   1860
ctcacctcag ctactcagga ggctgaggca ggagaatagc ttgaacccag gaggcggaag   1920
ttgcagtgag ccgagatcgc gccattgcac tccagcctgg gcaaaagagc aaaactccat   1980
ctaaaaaaaa aaaaaaaaag gccacatgtg ctcgagctgc ag                       2022
```

<210> SEQ ID NO 61
<211> LENGTH: 2437
<212> TYPE: DNA
<213> ORGANISM: Homo sapiens

<400> SEQUENCE: 61

```
gttacttctg ctctaaaagc tgcggaattc ctcgagcact gttggcctac tgggtgtact     60
gtggagactg tcaaagtctc ccggagccca atttccggaa gcggtgagtt ctgaaagaag    120
ttcctgcacc gtagtttccc aagtctgcga atccccaacc atgagcgcct cgggcgtact    180
gtcctttacc cagcaaggat gggagcaggt gctggccaaa gtgaaacggg ctgtggttta    240
cctggacgcc gcctgcgccg agagcctgca ctggggctgc ggatccaccc gtctcctgga    300
ggcggtgggg ggccctgact gtcacctgcg agagttcgag cccgacgcaa ttggtggtgg    360
agccaagcag cccaaggcag tgtttgtgct gagctgcctg ctgaaaggcc ggaccgtgga    420
gatcctacgg gacatcatct gccgcagtca cttccagtat tgtgtggtgg tcacaaccgt    480
gagccacgct gtccacctca cagctaatca tgtcccagcg gcggcagcgg ccgagatgga    540
ggggcagcag ccggtgttcg agcagctgga ggagaagctg tgtgaatgga tgggcaacat    600
gaactacacg gccgaggtgt tccatgtccc gttattgctt gcccctgttg ctccccactt    660
```

```
tgccttgact ccagcttttg catccctttt cccactgcta ccccaggatg tgcacctcct    720
taatagcgcc cgaccggaca agaggaagct gggaagcctg ggtgatgtgg actccactac    780
gctaacccca gagctgctgc tgcagatcag atgcctagtg tcaggcctca gttctctgtg    840
tgaacattta ggagtacggg aggagtgttt tgctgtaggt tccttaagtc aggtcatcgc    900
tgcggatctg gccaattatg cccctgcaaa gaacaggaag aagactgctg caggcagggc    960
atcagtggtt tttgtggaca gaaccctgga tctcacagga gcagttggac atcatggaga   1020
caacttagta gagaagatca tttcagcact tccccagctc ccaggccaca caaatgatgt   1080
gatggttaac atgatagcgc tcactgcact ccatactgag gaggaaaatt ataatgtggt   1140
tgcaccaggc tgtctttcac aattcagtga caccacagcc aaagccctat gggaagcttt   1200
actgaacact aagcacaaag aggcagtgat ggaagttcgg agacatctag tggaagcggc   1260
aagcagagaa aacctgccaa tcaagatgag tatggggaga gtcacaccgg gacagctcat   1320
gtcctatatt cagctcttca agaacaacct caaagctcta atgaatcatt gtggcctcct   1380
ccagcttgga ctggccacag ctcaaacgtt gaaacaccca cagactgcca agtgggacaa   1440
ctttctggct tttgaaaggc tccttcttca gagcattggg gagtcagcaa tgtccgttgt   1500
gttaaatcag ctgctgccca tgattaagcc tgtaacccag agaaccaacg aggactacag   1560
ccctgaggaa ctgctgatcc ttctcatata tatttattct gtcactggag agctcacggt   1620
agacaaagac ctgtgtgaag cagaagaaaa agtcaagaaa gcattggctc aggtcttctg   1680
tgaggaatct ggattgtcac ctttgctgca aaaaattacg gactgggact cttcaattaa   1740
tctgacattt cacaaatcca aaattgccgt ggatgaactc tttacttcac ttcgggatat   1800
tgctggagct cggagtctcc tgaaacagtt taagtctgta tatgttcctg gaaatcatac   1860
ccaccaggca tcttataagc cattgttgaa gcaagttgtg gaggaaatat ttcatcccga   1920
gaggccagat tccgttgata ttgaacacat gtcttcaggc ctcactgatc tccttaaaac   1980
tggatttagc atgttcatga aggtgagccg gcctcatcct agtgactacc ccctcctgat   2040
cctctttgtg gtaggtgggg tcacagtctc tgaagtgaaa atggtcaaag atcttgtggc   2100
atcgttgaag ccaggaaccc aggtaatcgt gctgtccaca cgactcctga agccacttaa   2160
cattcctgag ctgttatttg caactgaccg actgcatcca gaccttggct tctgagcatc   2220
cgctaagaag ataagaccta ctcaagctgg aaatgccgat gcaattttct gccaccactc   2280
caaatactcc tccacaacca gcgtccctgt cactaattgc gagaatgatg gaattctgcc   2340
tgaagggtct tgatacctac tcagtgaggt actttgcttg gattgctgtg attcttaaaa   2400
aaaaaaaaaa aaaaggccac atgtgctcga gctgcag                            2437
```

<210> SEQ ID NO 62
<211> LENGTH: 1946
<212> TYPE: DNA
<213> ORGANISM: Homo sapiens

<400> SEQUENCE: 62

```
gcctgtacgg aagtgttact tctgctctaa aagctgcgga attcctcgag cactgttggc     60
ctactggctg aggcttatct gacatctcat tgtcccctgg tgtgtgtgtg tgtgtgtggt    120
gtttttgtgt gtgtggggtg tgagtgtggc agagaggaaa ggggagctgt ttgattctgt    180
agttcctttt ctgccttctt cctttctctg taaactttgg atacttatcc aaattactaa    240
cggcagattg agccctatgc agatggcatg tgtctgtgac aacctctgct ctccacatct    300
```

-continued

```
cttgggcctg tttacctgcg ctcccagagc ctccgccagc atcccagaat ctccatcccc    360

atctctcact tatacacaca tcagtcatcg gttatccatt agctaaaccg ccttccttaa    420

tagctttaca ctgtttgctt tctctggaac atttttagtt aaaatttcat aatgcagttg    480

cacacaaatg aagacacaga tggctgcatc ctccgtctct tcccctcgtt tacaggaagc    540

tgcggatcag ggaggggtgt tagggttacc cacatggtaa gggcagagac aagaggggac    600

cccagttttc catgctgcac atggtcattg ctggggactg aggtttgcac atcaccctgc    660

cctgttctcc ctccgctggg gagaaagtca gggatggagc aagctgcagc atcttctgaa    720

aaagaaaagg tggccttgtc tccaggtctc ccctcaagtc ccaccttccc atagttttct    780

gccacttctc ttgattttcc tctctgccac ttctcttgat ttcctctct gccacttctc    840

ttgattttcc tctctgcagc tgctttgagg tgggttttct ccagatgcac actttcccct    900

gctttgcgtc cttattctgg tagaagcaca atctaaagct cattaaggga actaatcaat    960

tctgtgcatg gcgctagctc agcagatcac cacacaggca gcactattag caagtcggtg   1020

cttaacacat ggcacttcca tgaatcgata tggagcccgt gtagaacaag gcatgggttt   1080

ttttctcttc ccattaagaa aaactgatgc caaaaataac ttctcagata ttttcaagta   1140

tgacttttat gaagggaaaa agcatttttg tttgcaaaat catgcttcag tgcaggccag   1200

ttgtgaattg tgatggcttt tatttctcct ggggctgtaa ctttaagggt ttagaatttg   1260

gaaccacagc ctagctaatc atgacacaca cacacacaca cacacatgca cacacataca   1320

catacacaaa gcatcacgaa gaaccataca aattgtacat tattttacac atggaggctc   1380

actctaaaat agataccatt ttaaatatta actaaaactt gtgctcattg tatgttcatt   1440

ctatatgtac tgatttgtta ttcacatttc tttcaaaatc gttcaaattt ctagcccaca   1500

tcaattaaat attaatagta ctttctacaa acatgagcgc acaaaataaa ttcaaatcta   1560

tttttcccac tggtgttatc aatactgctc atactttgtc agtaactaag tatcacatga   1620

tcttaaaact aatgtcacat actaaaaagc ttctgaggca aattgtagaa agaactctca   1680

acatcattgt tctactggac aacatacata aaattatttt acagtgatgg gagagaaata   1740

ggctcctcat cctaaaagct gcgaagacag tagcggtgcc gtgttttggc gttactcccc   1800

tgtggatccc agcgacgggt ggatttctcc tgtgctttat catcagacac aaaatggacc   1860

aaaatggacc aaaatggacg agtgtgaggg acacagaggc tgctgtaaaa aaaaaaaaaa   1920

aaaggccaca tgtgctcgag ctgcag                                        1946
```

<210> SEQ ID NO 63
<211> LENGTH: 1813
<212> TYPE: DNA
<213> ORGANISM: Homo sapiens

<400> SEQUENCE: 63

```
tgtacggaag tgttacttct gctctaaaag ctgcggaatt cctcgagcac tgttggccta     60

ctggtacgta ggcacctgtg ggtttgagtg cgttcaatat acagactgca gtaggaggct    120

ggcactgact ctgctgactc cagtacactc cttcactgct gttctgacaa tttctccact    180

gtccagaaga caaacaaaat ggtgcagcac gtacagggct tgggaaaaag ataaccgtca    240

atatgatcca gaggtgagtt tgctacagtg aacaggagag aaaattgtta acaagataaa    300

agccttggat gtggttcagt atgtcagatg tcttcagctg ttttaatatt tggttctggc    360

cagtaaggat gaaactgttg tagttctaaa atcttcatgc cctctatata aagaggttca    420

ggtatattgc atttatagca ttactagatg catgcatggt agtttataaa catttatatt    480
```

```
tatactaaac atgtgtaatg tgtgtgtcta tatagatagg tgtttgtgaa ggttatatct     540

attaatactg gatttttaaa aagtaagcac ttttagtttt tatattttct ctgttgtaca     600

tttgttgcag ctcctgccaa tgtctctttc cctatattgt tcattttata atagcagaaa     660

acattagtag cgcactctgt ggtgagatat ggaaaatcag tagaatgaac cttggagttg     720

gcacttcata ttttattgat gactgtaatg cagtgtgagt tcgcattgca catagtcttg     780

atttaaatga ttacctcttt tatgaaagca aaatgtttgt aagaacggcc atgttgtaga     840

cagggagcat aaaataaagg agaggaagta ggacaagtaa catttctctg tccttggttt     900

cttgaacaat gttcagcatt gactcaaggc actgtcattt cagaagtaca gtatagaaac     960

aattgagcat caagcataga tgaaacatgg aggcttagtt tcccaccccc tccaaaagaa    1020

gcactttact tatgtactca catattttcg gtttctgtgg ctgtgttact gggtagctgt    1080

ccagttgaga cgagatgttt acttaagcca cacccagcag agtcagcttt taatgtgttg    1140

ggggcactat tttaatcctg tgctgatttg taaccatcat ctatgggatg cctttgagtt    1200

gtaaaaagag ggaaaatact agattcacag gttgcagctt actatgtttt tgaatatttg    1260

agttgctgta ttaatagcac agaagagcag tatttaagtt atgcagcatt tatctatggc    1320

agagagagat agagaatatg tgtatggttc cattacaagt gtaatgcaag tattctgatc    1380

atatagctaa aaatgctgct ggtatattat tttagttagt gttgtgggta gtaaattgga    1440

gtatgacatt cagagttcag attttcttat ttgagaaaat atttgtccaa acattttaaa    1500

tacttaattt ttctgtgctt ttaaaagatt tgcaaaggat tcagcctgag cttagaaatg    1560

tataatgttt tattccatgc taaagacatt ttgtatgtga taagaattaa caactgtatg    1620

gctggctggc tgccactgtg ttggattacc ttacccacct tactgtagac aaaaataata    1680

aggattcagc actaatccta gtagtctcca tagtactcat attgtatatt ttcagaaact    1740

cctttttttat agccaaagca aagtgttctc cccaaaaaaa aaaaaaaaaa ggccacatgt    1800

gctcgagctg cag                                                       1813
```

```
<210> SEQ ID NO 64
<211> LENGTH: 2120
<212> TYPE: DNA
<213> ORGANISM: Homo sapiens

<400> SEQUENCE: 64

taggcctgta cggaagtgtt acttctgctc taaaagctgc ggaattcctc gagcactgtt      60

ggcctactgg agtgctgaag taggcgcgga cgtgcccggt gcctggcgcg tggtagcagg     120

cgcccggtgc cccggccggc gaagaccatg gcgttcatgg tgaagaccat ggtgggcggc     180

cagctgaaga acctcactgg gagcctggga ggcggcgagg ataagggaga tggggacaag     240

tcggcagccg aagctcaggg catgagccgg gaggagtacg aggagtatca gaagcaactc     300

gtggaagaga agatggagcg ggatgcacag ttcacacaga ggaaggcaga gcgggccaca     360

ctgcggagcc acttccgaga caaataccgg ctacccaaga acgagacaga tgagagccag     420

atccagatgg caggtggaga cgtggagctg ccccgggagc tggccaagat gatcgaggag     480

gacacagagg aggaggagga gaaggcctca gtccttgggc agctggccag ccttcctggc     540

ttgaacctgg gctcactcaa ggacaaggcc caggccacac tgggggatct caagcaatca     600

gctgagaagt gtcacgtcat gtgaccactt ccccggggtt acccactggg ctgggccccc     660

atgagggcta agagtgtgtc aacttccagg gacccatact ccatttgggg ctttgtttcc     720
```

-continued

```
cttgccccat cctagttcca agacctttcc catccatgcc ccaagcctat cttctggttt    780

cttcctctcc gctgggagta aagtccccat cttcactcta cccttcagga ccctccccac    840

cagctcagcc tgtggaggcc tcccaagatt gtaggaatag gcccatccct ctctggccat    900

ggccccaagt tcctgcacac aggagcaccc acagagagac acacacagga cacaaaaccc    960

ctggcacgtt cagagacaga agccacagac acatcccggc acagacagac acacacgagg   1020

ccagctccct tgcgtgtcca gcccctccag acaccaccac tcagaaactc tgagagagag   1080

catgggcaga caccctcagc agacaggagg cctgagttcc agtctccacc tttattgttc   1140

ttgaaagccc ctgctctctc tgagccttat ttcatcatct gtaaaatggg aatgtcctga   1200

atgacttcta aggctctttc tggcttgaac tgtcagagcc aagcccacat ccctccttgg   1260

gcagggcagc agctgctgcc acagcctcca gcggctgcca ctgtgggctc tgggagccgg   1320

agcgatgctg tgtgagaggc agagtgccaa ggatgaagct ggcactgaac agtaagcggc   1380

tccaggcctc ctctgggccc agggcccagc caatttctgt tctgttcctg tagaacgctc   1440

tctggattcc atagctggaa tctcctctct tagctcagtg aaaaataaaa atcccaaatg   1500

gtgtgcctac cttcccactt cttactggct tccaggagtc ttggagttca tagccccccg   1560

agcctgcctt aaaggggtgt cctccacccc ccacctacag cttcacagga ggggagaggg   1620

catccagtgc taggagtaga agtgtctcca gctctgttct cttggggccc tgggtgaagg   1680

tggggtctgg ggcttatgaa ataggtctgg gctttgagga ggatggagca gcctcattat   1740

gtggggaaga tggggcctct ggggcgtcac tgagaccaca ggtggggccg gggctggacc   1800

gcagctgtct tgggtgcctg tgcctgcacc cctcctcacc ctagagacgg aagatgtgca   1860

aaaagaaaga aggaagggca actgcattcc agccccacac tgtgatgact ttgagcctgt   1920

cctttccctc cttgagcctg tcttgcttgt cccctgtaaa atgaacagtc cccctctccc   1980

ccaaatagta ataatacatg tttcaaaggg tgaccattta taaagcatat gacaaaccat   2040

atcaataaat gtaactcatt cttttaaaaa aaaaaaaaaa aggccacatg tgctcgagct   2100

gcaggtcgcg gccgctagac                                               2120
```

<210> SEQ ID NO 65
<211> LENGTH: 779
<212> TYPE: DNA
<213> ORGANISM: Homo sapiens
<220> FEATURE:
<221> NAME/KEY: modified_base
<222> LOCATION: (2)..(3)
<223> OTHER INFORMATION: n is a, c, g, or t
<220> FEATURE:
<221> NAME/KEY: modified_base
<222> LOCATION: (5)..(7)
<223> OTHER INFORMATION: n is a, c, g, or t
<220> FEATURE:
<221> NAME/KEY: modified_base
<222> LOCATION: (607)..(607)
<223> OTHER INFORMATION: n is a, c, g, or t
<220> FEATURE:
<221> NAME/KEY: modified_base
<222> LOCATION: (652)..(652)
<223> OTHER INFORMATION: n is a, c, g, or t
<220> FEATURE:
<221> NAME/KEY: modified_base
<222> LOCATION: (694)..(694)
<223> OTHER INFORMATION: n is a, c, g, or t
<220> FEATURE:
<221> NAME/KEY: modified_base
<222> LOCATION: (726)..(727)
<223> OTHER INFORMATION: n is a, c, g, or t

<400> SEQUENCE: 65

```
gnngnnnttg attcctcgag cctgttggcc tactggatat gaaatgtttt aatatacccc     60

agggacagac attcagaatt aagacggaga tggagagaga atgttatcaa caacaacaaa    120

aaatttcaga tagctgcccc tctcaaatgg gaagaaagtt agtatcatta gcaggaaaat    180

taggtgacac ttatgctgat acatttgttg tttccctcta gagacaacag tctatcccaa    240

tatgctgtgc cagggctggg ataactatcc ttgtggtctg aggacaatgt gtttattatg    300

gccttagaaa tagaaactgg ggctgtgcta taaatcctat cagatattga atggatgctt    360

tcaccttctt cttaagataa gccagaagtt tcattctttt aagaaaaatg agaaagtgcc    420

ttgtttattg tgagaacaca ggtcacctga aaaggcaaac agttttcaaa ttaaaggtgg    480

tatcttgtgt attatagaaa acaggaatgt atgggtttcc agagtttcag gaaaagcaca    540

actatctggt tgggggctgc tgctgctgcc tatcttggga accaccctta gccacttaat    600

cttttangac ttcagtcttt caacttccaa gtgggaaagg taattttcct gnatcatggt    660

aaaggattaa ctgtacaata atggatataa atgngctctg tgcactctac agcattgggc    720

aattgnnaag ggagtgtgca cactggtgtg gtggccaggt aattggacct gggaattcc     779
```

<210> SEQ ID NO 66
<211> LENGTH: 909
<212> TYPE: DNA
<213> ORGANISM: Homo sapiens
<220> FEATURE:
<221> NAME/KEY: modified_base
<222> LOCATION: (5)..(5)
<223> OTHER INFORMATION: n is a, c, g, or t
<220> FEATURE:
<221> NAME/KEY: modified_base
<222> LOCATION: (11)..(11)
<223> OTHER INFORMATION: n is a, c, g, or t
<220> FEATURE:
<221> NAME/KEY: modified_base
<222> LOCATION: (734)..(734)
<223> OTHER INFORMATION: n is a, c, g, or t
<220> FEATURE:
<221> NAME/KEY: modified_base
<222> LOCATION: (739)..(739)
<223> OTHER INFORMATION: n is a, c, g, or t
<220> FEATURE:
<221> NAME/KEY: modified_base
<222> LOCATION: (750)..(750)
<223> OTHER INFORMATION: n is a, c, g, or t
<220> FEATURE:
<221> NAME/KEY: modified_base
<222> LOCATION: (753)..(753)
<223> OTHER INFORMATION: n is a, c, g, or t
<220> FEATURE:
<221> NAME/KEY: modified_base
<222> LOCATION: (765)..(765)
<223> OTHER INFORMATION: n is a, c, g, or t
<220> FEATURE:
<221> NAME/KEY: modified_base
<222> LOCATION: (803)..(803)
<223> OTHER INFORMATION: n is a, c, g, or t
<220> FEATURE:
<221> NAME/KEY: modified_base
<222> LOCATION: (819)..(819)
<223> OTHER INFORMATION: n is a, c, g, or t
<220> FEATURE:
<221> NAME/KEY: modified_base
<222> LOCATION: (822)..(822)
<223> OTHER INFORMATION: n is a, c, g, or t
<220> FEATURE:
<221> NAME/KEY: modified_base
<222> LOCATION: (829)..(829)
<223> OTHER INFORMATION: n is a, c, g, or t
<220> FEATURE:
<221> NAME/KEY: modified_base
<222> LOCATION: (866)..(866)

<223> OTHER INFORMATION: n is a, c, g, or t
<220> FEATURE:
<221> NAME/KEY: modified_base
<222> LOCATION: (872)..(872)
<223> OTHER INFORMATION: n is a, c, g, or t
<220> FEATURE:
<221> NAME/KEY: modified_base
<222> LOCATION: (880)..(880)
<223> OTHER INFORMATION: n is a, c, g, or t

<400> SEQUENCE: 66

```
gttgntcctc ngcctgttgg cctactggat actatcctct ccatgaatgt ctgccccacc     60

attcttaact ggcacacatt acagtttggc tccactaaac aaaaaaacca gtcataatta    120

tgaaaactgg ttttgtacaa aaaccagcat gaatgtaatg ggagaatggc tgtttgaaat    180

ttattaagag agtatgtgaa ttctgaccct cttcattttt ttcagcttga aactataatc    240

aacttcccta acttcttggt atctctcttc ctcatttgtg gtatcatttt ttactttta    300

cttccttgta ttactgtgat cctttttact ttacacctcc ttgtattact tccatgattt    360

cttaccagct actattctct attcttttcc aaaactttga atgctctttt tggttgcaga    420

cccagcctat agtatctgtg gagcctgata agaagcttct gtacctgtgg gaaagtagcc    480

tgtaggtttt cacaggtcaa agtgttcaag agtatcaggg cttttgatct cttattattg    540

gacatataaa tgaaattttg cagaaatttt attctgggtc accagattta aagtattatt    600

ccattggcat taacaaatct gtagataccc tgtttaaagc catgttacta aaaacagaac    660

taggatttca catgaacaaa atattttcat attctttatt ttctcaaaga agtctctaag    720

aagaacaagc cccngttgnc ctattaaatn agnaaaagca taganggttt attggcttat    780

aatgcatggg gtattttctt tcnattttac tgaattttng tngaccaana aaatctcttt    840

ttggttttgg gaaactaaga tgagancatt gntttaatcn ggaataatga aaagaaaacc    900

aaggggaag                                                             909
```

<210> SEQ ID NO 67
<211> LENGTH: 909
<212> TYPE: DNA
<213> ORGANISM: Homo sapiens
<220> FEATURE:
<221> NAME/KEY: modified_base
<222> LOCATION: (686)..(686)
<223> OTHER INFORMATION: n is a, c, g, or t
<220> FEATURE:
<221> NAME/KEY: modified_base
<222> LOCATION: (689)..(689)
<223> OTHER INFORMATION: n is a, c, g, or t
<220> FEATURE:
<221> NAME/KEY: modified_base
<222> LOCATION: (713)..(713)
<223> OTHER INFORMATION: n is a, c, g, or t
<220> FEATURE:
<221> NAME/KEY: modified_base
<222> LOCATION: (732)..(732)
<223> OTHER INFORMATION: n is a, c, g, or t
<220> FEATURE:
<221> NAME/KEY: modified_base
<222> LOCATION: (750)..(750)
<223> OTHER INFORMATION: n is a, c, g, or t
<220> FEATURE:
<221> NAME/KEY: modified_base
<222> LOCATION: (770)..(770)
<223> OTHER INFORMATION: n is a, c, g, or t
<220> FEATURE:
<221> NAME/KEY: modified_base
<222> LOCATION: (796)..(796)
<223> OTHER INFORMATION: n is a, c, g, or t
<220> FEATURE:
<221> NAME/KEY: modified_base
<222> LOCATION: (809)..(809)
<223> OTHER INFORMATION: n is a, c, g, or t
<220> FEATURE:
<221> NAME/KEY: modified_base
<222> LOCATION: (816)..(816)
<223> OTHER INFORMATION: n is a, c, g, or t
<220> FEATURE:
<221> NAME/KEY: modified_base
<222> LOCATION: (829)..(829)
<223> OTHER INFORMATION: n is a, c, g, or t
<220> FEATURE:
<221> NAME/KEY: modified_base
<222> LOCATION: (847)..(848)
<223> OTHER INFORMATION: n is a, c, g, or t
<220> FEATURE:
<221> NAME/KEY: modified_base
<222> LOCATION: (853)..(853)
<223> OTHER INFORMATION: n is a, c, g, or t
<220> FEATURE:
<221> NAME/KEY: modified_base
<222> LOCATION: (864)..(864)
<223> OTHER INFORMATION: n is a, c, g, or t
<220> FEATURE:
<221> NAME/KEY: modified_base
<222> LOCATION: (899)..(900)
<223> OTHER INFORMATION: n is a, c, g, or t
<220> FEATURE:
<221> NAME/KEY: modified_base
<222> LOCATION: (907)..(908)
<223> OTHER INFORMATION: n is a, c, g, or t

<400> SEQUENCE: 67

```
tgtggccttt tttttttttt ttttttggta gaaacggggt ttcctcatgt tgctcaggct     60

ggtcctgaac tcctgggctc aagtgatcct ctagcctcag cctccccaaa tgctggaatt    120

atgtaattat ttatgtaagc atcagcccct gtgctctgcc ccactactgc acgtttttaa    180

gaagaggagt gactgatcaa attcatagtt tagaaagatc aatctgacaa agcagtatga    240

caaatggatt atataaggac aatataaggt gtatagggat ttatgaggcc tttaagatat    300

ttcaggtgaa aaatgatgag aacctaaaaa gtatcagtgt ctataaaaag gagagaatga    360

acaccaaact tacacttgca atataaagcc aatctatttt gacgacatca tagatgtagt    420

gtccactaat tggggatggt ttaggttgga ttgggatgag aatggaatga tgcagttatt    480

gaggcaaagg aaaatatgta agatgacagt cagttttcta gcttggtagt cattcttttt    540

cactagtcat tatggggtca aatggagtgc ctactgatcc ataagatgtg ctaattgtta    600

ccatcgacta cagttaactt gaattccatg tgtctagtct gcctctactc aacaattaca    660

agagtttctt ggagcttcag aattgntang ggaaccatgt tagttttggt tgnaatttaa    720

taaaaagtac cnaaaaagcc ccaagagatn tggaacaaga aaggcttttn tccttgaaag    780

aaacacaagg ggtttnccct tttagtccnt gctttnttaa aaaccaagnt acatttgggt    840

acccaannct agngggttgc tgtnggggaa aaattaaggg gcctatcttt tgtttggtnn    900

ccccttnng                                                            909
```

<210> SEQ ID NO 68
<211> LENGTH: 1020
<212> TYPE: DNA
<213> ORGANISM: Homo sapiens
<220> FEATURE:
<221> NAME/KEY: modified_base
<222> LOCATION: (12)..(12)
<223> OTHER INFORMATION: n is a, c, g, or t
<220> FEATURE:
<221> NAME/KEY: modified_base
<222> LOCATION: (694)..(694)
<223> OTHER INFORMATION: n is a, c, g, or t
<220> FEATURE:

<221> NAME/KEY: modified_base
<222> LOCATION: (702)..(702)
<223> OTHER INFORMATION: n is a, c, g, or t
<220> FEATURE:
<221> NAME/KEY: modified_base
<222> LOCATION: (727)..(727)
<223> OTHER INFORMATION: n is a, c, g, or t
<220> FEATURE:
<221> NAME/KEY: modified_base
<222> LOCATION: (740)..(740)
<223> OTHER INFORMATION: n is a, c, g, or t
<220> FEATURE:
<221> NAME/KEY: modified_base
<222> LOCATION: (749)..(749)
<223> OTHER INFORMATION: n is a, c, g, or t
<220> FEATURE:
<221> NAME/KEY: modified_base
<222> LOCATION: (760)..(760)
<223> OTHER INFORMATION: n is a, c, g, or t
<220> FEATURE:
<221> NAME/KEY: modified_base
<222> LOCATION: (767)..(767)
<223> OTHER INFORMATION: n is a, c, g, or t
<220> FEATURE:
<221> NAME/KEY: modified_base
<222> LOCATION: (769)..(769)
<223> OTHER INFORMATION: n is a, c, g, or t
<220> FEATURE:
<221> NAME/KEY: modified_base
<222> LOCATION: (826)..(826)
<223> OTHER INFORMATION: n is a, c, g, or t
<220> FEATURE:
<221> NAME/KEY: modified_base
<222> LOCATION: (829)..(829)
<223> OTHER INFORMATION: n is a, c, g, or t
<220> FEATURE:
<221> NAME/KEY: modified_base
<222> LOCATION: (831)..(831)
<223> OTHER INFORMATION: n is a, c, g, or t
<220> FEATURE:
<221> NAME/KEY: modified_base
<222> LOCATION: (835)..(835)
<223> OTHER INFORMATION: n is a, c, g, or t
<220> FEATURE:
<221> NAME/KEY: modified_base
<222> LOCATION: (841)..(841)
<223> OTHER INFORMATION: n is a, c, g, or t
<220> FEATURE:
<221> NAME/KEY: modified_base
<222> LOCATION: (856)..(857)
<223> OTHER INFORMATION: n is a, c, g, or t
<220> FEATURE:
<221> NAME/KEY: modified_base
<222> LOCATION: (871)..(871)
<223> OTHER INFORMATION: n is a, c, g, or t
<220> FEATURE:
<221> NAME/KEY: modified_base
<222> LOCATION: (875)..(875)
<223> OTHER INFORMATION: n is a, c, g, or t
<220> FEATURE:
<221> NAME/KEY: modified_base
<222> LOCATION: (883)..(883)
<223> OTHER INFORMATION: n is a, c, g, or t
<220> FEATURE:
<221> NAME/KEY: modified_base
<222> LOCATION: (891)..(891)
<223> OTHER INFORMATION: n is a, c, g, or t
<220> FEATURE:
<221> NAME/KEY: modified_base
<222> LOCATION: (899)..(899)
<223> OTHER INFORMATION: n is a, c, g, or t
<220> FEATURE:
<221> NAME/KEY: modified_base
<222> LOCATION: (913)..(913)
<223> OTHER INFORMATION: n is a, c, g, or t
<220> FEATURE:
<221> NAME/KEY: modified_base
<222> LOCATION: (915)..(915)
<223> OTHER INFORMATION: n is a, c, g, or t
<220> FEATURE:
<221> NAME/KEY: modified_base
<222> LOCATION: (921)..(921)
<223> OTHER INFORMATION: n is a, c, g, or t
<220> FEATURE:
<221> NAME/KEY: modified_base
<222> LOCATION: (934)..(934)
<223> OTHER INFORMATION: n is a, c, g, or t
<220> FEATURE:
<221> NAME/KEY: modified_base
<222> LOCATION: (938)..(938)
<223> OTHER INFORMATION: n is a, c, g, or t
<220> FEATURE:
<221> NAME/KEY: modified_base
<222> LOCATION: (951)..(951)
<223> OTHER INFORMATION: n is a, c, g, or t
<220> FEATURE:
<221> NAME/KEY: modified_base
<222> LOCATION: (959)..(959)
<223> OTHER INFORMATION: n is a, c, g, or t
<220> FEATURE:
<221> NAME/KEY: modified_base
<222> LOCATION: (965)..(966)
<223> OTHER INFORMATION: n is a, c, g, or t
<220> FEATURE:
<221> NAME/KEY: modified_base
<222> LOCATION: (979)..(980)
<223> OTHER INFORMATION: n is a, c, g, or t
<220> FEATURE:
<221> NAME/KEY: modified_base
<222> LOCATION: (1004)..(1004)
<223> OTHER INFORMATION: n is a, c, g, or t
<220> FEATURE:
<221> NAME/KEY: modified_base
<222> LOCATION: (1019)..(1019)
<223> OTHER INFORMATION: n is a, c, g, or t

<400> SEQUENCE: 68

```
gttgattcct cngcactgtt ggcctactgg gacaataaag cagctcatct ttacttccta     60

agagaattcc acactcagtg aagatcaaaa cttacaatga aaacatttta atgaatcaca    120

gaaaatcagt tttctgttt gtttggttgt tggttttgtg tctttcctgg tgtgagctcc    180

ccaagcttac agatgagctg atgctactag ttggtaccag taatccatca gaagacagat    240

gaaactttgt aagagaaact gtatttgata aagctgaaag ctaacttgct tcaatctttt    300

tagaaaatgt tttattcatc ttcatagaga cccaaaggaa aaataatttg gacagggatg    360

gcaattctgt gacagtttat catccctcct tagcaatgga ccaaagagag aaacaaatag    420

gaagtcaaaa atttcctcgt ttcctggtct gtgacaaccc caaagattcc aaagagagtt    480

ggagaatagc ttgcttgcaa aagtgagcag gtctcacata ctcccttcaa ctccatctcc    540

taaaaagtaa tttaaatttc aggggtatca tctgtatagc cacataaaga ggacattgtc    600

catatttaaa actgagaaat atccatcatt catatcagta acattttcat cttattattc    660

tgcttttta aacttacatt tctgtccccc tgcngtattc angtcagttg tatacccaag    720

aatcgtngta agtgcttttn ttaagtggnc aggatatttn aatgccncna agaaaatggg    780

gtaatttaat ttaatttcct tccaaacatt ttaatttttc tgccanganc nttangtttt    840

nccattccaa gggggnncct atttccttta naacnatttc ttnaggggtt nccaaaagng    900

ggggggattt tcntncatta naattttctt tagncccntt tttacccagt nctctggtnc    960

cctgnngggg ggaattttnn ctttgggggg gggaaaaaaa aaancccaat ttgggattnt   1020
```

<210> SEQ ID NO 69
<211> LENGTH: 938
<212> TYPE: DNA
<213> ORGANISM: Homo sapiens
<220> FEATURE:

<221> NAME/KEY: modified_base
<222> LOCATION: (3)..(3)
<223> OTHER INFORMATION: n is a, c, g, or t
<220> FEATURE:
<221> NAME/KEY: modified_base
<222> LOCATION: (757)..(757)
<223> OTHER INFORMATION: n is a, c, g, or t
<220> FEATURE:
<221> NAME/KEY: modified_base
<222> LOCATION: (764)..(764)
<223> OTHER INFORMATION: n is a, c, g, or t
<220> FEATURE:
<221> NAME/KEY: modified_base
<222> LOCATION: (772)..(772)
<223> OTHER INFORMATION: n is a, c, g, or t
<220> FEATURE:
<221> NAME/KEY: modified_base
<222> LOCATION: (818)..(818)
<223> OTHER INFORMATION: n is a, c, g, or t
<220> FEATURE:
<221> NAME/KEY: modified_base
<222> LOCATION: (823)..(824)
<223> OTHER INFORMATION: n is a, c, g, or t
<220> FEATURE:
<221> NAME/KEY: modified_base
<222> LOCATION: (831)..(831)
<223> OTHER INFORMATION: n is a, c, g, or t
<220> FEATURE:
<221> NAME/KEY: modified_base
<222> LOCATION: (836)..(836)
<223> OTHER INFORMATION: n is a, c, g, or t
<220> FEATURE:
<221> NAME/KEY: modified_base
<222> LOCATION: (843)..(843)
<223> OTHER INFORMATION: n is a, c, g, or t
<220> FEATURE:
<221> NAME/KEY: modified_base
<222> LOCATION: (856)..(856)
<223> OTHER INFORMATION: n is a, c, g, or t
<220> FEATURE:
<221> NAME/KEY: modified_base
<222> LOCATION: (865)..(865)
<223> OTHER INFORMATION: n is a, c, g, or t
<220> FEATURE:
<221> NAME/KEY: modified_base
<222> LOCATION: (868)..(869)
<223> OTHER INFORMATION: n is a, c, g, or t
<220> FEATURE:
<221> NAME/KEY: modified_base
<222> LOCATION: (881)..(881)
<223> OTHER INFORMATION: n is a, c, g, or t
<220> FEATURE:
<221> NAME/KEY: modified_base
<222> LOCATION: (886)..(886)
<223> OTHER INFORMATION: n is a, c, g, or t
<220> FEATURE:
<221> NAME/KEY: modified_base
<222> LOCATION: (897)..(897)
<223> OTHER INFORMATION: n is a, c, g, or t
<220> FEATURE:
<221> NAME/KEY: modified_base
<222> LOCATION: (906)..(906)
<223> OTHER INFORMATION: n is a, c, g, or t
<220> FEATURE:
<221> NAME/KEY: modified_base
<222> LOCATION: (912)..(912)
<223> OTHER INFORMATION: n is a, c, g, or t
<220> FEATURE:
<221> NAME/KEY: modified_base
<222> LOCATION: (935)..(935)
<223> OTHER INFORMATION: n is a, c, g, or t
<220> FEATURE:
<221> NAME/KEY: modified_base
<222> LOCATION: (938)..(938)
<223> OTHER INFORMATION: n is a, c, g, or t

<400> SEQUENCE: 69
gtngggcctt tttttttttt tttttgtaga gaagagtttt cctatgttgc ccagactggt 60

```
cttgaactcc tgggcttaaa tactccacct gccttggcct cccaaagtgc tgggattaca    120

gacatgagcc actgtgcctg gctcagaatt tttcaattag aaccgctaca taaaatcaag    180

tttcctaaat ccataccaga tgatgtccag gcactgtgtt tcacacacct tgccttagat    240

cgacaagaaa ttacactttg aagtacacta gtggcaagaa tctgagtctt cttctcaaag    300

aggagtcaga aagcaatggt gtaaattttt ggcttctttc agtgctttgg gtacttgctt    360

tactgtacac atatgaatga gcctactgtt tacccaaagc ccagaccatt tgaagttatg    420

aatggggaga agtcacataa aactagagaa ctatcactcg gtgttttcat ggacccactt    480

ccttaccaca aggtactatg attttggcag acatcataag ctagatgttg ccatttgacc    540

aatctaacaa tctacctgtg attctaccca gattttttac taccttttta ggtaaatgtc    600

aaatgaaata ggatggtgta gggcatatga tttaaacata aaatgtttcc ctttcgatga    660

cagatttttg ctcatgctag ccaacaggat aggtatagac cctttgggat gccattactg    720

gacttctttt cattagtctt gggccctaat cttatgnttt tcangccttt tnctttttcca    780

ttttccccca aaaaacccaa ccccttaagg cttgttangc ttnnctgggg ngaaantaac    840

cgntacgggg gacctnttgg aaaanggnnc ccatttcctt natggnggtt gggggancaa    900

tggctnttaa cnccttttt ttttggttta agggntcn                             938
```

```
<210> SEQ ID NO 70
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70

agcaucgagu cggccuuggc cuacugg                                         27


<210> SEQ ID NO 71
<211> LENGTH: 42
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 71

gcggctgaag acggcctatg tggccttttt tttttttttt tt                        42


<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 72

agcatcgagt cggccttgtt g                                               21


<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence:
      Synthetic primer
```

<400> SEQUENCE: 73
gcgctgaaga cggcctatgt 20

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
tcagaaggct tcgagactg 19

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
gcagatatct tgtcaaaggt 20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
ggtgagccct aacatccaca 20

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
agcccgtaag ccatcaatc 19

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
atcatggtga aaggcacgtc 20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
cataatttcc acgtgttgtg 20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
agaggttagc cctgagacag 20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
tctatgcttc cagcaggtac 20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
cctttatatt agaacgtggc 20

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
taggttttca ggacttgg 18

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
gcaggatagc aaccttgaca 20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 85

-continued atgcatgctt tcgtgtgttc 20

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence:
Synthetic primer

<400> SEQUENCE: 86
caccctggag aaacacaaac tc 22

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 87
atgccgtcca tcttcatcac 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 88
aacatgaatc tgtgggtgac 20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 89
tcaatcgctt gaccttcctc 20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 90
aagcattgaa gtaacaaccg 20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 91
tgcatttgac atatgagagc 20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
tattagaacg tggccctcca 20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
tcgggactag caggacagaa 20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
taaaccagca accctaacag 20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
actagaatca gacctgcctt 20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 96
aactggcagc aaagaaggtc 20

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
agcagaagca cgtcagtaag g 21

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
tcacccagaa tgagacatgg 20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
gtcagaaggt gacacggtga 20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 100
cccaaggagg taagagcctg 20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 101
aagcgctgga gcttgtcggt 20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 102
agaacggtgt aattcagaga 20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
gtcatcagca agctcgaata 20

-continued

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
tttatattag aacgtggccc 20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
aggacttggt agcttctcgg 20

<210> SEQ ID NO 106
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
aattttaaaa aggcaggata tacaac 26

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
aaggagaggt agcattttat gtgc 24

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
ggcatcctca tctcctcaga 20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
tctgaagcag ttcgaagcac 20

<210> SEQ ID NO 110

<211> LENGTH: 21
<212> TYPE: DNA
<213> ORGANISM: Artificial Sequence
<220> FEATURE:
<223> OTHER INFORMATION: Description of Artificial Sequence:
Synthetic primer

<400> SEQUENCE: 110
tggttcaaac tcttccctcc t 21

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 111
cttccacctg tgcgttttct 20

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence:
Synthetic primer

<400> SEQUENCE: 112
tgggaaatcc acctgcatc 19

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 113
accagctcac cctgaatgtg 20

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence:
Synthetic primer

<400> SEQUENCE: 114
cgtggcaaca cctttttatt c 21

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence:
Synthetic primer

<400> SEQUENCE: 115
acacggcatg ggtttgtt 18

<210> SEQ ID NO 116
<211> LENGTH: 21

```
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 116

tgaggagttg aatgctgacc t                                               21


<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 117

catcggggtt aatgctcttg                                                 20


<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 118

acttgctcat ggtgctgtct c                                               21


<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 119

cgcagagcct ggtaatcttc                                                 20


<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 120

cctcaagaac cagaccaagc                                                 20


<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 121

ctgatgctga ggagctgaca                                                 20


<210> SEQ ID NO 122
<211> LENGTH: 19
<212> TYPE: DNA
```

<213> ORGANISM: Artificial Sequence
<220> FEATURE:
<223> OTHER INFORMATION: Description of Artificial Sequence:
Synthetic primer

<400> SEQUENCE: 122
ggccaccaga gaggtaatg 19

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence:
Synthetic primer

<400> SEQUENCE: 123
gtgctgacct aagacccaaa g 21

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 124
ctgcctttga gatggtgatg 20

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence:
Synthetic primer

<400> SEQUENCE: 125
tgtagtgctt tgcattgttg g 21

<210> SEQ ID NO 126
<211> LENGTH: 19
<212> TYPE: DNA
<213> ORGANISM: Artificial Sequence
<220> FEATURE:
<223> OTHER INFORMATION: Description of Artificial Sequence:
Synthetic primer

<400> SEQUENCE: 126
tacctcttcg gctggatgg 19

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence:
Synthetic primer

<400> SEQUENCE: 127
gcttgggcag gatgaatg 18

<210> SEQ ID NO 128
<211> LENGTH: 20
<212> TYPE: DNA
<213> ORGANISM: Artificial Sequence

```
<220> FEATURE:
<223> OTHER INFORMATION: Description of Artificial Sequence:
      Synthetic primer

<400> SEQUENCE: 128

agccgatgaa gtgtctgctt                                              20


<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 129

ragccacaaa agcaggttag g                                            21


<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 130

gcagcagata tagggacaca ga                                           22


<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 131

cacgcataaa tggctacacc                                              20


<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 132

agattattca cctgtaagc                                               19


<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 133

ttttccacat gtccagcacc                                              20


<210> SEQ ID NO 134
<211> LENGTH: 20
<212> TYPE: DNA
<213> ORGANISM: Artificial Sequence
<220> FEATURE:
```

```
<223> OTHER INFORMATION: Description of Artificial Sequence:
      Synthetic primer

<400> SEQUENCE: 134

gtgaccagca aggaaacaca                                              20


<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 135

gaggattcag ccacgaaca                                               19


<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 136

gcatggagga aaccattagg                                              20


<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 137

tggctcttca accaaacctt                                              20


<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 138

atgacctggc actaggcttg                                              20


<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 139

aacacatctg ctggcttctg                                              20


<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence:
```

Synthetic primer

<400> SEQUENCE: 140
acgacgacac tgacaaccac 20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 141
gcttgacctc cgactcatct 20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 142
cacccatctg tgtctgtggt 20

<210> SEQ ID NO 143
<211> LENGTH: 19
<212> TYPE: DNA
<213> ORGANISM: Artificial Sequence
<220> FEATURE:
<223> OTHER INFORMATION: Description of Artificial Sequence:
Synthetic primer

<400> SEQUENCE: 143
cgtgctgacg atgatgttg 19

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence:
Synthetic primer

<400> SEQUENCE: 144
gtgtttggca ctacatcacc a 21

<210> SEQ ID NO 145
<211> LENGTH: 19
<212> TYPE: DNA
<213> ORGANISM: Artificial Sequence
<220> FEATURE:
<223> OTHER INFORMATION: Description of Artificial Sequence:
Synthetic primer

<400> SEQUENCE: 145
ccgggttttc cattttcac 19

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 146
tacagtggga actgcgtttg 20

<210> SEQ ID NO 147
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
cagggttcgt atgcaggag 19

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
agccattaca ggtggcaaga 20

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
gttgggtcga tcttaggagg tag 23

<210> SEQ ID NO 150
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
taacaactct agcaccatc 19

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
tacttagcag aacagaagag 20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
gtggacacca agaatgcaag 20

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence:
Synthetic primer

<400> SEQUENCE: 153
cagccaactg tggtaagaag g 21

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 154
cagtgcagcc ttggaagtgt 20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 155
tcaaaagctg cgtgtgtctc 20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 156
ttagtgagta cacgagctgg 20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 157
acttaaccca gactgaccac 20

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence:
Synthetic primer

<400> SEQUENCE: 158

-continued

```
agatgtttaa gggcaaacc                                                    19


<210> SEQ ID NO 159
<211> LENGTH: 18
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 159

tggagcctct tggatctc                                                     18


<210> SEQ ID NO 160
<211> LENGTH: 19
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 160

aacatcctgg tggaacagc                                                    19


<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 161

ctctatagta acgaccaaac                                                   20


<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 162

gcttgaggac agtgaaaacc a                                                 21


<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 163

tggagtgaga ggatgggaag                                                   20


<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 164
```

gcaggggaca caggactcta c 21

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 165
aagctccttc tggctcaaca 20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
ccgagatctt ctgccttcat 20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 167
tccttgccgt ctcaaactct 20

<210> SEQ ID NO 168
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 168
atctctctag tgccatgac 19

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 169
agtcttgcta agactttcag 20

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 170
cagtgcggtt gtggtctatc t 21

```
<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 171

tgaggcgttg actttctgg                                                19


<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 172

ttcagcaggt cctagccaag                                               20


<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 173

rtggaagctg ctgaagaaac a                                             21


<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 174

gcctttcttt gtctggaacg                                               20


<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 175

gggtgaagca atttcacagg                                               20


<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 176

aaatggcagt ttgactgtgg                                               20
```

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 177
ttggctgagt tctccctcat 20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 178
attaatcctg cactcttacg 20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 179
agttccattt ctacagcaag 20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 180
ttggtcgtga ggtggattct 20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 181
atcttgccag ccacagactt 20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 182
agagtcacct gcgaccctta 20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 183
agctctagca gccagcacat 20

<210> SEQ ID NO 184
<211> LENGTH: 22
<212> TYPE: DNA
<213> ORGANISM: Artificial Sequence
<220> FEATURE:
<223> OTHER INFORMATION: Description of Artificial Sequence:
Synthetic primer

<400> SEQUENCE: 184
cataatcttc tccggcttca tc 22

<210> SEQ ID NO 185
<211> LENGTH: 22
<212> TYPE: DNA
<213> ORGANISM: Artificial Sequence
<220> FEATURE:
<223> OTHER INFORMATION: Description of Artificial Sequence:
Synthetic primer

<400> SEQUENCE: 185
gtctggtatt tccgtgaggt tt 22

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 186
atctcccatc gactcactgc 20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 187
tggctttact ggtcatacag 20

<210> SEQ ID NO 188
<211> LENGTH: 19
<212> TYPE: DNA
<213> ORGANISM: Artificial Sequence
<220> FEATURE:
<223> OTHER INFORMATION: Description of Artificial Sequence:
Synthetic primer

<400> SEQUENCE: 188
tgattctcca aggcaaggt 19

<210> SEQ ID NO 189

```
<211> LENGTH: 19
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 189

gatttcccca ttgactgct                                          19


<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 190

agcctttgct accctcttcc                                         20


<210> SEQ ID NO 191
<211> LENGTH: 19
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 191

ggcgaaacac tcctctcgt                                          19


<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 192

aacctcgtaa aaaccatggc                                         20


<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 193

agcagtgact tgagcatttg                                         20


<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 194

cgacacctct cattgcacac                                         20


<210> SEQ ID NO 195
<211> LENGTH: 20
```

<212> TYPE: DNA
<213> ORGANISM: Artificial Sequence
<220> FEATURE:
<223> OTHER INFORMATION: Description of Artificial Sequence:
Synthetic primer

<400> SEQUENCE: 195
tccgtctcaa atccacacac 20

<210> SEQ ID NO 196
<211> LENGTH: 19
<212> TYPE: DNA
<213> ORGANISM: Artificial Sequence
<220> FEATURE:
<223> OTHER INFORMATION: Description of Artificial Sequence:
Synthetic primer

<400> SEQUENCE: 196
agcacaattc cccagacac 19

<210> SEQ ID NO 197
<211> LENGTH: 22
<212> TYPE: DNA
<213> ORGANISM: Artificial Sequence
<220> FEATURE:
<223> OTHER INFORMATION: Description of Artificial Sequence:
Synthetic primer

<400> SEQUENCE: 197
ctgtagccct tactgtttga cc 22

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 198
ctgtgttctg atgccaatgc 20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 199
tgcaactttc tccaccaaga 20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 200
ggagctagcc aagatgatcg 20

<210> SEQ ID NO 201
<211> LENGTH: 20
<212> TYPE: DNA

```
<213> ORGANISM: Artificial Sequence
<220> FEATURE:
<223> OTHER INFORMATION: Description of Artificial Sequence:
      Synthetic primer

<400> SEQUENCE: 201

ctggccatcc tagaggagaa                                                 20


<210> SEQ ID NO 202
<211> LENGTH: 26
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 202

aattttaaaa aggcaggata tacaac                                          26


<210> SEQ ID NO 203
<211> LENGTH: 24
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 203

aaggagaggt agcattttat gtgc                                            24


<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 204

aatcttcctc ccaacccatg                                                 20


<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 205

tgaccctgct gaaggaagcg                                                 20


<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 206

ccctgaatgt tgaacgagtg                                                 20


<210> SEQ ID NO 207
<211> LENGTH: 20
<212> TYPE: DNA
<213> ORGANISM: Artificial Sequence
```

<220> FEATURE:
<223> OTHER INFORMATION: Description of Artificial Sequence:
Synthetic primer

<400> SEQUENCE: 207
tgcacattga agaggcaaac 20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 208
ccgaggtcaa catttgttcc 20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 209
gagcagagca cagacagtgg 20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 210
ctggaatcat ccaggctttg 20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 211
gcgtccagga taacagcact 20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 212
gtcttcaagc agcgacagtg 20

<210> SEQ ID NO 213
<211> LENGTH: 20
<212> TYPE: DNA
<213> ORGANISM: Artificial Sequence
<220> FEATURE:

```
<223> OTHER INFORMATION: Description of Artificial Sequence:
      Synthetic primer

<400> SEQUENCE: 213

ccttcagggt ctggttgatg                                              20


<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 214

gggaccacta accagctgaa                                              20


<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 215

aaatgtctga cccctcctca                                              20


<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 216

ccaggatgga gtagccaaga                                              20


<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 217

gccagtgatc tccaggtttg                                              20


<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 218

actggggagg aatggctagt                                              20


<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence:
```

Synthetic primer

<400> SEQUENCE: 219
ctggctggag gaaaaaggac 20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 220
ctgaggtgct gatgatcctg 20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 221
ccaaactcct gctcttctcg 20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 222
agcagtttgg tgctgttggt 20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 223
gcttgttcca tggttggact 20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 224
acgaggacca caggactcaa 20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 225
tgggctccat agtttgttcc 20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 226
attctctctg gaggcgatga 20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 227
tttcctcaca gctccctctc 20

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 228
tttagctgtt tgcaaataag atgt 24

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 229
aatgcagtgt gtgggatgtg 20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 230
tccgacatga tggttctcct 20

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 231
agatccagga gtcacccaaa 20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 232
cacaggtgtc aaagcacgtt 20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 233
tgtagcactc gctgttgctc 20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 234
tcctgaagcc ttcttgccta 20

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 235
gcttgtggca accagaaagt 20

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 236
aggtgggagt cgacctttct 20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 237
gcatccttca acttggtcct 20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 238
gcagcaagga agaggacaag 20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 239
agcaatcttc gtctgggaag 20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 240
agaaggacct cctcccaaag 20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 241
tgcaacagtc ctcttccttg 20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 242
attagttggg acctgccttg 20

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 243
gcccattttc ttcagcagag 20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 244
agagcagctc agctaccaca 20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 245
gaaggcaact ttggtgttgg 20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 246
aaacgggtac aggatggaga 20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 247
caactggagg tcggaggata 20

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence:
Synthetic primer

<400> SEQUENCE: 248
tggtctgttt aacaattgac ctg 23

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence:
Synthetic primer

<400> SEQUENCE: 249
gctgcatctt ccaacattct t 21

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 250
ccgtgcagtt tgacatgaat 20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 251
tgtggcatct cattcagcat 20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 252
caccctttga agtgacggta 20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 253
ctgaaaaacc agcccacact 20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 254
ctctgtggga tgacacatgc 20

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 255
tttggcacct tgtcattttg 20

<210> SEQ ID NO 256
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 256
cctgcttaag agtaagcctg gt 22

<210> SEQ ID NO 257
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 257
agttctgtgg gctataggat cg 22

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 258
tgtgtcttcc gactttctgg 20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 259
tctttccctg agtgcttggt 20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 260
agaggtggaa gcacttcagg 20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 261
aaagtccttg gtgctctcgt 20

-continued

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 262
ctggagcctg tttgatggtt 20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 263
tgctttcctt actggcaggt 20

<210> SEQ ID NO 264
<211> LENGTH: 19
<212> TYPE: DNA
<213> ORGANISM: Artificial Sequence
<220> FEATURE:
<223> OTHER INFORMATION: Description of Artificial Sequence:
Synthetic primer

<400> SEQUENCE: 264
gaacatgggc actgactgg 19

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 265
catcagggct aggagactcg 20

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence:
Synthetic primer

<400> SEQUENCE: 266
cagcaatgaa tcctccaatg t 21

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 267
tggtggttct ccctgtgatt 20

<210> SEQ ID NO 268

<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 268
agaccagtgg ctcgtcaaac 20

<210> SEQ ID NO 269
<211> LENGTH: 19
<212> TYPE: DNA
<213> ORGANISM: Artificial Sequence
<220> FEATURE:
<223> OTHER INFORMATION: Description of Artificial Sequence:
Synthetic primer

<400> SEQUENCE: 269
ttgcagacat caggggtgt 19

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 270
tctgcaccag agaatccaca 20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 271
atagggcttt tctcccgtgt 20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 272
cagaaaaacg gtggaggact 20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 273
ccctgccttg ttctccataa 20

<210> SEQ ID NO 274
<211> LENGTH: 20

<212> TYPE: DNA
<213> ORGANISM: Artificial Sequence
<220> FEATURE:
<223> OTHER INFORMATION: Description of Artificial Sequence: Synthetic primer

<400> SEQUENCE: 274
caagcatgca ggaagaactc 20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 275
aatgttcgta gccgatccag 20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 276
tgtgtttgct ggggagtatg 20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 277
tcatttgcag ccactctacg 20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 278
tggagctcag aagaggagga 20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 279
cgcaacatga agtccatcag 20

<210> SEQ ID NO 280
<211> LENGTH: 20
<212> TYPE: DNA

-continued

```
<213> ORGANISM: Artificial Sequence
<220> FEATURE:
<223> OTHER INFORMATION: Description of Artificial Sequence:
      Synthetic primer

<400> SEQUENCE: 280

caaagtccct ctccttcagc                                                    20


<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 281

ccctagtggc caactctgat                                                    20


<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 282

ttacccaggt ggttcagcat                                                    20


<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 283

tacccatcag ggtgatgaca                                                    20


<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 284

gccaggaagt gaggaatgag                                                    20


<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 285

cccggatgac ctgaatgtag                                                    20


<210> SEQ ID NO 286
<211> LENGTH: 20
<212> TYPE: DNA
<213> ORGANISM: Artificial Sequence
```

-continued

```
<220> FEATURE:
<223> OTHER INFORMATION: Description of Artificial Sequence:
      Synthetic primer

<400> SEQUENCE: 286

aacacactgg cgttcatctg                                              20


<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 287

gactcccact tgcgtctctg                                              20


<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 288

gacatggaag gcatgctgta                                              20


<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 289

gacagacgct tcagcgaaat                                              20


<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 290

agccttggtg ctgaagatgt                                              20


<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 291

cttatgtgac cgtgcacctg                                              20


<210> SEQ ID NO 292
<211> LENGTH: 20
<212> TYPE: DNA
<213> ORGANISM: Artificial Sequence
<220> FEATURE:
```

<223> OTHER INFORMATION: Description of Artificial Sequence:
Synthetic primer

<400> SEQUENCE: 292
cgcctgacaa tctcaattcc 20

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 293
ctcacgtgtc tgcgtttgat 20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 294
aggggatccg gaagtatgac 20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 295
aagccgctca tctggtagag 20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 296
tgagaaaacg gtcctgaagc 20

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 297
tgtcagaccc ttggcatctt 20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence:

Synthetic primer

<400> SEQUENCE: 298
tacctgagtc ggacacgatg 20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 299
gagagccaga caagctttgg 20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 300
acaaggaccc ctgtgctaac 20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 301
tgaggacagt ggcaggtgta 20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 302
tgcgaggatt aactccaagg 20

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 303
ggcaactttg gctgaagagt 20

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 304
agtccccatt gggatactgc 20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 305
tgggcaataa tttggaaacc 20

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 306
agccacactg ttagcagcaa 20

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 307
cgaatgtcca gaagggagag 20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 308
cagcctgtga atggtgtgaa 20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 309
tgagggaagc tgtggaagag 20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 310
tgacatctgc ttgtccttgg 20

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 311
ggacggcagt accaagagtg 20

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 312
gagtctgcca ttggctttgt 20

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 313
ctgcttgctc tgttccactg 20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 314
agacagggtc tggctgtgtt 20

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 315
tgaggccagg agttcaagac 20

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 316
ctggcacaat gtcttcacaa 20

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 317
ttgaaagggg agattcctga 20

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 318
cgacagatga ccttgattcg 20

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 319
gcctcagaag cctttctcaa 20

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 320
gttggcgagc tagcaaaact 20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 321
tgccatcctt ctcacagatg 20

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 322

```
ttacccataa tgccctccac                                                20


<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 323

caaaacgaca gcagcagaac                                                20


<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 324

ggcattggag gttgtcattc                                                20


<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 325

gcttgctctt caccaggaac                                                20


<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 326

gaagaccctg gtttttgcag                                                20


<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 327

caactcggtt ggtgaaatca g                                              21


<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 328

aggagaagcc tcatcaacca                                                20
```

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 329
tcaggcagac attcccagat 20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 330
aatgtgccgg ttttctcatc 20

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 331
ccaacccctt agacatgcac 20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 332
tctgtgaaag ggcatgtgag 20

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 333
ggagggattt cattgctctg 20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 334
tctcagttgg gtttggaagc 20

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 335
ggagaaaagc cagagtgtcg 20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 336
cacgggaacc catttgtatg 20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 337
gtggaaggag ccgttgataa 20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 338
atcggcagag tgcatacctt 20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 339
tctgtggctc aatacgcttg 20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 340
ttcccaccaa atcagtctcc 20

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 341
tggccactga agtctcaggt 20

<210> SEQ ID NO 342
<211> LENGTH: 21
<212> TYPE: DNA
<213> ORGANISM: Artificial Sequence
<220> FEATURE:
<223> OTHER INFORMATION: Description of Artificial Sequence:
Synthetic primer

<400> SEQUENCE: 342
atggtgaaag tggttcagtg c 21

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 343
tgcatttgct gtggattacc 20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 344
gtggcacagt gggagctatt 20

<210> SEQ ID NO 345
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 345
gcccaatcct ctaaacaacg 20

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 346
gtaaacagcc ccttggtcag 20

<210> SEQ ID NO 347

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 347
atgtgcagtg ttccccactt 20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 348
caagcggtgg agtacttgaa 20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 349
cctgcagttc ccagtctttc 20

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 350
cccagccagc caagtagata 20

<210> SEQ ID NO 351
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 351
accccactct ttgggtctct 20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 352
actgggcatc tggatagcag 20

<210> SEQ ID NO 353
<211> LENGTH: 20

<212> TYPE: DNA
<213> ORGANISM: Artificial Sequence
<220> FEATURE:
<223> OTHER INFORMATION: Description of Artificial Sequence: Synthetic primer

<400> SEQUENCE: 353
cttcggaacc agccaactta 20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 354
tgaggggctt caagcagtag 20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 355
gcacactcac ttcccaagga 20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 356
cgtggtggtg tgtattttgg 20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 357
gcggtgacat aaaaggctga 20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 358
atggagaact tgcctgcact 20

<210> SEQ ID NO 359
<211> LENGTH: 20
<212> TYPE: DNA

<213> ORGANISM: Artificial Sequence
<220> FEATURE:
<223> OTHER INFORMATION: Description of Artificial Sequence:
Synthetic primer

<400> SEQUENCE: 359
tcagcttcac ccacactttg 20

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 360
ctgtggagga gtgggatgtt 20

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 361
gttgcttttg gtttcccatc 20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 362
tgtgagtcct cctgttgtgg 20

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 363
gagctgtcaa aatggcttcc 20

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 364
tcacagttgc tgccaaagag 20

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 365
cgtcccattt tccagagatg 20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 366
accagtgtga ggtggtcaga 20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 367
gtgggaggcc acaaacttag 20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 368
ggagcaatcc aaggagatga 20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 369
tggacagcct ccttcagttt 20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 370
ggtcgtttag gtggcaaatg 20

<210> SEQ ID NO 371
<211> LENGTH: 20
<212> TYPE: DNA
<213> ORGANISM: Artificial Sequence
<220> FEATURE:

<223> OTHER INFORMATION: Description of Artificial Sequence:
Synthetic primer

<400> SEQUENCE: 371
cccaggaatc tgcaaggata 20

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 372
gttgatggag caccacagaa 20

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 373
ctgcattgtt cagccaggtt 20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 374
caccaatgct gtgaacttgc 20

<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 375
tgacagtcca gcctcacaga 20

<210> SEQ ID NO 376
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 376
tggacacgca taagaagcag 20

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence:

Synthetic primer

<400> SEQUENCE: 377
tgtcgaagaa actcctgacg 20

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 378
gtggtgtgat gtctgccatt 20

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 379
ccttgttgga ccttgattcc 20

<210> SEQ ID NO 380
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 380
aaggctcttt ccaggaggtc 20

<210> SEQ ID NO 381
<211> LENGTH: 21
<212> TYPE: DNA
<213> ORGANISM: Artificial Sequence
<220> FEATURE:
<223> OTHER INFORMATION: Description of Artificial Sequence:
Synthetic primer

<400> SEQUENCE: 381
ccttcaggac acacaggctt a 21

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 382
tagtccccaa acctgctgtt 20

<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 383
ggcgaagaag aatttgaacg 20

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 384
gcctgtggtc aaaatccagt 20

<210> SEQ ID NO 385
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 385
ctttgcctca gtggctcttc 20

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 386
tttccaggag gtcaggtttg 20

<210> SEQ ID NO 387
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 387
ccttcaggac acacaggctt a 21

<210> SEQ ID NO 388
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 388
tgacaaagac gctgaactgg 20

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 389
gggttgtcag aaagcctgag 20

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 390
taatgggagt gctgcctctg 20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 391
catctttaag gctaacatgc 20

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 392
aaggagcgca ccaacagtat 20

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 393
atagggtggc tcagggaaat 20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 394
gcacttggac ctcccttgta 20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence:
Synthetic primer

<400> SEQUENCE: 395

```
ggtcctgcac atttcaacag                                              20


<210> SEQ ID NO 396
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 396

gggcaggaca ataagactgc                                              20


<210> SEQ ID NO 397
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 397

tgtccacagc agacacccta                                              20


<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 398

aagaaggctc cgagctcaat                                              20


<210> SEQ ID NO 399
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 399

tctgtgagct ccaggcagta                                              20


<210> SEQ ID NO 400
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 400

gcagcattct gagacacagg                                              20


<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 401
```

```
gctggagaga cccaaggact                                                 20


<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 402

caggggataa ccttcgtcaa                                                 20


<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 403

aagcagcaac gtgggataac                                                 20


<210> SEQ ID NO 404
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 404

acattgacaa ccctcccaag                                                 20


<210> SEQ ID NO 405
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 405

aaagcagcag cctcagagaa                                                 20


<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 406

aaacgcttga gctcttccac                                                 20


<210> SEQ ID NO 407
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 407

agctcagcaa ccgctctaaa                                                 20
```

```
<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 408

agaggggcca agggatataa                                              20


<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 409

tacgagggcc tgtttcagat                                              20


<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 410

ttcagagcat cgagttcacg                                              20


<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 411

tcatcctcct gggtgaagtt                                              20


<210> SEQ ID NO 412
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 412

tcaccaaaac tggcacagag                                              20


<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 413

tcggactgtg ctgcattcta                                              20
```

-continued

```
<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 414

ctgcacacct ctcaatgcag                                              20


<210> SEQ ID NO 415
<211> LENGTH: 18
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 415

gaagcagccc gatgtgtt                                                18


<210> SEQ ID NO 416
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 416

cagagcagta accgtgacca                                              20


<210> SEQ ID NO 417
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 417

accaggacgg acactgttgt                                              20
```